US007217794B2

(12) United States Patent
Abdel-Meguid et al.

(10) Patent No.: US 7,217,794 B2
(45) Date of Patent: May 15, 2007

(54) COMPOUNDS AND METHODS FOR TREATMENT OF THROMBOSIS

(75) Inventors: Sherin S. Abdel-Meguid, Exton, PA (US); Robert E. Babine, Franklin, MA (US); Hongfeng Deng, Acton, MA (US); Lei Jin, Wellesley, MA (US); Jian Lin, Walpole, MA (US); Scott R. Magee, Somerville, MA (US); Harold V. Meyers, Weston, MA (US); Pramod Pandey, Canton, MA (US); Michael J. Rynkiewicz, Boston, MA (US); David T. Weaver, Newton, MA (US); Zihong Gho, Southbury, CT (US); Thomas D. Bannister, Northborough, MA (US)

(73) Assignee: Daiamed, Inc., Cambridge, MA (US)

( * ) Notice: Subject to any disclaimer, the term of this patent is extended or adjusted under 35 U.S.C. 154(b) by 0 days.

(21) Appl. No.: 10/817,248

(22) Filed: Apr. 2, 2004

(65) Prior Publication Data

US 2005/0143317 A1 Jun. 30, 2005

Related U.S. Application Data

(60) Provisional application No. 60/459,910, filed on Apr. 2, 2003.

(51) Int. Cl.
*C07K 14/745* (2006.01)
*C07K 1/00* (2006.01)
*C07K 14/00* (2006.01)

(52) U.S. Cl. .................. 530/384; 530/350; 530/380; 530/381; 530/412

(58) Field of Classification Search .............. None
See application file for complete search history.

(56) References Cited

U.S. PATENT DOCUMENTS

| 4,461,724 | A | * | 7/1984 | Konishi ................ 530/330 |
| 4,904,659 | A | | 2/1990 | Atwell et al. ............ 514/235.2 |
| 5,286,637 | A | * | 2/1994 | Veronese et al. ........... 435/183 |
| 5,658,902 | A | | 8/1997 | Ahn et al. .................. 51/234.8 |
| 5,919,589 | A | * | 7/1999 | Kawakami et al. ....... 429/231.8 |
| 5,942,620 | A | | 8/1999 | Krantz et al. ............. 546/166 |
| 6,048,720 | A | * | 4/2000 | Dalborg et al. ............ 435/219 |
| 6,258,822 | B1 | | 7/2001 | Geyer et al. ............... 514/275 |
| 6,284,796 | B1 | | 9/2001 | Geyer et al. ............... 514/275 |
| 6,608,026 | B1 | * | 8/2003 | Wang et al. ................ 514/2 |
| 2005/0143317 | A1 | * | 6/2005 | Abdel-Meguid et al. ...... 514/19 |

FOREIGN PATENT DOCUMENTS

| EP | 0206802 | 9/1993 |
| WO | WO 96/18644 | 6/1996 |
| WO | WO 00/32590 | 6/2000 |
| WO | WO 00/66545 | 11/2000 |
| WO | WO 00/69832 | 11/2000 |
| WO | WO 02/24667 | 3/2002 |

OTHER PUBLICATIONS

M.-F. Sun, et al. J. Biol. Chem. (1999), 274(51), pp. 36373-36378.*
J. Rudinger. In: Peptide Hormones, JA Parsons, Ed. (1976) 1-7.*
H.J.C. Berendsen. A Glimpse of the Holy Grail? Science (1998) 282, pp. 642-643.*
D. Voet and J.G. Voet. Biochemistry, 2nd Edition.(1995), pp. 235-241.*
D.E. Smilek, et al. Proc. Natl. Acad. Sci. USA (1991) 88, pp. 9633-9637.*
Y. Inada, et al. Methods Enzymol. (1994) 242, pp. 65-90.*
H.F. Gaertner and R.E. Offord. Bioconj. Chem. (1996) 7(1), pp. 38-44.*
T.M. Penning, et al. J. Biol. Chem. (1982) 257(21), pp. 12589-12593.*
J.L. Strominger, et al. J. Am. Chem. Soc. (1959), 81, pp. 3803-3804.*
Granberg et al., X-ray crystallographic studies of des-Gla-FVIIa/sTF complexes and their use in structure based design. Poster MEDI 85 American Chemical Society 226th National Meeting, Sep. 8, 2003.
Holmes et al., "Site specific 1:1 opioid:albumin conjugate with in vitro activity and long in vivo duration," *Bioconjug. Chem.* 11(4):439-444 (2000).
Johansson-Zetterberg et al., Search for bensamidine P1-replacement in FVIIa dipeptide Inhibitors. Poster MEDI 83 American Chemical Society 226th National Meeting, Sep. 8, 2003.
Klinghofer et al., "Species specificity of amidine-based urokinase inhibitors," *Biochemistry* 40(31):9125-9131 (2001).
Meijers et al., "High levels of coagulation factor XI as a risk factor for venous thrombosis," *N. Engl. J. Med.* 342(10):696-701 (2000).
Outt et al., "A General Synthesis of 4-Substituted 6-(2-Imidazolinylamino)-5,8-dimethylquinolines," *J. Org. Chem.* 63(17):5762-5768 (1998).
Parlow et al., "Polymer-assisted solution-phase library synthesis and crystal structure of alpha-ketothiazoles as tissue factor VIIa inhibitors," *J. Med. Chem.* 46(19):4043-4049 (2003).
Veale et al., "Nonpeptidic inhibitors of human leukocyte elastase. 5.Design, synthesis, and X-ray crystallography of a series of orally active 5-aminopyrimidin-6-one-containing trifluoromethyl ketones," *J. Med. Chem.* 38(1):98-108 (1995).

(Continued)

*Primary Examiner*—Cecilia J. Tsang
*Assistant Examiner*—Andrew D. Kosar
(74) *Attorney, Agent, or Firm*—Clark & Elbing, LLP; Paul T. Clark

(57) ABSTRACT

The present invention provides compounds that inhibit Factor XIa and methods of preventing or treating undesired thrombosis by administering a compound of the invention to a mammal. The invention also provides three-dimensional structures of Factor XIa and methods for designing or selecting additional Factor XIa inhibitors using these structures.

6 Claims, 21 Drawing Sheets

OTHER PUBLICATIONS

Baird and Walsh, "The Interaction of Factor XIa with Activated Platelets but Not Endothelial Cells Promotes the Activation of Factor IX in the Consolidation Phase of Blood Coagulation," *The Journal of Biological Chemistry* 277:38462-38467 (2002).

Minnema et al., "Activation of Clotting Factor XI Without Detectable Contact Activation in Experimental Human Endotoxemia," *Blood* 92:3284-3301 (1998).

Salomon et al., "Prevalence, Causes, and Characterization of Factor XI Inhibitors in Patients with Inherited Factor XI Deficiency," *Blood* 101:4783-4788 (2003).

Zivelin et al., "Factor XI Deficiency in French Basques is Caused Predominantly by an Ancestral Cys38Arg Mutation in the Factor XI Gene," *Blood* 99:2448-2454 (2002).

Information, Applicant's Statement, Jun. 2006.

* cited by examiner

| FXIcat | Residue | Trypsin | FXIcat | Residue | Trypsin | FXIcat | Residue | Trypsin |
|---|---|---|---|---|---|---|---|---|
| 370 | ILE | 16 | 410 | THR | 54 | 450 | ILE | 90 |
| 371 | VAL | 17 | 411 | ALA | 55 | 451 | HIS | 91 |
| 372 | GLY | 18 | 412 | ALA | 56 | 452 | ASP | 92 |
| 373 | GLY | 19 | 413 | HIS | 57 | 453 | GLN | 93 |
| 374 | THR | 20 | 414 | CYS | 58 | 454 | TYR | 94 |
| 375 | ALA | 21 | 415 | PHE | 59 | 455 | LYS | 95 |
| 376 | SER | 22 | 416 | TYR | 5901 | 456 | MET | 96 |
| 377 | VAL | 23 | 417 | GLY | 5902 | 457 | ALA | 97 |
| 378 | ARG | 24 | 418 | VAL | 5903 | 458 | GLU | 98 |
| 379 | GLY | 25 | 419 | GLU | 60 | 459 | SER | 99 |
| 380 | GLU | 26 | 420 | SER | 61 | 460 | GLY | 100 |
| 381 | TRP | 27 | 421 | PRO | 62 | 461 | TYR | 101 |
| 382 | PRO | 28 | 422 | LYS | 63 | 462 | ASP | 102 |
| 383 | TRP | 29 | 423 | ILE | 64 | 463 | ILE | 103 |
| 384 | GLN | 30 | 424 | LEU | 65 | 464 | ALA | 104 |
| 385 | VAL | 31 | 425 | ARG | 66 | 465 | LEU | 105 |
| 386 | THR | 32 | 426 | VAL | 67 | 466 | LEU | 106 |
| 387 | LEU | 33 | 427 | TYR | 68 | 467 | LYS | 107 |
| 388 | HIS | 34 | 428 | SER | 69 | 468 | LEU | 108 |
| 389 | THR | 35 | 429 | GLY | 70 | 469 | GLU | 109 |
| 390 | THR | 36 | 430 | ILE | 71 | 470 | THR | 110 |
| 391 | SER | 37 | 431 | LEU | 72 | 471 | THR | 111 |
| 392 | PRO | 3701 | 432 | ASN | 73 | 472 | VAL | 112 |
| 393 | THR | 3702 | 433 | GLN | 74 | 473 | ASN | 113 |
| 394 | GLN | 3703 | 434 | SER | 75 | 474 | TYR | 114 |
| 395 | ARG | 3704 | 435 | GLU | 76 | 475 | THR | 115 |
| 396 | HIS | 38 | 436 | ILE | 77 | 476 | ASP | 116 |
| 397 | LEU | 39 | 437 | LYS | 78 | 477 | SER | 117 |
| 398 | CYS | 40 | 438 | GLU | 79 | 478 | GLN | 118 |
| 399 | GLY | 41 | 439 | ASP | 80 | 479 | ARG | 119 |
| 400 | GLY | 42 | 440 | THR | 81 | 480 | PRO | 121 |
| 401 | SER | 43 | 441 | SER | 8101 | 481 | ILE | 122 |
| 402 | ILE | 44 | 442 | PHE | 82 | 482 | CYS | 123 |
| 403 | ILE | 45 | 443 | PHE | 83 | 483 | LEU | 124 |
| 404 | GLY | 46 | 444 | GLY | 84 | 484 | PRO | 125 |
| 405 | ASN | 47 | 445 | VAL | 85 | 485 | SER | 126 |
| 406 | GLN | 48 | 446 | GLN | 86 | 486 | LYS | 127 |
| 407 | TRP | 51 | 447 | GLU | 87 | 487 | GLY | 128 |
| 408 | ILE | 52 | 448 | ILE | 88 | 488 | GLU | 129 |
| 409 | LEU | 53 | 449 | ILE | 89 | 489 | ARG | 130 |

Figure 2

SEQ ID NO: 9

| | | | | | | | | |
|---|---|---|---|---|---|---|---|---|
| 490 | ASN | 131 | 530 | ARG | 171 | 570 | HIS | 204 |
| 491 | VAL | 132 | 531 | TYR | 172 | 571 | LEU | 209 |
| 492 | ILE | 13201 | 532 | ARG | 173 | 572 | VAL | 210 |
| 493 | TYR | 133 | 533 | GLY | 17301 | 573 | GLY | 211 |
| 494 | THR | 134 | 534 | HIS | 174 | 574 | ILE | 212 |
| 495 | ASP | 135 | 535 | LYS | 175 | 575 | THR | 213 |
| 496 | CYS | 136 | 536 | ILE | 176 | 576 | SER | 214 |
| 497 | TRP | 137 | 537 | THR | 177 | 577 | TRP | 215 |
| 498 | VAL | 138 | 538 | HIS | 178 | 578 | GLY | 216 |
| 499 | THR | 139 | 539 | LYS | 179 | 579 | GLU | 217 |
| 500 | GLY | 140 | 540 | MET | 180 | 580 | GLY | 218 |
| 501 | TRP | 141 | 541 | ILE | 181 | 581 | CYS | 219 |
| 502 | GLY | 142 | 542 | CYS | 182 | 582 | ALA | 220 |
| 503 | TYR | 143 | 543 | ALA | 183 | 583 | GLN | 221 |
| 504 | ARG | 144 | 544 | GLY | 184 | 584 | ARG | 222 |
| 505 | LYS | 145 | 545 | TYR | 18401 | 585 | GLU | 223 |
| 506 | LEU | 146 | 546 | ARG | 185 | 586 | ARG | 224 |
| 507 | ARG | 147 | 547 | GLU | 186 | 587 | PRO | 225 |
| 508 | ASP | 148 | 548 | GLY | 187 | 588 | GLY | 226 |
| 509 | LYS | 149 | 549 | GLY | 188 | 589 | VAL | 227 |
| 510 | ILE | 151 | 550 | LYS | 18801 | 590 | TYR | 228 |
| 511 | GLN | 152 | 551 | ASP | 189 | 591 | THR | 229 |
| 512 | ASN | 153 | 552 | ALA | 190 | 592 | ASN | 230 |
| 513 | THR | 154 | 553 | CYS | 191 | 593 | VAL | 231 |
| 514 | LEU | 155 | 554 | LYS | 192 | 594 | VAL | 232 |
| 515 | GLN | 156 | 555 | GLY | 193 | 595 | GLU | 233 |
| 516 | LYS | 157 | 556 | ASP | 194 | 596 | TYR | 234 |
| 517 | ALA | 158 | 557 | SER | 195 | 597 | VAL | 235 |
| 518 | LYS | 159 | 558 | GLY | 196 | 598 | ASP | 236 |
| 519 | ILE | 160 | 559 | GLY | 197 | 599 | TRP | 237 |
| 520 | PRO | 161 | 560 | PRO | 198 | 600 | ILE | 238 |
| 521 | LEU | 162 | 561 | LEU | 19801 | 601 | LEU | 239 |
| 522 | VAL | 163 | 562 | SER | 19802 | 602 | GLU | 240 |
| 523 | THR | 164 | 563 | CYS | 201 | 603 | LYS | 241 |
| 524 | ASN | 165 | 564 | LYS | 202 | 604 | THR | 242 |
| 525 | GLU | 166 | 565 | HIS | 20201 | 605 | GLN | 243 |
| 526 | GLU | 167 | 566 | ASN | 20202 | 606 | ALA | 244 |
| 527 | CYS | 168 | 567 | GLU | 20203 | 607 | VAL | |
| 528 | GLN | 169 | 568 | VAL | 20204 | | | |
| 529 | LYS | 170 | 569 | TRP | 203 | SEQ ID NO: 9 | | |

Figure 2 (Continued)

| COLUMNS | DATA TYPE | FIELD | DEFINITION |
|---|---|---|---|
| 1 – 6 | Record name | "ATOM" | |
| 7 – 11 | Integer | serial | Atom serial number. |
| 13 – 16 | Atom | name | Atom name. |
| 17 | Character | altLoc | Alternate location indicator. |
| 18 -20 | Residue name | resName | Residue name. |
| 22 | Character | chainID | Chain identifier. |
| 23 – 26 | Integer | resSeq | Residue sequence number. |
| 27 | AChar | iCode | Code for insertion of residues. |
| 31 – 38 | Real (8.3) | x | Orthogonal coordinates for X in Angstroms. |
| 39 – 46 | Real (8.3) | y | Orthogonal coordinates for Y in Angstroms. |
| 47 – 54 | Real (8.3) | z | Orthogonal coordinates for Z in Angstroms. |
| 55 – 60 | Real (6.2) | occupancy | Occupancy. |
| 61 – 66 | Real (6.2) | tempFactor | Temperature factor. |
| 73 – 76 | LString(4) | segID | Segment identifier, left-justified. |
| 77 - 78 | LString(2) | element | Element symbol, right-justified. |

Figure 3

| FXIcat Residue Substitutions | Activity* | Crystal Type |
|---|---|---|
| WT | 1.2 | N.D. |
| S434A | N.D. | N.D. |
| T475A | N.D. | N.D. |
| S434A,T475A | N.D. | Needles, Solved w/Ecotin |
| S434A,T475A,K422A | N.D. | Needles |
| S434A,T475A,K437A | 1.3 | Needles, Cubic/ Solved w/benzamidine, Plates |
| S434A,T475A,K486A | N.D. | N.D. |
| S434A,T475A,K505A | 1.1 | Needles w/SPRL cmpds; Cubic/ Solved w/benzamidine |
| S434A,T475A,K509A | N.D. | Needles |
| S434A,T475A,C482S | N.D. | Needles |
| S434A,T475A,C482S,K437A | 1.4 | Needles & Cubic crystals, with benz. and SPRL cmpds |
| S434A,T475A,C482S,R479A | N.D. | Needles |
| S434A,T475A,C482S,K505A | N.D. | Needles and Cubic crystals |
| S434A,T475A,C482S,D476A | 0.7 | Needles and plates |
| S434A,T475A,AVC terminal truncation | N.D. | Needles |
| S434A,T475A,C482S,Y416S | N.D. | N.D. |

*ratio of FXIcat mutant $K_{cat}$/native Factor XIa $K_{cat}$

Figure 4A

| Inhibitor | Resolution | Space Group | Lattice Constants | Mutant* | Condition† |
|---|---|---|---|---|---|
| Ecotin M84R | 2.2 Å | $P2_12_12_1$ | a=44.6 Å, b=92.7 Å, c=186.9 Å, α=β=γ=90° | WT-degly | 1 |
| WT Ecotin | 2.6 Å | $P2_12_12_1$ | a=44.3 Å, b=91.9 Å, c=186.2 Å, α=β=γ=90° | WT-degly | 1 |
| Ecotin IX-D | 3.0 Å | $P2_12_12_1$ | a=45.4 Å, b=91.4 Å, c=188.6 Å, α=β=γ=90° | 2m | 2 |
| Benzamidine | 2.0 Å | I23 | a=b=c=120.1 Å, α=β=γ=90° | 3m-K455A | 3 |
| SPRL-122599 | 2.8 Å | I23 | a=b=c=121.5 Å, α=β=γ=90° | 3m-K455A | 4 |
| SPRL-121995 | 2.1 Å | I23 | a=b=c=121.2 Å, α=β=γ=90° | 3m-K455A | 5 |
| SPRL-124336 | 3.0 Å | $P3_2$ | a=b=41.9 Å, c=103.8 Å, α=β=γ=90° | 3m-K455A | 6 |
| SPRL-123682 | 2.0 Å | I23 | a=b=c=121.3 Å, α=β=γ=90° | 3m-K455A | 7 |
| SPRL-123672 | 2.2 Å | I23 | a=b=c=121.4 Å, α=β=γ=90° | 3m-K455A | 3 |
| SPRL-123545 | 2.1 Å | I23 | a=b=c=120.7 Å, α=β=γ=90° | 3m-K455A | 8 |
| SPRL-122624 | 2.1 Å | I23 | a=b=c=122.4 Å, α=β=γ=90° | 3m-K455A | 9 |
| SPRL-123586 | 2.7 Å | $P2_1$ | a=55.8 Å, b=70.3 Å, c=62.1 Å, α=γ= 90°, β=102.2° | 3m-K455A | 10 |

*WT-degly=wide type FXIcat that is chemically deglycosylated; 2m=FXIcat with mutations of S452A, T493A; 2m-K523A=FXIcat with mutations of S452A, T493A and K523A; 3m-K455A=FXIcat with mutations of S452A, T493A, C500S and K455A.

†Crystallization conditions:
1. 20% (w/v) PEG 1000, 0.1 M Na/K phosphate, pH 6.2.
2. 22% (w/v) PEGMME 2000, 0.1 M $(NH_4)_2SO_4$, 0.1 M Na cacodylate, pH 6.2
3. 2.0 M ammonium sulfate, 0.1 M Tris-HCl, pH 8.5.
4. 23% (w/v) PEG 4000, 0.2 M $Li_2SO_4$, 0.1 M Tris-HCl, pH 8.5.
5. 24% (w/v) PEG 4000, 0.16 M $Li_2SO_4$, 80 mM Tris-HCl, pH 8.5.
6. 30% (w/v) PEGMME 5000, 0.2 M $(NH_4)_2SO_4$, 0.1 M Tris-HCl, pH 7.6.
7. 18% (w/v) PEG 4000, 0.2 M $Li_2SO_4$, 0.1 M Tris-HCl, pH 8.5.
8. 30% (w/v) PEG 4000, 0.2 M $Li_2SO_4$, 0.1 M Tris-HCl, pH 8.5.
9. 20% (w/v) PEGMME 2000, 0.2 M $(NH_4)_2SO_4$, 0.1 M Tris-HCl, pH 7.6.
10. 1.4 M tri-sodium citrate, 0.1 M HEPES, pH 7.5.

Figure 4B

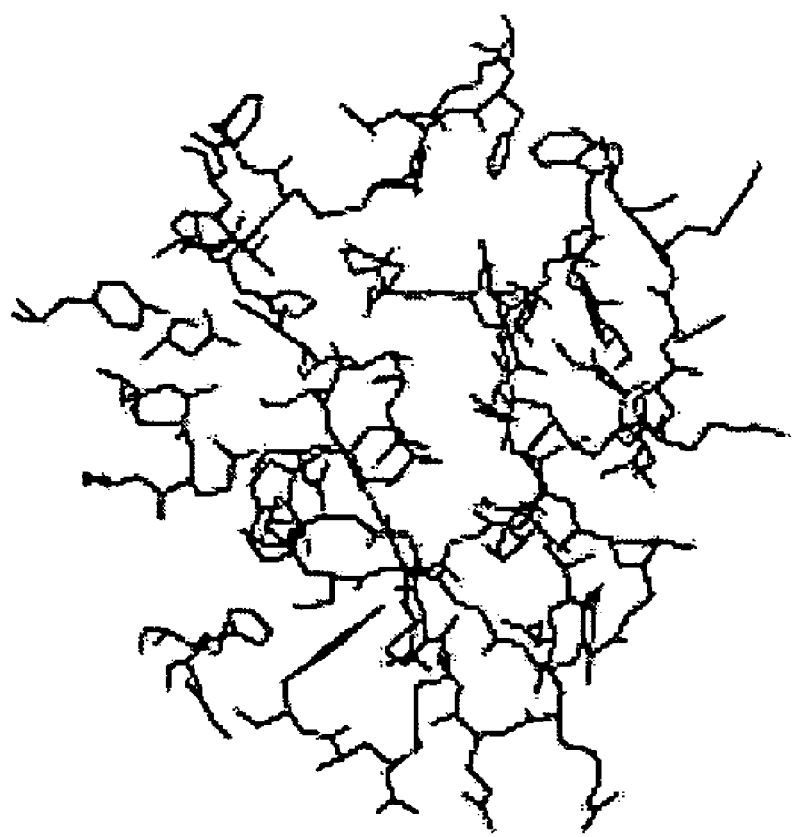
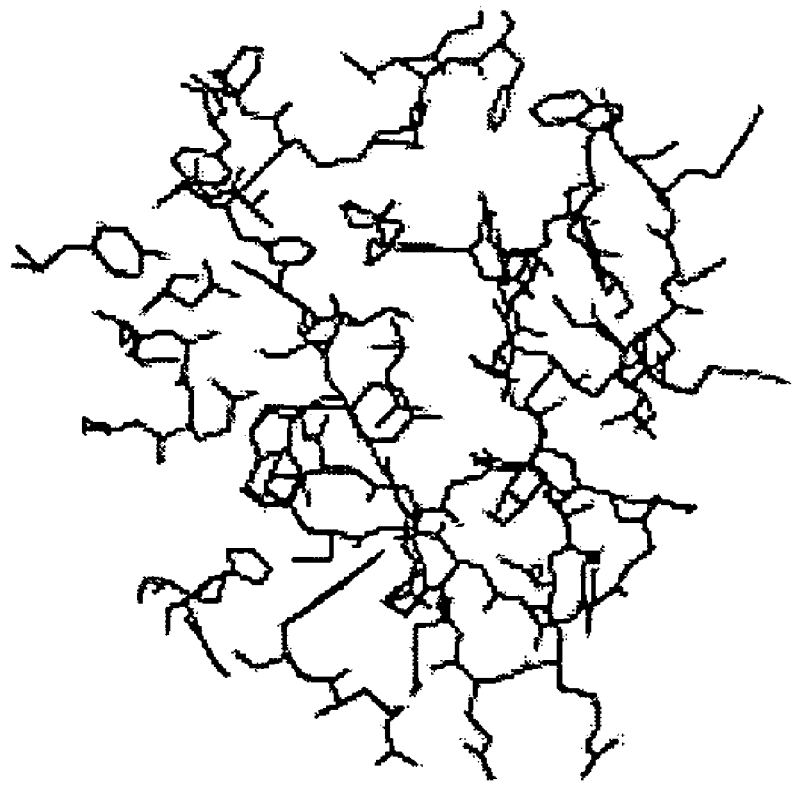
Figure 5C

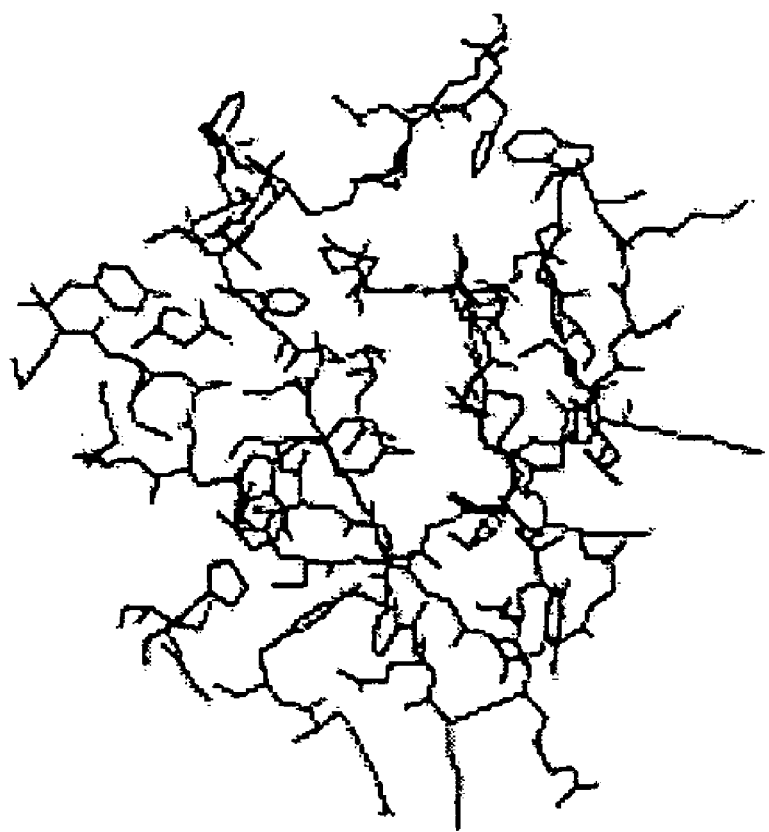
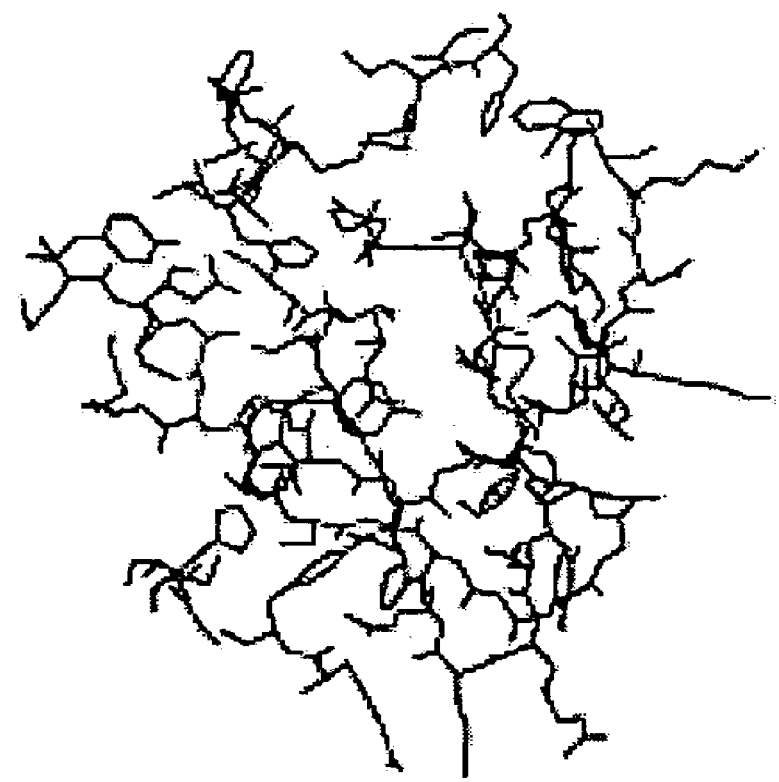
Figure 5D

Rat FXIcat sequence

|GTGTTCGGAGGAGCTGCGTC|TGTTCACGGCGAGTGGCCATGGCAGGTGACCCTGCA
CACCACCCAGGGACACCTGTGTGGAGGCTCCATCATTGGAAACCGGTGGATATTGA
CAGCGGCTCATTGTTTCTCTGGGACAGAGACACCTAAAACTCTGCGTGTCTACGGTG
GTATTGTAAATCAATCAGAAATAAATGAAGATACCACTTTCTTCAGGGTTCAAGAAA
TGATAATTCATGATCAATATACATCGGCAGAAAGTGGGTTTGACATTGCCCTCTTAA
AACTGGAACCGGCCATGAATTACACAGATTTTCAGCGGCCAATATGCCTGCCTTCCA
AAGGAGACAGAAACGTAGTTCACACAGAATGCTGGGTGACTGGATGGGGATACACA
AAATCAAGAGATGAAGTACAAAGTACTCTCCAGAAAGCCAAGGTACCATTGGTGTC
GAATGAAGAATGTCAAACAAGATACAGAAAACATAAAATAACCAACAAGGTGATCT
GTGCAGGATATAAGGAAGGAGGGAAGGATACGTGTAAGGGAGATTCTGGAGGGCC
CCTGTCCTGCAAACACAATGGGGTCTGGCACTTGGTGGGCATCACAAGCTGGGGTG
AAGGCTGCGGCCAGAAAGAGAGGCCGGGTGTCTACACCAACGTGGCCAAGTATGTG
GACTGGATTTTGG|AGAAAACTCAGTCGGAATGA|     SEQ ID NO: 4

Oligonucleotide positions used for cloning are indicated by the boxes

Figure 6

```
IVGGTASVRGEWPWQVTLHTTSPTQRHLCGGSIIGNQWILTAAHCFYGVE  Human   SEQ ID NO:9
VVGGAASVHGEWPWQVTLHIS---QGHLCGGSIIGNQWILTAAHCFSGIE  Mouse   SEQ ID NO:10
IVGGSASLPGEWPWQVTLHTVSPTQRHLCGGSIIGNQWILTAAHCFYGIE  Rabbit  SEQ ID NO:11
VFGGAASVHGEWPWQVTLHTT---QGHLCGGSIIGNRWILTAAHCFSGTE  Rat     SEQ ID NO:12

SPKILRVYSGILNQSEIKEDTSFFGVQEIIIHDQYKMAESGYDIALLKLE  Human
TPKKLRVYGGIVNQSEINEGTAFFRVQEMIIHDQYTTAESGYDIALLKLE  Mouse
SPKILRVYGGILNQSEIKEDTAFFGVQEIIIHDQYKTAESGYDIALLKLE  Rabbit
TPKTLRVYGGIVNQSEINEDTTFFRVQEMIIHDQYTSAESGFDIALLKLE  Rat TTVNYTDSQRPICLPSKGDRNVIYTDCWVTGWGYRKLRDKIQNTLQKAKI  Human
SAMNYTDFQRPICLPSKGDRNAVHTECWVTGWGYTALRGEVQSTLQKAKV  Mouse
TTMNYTDSQRPICLPSKGDRNVIYTDCWVTGWGYRKLRDKIQNTLQKAKI  Rabbit
PAMNYTDFQRPICLPSKGDRNVVHTECWVTGWGYTKSRDEVQSTLQKAKV  Rat PLVTNEECQKRYRGHKITHKMICAGYREGGKDACKGDSGGPLSCKHNEVW  Human
PLVSNEECQTRYRRHKITNKMICAGYKEGGKDTCKGDSGGPLSCKYNGVW  Mouse
PLLSNEECQKRYQRHEITSGMICAGYKEGGKDACKGDSGGPLSCKHNEVW  Rabbit
PLVSNEECQTRYRKHKITNKVICAGYKEGGKDTCKGDSGGPLSCKHNGVW  Rat HLVGITSWGEGCAQRERPGVYTNVVEYVDWILEKTQAV              Human
HLVGITSWGEGCGQKERPGVYTNVAKYVDWILEKTQTV              Mouse
HLVGITSWGEGCAQRERPGIYTNVVKYLDWILEKTQAP              Rabbit
HLVGITSWGEGCGQKERPGVYTNVAKYVDWILEKTQSE              Rat
```

Figure 7

```
              Kex-2    ↓
   ...GTA TCT CTC GAG AAA AGA ATC GTT GGA GGA...   SEQ ID NO: 13
      V   S   L   E   K   R   I   V   G   G       SEQ ID NO: 14
      ─────────────────────   ───────────────
            α-Factor                FXIa
```

Figure 9

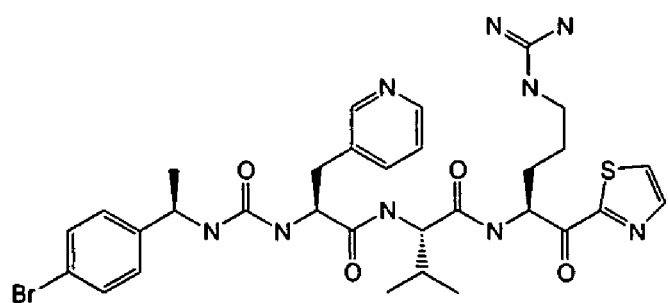
SPRL-123529
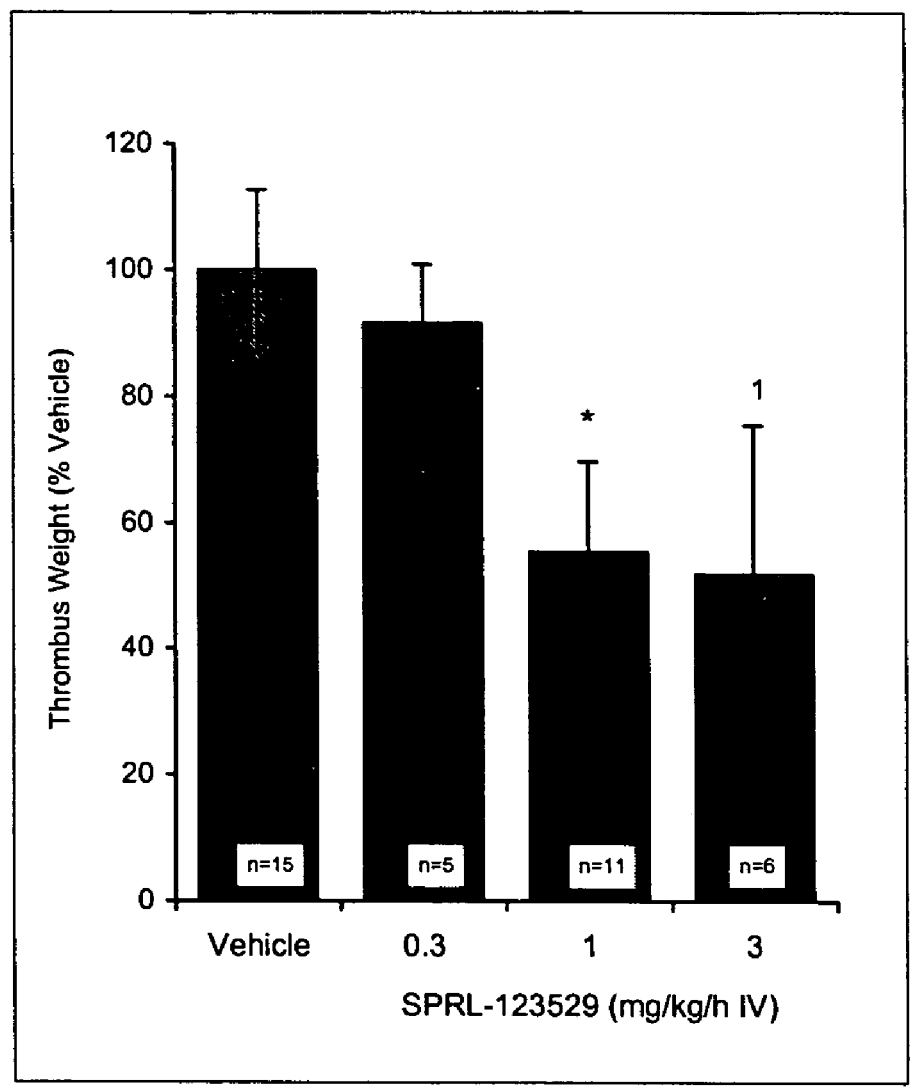
Figure 10

|  | M84R | wild type | IX-D | benz | 122599 | 121995 | 124336 | 123682 | 123672 | 123545 | 122624 |
|---|---|---|---|---|---|---|---|---|---|---|---|
| rms/loop | 2.88/48 | 2.66/48 | 2.85/48 | 2.96/48 | 3.05/48 | 3.02/48 | 3.27/48 | 2.99/48 | 3.18/48 | 2.78/48 | 3.13/48 |
| rms/fit | 0.97/944 | 1.12/936 | 0.94/944 | 0.89/944 | 0.89/944 | 0.87/944 | 0.96/928 | 0.86/944 | 0.54/912 | 0.84/944 | 0.89/944 |
| rms/loop | 2.96/48 | 2.75/48 | 2.94/48 | 3.05/48 | 3.13/48 | 3.10/48 | 3.39/48 | 3.06/48 | 3.18/48 | 2.84/48 | 3.22/48 |
| rms/fit | 0.75/920 | 0.98/916 | 0.70/916 | 0.55/908 | 0.51/908 | 0.48/908 | 0.59/896 | 0.47/908 | 0.54/912 | 0.51/908 | 0.48/908 |

Figure 12

|        | M84R | wild type | IX-D | benz | 122599 | 121995 | 124336 | 123682 | 123672 | 123545 | 122624 |
|---|---|---|---|---|---|---|---|---|---|---|---|
| M84R     |      | 2952 | 2948 | 932 | 936 | 940 | 928 | 940 | 940 | 940 | 936 |
| wild type | 0.53 |      | 2928 | 924 | 928 | 924 | 920 | 924 | 924 | 928 | 924 |
| IX-D     | 0.84 | 0.95 |      | 928 | 936 | 940 | 924 | 940 | 944 | 936 | 936 |
| benz     | 0.66 | 0.80 | 0.70 |     | 948 | 948 | 932 | 948 | 948 | 948 | 948 |
| 122599   | 0.66 | 0.88 | 0.69 | 0.29 |     | 948 | 932 | 948 | 948 | 948 | 948 |
| 121995   | 0.65 | 0.86 | 0.68 | 0.27 | 0.17 |     | 928 | 948 | 948 | 948 | 948 |
| 124336   | 0.63 | 0.58 | 0.64 | 0.65 | 0.55 | 0.49 |     | 928 | 932 | 932 | 928 |
| 123682   | 0.64 | 0.86 | 0.67 | 0.28 | 0.19 | 0.11 | 0.50 |     | 948 | 948 | 948 |
| 123672   | 0.68 | 0.89 | 0.72 | 0.33 | 0.19 | 0.22 | 0.52 | 0.21 |     | 948 | 948 |
| 123545   | 0.65 | 0.81 | 0.70 | 0.28 | 0.33 | 0.30 | 0.65 | 0.27 | 0.35 |     | 948 |
| 122624   | 0.66 | 0.91 | 0.68 | 0.31 | 0.27 | 0.23 | 0.48 | 0.22 | 0.26 | 0.37 |     |

Figure 13

|  | M84R | wild type | IX-D | benz | 122599 | 121995 | 124336 | 123682 | 123672 | 123545 | 122624 |
|---|---|---|---|---|---|---|---|---|---|---|---|
| M84R |  | 0.54 | 0.88 | 0.77 | 0.76 | 0.73 | 0.66 | 0.71 | 0.74 | 0.71 | 0.75 |
| wild type | 2964 |  | 0.99 | 0.86 | 0.92 | 0.92 | 0.89 | 0.92 | 0.89 | 0.85 | 0.97 |
| IX-D | 2968 | 2948 |  | 0.82 | 0.77 | 0.74 | 0.70 | 0.73 | 0.87 | 0.76 | 0.75 |
| benz | 948 | 936 | 948 |  | 0.29 | 0.27 | 0.65 | 0.28 | 0.33 | 0.28 | 0.31 |
| 122599 | 948 | 936 | 948 | 948 |  | 0.17 | 0.55 | 0.19 | 0.19 | 0.33 | 0.27 |
| 121995 | 948 | 936 | 948 | 948 | 932 |  | 0.51 | 0.11 | 0.22 | 0.30 | 0.23 |
| 124336 | 932 | 924 | 932 | 932 | 948 | 932 |  | 0.52 | 0.52 | 0.65 | 0.50 |
| 123682 | 948 | 936 | 948 | 948 | 948 | 948 | 932 |  | 0.21 | 0.27 | 0.22 |
| 123672 | 948 | 924 | 952 | 948 | 948 | 948 | 932 | 948 |  | 0.35 | 0.26 |
| 123545 | 948 | 936 | 948 | 948 | 948 | 948 | 932 | 948 | 948 |  | 0.37 |
| 122624 | 948 | 936 | 948 | 948 | 948 | 948 | 932 | 948 | 948 | 948 |  |

Figure 14

|  | M84R | wild type | IX-D | benz | 122599 | 121995 | 124336 | 123682 | 123672 | 123545 | 122624 |
|---|---|---|---|---|---|---|---|---|---|---|---|
| M84R | ■ | 0.21 | 0.45 | 0.26 | 0.25 | 0.28 | 0.42 | 0.27 | 0.28 | 0.28 | 0.35 |
| wild type | 0.22 | ■ | 0.32 | 0.42 | 0.38 | 0.41 | 0.34 | 0.42 | 0.45 | 0.42 | 0.50 |
| IX-D | 0.37 | 0.32 | ■ | 0.40 | 0.29 | 0.30 | 0.36 | 0.28 | 0.31 | 0.26 | 0.34 |
| benz | 0.31 | 0.47 | 0.28 | ■ | 0.20 | 0.20 | 0.30 | 0.17 | 0.21 | 0.16 | 0.20 |
| 122599 | 0.28 | 0.43 | 0.32 | 0.19 | ■ | 0.04 | 0.24 | 0.08 | 0.06 | 0.24 | 0.22 |
| 121995 | 0.32 | 0.45 | 0.34 | 0.20 | 0.04 | ■ | 0.22 | 0.08 | 0.07 | 0.25 | 0.17 |
| 124336 | 0.43 | 0.33 | 0.36 | 0.29 | 0.23 | 0.22 | ■ | 0.23 | 0.21 | 0.34 | 0.24 |
| 123682 | 0.31 | 0.46 | 0.31 | 0.17 | 0.08 | 0.08 | 0.22 | ■ | 0.11 | 0.21 | 0.13 |
| 123672 | 0.31 | 0.45 | 0.34 | 0.21 | 0.06 | 0.07 | 0.20 | 0.11 | ■ | 0.26 | 0.17 |
| 123545 | 0.32 | 0.45 | 0.28 | 0.16 | 0.23 | 0.25 | 0.35 | 0.20 | 0.26 | ■ | 0.22 |
| 122624 | 0.39 | 0.55 | 0.39 | 0.20 | 0.17 | 0.17 | 0.23 | 0.13 | 0.17 | 0.23 | ■ |

Figure 15

ATOMIC COORDINATE LISTINGS

Figure 16

SEQUENCE LISTING

```
<160> NUMBER OF SEQ ID NOS: 8

<210> SEQ ID NO 1
<211> LENGTH: 625
<212> TYPE: PRT
<213> ORGANISM: Homo sapiens

<400> SEQUENCE: 1

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30

Gly Asp Ile Thr Thr Val Phe Thr Pro Ser Ala Lys Tyr Cys Gln Val
        35                  40                  45

Val Cys Thr Tyr His Pro Arg Cys Leu Leu Phe Thr Phe Thr Ala Glu
    50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
```

-continued

```
                  85                  90                  95
Gly Tyr Ser Phe Lys Gln Cys Ser His Gln Ile Ser Ala Cys Asn Lys
                100                 105                 110
Asp Ile Tyr Val Asp Leu Asp Met Lys Gly Ile Asn Tyr Asn Ser Ser
                115                 120                 125
Val Ala Lys Ser Ala Gln Glu Cys Gln Glu Arg Cys Thr Asp Asp Val
                130                 135                 140
His Cys His Phe Phe Thr Tyr Ala Thr Arg Gln Phe Pro Ser Leu Glu
145                 150                 155                 160
His Arg Asn Ile Cys Leu Leu Lys His Thr Gln Thr Gly Thr Pro Thr
                165                 170                 175
Arg Ile Thr Lys Leu Asp Lys Val Val Ser Gly Phe Ser Leu Lys Ser
                180                 185                 190
Cys Ala Leu Ser Asn Leu Ala Cys Ile Arg Asp Ile Phe Pro Asn Thr
                195                 200                 205
Val Phe Ala Asp Ser Asn Ile Asp Ser Val Met Ala Pro Asp Ala Phe
                210                 215                 220
Val Cys Gly Arg Ile Cys Thr His His Pro Gly Cys Leu Phe Phe Thr
225                 230                 235                 240
Phe Phe Ser Gln Glu Trp Pro Lys Glu Ser Gln Arg Asn Leu Cys Leu
                245                 250                 255
Leu Lys Thr Ser Glu Ser Gly Leu Pro Ser Thr Arg Ile Lys Lys Ser
                260                 265                 270
Lys Ala Leu Ser Gly Phe Ser Leu Gln Ser Cys Arg His Ser Ile Pro
                275                 280                 285
Val Phe Cys His Ser Ser Phe Tyr His Asp Thr Asp Phe Leu Gly Glu
                290                 295                 300
Glu Leu Asp Ile Val Ala Ala Lys Ser His Glu Ala Cys Gln Lys Leu
305                 310                 315                 320
Cys Thr Asn Ala Val Arg Cys Gln Phe Phe Thr Tyr Thr Pro Ala Gln
                325                 330                 335
Ala Ser Cys Asn Glu Gly Lys Gly Lys Cys Tyr Leu Lys Leu Ser Ser
                340                 345                 350
Asn Gly Ser Pro Thr Lys Ile Leu His Gly Arg Gly Gly Ile Ser Gly
                355                 360                 365
Tyr Thr Leu Arg Leu Cys Lys Met Asp Asn Glu Cys Thr Thr Lys Ile
                370                 375                 380
Lys Pro Arg Ile Val Gly Gly Thr Ala Ser Val Arg Gly Glu Trp Pro
385                 390                 395                 400
Trp Gln Val Thr Leu His Thr Thr Ser Pro Thr Gln Arg His Leu Cys
                405                 410                 415
Gly Gly Ser Ile Ile Gly Asn Gln Trp Ile Leu Thr Ala Ala His Cys
                420                 425                 430
Phe Tyr Gly Val Glu Ser Pro Lys Ile Leu Arg Val Tyr Ser Gly Ile
                435                 440                 445
Leu Asn Gln Ser Glu Ile Lys Glu Asp Thr Ser Phe Phe Gly Val Gln
                450                 455                 460
Glu Ile Ile Ile His Asp Gln Tyr Lys Met Ala Glu Ser Gly Tyr Asp
465                 470                 475                 480
Ile Ala Leu Leu Lys Leu Glu Thr Thr Val Asn Tyr Thr Asp Ser Gln
                485                 490                 495
Arg Pro Ile Cys Leu Pro Ser Lys Gly Asp Arg Asn Val Ile Tyr Thr
                500                 505                 510
```

```
Asp Cys Trp Val Thr Gly Trp Gly Tyr Arg Lys Leu Arg Asp Lys Ile
            515                 520                 525

Gln Asn Thr Leu Gln Lys Ala Lys Ile Pro Leu Val Thr Asn Glu Glu
        530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
            580                 585                 590

Thr Ser Trp Gly Glu Gly Cys Ala Gln Arg Glu Arg Pro Gly Val Tyr
        595                 600                 605

Thr Asn Val Val Glu Tyr Val Asp Trp Ile Leu Glu Lys Thr Gln Ala
    610                 615                 620

Val
625

<210> SEQ ID NO 2
<211> LENGTH: 624
<212> TYPE: PRT
<213> ORGANISM: Oryctolagus cuniculus

<400> SEQUENCE: 2

Met Ile Leu Ser Tyr Gln Met Leu His Phe Ile Leu Val Ala Ser Val
1               5                   10                  15

Ser Gly Glu Cys Val Ile Lys Leu Phe Ser Asp Ile Tyr Phe Gln Gly
            20                  25                  30

Gly Asp Ile Thr Thr Val Tyr Thr Pro Asn Ala Lys His Cys Gln Val
        35                  40                  45

Val Cys Thr Tyr His Pro Arg Cys Leu Leu Phe Thr Phe Met Ala Glu
    50                  55                  60

Ser Ser Val Asp Ser Thr Lys Trp Phe Ser Cys Ile Leu Lys Asp Ser
65                  70                  75                  80

Val Thr Glu Ser Leu Pro Lys Val Asn Met Thr Gly Ala Ile Ser Gly
                85                  90                  95

Tyr Ser Phe Lys Gln Cys Pro His Gln Leu Ser Ala Cys Asn Lys Asp
            100                 105                 110

Ile Tyr Val Asp Leu Asp Met Gln Gly Met Asn Tyr Asn Gly Ser Val
        115                 120                 125

Thr Lys Asn Ala Gln Glu Cys Gln Glu Arg Cys Thr Asn Asp Ala His
    130                 135                 140

Cys His Phe Phe Thr Tyr Ala Thr Arg Gln Phe Pro Ser Ala Glu His
145                 150                 155                 160

Arg Asn Ile Cys Leu Leu Lys Tyr Thr Gln Thr Gly Ala Pro Thr Gly
                165                 170                 175

Ile Arg Lys Leu Lys Lys Val Ser Gly Phe Ser Leu Lys Ser Cys
            180                 185                 190

Ala Leu Ser Asn Leu Ala Cys Ile Arg Asp Ile Phe Pro Ser Thr Val
        195                 200                 205

Phe Ala Asp Asn Ile Asp Ser Val Val Ala Pro Asp Ala Leu Val
    210                 215                 220

Cys Arg Arg Ile Cys Thr His His Pro Asn Cys Leu Phe Phe Thr Phe
225                 230                 235                 240

Phe Ser Gln Glu Trp Pro Lys Glu Ser His Arg Asn Leu Cys Leu Leu
```

```
                    245                 250                 255
Lys Thr Ser Glu Ser Gly Leu Pro Ser Thr Arg Ile His Lys Asn Gln
                260                 265                 270

Ala Leu Ser Gly Phe Ser Leu Gln Asn Cys Arg His Ser Ile Pro Val
            275                 280                 285

Phe Cys His Ser Ser Phe Tyr Tyr Asp Thr Asp Phe Leu Gly Glu Glu
        290                 295                 300

Leu Asp Ile Val Asp Val Lys Gly His Glu Ala Cys Gln Lys Met Cys
305                 310                 315                 320

Thr Ser Ala Ile Arg Cys Gln Phe Phe Thr Tyr Ser Ser Ser Gln Glu
                325                 330                 335

Ser His Asn Lys Gly Lys Gly Thr Cys Tyr Leu Lys Leu Ser Ser Asn
            340                 345                 350

Gly Ser Pro Thr Lys Ile Leu His Gly Arg Gly Gly Ile Ser Gly Tyr
        355                 360                 365

Thr Leu Arg Leu Cys Lys Met Asp Asn Val Cys Thr Thr Lys Ile Lys
        370                 375                 380

Pro Arg Ile Val Gly Gly Ser Ala Ser Leu Pro Gly Glu Trp Pro Trp
385                 390                 395                 400

Gln Val Thr Leu His Thr Val Ser Pro Thr Gln Arg His Leu Cys Gly
                405                 410                 415

Gly Ser Ile Ile Gly Asn Gln Trp Ile Leu Thr Ala Ala His Cys Phe
            420                 425                 430

Tyr Gly Ile Glu Ser Pro Lys Ile Leu Arg Val Tyr Gly Gly Ile Leu
        435                 440                 445

Asn Gln Ser Glu Ile Lys Glu Asp Thr Ala Phe Phe Gly Val Gln Glu
    450                 455                 460

Ile Ile Ile His Asp Gln Tyr Lys Thr Ala Glu Ser Gly Tyr Asp Ile
465                 470                 475                 480

Ala Leu Leu Lys Leu Glu Thr Thr Met Asn Tyr Thr Asp Ser Gln Arg
                485                 490                 495

Pro Ile Cys Leu Pro Ser Lys Gly Asp Arg Asn Val Ile Tyr Thr Asp
            500                 505                 510

Cys Trp Val Thr Gly Trp Gly Tyr Arg Lys Leu Arg Asp Lys Ile Gln
        515                 520                 525

Asn Thr Leu Gln Lys Ala Lys Ile Pro Leu Leu Ser Asn Glu Glu Cys
    530                 535                 540

Gln Lys Arg Tyr Gln Arg His Glu Ile Thr Ser Gly Met Ile Cys Ala
545                 550                 555                 560

Gly Tyr Lys Glu Gly Gly Lys Asp Ala Cys Lys Gly Asp Ser Gly Gly
                565                 570                 575

Pro Leu Ser Cys Lys His Asn Glu Val Trp His Leu Val Gly Ile Thr
            580                 585                 590

Ser Trp Gly Glu Gly Cys Ala Gln Arg Glu Arg Pro Gly Ile Tyr Thr
        595                 600                 605

Asn Val Val Lys Tyr Leu Asp Trp Ile Leu Glu Lys Thr Gln Ala Pro
    610                 615                 620

<210> SEQ ID NO 3
<211> LENGTH: 624
<212> TYPE: PRT
<213> ORGANISM: Mus musculus

<400> SEQUENCE: 3
```

-continued

```
Met Thr Ser Leu His Gln Val Leu Tyr Phe Ile Phe Ala Ser Val
  1               5                  10                 15

Ser Ser Glu Cys Val Thr Lys Val Phe Lys Asp Ile Ser Phe Gln Gly
             20                  25                  30

Gly Asp Leu Ser Thr Val Phe Thr Pro Ser Ala Thr Tyr Cys Arg Leu
             35                  40                  45

Val Cys Thr His His Pro Arg Cys Leu Leu Phe Thr Phe Met Ala Glu
 50                  55                  60

Ser Ser Ser Asp Asp Pro Thr Lys Trp Phe Ala Cys Ile Leu Lys Asp
 65              70                  75                  80

Ser Val Thr Glu Ile Leu Pro Met Val Asn Met Thr Gly Ala Ile Ser
                 85                  90                  95

Gly Tyr Ser Phe Lys Gln Cys Pro Gln Gln Leu Ser Thr Cys Ser Lys
             100                 105                 110

Asp Glu Tyr Val Asn Leu Asp Met Lys Gly Met Asn Tyr Asn Ser Ser
             115                 120                 125

Val Val Lys Asn Ala Arg Glu Cys Gln Glu Arg Cys Thr Asp Asp Ala
 130                 135                 140

His Cys Gln Phe Phe Thr Tyr Ala Thr Gly Tyr Phe Pro Ser Val Asp
145                 150                 155                 160

His Arg Lys Met Cys Leu Leu Lys Tyr Thr Arg Thr Gly Thr Pro Thr
                 165                 170                 175

Thr Ile Thr Lys Leu Asn Gly Val Val Ser Gly Phe Ser Leu Lys Ser
             180                 185                 190

Cys Gly Leu Ser Asn Leu Ala Cys Ile Arg Asp Ile Phe Pro Asn Thr
             195                 200                 205

Val Leu Ala Asp Leu Asn Ile Asp Ser Val Val Ala Pro Asp Ala Phe
 210                 215                 220

Val Cys Arg Arg Ile Cys Thr His His Pro Thr Cys Leu Phe Phe Thr
225                 230                 235                 240

Phe Phe Ser Gln Ala Trp Pro Lys Glu Ser Gln Arg His Leu Cys Leu
                 245                 250                 255

Leu Lys Thr Ser Glu Ser Gly Leu Pro Ser Thr Arg Ile Thr Lys Ile
             260                 265                 270

His Ala Leu Ser Gly Phe Ser Leu Gln His Cys Arg His Ser Val Pro
             275                 280                 285

Val Phe Cys His Pro Ser Phe Tyr Asn Asp Thr Asp Phe Leu Gly Glu
 290                 295                 300

Glu Leu Asp Ile Val Asp Val Lys Gly Gln Glu Thr Cys Gln Lys Thr
305                 310                 315                 320

Cys Thr Asn Asn Ala Arg Cys Gln Phe Phe Thr Tyr Tyr Pro Ser His
                 325                 330                 335

Arg Leu Cys Asn Glu Arg Asn Arg Arg Gly Arg Cys Tyr Leu Lys Leu
             340                 345                 350

Ser Ser Asn Gly Ser Pro Thr Arg Ile Leu His Gly Arg Gly Gly Leu
             355                 360                 365

Ser Gly Tyr Ser Leu Arg Leu Cys Lys Met Asp Asn Val Cys Thr Thr
             370                 375                 380

Lys Ile Asn Pro Arg Val Val Gly Gly Ala Ala Ser Val His Gly Glu
385                 390                 395                 400

Trp Pro Trp Gln Val Thr Leu His Ile Ser Gln Gly His Leu Cys Gly
                 405                 410                 415

Gly Ser Ile Ile Gly Asn Gln Trp Ile Leu Thr Ala Ala His Cys Phe
```

```
                420             425             430
Ser Gly Ile Glu Thr Pro Lys Lys Leu Arg Val Tyr Gly Gly Ile Val
        435                 440                 445
Asn Gln Ser Glu Ile Asn Glu Gly Thr Ala Phe Phe Arg Glu Gln Glu
450                 455                 460
Met Ile Ile His Asp Gln Tyr Thr Thr Ala Glu Ser Gly Tyr Asp Ile
465                 470                 475                 480
Ala Leu Leu Lys Leu Glu Ser Ala Met Asn Tyr Thr Asp Phe Gln Arg
                485                 490                 495
Pro Ile Cys Leu Pro Ser Lys Gly Asp Arg Asn Ala Val His Thr Glu
            500                 505                 510
Cys Trp Val Thr Gly Trp Gly Tyr Thr Ala Leu Arg Gly Glu Val Gln
            515                 520                 525
Ser Thr Leu Gln Lys Ala Lys Val Pro Leu Val Ser Asn Glu Glu Cys
        530                 535                 540
Gln Thr Arg Tyr Arg Arg His Lys Ile Thr Asn Lys Met Ile Cys Ala
545                 550                 555                 560
Gly Tyr Lys Glu Gly Gly Lys Asp Thr Cys Lys Gly Asp Ser Gly Gly
                565                 570                 575
Pro Leu Ser Cys Lys Tyr Asn Gly Val Trp His Leu Val Gly Ile Thr
            580                 585                 590
Ser Trp Gly Glu Gly Cys Gly Gln Lys Glu Arg Pro Gly Val Tyr Thr
        595                 600                 605
Asn Val Ala Lys Tyr Val Asp Trp Ile Leu Glu Lys Thr Gln Thr Val
    610                 615                 620
```

<210> SEQ ID NO 4
<211> LENGTH: 708
<212> TYPE: DNA
<213> ORGANISM: Rattus Norvegicus

<400> SEQUENCE: 4

```
gtgttcggag gagctgcgtc tgttcacggc gagtggccat ggcaggtgac cctgcacacc      60
acccagggac acctgtgtgg aggctccatc attggaaacc ggtggatatt gacagcggct     120
cattgtttct ctgggacaga gacacctaaa actctgcgtg tctacggtgg tattgtaaat     180
caatcagaaa taaatgaaga taccactttc ttcagggttc aagaaatgat aattcatgat     240
caatatacat cggcagaaag tgggtttgac attgccctct aaaactgga accggccatg     300
aattacacag attttcagcg gccaatatgc ctgccttcca aaggagacag aaacgtagtt     360
cacacagaat gctgggtgac tggatgggga tacacaaaat caagagatga agtacaaagt     420
actctccaga aagccaaggt accattggtg tcgaatgaag aatgtcaaac aagatacaga     480
aaacataaaa taaccaacaa ggtgatctgt gcaggatata aggaaggagg gaaggatacg     540
tgtaagggag attctggagg gcccctgtcc tgcaaacaca tggggtctg gcacttggtg     600
ggcatcacaa gctggggtga aggctgcggc cagaaagaga ggccgggtgt ctacaccaac     660
gtggccaagt atgtggactg gattttggag aaaactcagt cggaatga                 708
```

<210> SEQ ID NO 5
<211> LENGTH: 33
<212> TYPE: DNA
<213> ORGANISM: Rattus Norvegicus

<400> SEQUENCE: 5

```
gtgttcggag gagctgcgtc tgttcacggc gag                                    33
```

```
<210> SEQ ID NO 6
<211> LENGTH: 36
<212> TYPE: DNA
<213> ORGANISM: Rattus Norvegicus

<400> SEQUENCE: 6
gtggactgga ttttggagaa aactcagtcg gaatga                         36

<210> SEQ ID NO 7
<211> LENGTH: 27
<212> TYPE: DNA
<213> ORGANISM: Rattus Norvegicus

<400> SEQUENCE: 7
atggataatg tgtgcacaac taaaatc                                   27

<210> SEQ ID NO 8
<211> LENGTH: 30
<212> TYPE: DNA
<213> ORGANISM: Rattus Norvegicus

<400> SEQUENCE: 8
tccagggcca caaagtgata ccagttgaac                                30
```

COMPOUNDS AND METHODS FOR TREATMENT OF THROMBOSIS

CROSS REFERENCE TO RELATED APPLICATIONS

This application claims priority under 35 U.S.C. 119 from provisional application U.S. Ser. No. 60/459,910 filed Apr. 2, 2003, the contents of which are incorporated herein by reference.

REFERENCE TO SEQUENCE LISTING ON COMPACT DISC

This application refers to a "Table of FIG. 16 listings", which is provided as an electronic document on two identical compact discs (CD-R), labeled "Copy 1" and "Copy 2." These compact discs each contain the file "50201.003002 Listing of FIG. 163.txt" (3,676,752 bytes, created on Aug. 3, 2004), which is incorporated by reference in its entirety.

BACKGROUND OF THE INVENTION

Blood coagulation is the first line of defense against blood loss following injury. The blood coagulation "cascade" involves a number of circulating serine protease zymogens, regulatory cofactors and inhibitors, as shown in FIG. 1. Each enzyme, once generated from its zymogen, specifically cleaves the next zymogen in the cascade to produce an active protease. This process is repeated until finally thrombin cleaves the fibrinopeptides from fibrinogen to produce fibrin that polymerizes to form a blood clot. Although efficient clotting limits the loss of blood at a site of trauma, it also poses the risk of systemic coagulation resulting in massive thrombosis. Under normal circumstances, hemostasis maintains a balance between clot formation (coagulation) and clot dissolution (fibrinolysis). However, in certain disease states such as acute myocardial infarction and unstable angina, the rupture of an established atherosclerotic plaque results in abnormal thrombus formation in the coronary arterial vasculature.

Despite the availability of a number of approved anticoagulant therapies, myocardial infarction, unstable angina, atrial fibrillation, stroke, pulmonary embolism, and deep vein thrombosis represent areas of major medical need. Cardiovascular diseases (e.g., acute myocardial infarction, stroke, and pulmonary embolism) disable or kill more people in the developed world than any other disease. Over two million patients are hospitalized each year in the U.S. for acute arterial thrombosis and stroke. The worldwide population for acute arterial antithrombotic therapy is five to six million, while over 25 million patients have chronic arterial thrombosis. Over 10 million individuals are candidates for venous thrombosis therapy.

A large medical need exists for novel anticoagulation drugs that lack some or all of the side effects of currently available drugs, such as the risk of bleeding episodes and patient-to-patient variability that results in the need for close monitoring and titration of therapeutic doses. Current anticoagulant therapies that dominate the market include injectable unfractionated and low molecular weight (LMW) heparin, and orally administered warfarin (coumadin).

Three phases of the coagulation cascade can be described, namely initiation, amplification, and propagation (see FIG. 1). Inhibiting enzymes of the propagation phase, i.e., Factor Xa and Factor IIa (thrombin), has been an area of active interest in the pharmaceutical industry for some time. The first generation of thrombin inhibitors to reach the clinic were polypeptides derived from natural sources, such as the potent anticoagulant, hirudin, which is a leech peptide. Potent, orally available, small molecule thrombin inhibitors have been discovered over the past few decades. Some of these are now in the clinic or are ready to be marketed. Efforts to develop potent Factor Xa inhibitors are not far behind. Targeting enzymes involved in propagation (e.g., hirudin) does not appear to be ideal since inhibitors of this phase of the coagulation cascade are associated with severe bleeding. This is further supported by findings that Factor V and Factor X deficiencies are associated with severe bleeding episodes.

Several new treatments under development are aimed at the initiation phase that involves Factor VII and tissue factor (TF). These include an active site-blocked Factor VIIa, a high affinity neutralizing antibody against TF, and a nematode protein (NAPcc) that inhibits Factor VIIa/TF. Because these approaches target the very start of the coagulation cascade, they may lead to bleeding episodes.

Due to the limited efficacy and adverse side-effects of some current therapeutics for the inhibition of undesirable thrombosis (e.g., deep vein thrombosis and stroke), improved compounds and methods are needed for preventing or treating undesirable thrombosis.

SUMMARY OF THE INVENTION

The present invention features compounds (e.g., peptidomimetics and non-peptides) that inhibit Factor XIa and methods for preventing or treating undesired thrombosis by administering one or more of these compounds alone or in combination with other molecules to a mammal. The invention also provides three-dimensional structures of Factor XIa and methods for designing or selecting additional Factor XIa inhibitors using these structures. Desirably, these compounds have certain structural, physical, and spatial characteristics that enable the compounds to interact with specific residues of the active site of Factor XIa.

Compounds of the Invention

Accordingly, in a first aspect, the invention features a compound of formula I, or a pharmaceutically acceptable salt or prodrug thereof:

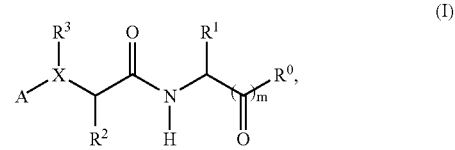

where $R^1$ is selected from the group consisting of:

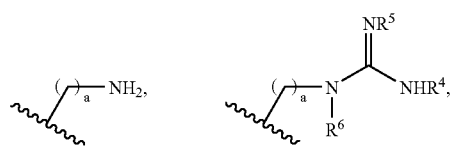

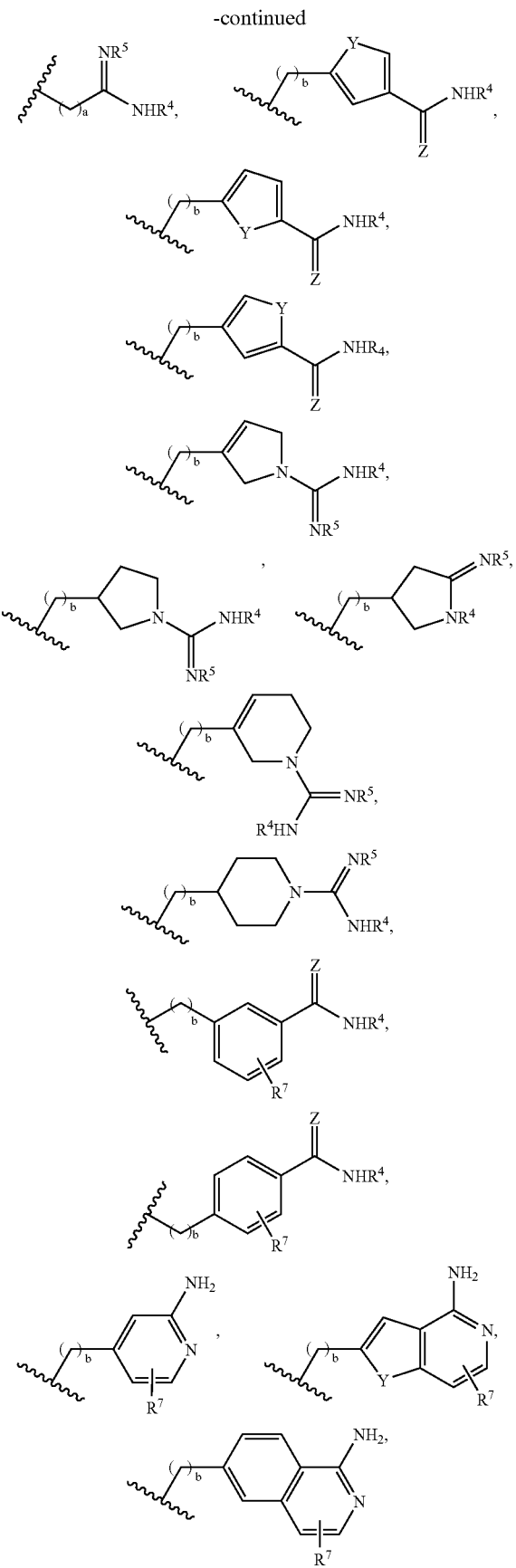

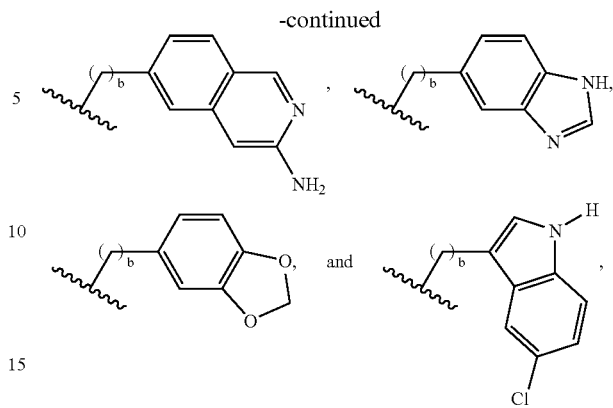

where R₄ is H or $C_{1-6}$ alkyl, $R^5$ is H, $C_{1-6}$ alkyl, OH, $NH_2$, $NO_2$, $CO_2R^{5a}$, where $R^{5a}$ is $C_{1-6}$ alkyl, or $R^5$ taken together with $R^4$ forms a 5- or 6-membered ring, $R^6$ is H, OH, $C_{1-6}$ alkyl, or when taken together with $R^4$, forms a 5- or 6-membered ring, $R^7$ is H, OH, SH, $NH_2$, $NO_2$, optionally substituted $C_{1-6}$ alkyl, halogen, or $CF_3$, Y is O, S, or $NR^4$, a is an integer from 0–5; b is an integer from 0–2, and Z is $NR^5$ or (H,H);

$R^2$ is H or an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{2-9}$ heterocyclyl, $C_{2-15}$ heteroaralkyl, or $C_{3-15}$ heteroaralkenyl, or when taken together with X and $R^3$ forms an optionally substituted $C_6$ aryl group or an optionally substituted $C_3$–$C_5$ heteroaryl group;

X is C or N; $R^3$ is H or optionally substituted $C_{1-6}$ alkyl, or together with X and A forms an optionally substituted $C_{3-5}$ heterocyclic ring, or together with X and $R^2$ forms an optionally substituted $C_6$ aryl group or an optionally substituted $C_2$–$C_5$ heteroaryl group;

A is $R^8$-$AA_2$, where $AA_2$ is a covalent bond or a peptide chain of one to five natural or unnatural alpha-amino acid residues of D- or L-configuration, preferably one or two residues, where $R^8$ is H, $C_{2-7}$ acyl, $C_{7-11}$ aroyl, $C_{3-10}$ heteroaroyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, aminocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{2-7}$ alkylthiocarbonyl, $C_{7-11}$ arylthiocarbonyl, $C_{3-10}$ heteroarylthiocarbonyl, $C_{2-7}$ alkoxythiocarbonyl, $C_{4-9}$ cycloalkoxythiocarbonyl, $C_{8-17}$ aralkoxythiocarbonyl, $C_7$ or $C_{11}$ aryloxythiocarbonyl, aminothiocarbonyl, $C_{2-7}$ alkylaminothiocarbonyl, $C_{3-13}$ dialkylaminothiocarbonyl, $C_{4-9}$ cycloalkylaminothiocarbonyl, $C_{8-17}$ aralkylaminothiocarbonyl, $C_7$ or $C_{11}$ arylaminothiocarbonyl, $C_{3-10}$ heterocyclylaminothiocarbonyl, $C_{3-16}$ heteroaralkylaminothiocarbonyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, or $C_{2-15}$ heteroaralkylsulfonyl, or A together with X and $R^3$ forms an optionally substituted $C_{2-5}$ heterocyclic ring; and m is an integer from 0–1, where when m is 1, $R^0$ is an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, $C_{3-15}$ heteroaralkenyl, or $C(O)R^9$, wherein $R^9$ is an optionally substituted $C_{1-6}$ alkyl, $C_{2-6}$ alkenyl, $C_{3-9}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, $C_{3-15}$ heteroaralkenyl, $C_{1-6}$ alkyloxy, $C_6$ or $C_{10}$ aryloxy, $C_{1-9}$ heteroaryloxy, $C_{7-16}$ aralkyloxy, $C_{1-6}$ alkylthio, $C_{3-8}$ cycloalkylthio, $C_6$ or $C_{10}$ arylthio, $C_{7-16}$ aralkylthio, $C_{1-6}$ alkylamino, $C_{2-12}$ dialkylamino, $C_{3-8}$ cycloalkylamino, $C_{7-16}$ aralkylamino, $C_6$ or $C_{10}$ arylamino, $C_{2-9}$ heterocyclylamino, or $C_{2-15}$ heteroaralkylamino, with the proviso that the amino acid of $AA_2$ that is covalently linked to X is not D-phenylalanine when $R^8$ is $C_{1-6}$ alkylsufonyl or $C_{7-16}$ aralkylsulfonyl. When m is 1, desirable $R^0$ heterocyclyl substituents include 2-thiazole, 2-(4-methylthiazole), 2-(5-methylthiazole), 2-(4,5-dimethylthiazole), 2-(5-(2-hydroxyethyl)thiazole), or 2-N-methylimidazole.

When m is 0, $R^0$ is H, CHO, CN, or $B(OR^9)_2$, wherein $R^9$ is H, $C_{1-6}$ alkyl, or taken together forms a $C_{2-4}$ cyclic boronate ester, or $R^0$ is an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, or $C_{3-15}$ heteroaralkenyl, with the proviso that the amino acid of $AA_2$ that is covalently linked to X is not D-cyclohexylglycine when $R^8$ is $C_{1-6}$ alkylsulfonyl or $C_{7-16}$ aralkylsulfonyl.

In one embodiment, $R^2$ is H or a substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, or $C_{3-15}$ heteroaralkenyl; X is N; a is an integer from 1–4; b is an integer from 0–2; $AA_2$ is a covalent bond and $R^8$ is $B-Y^1-(CH_2)_n-K-C(O)-$, wherein n is an integer from 0–6, K together with $-C(O)-$, X, and $R^3$ forms an optionally substituted $C_{2-5}$ heterocyclyl group or K is a single bond, $NR^9$, O, S, C(O), $CH(OR^{10})$, or $-CH(NHR^{11})$, wherein $R^9$ is H, OH, or $C_{1-6}$ alkyl, each of $R^{10}R^{11}$ is, independently, H, $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, $C_{3-15}$ heteroaralkenyl, $C_{2-7}$ acyl, $C_{7-11}$ aroyl, $C_{3-10}$ heteroaroyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, aminocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{2-7}$ alkylthiocarbonyl, $C_{7-11}$ arylthiocarbonyl, $C_{3-10}$ heteroarylthiocarbonyl, $C_{2-7}$ alkoxythiocarbonyl, $C_{4-9}$ cycloalkoxythiocarbonyl, $C_{8-17}$ aralkoxythiocarbonyl, $C_7$ or $C_{11}$ aryloxythiocarbonyl, aminothiocarbonyl, $C_{2-7}$ alkylaminothiocarbonyl, $C_{3-13}$ dialkylaminothiocarbonyl, $C_{4-9}$ cycloalkylaminothiocarbonyl, $C_{8-17}$ aralkylaminothiocarbonyl, $C_7$ or $C_{11}$ arylaminothiocarbonyl, $C_{3-10}$ heterocyclylaminothiocarbonyl, $C_{3-16}$ heteroaralkylaminothiocarbonyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, or $C_{2-15}$ heteroaralkylsulfonyl, $Y^1$ is O, S, $NR^{18}$, or a covalent bond, wherein $R^{18}$ is H or $C_{1-6}$ alkyl, wherein when $Y^1$ is a covalent bond, B is an optionally substituted $C_{1-6}$ alkyl, $C_{2-6}$ alkenyl, $C_{3-8}$ cycloalkyl, $C_6$ or $C_{10}$ aryl, $C_{1-9}$ heterocyclyl, $C_{7-16}$ aralkyl, $C_{8-16}$ aralkenyl, $C_{2-15}$ heteroaralkyl, $C_{3-15}$ heteroaralkenyl, $C_{1-6}$ alkylsulfonyl amino, and when $Y^1$ is O, S, or $NR^{18}$, and B is an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, $C_{3-15}$ heteroaralkenyl, $C_{2-7}$ acyl, $C_{7-11}$ aroyl, $C_{3-10}$ heteroaroyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, $C_{2-10}$ heterocyclyloxycarbonyl, aminocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{2-7}$ alkylthiocarbonyl, $C_{7-11}$ arylthiocarbonyl, $C_{3-10}$ heteroarylthiocarbonyl, $C_{2-7}$ alkoxythiocarbonyl, $C_{4-9}$ cycloalkoxythiocarbonyl, $C_{8-17}$ aralkoxythiocarbonyl, $C_7$ or $C_{11}$ aryloxythiocarbonyl, aminothiocarbonyl, $C_{2-7}$ alkylaminothiocarbonyl, $C_{3-13}$ dialkylaminothiocarbonyl, $C_{4-9}$ cycloalkylaminothiocarbonyl, $C_{8-17}$ aralkylaminothiocarbonyl, $C_7$ or $C_{11}$ arylaminothiocarbonyl, $C_{3-10}$ heterocyclylaminothiocarbonyl, $C_{3-16}$ heteroaralkylaminothiocarbonyl; $R^3$ is H or optionally substituted $C_{1-6}$ alkyl, or together with X and A forms an optionally substituted $C_{2-5}$ heterocyclic ring; and $R^0$ is -E-J, where when m is 0, E is a single bond to J, where J is H or an optionally substituted $C_{1-6}$ alkyl, and when m is 1, E is selected from the group consisting of a single bond to J, $-C(O)O-$, $-C(O)S-$, and $-C(O)NR^{10}-$, wherein $R^{10}$ is H or $C_{1-6}$ alkyl and J is an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, or $C_{3-15}$ heteroaralkenyl.

In one example of this embodiment, $R^8$ is $B-Y^1-(CH_2)_n-K-C(O)-$, K is oxo or CHOH, n is 0, where $Y^1$ is a covalent bond and B is phenyl, 4-chlorophenyl, 3-chlorophenyl, 3,4-dichlorophenyl, 3,5-dichlorophenyl, 3-fluorophenyl, 4-fluorophenyl, 3,4-difluorophenyl, and 3,5-difluorophenyl.

In another example, $AA_2$ is a covalent bond and $R^8$ is $B-Y^1-(CH_2)_n-K-C(O)-$, where n is 0 and K, $-C(O)-$, X, and $R^3$ together forms a heterocyclyl group having the formula X:

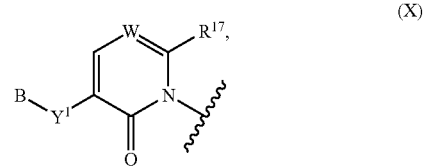

where W is CH or N, $R^{17}$ is hydrogen or an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, $C_{1-6}$ alkylthio, $C_{3-8}$ cycloalkylthio, $C_6$ or $C_{10}$ arylthio, $C_{7-16}$ aralkylthio, $C_{2-9}$ heterocyclylthio, $C_{2-15}$ heteroaralkylthio, $C_{1-6}$ alkylamino, $C_{2-12}$ dialkylamino $C_{3-8}$ cycloalkylamino, $C_{7-16}$ aralkylamino, $C_6$ or $C_{10}$ arylamino, or $C_{2-9}$ heterocyclylamino.

$Y^1$ is O, S, $NR^{18}$, or a covalent bond, where $R^{18}$ is H or $C_{1-6}$ alkyl. When $Y^1$ is a covalent bond, B is an optionally substituted $C_{1-6}$ alkyl, $C_{2-6}$ alkenyl, $C_{3-8}$ cycloalkyl, $C_6$ or $C_{10}$ aryl, $C_{1-9}$ heterocyclyl, $C_{7-16}$ aralkyl, $C_{8-16}$ aralkenyl, $C_{2-15}$ heteroaralkyl, $C_{3-15}$ heteroaralkenyl, $C_{1-6}$ alkylsulfonyl amino, $C_{3-8}$ cycloalkylsulfonylamino, $C_{7-16}$ aralkylsulfonylamino, $C_6$ or $C_{10}$ arylsulfonylamino, $C_{2-9}$ heterocyclylsulfonylamino, or $C_{2-15}$ heteroaralkylsulfonylamino. When $Y^1$ is O, S, or $NR^{18}$, B is an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{1-9}$ heterocyclyl, $C_{2-15}$ heteroaralkyl, $C_{3-15}$ heteroaralkenyl, $C_{2-7}$ acyl, $C_{7-11}$ aroyl, $C_{3-10}$ heteroaroyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, $C_{2-10}$ heterocyclyloxycarbonyl, aminocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{2-7}$ alkylthiocarbonyl, $C_{7-11}$ arylthiocarbonyl, $C_{3-10}$ heteroarylthiocarbonyl, $C_{2-7}$ alkoxythiocarbonyl, $C_{4-9}$ cycloalkoxythiocarbonyl, $C_{8-17}$ aralkoxythiocarbonyl, $C_7$ or $C_{11}$ aryloxythiocarbonyl, aminothiocarbonyl, C$_{2-7}$ alkylaminothiocarbonyl, C$_{3-13}$ dialkylaminothiocarbonyl, C$_{4-9}$ cycloalkylaminothiocarbonyl, C$_{8-17}$ aralkylaminothiocarbonyl, C$_7$ or C$_{11}$ arylaminothiocarbonyl, C$_{3-10}$ heterocyclylaminothiocarbonyl, C$_{3-16}$ heteroaralkylaminothiocarbonyl, or B is a natural or unnatural amino acid of L- or D-configuration substituted on the alpha-amine with H, C$_{2-7}$ acyl, C$_{7-11}$ aroyl, C$_{3-10}$ heteroaroyl, C$_{2-7}$ alkoxycarbonyl, C$_{4-9}$ cycloalkoxycarbonyl, C$_{8-17}$ aralkoxycarbonyl, C$_7$ or C$_{11}$ aryloxycarbonyl, C$_{2-10}$ heterocyclyloxycarbonyl, C$_{3-15}$ heteroaralkoxycarbonyl, aminocarbonyl, C$_{2-7}$ alkylaminocarbonyl, C$_{3-13}$ dialkylaminocarbonyl, C$_{4-9}$ cycloalkylaminocarbonyl, C$_{8-17}$ aralkylaminocarbonyl, C$_7$ or C$_{11}$ arylaminocarbonyl, C$_{3-10}$ heterocyclylaminocarbonyl, C$_{3-16}$ heteroaralkylaminocarbonyl, C$_{2-7}$ alkylthiocarbonyl, C$_{7-11}$ arylthiocarbonyl, C$_{3-10}$ heteroarylthiocarbonyl, C$_{2-7}$ alkoxythiocarbonyl, C$_{4-9}$ cycloalkoxythiocarbonyl, C$_{8-17}$ aralkoxythiocarbonyl, C$_7$ or C$_{11}$ aryloxythiocarbonyl, aminothiocarbonyl, C$_{2-7}$ alkylaminothiocarbonyl, C$_{3-13}$ dialkylaminothiocarbonyl, C$_{4-9}$ cycloalkylaminothiocarbonyl, C$_{8-17}$ aralkylaminothiocarbonyl, C$_7$ or C$_{11}$ arylaminothiocarbonyl, C$_{3-10}$ heterocyclylaminothiocarbonyl, C$_{3-16}$ heteroaralkylaminothiocarbonyl, C$_{1-6}$ alkylsulfonyl, C$_{3-8}$ cycloalkylsulfonyl, C$_{7-16}$ aralkylsulfonyl, C$_6$ or C$_{10}$ arylsulfonyl, C$_{2-9}$ heterocyclylsulfonyl, or C$_{2-15}$ heteroaralkylsulfonyl.

Desirable compounds include those where m is 1, R$^0$ is an optionally substituted 2-thiazole or 2-benzthiazole ring, R$^2$ is H or optionally substituted C$_{1-6}$ alkyl, R$^{17}$ is C$_6$ or C$_{10}$ aryl or C$_{1-9}$ heteroaryl, Y$^1$ is a bond, and B is an optionally substituted C$_{1-6}$ alkyl, C$_{7-16}$ aralkyl, C$_6$ or C$_{10}$ aryl, C$_{1-9}$ heterocyclyl, or C$_{2-15}$ heterocyclylalkyl; those where m is 1, R$^0$ is an optionally substituted 2-thiazole or 2-benzthiazole ring, R$^2$ is H or optionally substituted C$_{1-6}$ alkyl, R$^{17}$ is C$_6$ or C$_{10}$ aryl or C$_{1-9}$ heteroaryl, Y$^1$ is NH, and B is C$_{1-9}$ heterocyclyl or C$_{2-15}$ heterocyclylalkyl; those where m is 1, R$^0$ is 2-thiazole, R$^1$ is 3-guanidinopropyl, R$^2$ is H, R$^{17}$ is C$_6$ or C$_{10}$ aryl, or C$_{1-9}$ heteroaryl, Y$^1$ is NH, and B is C$_{1-9}$ heterocyclyl or C$_{2-15}$ heterocyclylalkyl; those where Y$^1$ is O or S; or those where R$^{17}$ is optionally substituted C$_6$ or C$_{10}$ aryl, C$_{1-9}$ heterocyclyl, C$_{1-6}$ alkylthio, C$_{3-8}$ cycloalkylthio, C$_6$ or C$_{10}$ arylthio, C$_{7-16}$ aralkylthio, C$_{2-9}$ heterocyclylthio, or C$_{2-15}$ heteroaralkylthio, Y$^1$ is NH, and B is C$_{1-9}$ heterocyclyl or C$_{2-15}$ heterocyclylalkyl.

In another embodiment of the first aspect, m is 1, X is N, R$^3$ is H, and R$^1$ is 3-guanidinopropyl, with the carbon bearing R$^1$ having an (R)- or (S)-configuration, and R$^2$ is selected from the group consisting of:

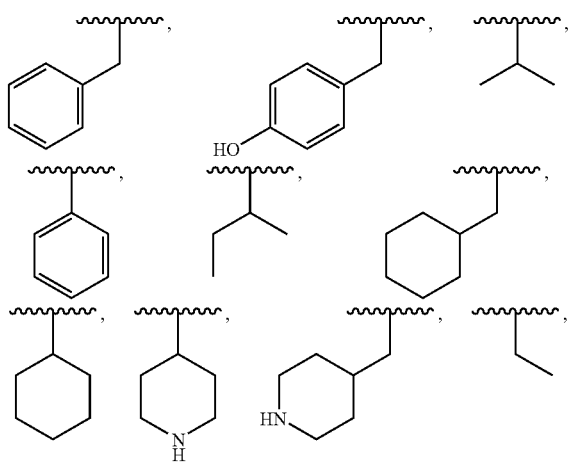

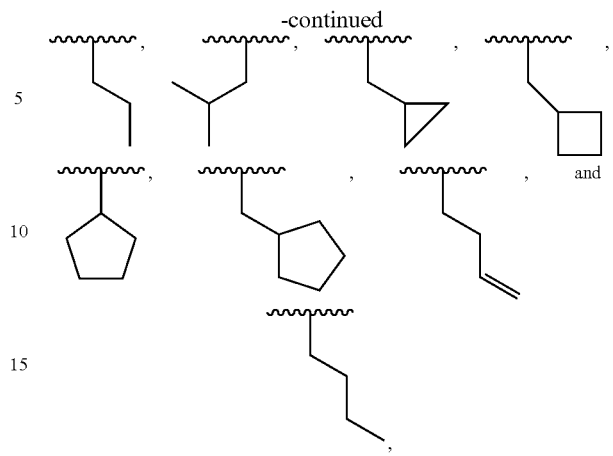

where the carbon bearing any of these substituents in either the (R)- or (S)-configuration. Preferably, the carbons bearing R$^1$ is of the (S)-configuration.

Preferably, A is R$^8$-AA$_2$, with R$^8$ is selected from the group consisting of:

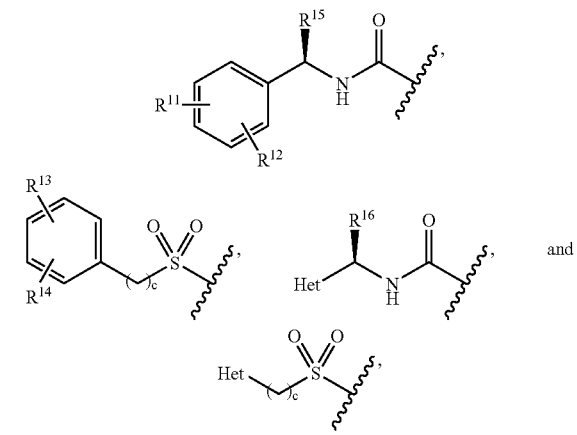

where c is 0 or 1; each of R$^{11}$, R$^{12}$, R$^{13}$, and R$^{14}$ is, independently, C$_{2-7}$ alkanoyl, C$_{1-6}$ alkyl, C$_{1-6}$ alkenyl, C$_{1-6}$ alkoxy, C$_{2-12}$ alkoxyalkyl, C$_{1-6}$ alkylsulfinyl, C$_{2-12}$ alkylsulfinylalkyl, C$_{1-6}$ alkylsulfonyl, C$_6$ or C$_{10}$ aryl, C$_{7-16}$ arylalkyl, amino, C$_{1-6}$ aminoalkyl, C$_7$ or C$_{11}$ aryloyl, azido, C$_{1-6}$ azidoalkyl, carboxaldehyde, carboxamide, carboxyl, C$_{2-7}$ (carboxaldehyde)alkyl, C$_{3-8}$ cycloalkyl, C$_{4-14}$ cycloalkylalkyl, halo, C$_{1-6}$ haloalkyl, C$_{1-9}$ heterocyclyl, C$_{1-9}$ (heterocyclyl)oxy, C$_{2-10}$ (heterocyclyl)oyl, hydroxy, C$_{1-6}$ hydroxyalkyl, nitro, C$_{1-6}$ nitroalkyl, N-protected amino, N-protected aminoalkyl, C$_{1-6}$ thioalkoxy, C$_{2-12}$ thioalkoxyalkyl, C$_{1-4}$ perfluoroalkyl, C$_{1-4}$ perfluoroalkoxy, C$_6$ or C$_{10}$ aryloxy, C$_{3-8}$ cycloalkoxy, C$_{4-14}$ cycloalkylalkoxy, or C$_{7-16}$ arylalkoxy, —(CH$_2$)$_q$CO$_2$R$^A$, wherein q is zero to four and R$^A$ is selected from the group consisting of (a) C$_{1-6}$ alkyl, (b) C$_6$ or C$_{10}$ aryl and (c) C$_{7-16}$ arylalkyl, wherein the alkylene group is of one to six carbon atoms, —(CH$_2$)$_q$CONR$^B$R$^C$, wherein q is zero to four and R$^B$ and R$^C$ are independently selected from the group consisting of (a) hydrogen, (b) C$_{1-6}$ alkyl, (c) C$_6$ or C$_{10}$ aryl and (d) C$_{7-16}$ arylalkyl, wherein the alkylene group is of one to six carbon atoms, —(CH$_2$)$_q$SO$_2$R$^D$, wherein q is zero to four and R$^D$ is selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_qSO_2NR^ER^F$, wherein q is zero to four and $R^E$ and $R^F$ are independently selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, or —$(CH_2)_qNR^GR^H$, wherein q is zero to four and $R^G$ and $R^H$ are independently selected from the group consisting of (a) hydrogen, (b) an N-protecting group, (c) alkyl of one to six carbon atoms, (d) alkenyl of two to six carbon atoms, (e) alkynyl of two to six carbon atoms, (f) $C_6$ or $C_{10}$ aryl, (g) $C_{7-16}$ arylalkyl, wherein the alkylene group is of one to six carbon atoms, (h) cycloalkyl of three to eight carbon atoms, and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; and each of $R^{15}$ and $R^{16}$ is, independently, H, $C_{1-6}$ alkyl; $C_{1-6}$ hydroxyalkyl; $C_{1-4}$ perfluoroalkyl, cyano, halo, —$(CH_2)_qCO_2R^A$, —$(CH_2)_qCONR^BR^C$, —$(CH_2)_qSO_2R^D$, —$(CH_2)_qSO_2NR^ER^F$, —$(CH_2)_qNR^GR^H$, wherein q is 0–2 and $R^A$, $R^B$, $R^C$, $R^D$, $R^E$, $R^F$, $R^G$, and $R^H$ are as defined above.

Most preferably, $AA_2$ is selected from the group consisting of:

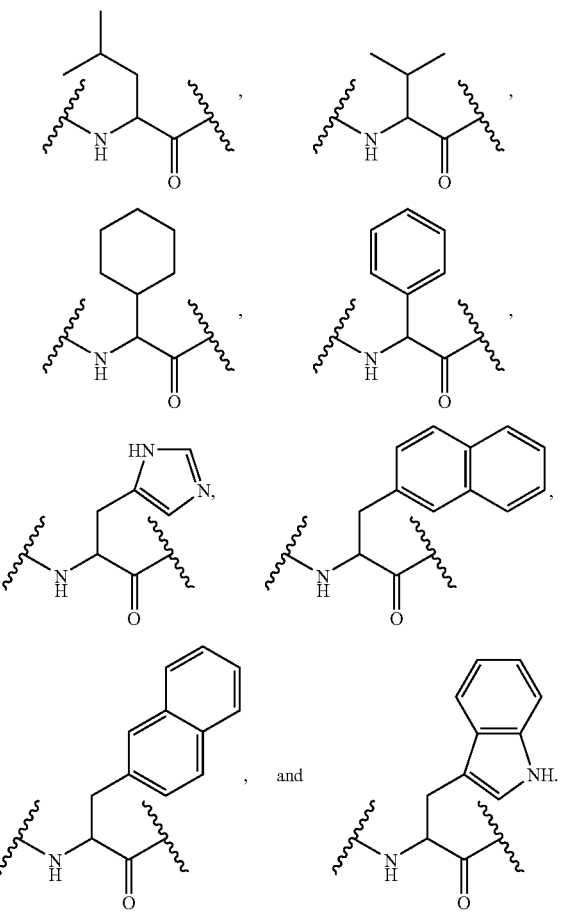

In one example, $AA_2$ is L-3-pyridylalanine, $R^8$ is

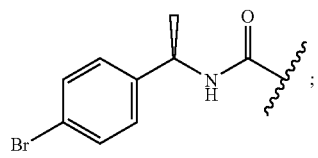

$R^2$ is 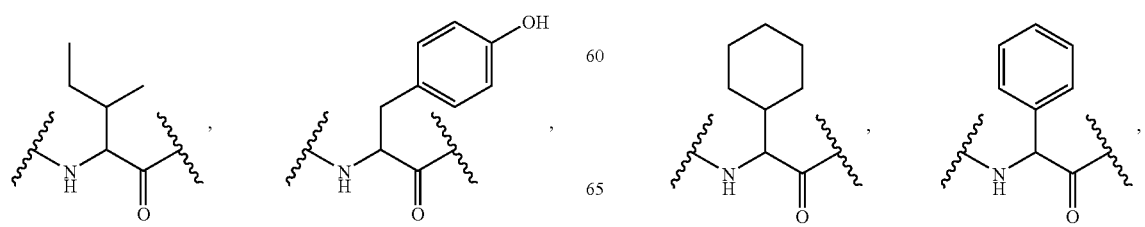

In other examples, $AA_2$ is

-continued
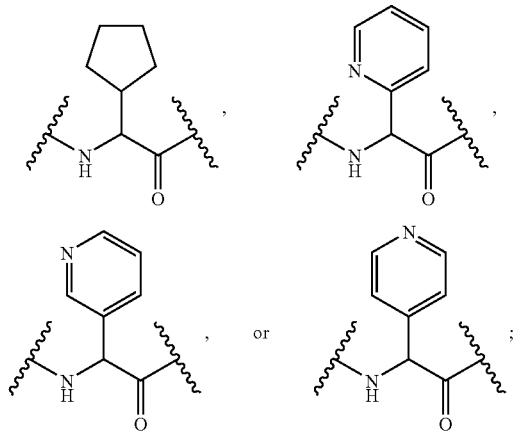
and $R^8$ is selected from the group consisting of: α-toluenesulfonyl, (methyl-3-benzoate)methanesulfonyl, 2-nitro-α-toluenesulfonyl, 1-propanesulfonyl, 3-carboxyl-α-toluenesulfonyl, and 3-chloropropanesulfonyl.
In other preferred compounds, A is selected from the group consisting of:
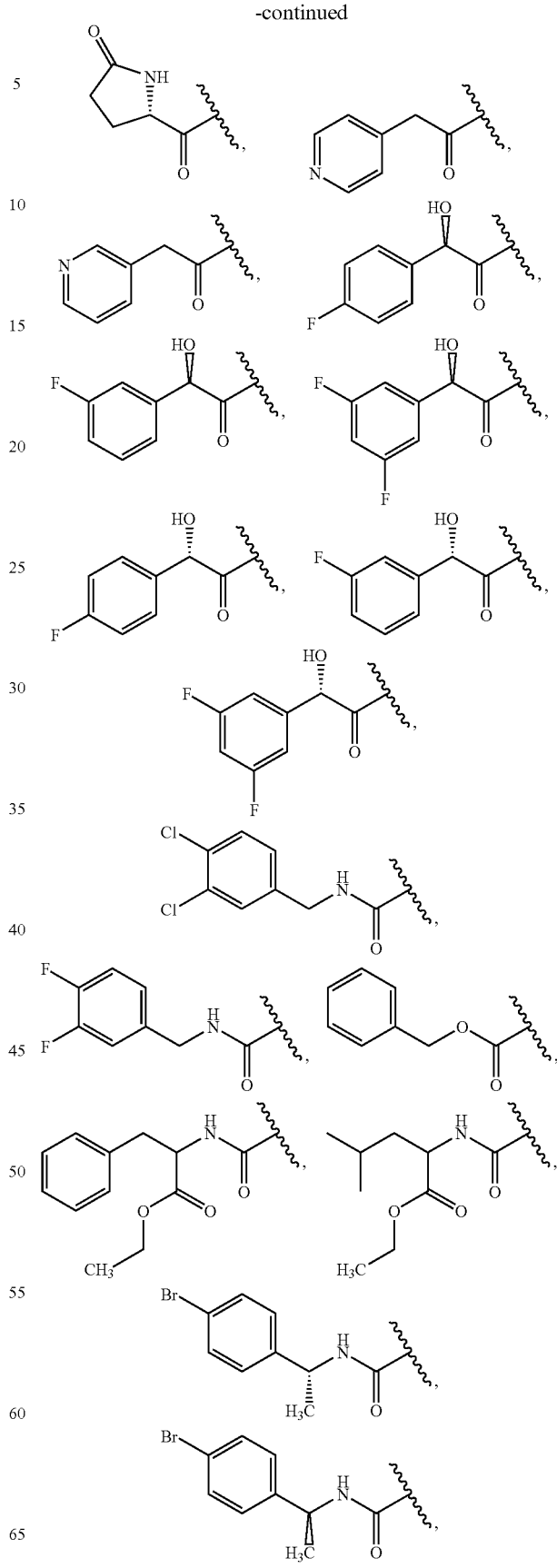

-continued
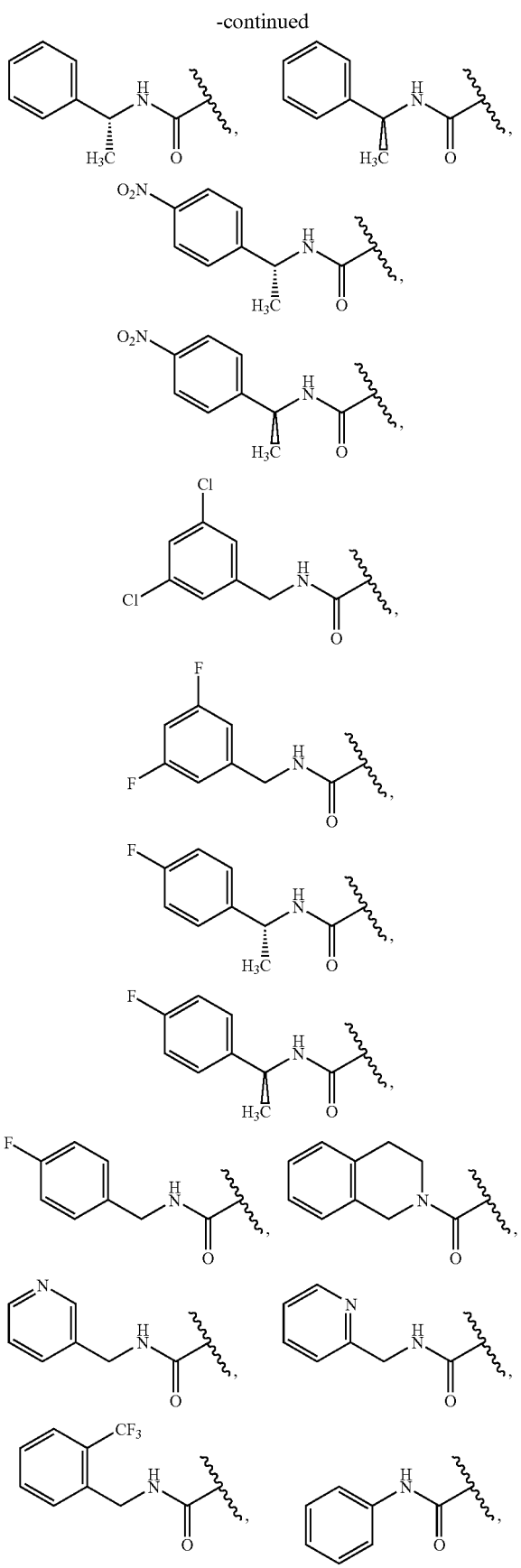
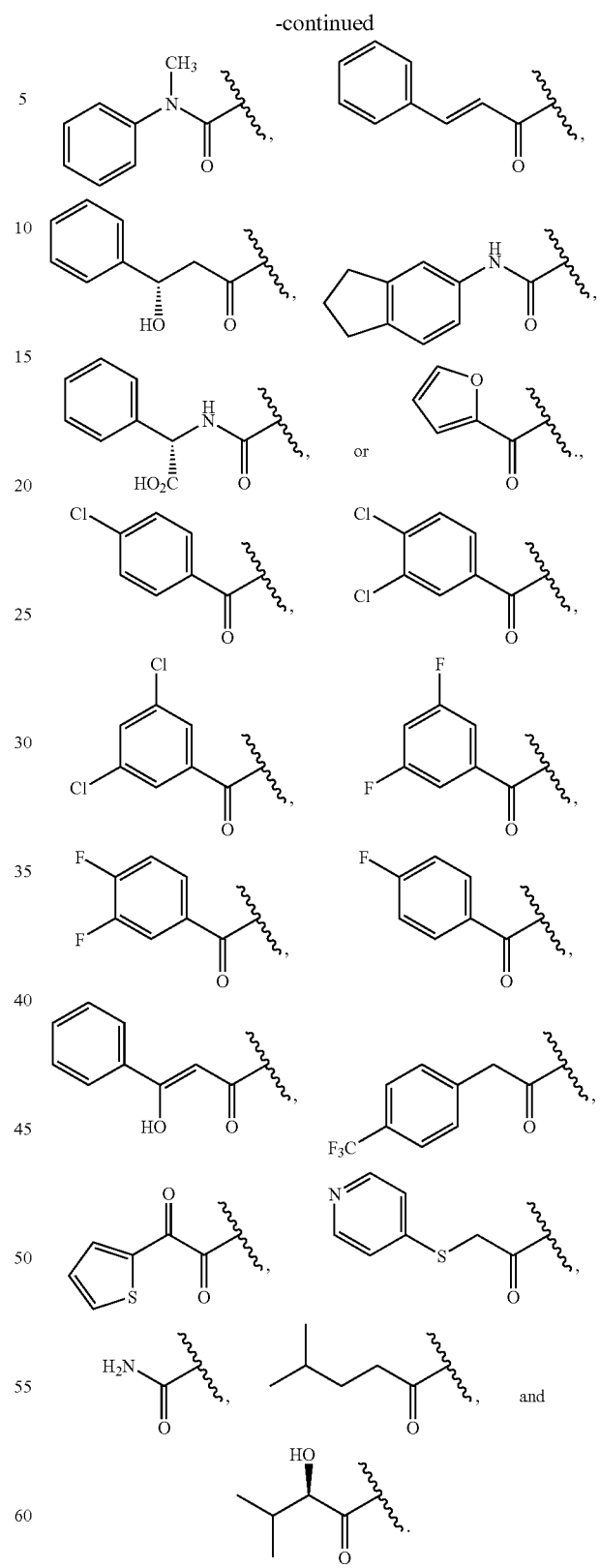
Preferably, m is 1, $R^0$ is an optionally substituted 2-thiazole or 2-benzthiazole ring; $R^2$ is H or optionally substituted $C_{1-6}$ alkyl, G is an optionally substituted $C_{1-6}$ alkyl, aralkyl, or B—Y—, wherein Y is NH and B is $C_{1-9}$ heterocyclyl or $C_{2-15}$ heteroaralkyl; and $R^{17}$ is $C_6$ or $C_{10}$ aryl, or $C_{1-9}$ heteroaryl.

In another embodiment of the first aspect, $R^1$ is selected from the group consisting of:

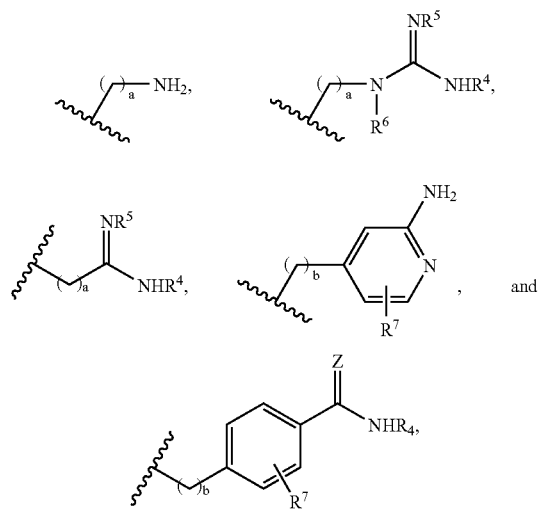

wherein a is an integer from 1–4, b is an integer from 0–2, $R^4$ and $R^5$ are H or $C_{1-6}$ alkyl, $R^6$ is H, OH, $C_{1-6}$ alkyl, or together with $R^4$ forms a 5- or 6-membered ring, and $R^7$ is H, OH, SH, $NH_2$, $NO_2$, optionally substituted $C_{1-6}$ alkyl, halogen, or $CF_3$;

$R^2$ is selected from the group consisting of:

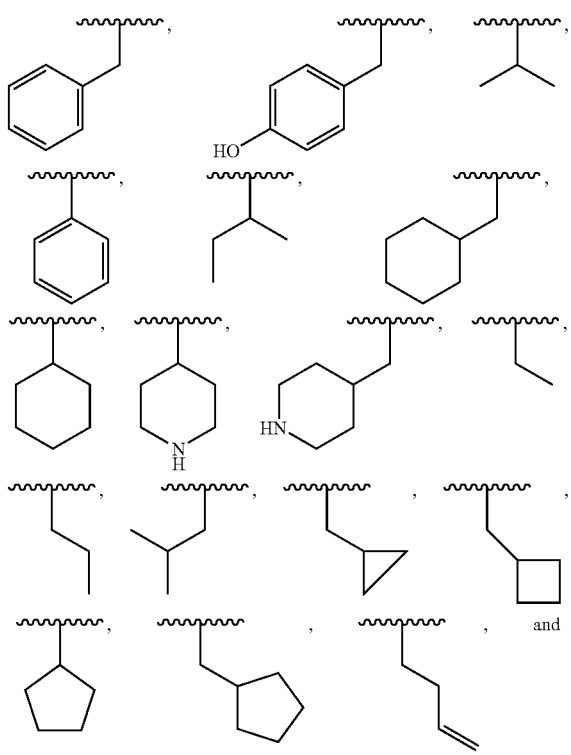

X is N; $R^3$ is H; and A is

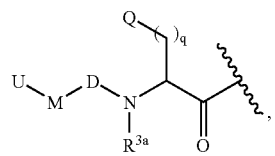

where $R^{3a}$ is H, $C_{1-6}$ alkyl, or together with M forms a 5- or 6-membered ring, D is C(O), C(S), or $S(O)_2$, q is an integer from 0–4, Q is an optionally substituted $C_{1-6}$ alkyl, $C_{3-8}$ cycloalkyl, $C_{1-9}$ heterocyclyl, $C_6$ or $C_{10}$ aryl, $C_{1-6}$ alkyloxy, $C_{3-8}$ cycloalkyloxy, $C_6$ or $C_{10}$ aryloxy, $C_{2-9}$ heterocyclyloxy, $C_{1-6}$ alkylthio, $C_{3-8}$ cycloalkylthio, $C_6$ or $C_{10}$ arylthio, $C_{1-6}$ alkylamino, $C_{2-12}$ dialkylamino, $C_{7-16}$ aralkylamino, $C_6$ or $C_{10}$ arylamino, $C_{2-9}$ heterocyclylamino, aminocarbonyl, $C_{2-7}$ alkylaminocarbonyl, $C_{3-13}$ dialkylaminocarbonyl, amino, amidino, guanidino, ureido, hydroxy, or carboxy, with the proviso that when q is 1, Q is not phenyl, M is single bond, $NR^{3b}$, O, or S, wherein $R^{3b}$ is H, $C_{1-6}$ alkyl, or when taken together with M, D, N, and $R^{3a}$ forms a 5- or 6-membered ring, and U is an optionally substituted $C_{1-6}$ alkyl, $C_{2-6}$ alkenyl, $C_{3-8}$ cycloalkyl, $C_{1-9}$ heterocyclyl, $C_{7-16}$ aralkyl, $C_{8-16}$ aralkenyl, $C_6$ or $C_{10}$ aryl, $C_{2-15}$ heterocyclylalkyl, or $C_{3-15}$ heteroaralkenyl, where when m is 1, $R^0$ is an optionally substituted $C_6$ or $C_{10}$ aryl or $C_{1-9}$ heterocyclyl, or when m is 0, $R^0$ is H or $C_{1-6}$ alkyl.

In some examples of preferred compounds, m is 1, $R^0$ is an optionally substituted 2-thiazole or 2-benzthiazole ring, $R^1$ is 3-guanidinopropyl, $R^2$ is 2-methylpropyl, $R^{3a}$ is H, D is $S(O)_2$, M is a single bond, q is 0, Q is phenyl, cyclohexyl, cyclopentyl, 4-pyridyl, 3-pyridyl, or 2-pyridyl, and U is selected from the group consisting of: benzyl, 3-methylcarboxybenzyl, 3-carboxybenzyl, 2-nitrobenzyl, 1-propyl, and 3-chloropropyl.

In other examples, m is 1, $R^0$ is an optionally substituted 2-thiazole or 2-benzthiazole ring, $R^1$ is 3-guanidinopropyl, $R^{3a}$ is H, D is C(O), M is $NR^{3b}$, where $R^{3b}$ is H, q is 0, Q is selected from the group consisting of:

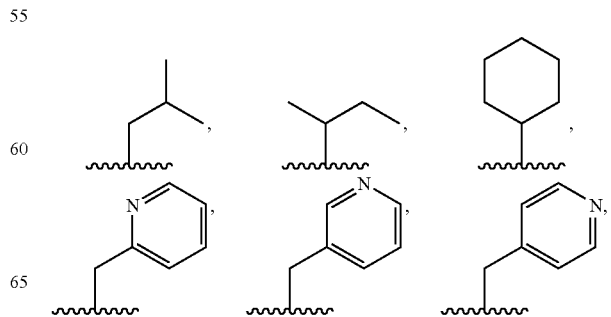

-continued

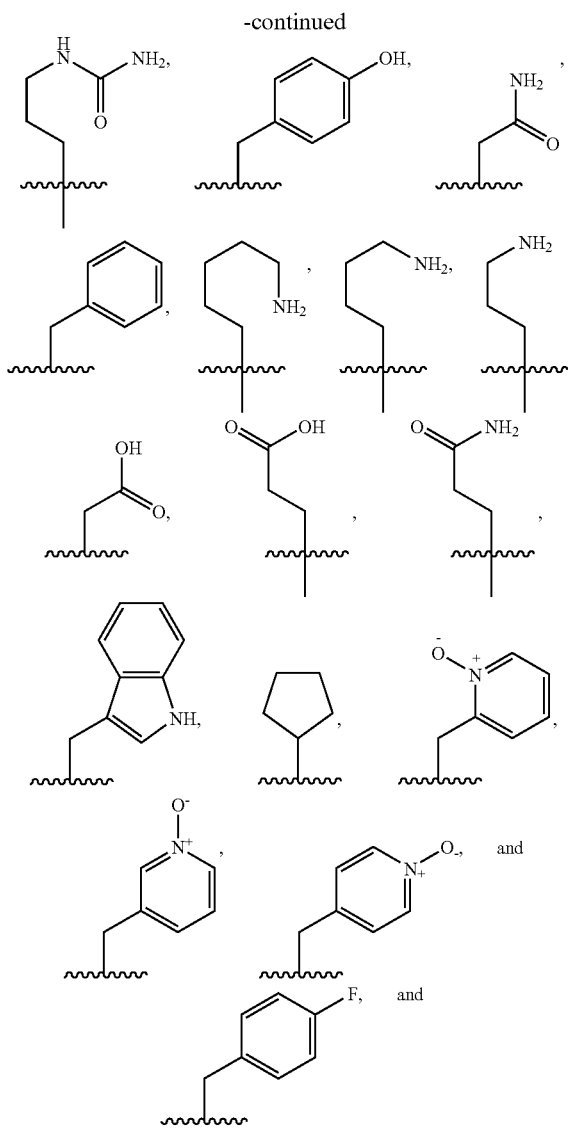

U is selected from the group consisting of: 2-chlorobenzyl, 3-chlorobenzyl, 4-chlorobenzyl, 2,3-dichlorobenzyl, 2,4-dichlorobenzyl, 2,5-dichlorobenzyl, 2,6-dichlorobenzyl, 3,4-dichlorobenzyl, 3,5-dichlorobenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, (R)-α-methyl-4-bromobenzyl, (S)-α-methyl-4-bromobenzyl, (R)-α-methyl-4-chlorobenzyl, (S)-α-methyl-4-chlorobenzyl, (R)-α-methyl-4-fluorobenzyl, (S)-α-methyl-4-fluorobenzyl, 2-trifluoromethylbenzyl, 2-methylbenzyl, 3-methylbenzyl, 4-methylbenzyl, 2-phenylacetic acid, 2-pyridylmethyl, 3-pyridylmethyl, 4-pyridylmethyl, phenyl, and indanyl. Preferred compounds include those where $R^2$ is isopropyl, Q is selected from the group consisting of: cyclohexyl, 2-pyridylmethyl, 3-ureidopropyl, 4-hydroxybenzyl, and acetamide, and U is (R)-α-methyl-4-bromobenzyl.

In still some other examples, U is $CHR^{3c}R^{3d}$, wherein $R^{3c}$ is an optionally substituted $C_6$ or $C_{10}$ aryl or $C_{1-9}$ heterocyclyl, and $R^{3d}$ is H, $C_{1-6}$ alkyl, C2–6 alkenyl, or together with $R^{3c}$ forms a fused bicyclic ring.

In yet another embodiment of the first aspect, m is 0 and $R^0$ is H. Preferred compounds include those where $R^2$ is H or an optionally substituted $C_{1-6}$ alkyl, $C_{2-6}$ alkenyl, $C_{3-8}$ cycloalkyl, $C_{7-16}$ aralkyl, $C_{8-16}$ aralkenyl, $C_6$ or $C_{10}$ aryl, $C_{2-9}$ heterocyclyl, $C_{2-15}$ heteroaralkyl, or $C_{3-15}$ heteroaralkenyl; $R^3$ is H or $C_{1-6}$ alkyl; X is N; and A is $R^8$-$AA_2$, wherein $AA_2$ is a single natural or unnatural alpha-amino acid residue and $R^8$ is selected from the group consisting of:

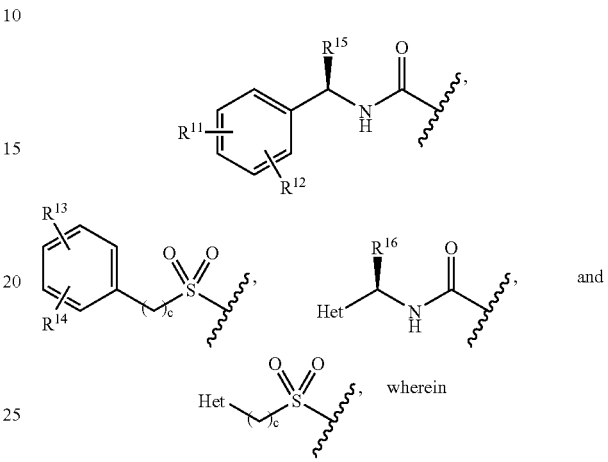

c is 0 or 1; each of $R^{11}$, $R^{12}$, $R^{13}$, and $R^{14}$ is, independently, $C_{2-7}$ alkanoyl, $C_{1-6}$ alkyl, $C_{1-6}$ alkenyl, $C_{1-6}$ alkoxy, $C_{2-12}$ alkoxyalkyl, $C_{1-6}$ alkylsulfinyl, $C_{2-12}$ alkylsulfinylalkyl, $C_{1-6}$ alkylsulfonyl, $C_6$ or $C_{10}$ aryl, $C_{7-16}$ arylalkyl, amino, $C_{1-6}$ aminoalkyl, $C_7$ or $C_{11}$ aryloyl, azido, $C_{1-6}$ azidoalkyl, carboxaldehyde, carboxamide, carboxyl, $C_{2-7}$ (carboxaldehyde)alkyl, $C_{3-8}$ cycloalkyl, $C_{4-14}$ cycloalkylalkyl, halo, $C_{1-6}$ haloalkyl, $C_{1-9}$ heterocyclyl, $C_{1-9}$ (heterocyclyl)oxy, $C_{2-10}$ (heterocyclyl)oyl, hydroxy, $C_{1-6}$ hydroxyalkyl, nitro, $C_{1-6}$ nitroalkyl, N-protected amino, N-protected aminoalkyl, $C_{1-6}$ thioalkoxy, $C_{2-12}$ thioalkoxyalkyl, —$(CH_2)_qCO_2R^A$, wherein q is zero to four and $R^A$ is selected from the group consisting of (a) $C_{1-6}$ alkyl, (b) $C_6$ or $C_{10}$ aryl and (c) $C_{7-16}$ arylalkyl, wherein the alkylene group is of one to six carbon atoms, —$(CH_2)_qCONR^BR^C$, wherein q is zero to four and $R^B$ and $R^C$ are independently selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_qSO_2R^D$, wherein q is zero to four and $R^D$ is selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_qSO_2NR^ER^F$, wherein q is zero to four and $R^E$ and $R^F$ are independently selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_qNR^GR^H$, wherein q is zero to four and $R^G$ and $R^H$ are independently selected from the group consisting of (a) hydrogen, (b) an N-protecting group, (c) alkyl of one to six carbon atoms, (d) alkenyl of two to six carbon atoms, (e) alkynyl of two to six carbon atoms, (f) $C_6$ or $C_{10}$ aryl, (g) $C_{7-16}$ arylalkyl, wherein the alkylene group is of one to six carbon atoms, (h) cycloalkyl of three to eight carbon atoms, and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group, $C_{1-4}$ perfluoroalkyl, $C_{1-4}$ perfluoroalkoxy; $C_6$ or $C_{10}$ aryloxy, $C_{3-8}$ cycloalkoxy, $C_{4-14}$ cycloalkylalkoxy, or $C_{7-16}$ arylalkoxy; and each of $R^{15}$ and $R^{16}$ is, independently, H, $C_{1-6}$ alkyl; $C_{1-6}$ hydroxyalkyl; $C_{1-4}$ perfluoroalkyl, cyano, halo, $-(CH_2)_q CO_2 R^A$, $-(CH_2)_q CONR^B R^C$, $-(CH_2)_q SO_2 R^D$, $-(CH_2)_q SO_2 NR^E R^F$, $-(CH_2)_q NR^G R^H$, wherein q is zero to two and $R^A$, $R^B$, $R^C$, $R^D$, $R^E$, $R^F$, $R^G$, and $R^H$ are as defined above.

Other preferred compounds include those where $R^1$ is selected from the group consisting of:

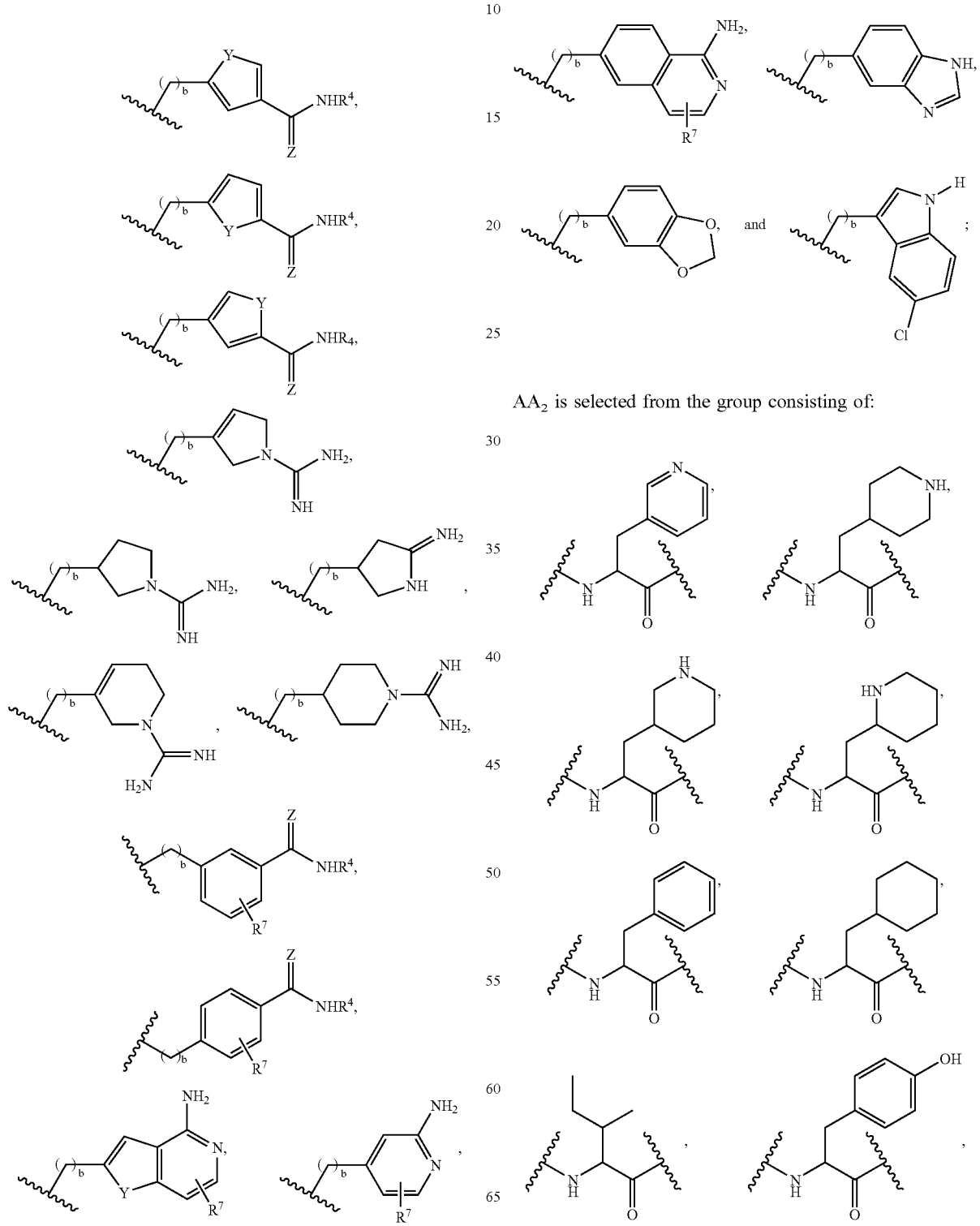

AA$_2$ is selected from the group consisting of:

-continued

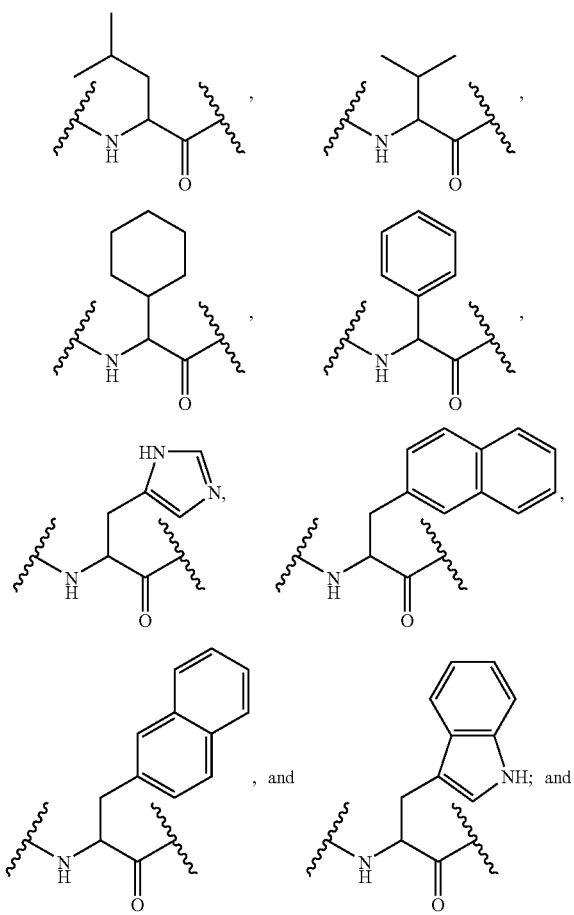

$R^2$ is selected from the group consisting of:

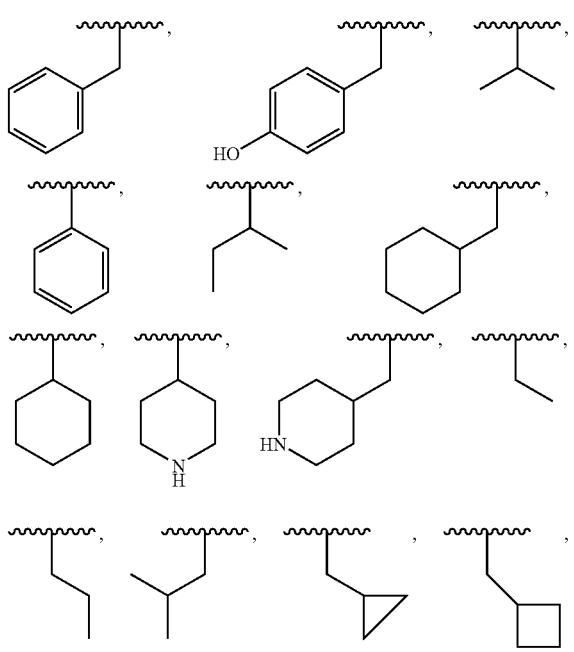

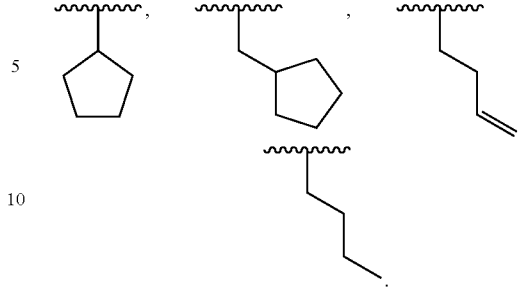

Most preferred compounds are those in which $R^1$ is

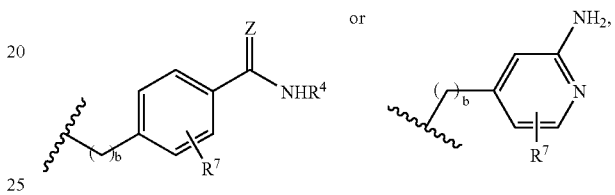

where b is 0 or 1 and $R^7$ is H, and A is $R^8$-$AA_2$, where $R^8$ is benzylsulfonyl, 3-methylcarboxybenzylsulfonyl, 3-carboxybenzylsulfonyl, 2-nitrobenzylsulfonyl, propylsulfonyl, and 3-chloropropylsulfonyl and $AA_2$ is as previously defined.

In a second aspect, the invention features a compound of formula II:

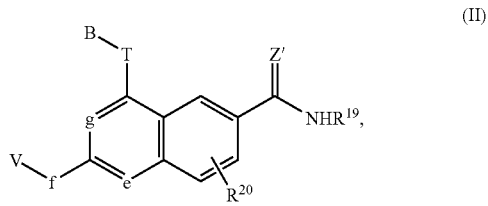

or a pharmaceutically acceptable salt or prodrug thereof, where $R^{19}$ is H, $C_{1-6}$ alkyl, OH, $NH_2$, $NO_2$, $CO_2R^{19a}$, wherein $R^{19a}$ is $C_{1-6}$alkyl; $R^{20}$ is H, OH, SH, $NH_2$, $NO_2$, optionally substituted $C_{1-6}$ alkyl, halogen, $C_{1-3}$ perfluoroalkyl, or when together with Z' forms a fused 5- or 6-membered ring; e is N, NO, or $CR^{21a}$, wherein $R^{21a}$ is H, halogen, or $C_{1-3}$ perfluoroalkyl; g is N, NO, or $CR^{21b}$, wherein $R^{21b}$ is H, halogen, $C_{1-6}$ alkyl, $C_{1-3}$ perfluoroalkyl, $C_{1-3}$ alkenyl, $C_{7-16}$ aralkyl, $C_{2-15}$ heteroaralkyl, $C_{1-6}$ alkoxy, $C_{7-16}$ aralkoxy, $C_{2-15}$ heteroaralkoxy, $C_{2-7}$ alkoxycarbonyl, $C_{8-17}$ aralkoxycarbonyl, $C_{3-16}$ heteroaralkoxycarbonyl, $C_{2-7}$ alkylaminocarbonyl, $C_{8-17}$ aralkylaminocarbonyl, $C_{3-16}$ heteroaralkylaminocarbonyl, $C_{1-6}$ alkylthio, $C_{7-16}$ aralkylthio, $C_{2-15}$ heteroaralkylthio, $C_{2-7}$ alkylthiocarbonyl, $C_{8-17}$ aralkylthiocarbonyl, $C_{3-16}$ heteroaralkylthiocarbonyl;

T is a bond, O, S, or $NR^{23}$, where $R^{23}$ is H, OH, or optionally substituted $C_{1-6}$ alkyl, $C_{1-6}$ alkenyl, $C_{7-11}$ aralkyl, $C_{8-16}$ aralkenyl, $C_{2-15}$ heteroaralkyl, or $C_{3-15}$ heteroaralkenyl.

When T is O, S, or $NR^{23}$, B is a natural or unnatural alpha-amino acid residue of D- or L-configuration, or an optionally substituted $C_{1-6}$ alkyl, $C_{3-8}$ cycloalkyl, $C_{1-6}$ alkenyl, $C_{7-16}$ aralkyl, $C_{8-17}$ aralkylcarbonyl, $C_{8-16}$ aralkenyl, $C_6$ or $C_{10}$ aryl, $C_{2-15}$ heteroaralkyl, $C_{3-16}$ heteroaralkylcarbonyl, $C_{3-15}$ heteroaralkenyl, $C_{2-7}$ acyl, $C_{4-9}$ cycloalkylcarbonyl, $C_{7-11}$ aroyl, $C_{2-10}$ heterocyclyloyl, $C_{4-9}$ cycloalkoxycarbonyl, $C_7$ or $C_{11}$ aryloxycarbonyl, $C_{3-10}$ heterocyclyloxycarbonyl, $C_{3-16}$ heteroaralkyloxycarbonyl, aminocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{2-7}$ alkylthiocarbonyl, $C_{4-9}$ cycloalkylthiocarbonyl, $C_{7-11}$ arylthiocarbonyl, $C_{8-17}$ aralkylthiocarbonyl, $C_{2-10}$ heterocyclylthiocarbonyl, $C_{3-16}$ heteroaralkylthiocarbonyl, aminothiocarbonyl, $C_{2-7}$ alkylaminothiocarbonyl, $C_{3-13}$ dialkylaminothiocarbonyl, $C_{4-9}$ cycloalkylaminothiocarbonyl, $C_{8-17}$ aralkylaminothiocarbonyl, $C_7$ or $C_{11}$ arylaminothiocarbonyl, $C_{3-10}$ heterocyclylaminothiocarbonyl, $C_{3-16}$ heteroaralkylaminothiocarbonyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, or $C_{2-15}$ heteroaralkylsulfonyl.

When T is a bond, B is OH, SH, $NH_2$, $NO_2$, $SO_3H$, $CO_2H$ or an optionally substituted $C_{1-6}$ alkyl, $C_{1-6}$ alkenyl, $C_{7-16}$ aralkyl, $C_{8-16}$ aralkenyl, $C_{2-15}$ heteroaralkyl, $C_{3-15}$ heteroaralkenyl, $C_{2-7}$ acyl, $C_{7-11}$ aroyl, $C_{3-10}$ heteroaroyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, $C_{3-16}$ heteroaralkyloxycarbonyl, $C_{2-10}$ heterocyclyloxycarbonyl, aminocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{2-7}$ alkylthiocarbonyl, $C_{4-9}$ cycloalkylthiocarbonyl, $C_{7-11}$ arylthiocarbonyl, $C_{8-17}$ aralkylthiocarbonyl, $C_{2-10}$ heterocyclylthiocarbonyl, $C_{3-16}$ heteroaralkylthiocarbonyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, or $C_{2-15}$ heteroaralkylsulfonyl.

f is a bond, O, S, or $NR^{24}$, wherein $R^{24}$ is H, OH, or $C_{1-6}$ alkyl.

When f is O, S, or $NR^{24}$, V is H or an optionally substituted $C_{1-6}$ alkyl, $C_{7-16}$ aralkyl, $C_{2-15}$ heteroaralkyl, $C_{2-7}$ acyl, $C_{7-11}$ aroyl, $C_{3-10}$ heteroaroyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, $C_{3-16}$ heteroaralkyloxycarbonyl, $C_{2-10}$ heterocyclyloxycarbonyl, aminocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{2-7}$ alkylthiocarbonyl, $C_{4-9}$ cycloalkylthiocarbonyl, $C_{7-11}$ arylthiocarbonyl, $C_{8-17}$ aralkylthiocarbonyl, $C_{2-10}$ heterocyclylthiocarbonyl, $C_{3-16}$ heteroaralkylthiocarbonyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, or $C_{2-15}$ heteroaralkylsulfonyl.

When f is a bond, V is H, OH, SH, $NH_2$, $SO_3H$, $CO_2H$, or an optionally substituted $C_{1-6}$ alkyl, hydroxy-$C_{1-6}$ alkyl, $C_{3-8}$ cycloalkyl, $C_{1-6}$ alkenyl, $C_{7-16}$ aralkyl, $C_{8-16}$ aralkenyl, $C_{2-15}$ heteroaralkyl, $C_{3-15}$ heteroaralkyl, $C_6$ or $C_{10}$ aryl, $C_{1-9}$ heterocyclyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{2-10}$ heterocyclylaminocarbonyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, $C_{3-10}$ heterocyclyloxycarbonyl, $C_{3-16}$ heteroaralkyloxycarbonyl, $C_{2-7}$ alkylthiocarbonyl, $C_{4-9}$ cycloalkylthiocarbonyl, $C_{7-11}$ arylthiocarbonyl, $C_{8-17}$ aralkylthiocarbonyl, $C_{2-10}$ heterocyclylthiocarbonyl, $C_{3-16}$ heteroaralkylthiocarbonyl, $C_{2-7}$ acyl, $C_{7-11}$ aroyl, $C_{3-10}$ heteroaroyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, $C_{2-15}$ heteroaralkylsulfonyl, $C_{1-6}$ alkylaminosulfonyl, $C_{3-8}$ cycloalkylaminosulfonyl, $C_{2-12}$ dialkylaminosulfonyl, $C_{7-17}$ aralkylaminosulfonyl, $C_6$ or $C_{10}$ arylaminosulfonyl, $C_{1-9}$ heterocyclylaminosulfonyl, $C_{2-15}$ heteraralkylaminosulfonyl, $C_{1-16}$ alkylsulfinyl, $C_{3-8}$ cycloalkylsulfinyl, $C_{7-16}$ aralkylsulfinyl, $C_6$ or $C_{10}$ arylsulfinyl, $C_{2-9}$ heterocyclylsulfinyl, or $C_{2-15}$ heteroaralkylsulfinyl.

In one embodiment, T is NH, B is an optionally substituted optionally substituted $C_{2-7}$ acyl, $C_{4-9}$ cycloalkylcarbonyl, $C_7$ or $C_{11}$ aroyl, $C_{2-10}$ heterocyclylcarbonyl, $C_{3-10}$ heteroaroyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, $C_{3-10}$ heterocyclyloxycarbonyl, $C_{3-16}$ heteroaralkyloxycarbonyl, $C_{2-7}$ alkylthiocarbonyl, $C_{4-9}$ cycloalkylthiocarbonyl, $C_{7-17}$ aralkylthiocarbonyl, $C_7$ or $C_{11}$ arylthiocarbonyl, $C_{3-16}$ heteroaralkylthiocarbonyl, $C_{3-10}$ heterocyclylthiocarbonyl, aminothiocarbonyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{3-10}$ heterocyclylaminocarbonyl, $C_{3-16}$ heteroaralkylaminocarbonyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, or $C_{2-15}$ heteroaralkylsulfonyl; and f is O, S, or $NR^{24}$.

In another embodiment, T is NH, and B is an optionally substituted $C_6$ or $C_{10}$ aroyl or an optionally substituted $C_{1-9}$ heteroaroyl. Examples include those compounds in which B is

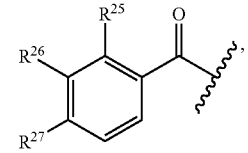

where each of $R^{25}$, $R^{26}$, and $R^{27}$ is, independently, H, $C_{2-7}$ alkanoyl, $C_{1-6}$ alkyl, $C_{1-6}$ alkenyl, $C_{1-6}$ alkoxy, $C_{2-12}$ alkoxyalkyl, $C_{1-6}$ alkylsulfinyl, $C_{2-12}$ alkylsulfinylalkyl, $C_{1-6}$ alkylsulfonyl, $C_6$ or $C_{10}$ aryl, $C_{7-16}$ arylalkyl, amino, $C_{1-6}$ aminoalkyl, $C_7$ or $C_{11}$ aryloyl, azido, $C_{1-6}$ azidoalkyl, carboxaldehyde, carboxamide, carboxyl, $C_{2-7}$ (carboxaldehyde)alkyl, $C_{3-8}$ cycloalkyl, $C_{4-14}$ cycloalkylalkyl, halo, $C_{1-6}$ haloalkyl, $C_{1-9}$ heterocyclyl, $C_{1-9}$ (heterocyclyl)oxy, $C_{2-10}$ (heterocyclyl)oyl, hydroxy, $C_{1-6}$ hydroxyalkyl, nitro, $C_{1-6}$ nitroalkyl, N-protected amino, N-protected aminoalkyl, $C_{1-6}$ thioalkoxy, $C_{2-12}$ thioalkoxyalkyl, thiol, $-(CH_2)_qCO_2R^A$, wherein q is zero to four and $R^A$ is selected from the group consisting of (a) $C_{1-6}$ alkyl, (b) $C_6$ or $C_{10}$ aryl and (c) $C_{7-16}$ arylalkyl, wherein the alkylene group is of one to six carbon atoms, $-(CH_2)_qCONR^BR^C$, wherein q is zero to four and $R^B$ and $R^C$ are independently selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, $-(CH_2)_qSO_2R^D$, wherein q is zero to four and $R^D$ is selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, $-(CH_2)_qSO_2NR^ER^F$, wherein q is zero to four and $R^E$ and $R^F$ are independently selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_q NR^G R^H$, wherein q is zero to four and $R^G$ and $R^H$ are independently selected from the group consisting of (a) hydrogen, (b) an N-protecting group, (c) alkyl of one to six carbon atoms, (d) alkenyl of two to six carbon atoms, (e) alkynyl of two to six carbon atoms, (f) $C_6$ or $C_{10}$ aryl, (g) $C_{7-16}$ arylalkyl, wherein the alkylene group is of one to six carbon atoms, (h) cycloalkyl of three to eight carbon atoms, and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group, $C_{1-4}$ perfluoroalkyl, $C_{1-4}$ perfluoroalkoxy; $C_6$ or $C_{10}$ aryloxy, $C_{3-8}$ cycloalkoxy, $C_{4-14}$ cycloalkylalkoxy, or $C_{7-16}$ arylalkoxy.

Preferred compounds in which B is a 2,3-disubstituted or 2,3,4-trisubstituted aryloyl include those in which f is a bond and V is an optionally substituted $C_{1-6}$ alkyl, hydroxy-$C_{1-6}$ alkyl, $C_{3-8}$ cycloalkyl, $C_{1-6}$ alkenyl, $C_{7-16}$ aralkyl, $C_{8-16}$ aralkenyl, $C_{2-15}$ heteroaralkyl, $C_{3-15}$ heteroaralkyl, $C_6$ or $C_{10}$ aryl, $C_{1-9}$ heterocyclyl, $C_{2-7}$ alkylaminocarbonyl, $C_{3-13}$ dialkylaminocarbonyl, $C_{4-9}$ cycloalkylaminocarbonyl, $C_{8-17}$ aralkylaminocarbonyl, $C_7$ or $C_{11}$ arylaminocarbonyl, $C_{2-10}$ heterocyclylaminocarbonyl, $C_{2-7}$ alkoxycarbonyl, $C_{4-9}$ cycloalkoxycarbonyl, $C_{8-17}$ aralkoxycarbonyl, $C_7$ or $C_{11}$ aryloxycarbonyl, $C_{3-10}$ heterocyclyloxycarbonyl, $C_{3-16}$ heteroaralkyloxycarbonyl, $C_{2-7}$ alkylthiocarbonyl, $C_{4-9}$ cycloalkylthiocarbonyl, $C_{7-11}$ arylthiocarbonyl, $C_{8-17}$ aralkylthiocarbonyl, $C_{2-10}$ heterocyclylthiocarbonyl, $C_{3-16}$ heteroaralkylthiocarbonyl, $C_{2-7}$ acyl, $C_{7-11}$ aroyl, $C_{3-10}$ heteroaroyl, $C_{1-6}$ alkylsulfonyl, $C_{3-8}$ cycloalkylsulfonyl, $C_{7-16}$ aralkylsulfonyl, $C_6$ or $C_{10}$ arylsulfonyl, $C_{2-9}$ heterocyclylsulfonyl, or $C_{2-15}$ heteroaralkylsulfonyl, $C_{1-6}$ alkylaminosulfonyl, $C_{3-8}$ cycloalkylaminosulfonyl, $C_{2-12}$ dialkylaminosulfonyl, $C_{7-17}$ aralkylaminosulfonyl, $C_6$ or $C_{10}$ arylaminosulfonyl, $C_{1-9}$ heterocyclylaminosulfonyl, $C_{2-15}$ heteraralkylaminosulfonyl, $C_{1-6}$ alkylsulfinyl, $C_{3-8}$ cycloalkylsulfinyl, $C_{7-16}$ aralkylsulfinyl, $C_6$ or $C_{10}$ arylsulfinyl, $C_{2-9}$ heterocyclylsulfinyl, or $C_{2-15}$ heteroaralkylsulfinyl. Most preferred compounds in which B is a 2,3-disubstituted or 2,3,4-trisubstituted aryloyl include those where f is a bond and V is optionally substituted $C_6$ or $C_{10}$ arylaminocarbonyl or $C_{7-17}$ aralkylaminocarbonyl.

In another embodiment of the second aspect, f is a bond and V is H. Examples include those compounds in which B is

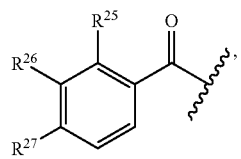

where each of $R^{25}$, $R^{26}$, and $R^{27}$ is, independently H, $C_{2-7}$ alkanoyl, $C_{1-6}$ alkyl, $C_{1-6}$ alkenyl, $C_{1-6}$ alkoxy, $C_{2-12}$ alkoxyalkyl, $C_{1-6}$ alkylsulfinyl, $C_{2-12}$ alkylsulfinylalkyl, $C_{1-6}$ alkylsulfonyl, $C_6$ or $C_{10}$ aryl, $C_{7-16}$ arylalkyl, amino, $C_{1-6}$ aminoalkyl, $C_7$ or $C_{11}$ aryloyl, azido, $C_{1-6}$ azidoalkyl, carboxaldehyde, carboxamide, carboxyl, $C_{2-7}$ (carboxaldehyde)alkyl, $C_{3-8}$ cycloalkyl, $C_{4-14}$ cycloalkylalkyl, halo, $C_{1-6}$ haloalkyl, $C_{1-9}$ heterocyclyl, $C_{1-9}$ (heterocyclyl)oxy, $C_{2-10}$ (heterocyclyl)oyl, hydroxy, $C_{1-6}$ hydroxyalkyl, nitro, cyano, $C_{1-6}$ nitroalkyl, N-protected amino, N-protected aminoalkyl, $C_{1-6}$ thioalkoxy, $C_{2-12}$ thioalkoxyalkyl, thiol, —$(CH_2)_q CO_2 R^A$, wherein q is zero to four and $R^A$ is selected from the group consisting of (a) $C_{1-6}$ alkyl, (b) $C_6$ or $C_{10}$ aryl and (c) $C_{7-16}$ arylalkyl, wherein the alkylene group is of one to six carbon atoms, —$(CH_2)_q CONR^B R^C$, wherein q is zero to four and $R^B$ and $R^C$ are independently selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_q SO_2 R^D$, wherein q is zero to four and $R^D$ is selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_q SO_2 NR^E R^F$, wherein q is zero to four and $R^E$ and $R^F$ are independently selected from the group consisting of (a) hydrogen, (b) $C_{1-6}$ alkyl, (c) $C_6$ or $C_{10}$ aryl and (d) $C_{7-16}$ arylalkyl, wherein the alkylene group is of one to six carbon atoms, —$(CH_2)_q NR^G R^H$, wherein q is zero to four and $R^G$ and $R^H$ are independently selected from the group consisting of (a) hydrogen, (b) an N-protecting group, (c) alkyl of one to six carbon atoms, (d) alkenyl of two to six carbon atoms, (e) alkynyl of two to six carbon atoms, (f) $C_6$ or $C_{10}$ aryl, (g) $C_{7-16}$ arylalkyl, wherein the alkylene group is of one to six carbon atoms, (h) cycloalkyl of three to eight carbon atoms, and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group, $C_{1-4}$ perfluoroalkyl, $C_{1-4}$ perfluoroalkoxy; $C_6$ or $C_{10}$ aryloxy, $C_{3-8}$ cycloalkoxy, $C_{4-14}$ cycloalkylalkoxy, or $C_{7-16}$ arylalkoxy.

A preferred B substituent for any of the compounds of formula II is a 2,3,-disubstituted aroyl group in which the 2-substituent is halo or $C_{1-6}$ alkyl and the 3-substituent is hydroxyl.

In an embodiment of either the first aspect or second aspect of the invention, a compound of the invention can further be attached to a linker (e.g. to any of the groups $R^0$, $R^2$, or A of compounds of formula I or to any of the groups B or V of formula II), where the linker is reactive to a blood component, such as, for example, an erythrocyte, a lymphocyte, a blood platelet, an immunoglobulin, serum albumin, ferritin, corticosteroid-binding globulin, sex hormone-binding globulin, transferrin, thyroxin-binding protein, and alpha-2-macroglobulin. Some examples of linkers attached to a group reactive to a blood component are maleimide-$(CH_2)_{bb}C(O)NHCH_2CH_2(OCH_2CH_2)_{aa}OCH_2C(O)$—, maleimide-$(CH_2)_{bb}C(O)NHCH_2CH_2(OCH_2CH_2)_{aa}$ NHCH_2C(O)—, maleimide-$(CH_2)_{bb}C(O)NHCH_2CH_2$ $(OCH_2CH_2)_{aa}NHC(S)$—, maleimide-$(CH_2)_{bb}NHC(S)$—, maleimide-$(CH_2)_{bb}C(O)$—, and maleimide $(CH_2)_{bb}$— where aa is 1–10 and bb is 1–4.

In another embodiment of either the first or second aspect, a compound of the invention can further be attached to a polyethylene glycol moiety (e.g. to any of the groups $R^0$, $R^2$, or A of compounds of formula I or to any of the groups B or V of formula II). Examples of polyethylene glycol moieties include $H(OCH_2CH_2)_{cc}O$—, $H_3C(OCH_2CH_2)_{cc}OC(O)$, $H(OCH_2CH_2)_{cc}OC(O)$, $H_3C(OCH_2CH_2)_{cc}NHC(O)$, $H(OCH_2CH_2)_{cc}NHC(O)$, $H_3C(OCH_2CH_2)_{cc}NHC(S)$, $H(OCH_2CH_2)_{cc}NHC(S)$, $H_3C(OCH_2CH_2)_{cc}C(O)$, $H(OCH_2CH_2)_{cc}C(O)$, $H_3C(OCH_2CH_2)_{cc}NHCH_2C(O)$, $H(OCH_2CH_2)_{cc}NHCH_2C(O)_2H_3C(OCH_2CH_2)_{cc}OC(O)C$ $(CH_3)_2$—, and $H(OCH_2CH_2)_{cc}OC(O)C(CH_3)_2$—, wherein cc is a range of numbers that results in an average molecular weight of said polyethylene glycol moiety of between 1,000–40,000, preferabley 20,000 or 40,000.

In another aspect, the invention features a pharmaceutical composition that includes a pharmaceutically acceptable carrier and a therapeutically effective amount of any compound of the invention, or a pharmaceutically acceptable salt or prodrug thereof.

The invention also features a method of treating a patient in need of thromboembolic disorder treatment that includes administering to the patient a therapeutically effective amount of any compound of the invention, or a pharmaceutically acceptable salt or prodrug thereof. The thromboembolic disorder can be arterial cardiovascular thromboembolic disorders, venous cardiovascular thromboembolic disorders, and thromboembolic disorders in the chambers of the heart; including unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (D) other procedures in which blood is exposed to an artificial surface that promotes thrombosis.

In addition to their use in anticoagulant therapy, Factor XIa inhibitors are useful in the treatment and prevention of other diseases in which the generation of thrombin has been implicated as playing a physiologic role. For example, thrombin has been implicated in contributing to the morbidity and mortality of chronic and degenerative diseases such as cancer, arthritis, atherosclerosis, and Alzheimer's disease by its ability to regulate many different cell types-through specific cleavage and activation of a cell surface thrombin receptor, mitogenic effects, diverse cellular functions such as cell proliferation, for example, abnormal proliferation of vascular cells resulting in restenosis or angiogenesis, release of PDGF, and DNA synthesis. Inhibition of Factor XIa effectively blocks thrombin generation and therefore neutralizes any physiologic effects of thrombin on various cell types. The representative indications discussed above include some, but not all, of the potential clinical situations amenable to treatment with a Factor XIa inhibitor.

Three-Dimensional Structures of Factor XIa and Methods for Designing or Selecting Additional Factor XIa Inhibitors Using These Structures For the purpose of comparison to other serine proteases in the trypsin superfamily, two distinct residue numbering systems are used herein. For three-dimensional structure related descriptions, FXIcat residues are assigned numbers corresponding to those of trypsin, these numbers are shown in regular type and apply only to residues in the FXIcat. For primary structure (sequence) related descriptions, e.g., mutations or catalytic domain termini, FXIcat is assigned numbers corresponding to those of the native zymogen found in the bloodstream. Thus, the initiator methionine is residue—18, and the protein begins with Glu1 (SEQ ID NO: 2). These numbers are shown in bold in the text. The 18 amino acid signal sequence, which is included in the translated sequence in Genbank, is removed co-translationally to yield the N-terminus of the mature enzyme. FIG. 2 shows the conversion between these two numbering systems.

Computer Systems

In one aspect, the invention features a computer system that includes (a) a memory having stored therein data indicative of atomic coordinates in any one of the files listed in FIG. 16, or surrogates thereof, of the non-hydrogen atoms of residues serine 195, histidine 57, and aspartic acid 102 of FXIcat or atomic coordinates that have a root mean square deviation from the backbone atoms of the residues of less than 0.6, 0.5, 0.4, 0.3, 0.2, or 0.1 Å, and (b) a processor in electrical communication with the memory. This processor includes a program for generating and displaying a three-dimensional model representative of FXIcat. In one example, the stored data is x-ray diffraction data.

In another aspect, the invention features a computer system that includes a memory having stored therein data indicative of a pharmacophore model of a Factor XIa ligand. The pharmacophore model includes a three-dimensional model that includes 3 or more of the following: (i) an electrophilic carbon atom that binds to the side chain oxygen atom (OG) of Ser195 such that the electrophilic carbon atom is 1.4–4.0 Å (e.g., 1.8 to 3.5 Å or 2 to 3 Å) from the oxygen atom; (ii) at least one hydrogen bond donor group to interact with Asp189 such that the non-hydrogen atoms of the hydrogen bond donor groups are within 2.0 to 4.2 Å (e.g., 2.5 to 3.5 Å or 2.8 to 3.2 Å) away from the side chain oxygens of Asp189; (iii) a hydrophobic group that makes van der Waals contacts with residues of the active site and is less than 5.0 Å (e.g., less than 4.5, 4, 3, 2, or 1 Å) away from the CB atom of Ala97; (iv) a hydrogen bond donor group which makes a hydrogen bond with the main chain carbonyl of Ser214 such that the distance between the hydrogen-bonded atoms is less than 4.0 Å (e.g., less than 3.5, 3, 2, or 1 Å); (v) a hydrogen bond donor group that makes a hydrogen bond with the main chain carbonyl of Gly216 such that the distance between the hydrogen-bonded atoms is less than 4.0 Å (e.g., less than 3.5, 3, 2, or 1 Å); (vi) a hydrogen bond acceptor group that makes a hydrogen bond with the main chain nitrogen of Gly216 such that the distance between the hydrogen-bonded atoms is less than 4.0 Å (e.g., less than 3.5, 3, 2, or 1 Å); (vii) a hydrogen bond acceptor group that makes a hydrogen bond with a side chain nitrogen of His57 such that the distance between the hydrogen-bonded atoms is less than 4.0 Å (e.g., less than 3.5, 3, 2, or 1 Å); (viii) a group that makes van der Waals contacts with the side chains of residues of Lys192 and/or Leu146; (ix) a group that makes van der Waals contacts with the side chains of residues of Cys191 and/or Cys219; and (x) a group or groups that make one or more polar interactions with the side chains of residues of His174, Glu98 and/or Glu217. The computer also has a processor that is in electrical communication with the memory and that has a program for generating the three-dimensional model.

In another aspect, the invention features a computer readable memory having stored therein data indicative of a pharmacophore model of the invention or atomic coordintes of the invention.

Methods for Identifying, Designing, Manufacturing, or Evaluating Factor XIa Ligands Information from the three-dimensional structure of FXIcat can be used in a variety of methods for identifying, manufacturing, or evaluating Factor XIa ligands. In one such aspect, the invention includes a method of selecting or designing a candidate ligand for Factor XIa. This method involves generating in a computer a three-dimensional structure of FXIcat based on the atomic coordinates in one or more of the files listed in FIG. 16, or surrogates thereof, of the non-hydrogen atoms of residues seine 195, histidine 57, and aspartic acid 102 or atomic coordinates that have a root mean square deviation from the backbone atoms of the residues of less than 0.6, 0.5, 0.4, 0.3, 0.2, or 0.1 Å. A candidate ligand that has sufficient surface complementarity to the structure to bind Factor XIa (e.g., binding in an aqueous solution such as an aqueous solution at pH 7.0) is designed, selected or identified. Surface complementarities can be assessed with a number of commercially available software packages, including, but not limited to, INSIGHT II® and QUANTA® (Accelrys Inc: P.O. Box 5350, Princeton, N.J. 08543-5350, USA), DOCK (Gschwend, D. A. and I. D. Kuntz, *J. Comput-Aided Mol. Design*, 1996) and SYBYL® (Tripos, Inc.: 1699 South Hanley Rd., St. Louis, Mo., 63144-2913, USA; Han et al., Bioorg. Med. Chem. Lett, 10:39–43, 2000). Designed ligands are then manufactured. If desired, the ability of any candidate ligand designed by the methods described herein to bind Factor XIa in vitro or in vivo can be optionally measured to confirm this binding and/or to compare the affinity of the ligand to other Factor XIa ligands. Compounds so prepared can also be used to determine their ability to inhibit Factor XIa, using inhibition assays as described herein.

In another aspect, the invention provides a method for manufacturing a Factor XIa ligand. This method includes crystallizing FXIcat or a mutant of FXIcat with a ligand and obtaining the atomic coordinates, or surrogates thereof, of at least a portion of FXIcat with at least a portion of the ligand. One or more moieties in the ligand are selected for modification such that the modified ligand maintains the ability to bind Factor XIa. The ligand is modified based on this determination. Such modifications include moieties known by those skilled in the art to improve aqueous solubility, improve pharmacodynamic properties, such as increased circulation half-life or cell membrane permeability. Modifications can also be made to increase ligant affinity to FXIcat, as described in more detail elsewhere herein.

In a related aspect, the invention provides another method for manufacturing a Factor XIa ligand. This method involves manufacturing a ligand that binds FXIcat and that is designed or selected based on information obtained using a model of the atomic coordinates, or surrogates thereof, of at least a portion of the three-dimensional structure of FXIcat. In some embodiments, the ligand is designed or selected using a computer system of the invention. In desirable embodiments, the method involves (i) using information from a model generated from the atomic coordinates, or surrogates thereof, of at least a portion of the three-dimensional structure of FXIcat and (ii) designing, selecting, and/or manufacturing a ligand for Factor XIa based on the information.

In yet another aspect, the invention features a method of evaluating the ability of a candidate ligand to bind Factor XIa. This method involves (a) generating in a computer a three-dimensional structure of FXIcat based on the atomic coordinates in any one of the files listed in FIG. 16, or surrogates thereof, of the non-hydrogen atoms of residues serine 195, histidine 57, and aspartic acid 102 or atomic coordinates that have a root mean square deviation from the backbone atoms of the residues of less than 0.6, 0.5, 0.4, 0.3, 0.2, or 0.1 Å, and (b) employing a computational means to measure the interaction between the candidate ligand and FXIcat.

In another aspect, the invention provides a method of identifying a candidate ligand for Factor XIa. This method includes generating a three-dimensional model of a pharmacophore model of a FXIcat ligand using a computer system of the invention, and selecting or designing a candidate ligand satisfying the criteria of the pharmacophore model.

The invention also provides methods for excluding a candidate compound from further drug development. For example, candidate compounds for indications other than excess or undesired thrombosis can be evaluated for their ability to inhibit Factor XIa. Candidate compounds that inhibit Factor XIa and that are being developed for other indications are desirably modified to reduce their affinity for Factor XIa or eliminated from further drug development. In one such aspect, the invention features a method of evaluating the ability of a candidate compound to bind Factor XIa. This method involves (a) generating in a computer a three-dimensional structure of FXIcat based on the atomic coordinates in one or more of the files listed in FIG. 16, or surrogates thereof, of the non-hydrogen atoms of residues serine 195, histidine 57, and aspartic acid 102 or atomic coordinates that have a root mean square deviation from the backbone atoms of the residues of less than 0.6, 0.5, 0.4, 0.3, 0.2, or 0.1 Å, and (b) employing a computational means to measure the interaction between the candidate compound and FXIcat or to measure the surface complementarity between the candidate compound and FXIcat. In some embodiments, the candidate compound inhibits the activity of another protease (e.g., tryptase and elastase) and is either subsequently modified to reduce its affinity for Factor XIa or eliminated from further drug development.

Methods for Determining the Structure of FXIcat

The three-dimensional structural information of the present invention can be used to model the three-dimensional structure of other proteins, such as FXIcat from other mammals of laboratory, domestic or veterinary interest (e.g., rat, rabbit, mouse, cat, dog, cow, goat, pig, or sheep). Additionally, the structure of FXIcat can be used to model the structure of related proteins, such as other proteases with at least 30, 40, 50, 60, 70, 80, 90, 95, or 100% sequence identity to the catalytic domain of human Factor XI or to full-length human Factor XI.

Accordingly, in one such aspect, the invention features a method of generating a three-dimensional model of a FXIcat of interest. This method includes homology modeling using at least a portion of the atomic coordinates in any one of the files listed in FIG. 16 (e.g., atomic coordinates of a structure of the invention), or surrogates thereof, and at least a portion of the amino acid sequence of the Factor XI of interest, thereby generating a model of the FXIcat of interest.

In a related aspect, the invention features a method for experimentally determining the three-dimensional structure of the FXIcat of interest. This method involves crystallizing a FXIcat of interest, generating an X-ray diffraction pattern from the crystallized FXIcat of interest, and (i) applying at least a portion of the atomic coordinates of the files listed in FIG. 16 (e.g., atomic coordinates of a structure of the invention), or surrogates thereof, to the diffraction pattern to generate a three-dimensional electron density map of at least a portion of the FXIcat of interest, or (ii) utilizing de novo crystallographic methods such as isomorphous replacement or MAD phasing to generate such an electron density map.

Desirable Embodiments Using the FXIa Three-Dimensional Structure

In some embodiments of any of the aspects of the invention in which information from the three-dimensional structure of FXIcat is used for identifying, manufacturing, or evaluating a Factor XIa ligand, the three-dimensional structure also includes the hydrogen atoms of residues serine 195, histidine 57, and/or aspartic acid 102. In certain embodiments, the three-dimensional structure further includes the non-hydrogen atoms, or both the non-hydrogen and hydrogen atoms, of one or more of the following residues Tyr5901, Ala97, Glu98, Asp102, Leu146, His174, Asp189, Ala190, Cys191, Lys192, Gly193, Asp194, Ser214, Trp215, Gly216, Glu217, and Gly218. In some embodiments, the three-dimensional structure further includes the non-hydrogen atoms, or both the non-hydrogen and hydrogen atoms, of one or more of the following residues: Arg3704, His38, Leu39, Cys40, Cys58, Tyr94, Gly142, Tyr143, Tyr172, Cys219, Ala220, and Arg224. In some embodiments, the three-dimensional structure further includes the non-hydrogen atoms, or both the non-hydrogen and hydrogen atoms, of one or more of the following residues: Phe59, Ile151, Ala183, Gly196, Gly197, Thr213, Pro225, Gly226, Val227, and Tyr228. In various embodiments, the structure further includes coordinates for the non-hydrogen or both the non-hydrogen and hydrogen atoms of one or more of the following residues: Arg3704, His38, Leu39, Cys40, His57, Cys58, Phe59, Tyr5901, Tyr94, Ala97, Glu98, Asp102, Gly142, Tyr143, Leu146, Ile151, Tyr172, His174, Ala183, Asp189, Ala190, Cys191, Lys192, Gly193, Asp194, Ser195, Gly196, Gly197, Thr213, Ser214, Trp215, Gly216, Glu217, Gly218, Cys219, Ala220, Arg224, Pro225, Gly226, Val227, and Tyr228. In desirable embodiments, the structure includes the coordinates for all of the residues in the FXIcat.

Desirably, the atomic coordinates have a root mean square deviation from the atomic coordinates of the backbone atoms of the corresponding residues in any one of the files listed in FIG. 16 of less than 1.2, 1.0, 0.9, 0.8, 0.7, 0.6, 0.5, 0.4, or 0.3 Å. In various embodiments, the resolution of the structure is at least 5, 4, 3, 2.5, 2.0, 1.8, or 1.5 Å (in order of increasing resolution and increasing preference). Exemplary surrogates for atomic coordinates of the invention include any modification (e.g., mathematical modification, addition of a constant or scaling) of the coordinates that preserves the relative relationships among the coordinates. Desirable portions of atomic coordinates of Factor XIcat include at least 50, 60, 70, 80, 90, 95, or 100% of the atomic coordinates for Factor XIcat. In some embodiments, the portion of the atomic coordinates of Factor XIcat includes at least 50, 60, 70, 80, 90, 95, or 100% of the atomic coordinates for the non-hydrogen atoms of Factor XIcat or for all the atoms of Factor XIcat.

In some embodiments, the compound possesses at least one hydrogen bond donor group that interacts (e.g., forms a hydrogen bond) with Asp189 of FXIcat. In some embodiments, the compound possesses an electrophilic carbon and at least one hydrogen bond donor group that interacts with Asp 189 of FXIcat. The electrophilic carbon of the compound is desirably separated by approximately 5.9 Å (e.g., 5.5 to 6.3 Å) and 8.3 Å (e.g., 8.0 to 8.6 Å) from the hydrogen bond donor group of the compound and Asp189, respectively. The electrophilic carbon atom is desirably 1.4 to 4.0 Å (e.g., 2 to 3.5 Å or 2.5 to 3 Å) from the side chain oxygen atom (OG) of Ser195. The non-hydrogen atoms of the hydrogen bond donor groups are desirably within 2.0 to 4.2 Å away from the side chain oxygens of Asp189. These groups can either interact directly with Asp 189 or interact indirectly through water molecules.

In various embodiments, the compound has one or more of the following: (i) an electrophilic carbon atom that binds to the side chain oxygen atom (OG) of Ser195 such that the electrophilic carbon atom is 1.4–4.0 Å from the oxygen atom; (ii) at least one hydrogen bond donor group to interact with Asp 189 such that the non-hydrogen atoms of the hydrogen bond donor groups are within 2.0 to 4.2 Å away from the side chain oxygens of Asp189; (iii) a hydrophobic group that makes van der Waals contacts with residues of the active site and is less than 5.0 Å (e.g., less than 4.5, 4, 3, 2, or 1 Å) of the CB atom of Ala97; (iv) a hydrogen bond donor group which makes a hydrogen bond with the main chain carbonyl of Ser214 such that the distance between the hydrogen-bonded atoms is less than 4.0 Å (e.g., less than 3.5, 3, 2, or 1 Å); (v) a hydrogen bond donor group that makes a hydrogen bond with the main chain carbonyl of Gly216 such that the distance between the hydrogen-bonded atoms is less than 4.0 Å (e.g., less than 3.5, 3, 2, or 1 Å); (vi) a hydrogen bond acceptor group that makes a hydrogen bond with the main chain nitrogen of Gly216 such that the distance between the hydrogen-bonded atoms is less than 4.0 Å (e.g., less than 3.5, 3, 2, or 1 Å); (vii) a hydrogen bond acceptor group that makes a hydrogen bond with a side chain nitrogen of His57 such that the distance between the hydrogen-bonded atoms is less than 4.0 Å (e.g., less than 3.5, 3, 2, or 1 Å); (viii) a group that makes van der Waals contacts with the side chains of residues of Lys192 and/or Leu146; (ix) a group that makes van der Waals contacts with the side chains of residues of Cys191 and/or Cys219; and (x) a group or groups that make one or more polar interactions with the side chains of residues of His174, Glu98 and/or Glu217. Desirably, the inhibitors of Factor XIa used in the present invention comprise 3, 4, 5, or 6 or more of the above.

In other embodiments, the compound has at least one hydrogen bond donor group that interacts with Asp189. In this compound, the non-hydrogen atoms of the hydrogen bond donor groups are desirably within 2.0 to 4.2 Å away from the side chain oxygens of Asp189.

In a desirable embodiment of any of the aspects of the invention in which information from the three-dimensional structure of FXIcat is used for identifying, manufacturing, or evaluating a Factor XIa ligand, the method also includes determining the ability of the candidate ligand to bind Factor XIa in vitro or in vivo. In some embodiments, the method further includes determining the ability of the candidate ligand to inhibit the enzymatic activity of Factor XIa in vitro or in vivo. Desirably, the affinity of the candidate ligand for Factor XIa is at least 2, 5, 10, 20, or 30-fold higher than its affinity for another protease such as thrombin, trypsin, Factor IXa, Factor VIIa and/or Factor Xa. Affinity can be reported as, e.g., $K_m$, $K_d$, $K_i$ or $IC_{50}$ values in which lower values indicate higher affinity. Desirably, the affinity of the candidate ligand for Factor XIa is at least 10 µM, 1 µM, 100 nM, 10 nM, or 1 nM. In various embodiments, the amino acid sequence of FXIcat present in the structure is at least 70, 80, 92, 94, 96, 98, or 100% identical to the amino acid sequence of the corresponding region of human Factor XI (SEQ ID NO: 2).

FXIcat Crystals

The invention also features crystals of FXIcat that are useful for determining the three-dimensional structure of FXIcat or a protein with substantial sequence identity (e.g., at least 30, 40, 50, 60, 70, 80, 90, 95, or 100% sequence identity) to FXIcat. In one such aspect, the invention features a crystal (e.g., a cubic crystal) of FXIcat that is at least 10, 12, 15, 18, 20, or 25µ in the shortest dimension and diffracts to better than 3.5, 3.2, 3.0, 2.8, 2.5, or 2.0 Å resolution, or a crystal (e.g, a needle-like crystal) that has a size of at least 10, 12, 15, 18, 20, or 25µ in the smallest dimension and diffracts to 3.5, 3.2, 3.0, 2.8, 2.5, or 2.0 Å resolution or better.

The invention also features crystals of a quadruple mutant FXIcat protein in which each of residues Ser434, Thr475 and Lys437 has been mutated to an alanine, and Cys482 has been mutated to serine (FXIcat-S434A, T475A, K437A, C482S) that are useful for determining the three-dimensional structure. In one such aspect, the invention features a crystal (e.g., a cubic crystal) that is at least 10, 12, 15, 18, 20, or 25μ in the shortest dimension and diffracts to better than 3.5, 3.2, 3.0, 2.8, 2.5, or 2.0 Å resolution, or a crystal (e.g., a needle-like crystal) that is at least 10, 12, 15, 18, 20, or 25 g in the smallest dimension and diffracts to 3.5, 3.2, 3.0, 2.8, 2.5, or 2.0 Å resolution or better.

The invention further features crystals of a mutant FXIcat protein in which one or more of the following residues Ser434, Thr475, Lys422, Lys437, Lys486, Lys505, Lys509, Arg479 and/or Asp476 are mutated (e.g., mutated to alanine), and/or Cys482 has been mutated (e.g., mutated to serine) and that are useful for determining the three-dimensional structure. In one such aspect, the invention features a crystal (e.g., a cubic crystal) of FXIcat-S434A, T475A, C482S, K505A that is at least 10, 12, 15, 18, 20, or 25μ in the shortest dimension and diffracts to better than 3.5, 3.2, 3.0, 2.8, 2.5, or 2.0 Å resolution, or a crystal (e.g., a plate-like crystal) of FXIcat-S434A, T475A, C482S, D476A that is at least 10, 12, 15, 18, 20, or 25μ in the smallest dimension and diffracts to 3.5, 3.2, 3.0, 2.8, 2.5, or 2.0 Å resolution or better.

Factor XIa Proteins and Nucleic Acids

In one aspect, the invention provides a purified, less than full-length protein fragment of Factor XI, such as a protein consisting essentially of the catalytic domain of Factor XI. The catalytic domain is identified as the residues carboxyl to the activating protease cleavage site designated as KPR↓IVG (where the arrow denotes the proteolytic cleavage). The residues that make up this domain are 370–607 for the human, 372–606 for the mouse and 369–606 for the rabbit. The sequence for entire Factor XI rat gene is not yet known, but the catalytic domain comprises residues 1–234. In some embodiments, the human protein fragment consists of residues 370–607 of SEQ ID NO: 1 (GenBank Accession No. P03951). For the rabbit, the protein fragment consists of residues 369–606 of SEQ ID NO: 2 (GenBank Accession No. AF395821). For the mouse, the protein fragment consists of residues 372–606 of SEQ ID NO: 3 (GenBank Accession No. AF356627). For the rat, the protein fragment consists of residues 1–234 of SEQ ID NO: 4.

In another aspect, the invention features a purified Factor XI protein or fragment thereof including (a) a mutation of a residue that is otherwise post-translationally modified either naturally or in an organism used for recombinant expression, (b) a mutation that alters the charge of Factor XI, (c) a mutation that eliminates a free, reactive sulfhydryl group of a cysteine, (d) a combination of mutations that together alter the distribution of charge density without altering the overall charge of Factor XI, (e) a mutation of the $NH_2$— or COOH-terminal residue of Factor XI, and/or (f) a mutation that alters the folding and/or crystal packing of Factor XI. In certain embodiments, the protein is enzymatically de-glycosylated. In other embodiments, one or more residues that would otherwise lead to glycosylation are mutated to another residue that results in no glycosylation. In some embodiments, the protein has at least 2, 3, 4, 5, 6, 7, 8, or 9 residues that are mutated compared to a naturally occurring Factor XI protein or the catalytic domain of a naturally-occurring Factor XI protein. In desirable embodiments, the mutation(s) allow crystallization or increase the resolution of the corresponding three-dimensional structure of the mutant protein compared to the structure of Factor XI without the mutation(s). For example, the mutations may increase the size or order of the resulting crystals, resulting in a higher resolution structure. Desirable mutant Factor XI proteins or fragments are at least 80, 85, 90, 92, 94, 96, 98, or 99% identical to any one of SEQ ID NOs: 1–4.

In another aspect, the invention provides a purified protein including a region that is at least 92, 94, 96, 98, or 100% identical to the amino acid sequence of SEQ ID NO: 1 (human Factor XI) or SEQ ID NO: 3 (rat Factor XI). In some embodiments, the protein has an amino acid sequence at least 92, 94, 96, 98, or 100% identical to the amino acid sequence of SEQ ID NO: 1, over the entire length of SEQ ID NO: 1 or 3.

In another aspect, the invention features a purified nucleic acid encoding one or more of the proteins or protein fragments of the invention. Desirably, the nucleic acid is contained within a vector and operably linked to a promoter that regulates transcription of the nucleic acid.

Definitions

As used throughout this specification and the appended claims, the following terms have the meanings specified:

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups are of from 2 to 7 carbons.

The term "acylamino," as used herein, represents an acyl group attached to the parent molecular group through a nitrogen atom. Exemplary unsubstituted acylamino groups are of from 2 to 7 carbons.

The term "acyloxy," as used herein, represents an acyl group attached to the parent molecular group through an oxygen atom. Exemplary unsubstituted acyloxy groups are of from 2 to 7 carbons.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy, wherein the alkylene group is of one to six carbon atoms; (7) aryloyl; (8) azido; (9) carboxaldehyde; (10) cycloalkyl of three to eight carbon atoms; (11) halo; (12) heterocycle; (13) (heterocycle)oxy; (14) (heterocycle)oyl; (15) hydroxy; (16) N-protected amino; (17) nitro; (18) oxo; (19) spiroalkyl of three to eight carbon atoms; (20) thioalkoxy of one to six carbon atoms; (21) thiol; (22) —$CO_2R^A$, wherein $R^A$ is selected from the group consisting of (a) alkyl, (b) aryl and (c) arylalkyl, wherein the alkylene group is of one to six carbon atoms; (23) —$C(O)NR^BR^C$, wherein $R^B$ and $R^C$ are independently selected from the group consisting of (a) hydrogen, (b) alkyl, (c) aryl and (d) arylalkyl, wherein the alkylene group is of one to six carbon atoms; (24) —$SO_2R^D$, wherein $R^D$ is selected from the group consisting of (a) alkyl, (b) aryl and (c) arylalkyl, wherein the alkylene group is of one to six carbon atoms; (25) —$SO_2NR^ER^F$, wherein $R^E$ and $R^F$ are independently selected from the group consisting of (a) hydrogen, (b) alkyl, (c) aryl and (d) arylalkyl, wherein the alkylene group is of one to six carbon atoms; and (26) —$NR^GR^H$, wherein $R^G$ and $R^H$ are independently selected from the group consisting of (a) hydrogen; (b) an N-protecting group; (c) alkyl of one to six carbon atoms; (d)

alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group.

The terms "alkoxy" or "alkyloxy," as used interchangeably herein, represent an alkyl group attached to the parent molecular group through an oxygen atom. Exemplary unsubstituted alkoxy groups are of from 1 to 6 carbons.

The terms "alkoxyalkyl" or "alkyloxyalkyl," as used interchangeably herein, represent an alkyl group to which is attached an alkoxy group. Exemplary unsubstituted alkoxyalkyl groups are of from 2 to 12 carbons.

The terms "alkoxycarbonyl" or "alkyloxycarbonyl," as used interchangeably herein, represent an ester group; i.e. an alkoxy group, attached to the parent molecular group through a carbonyl group and is exemplified by methoxycarbonyl, ethoxycarbonyl and the like. Exemplary unsubstituted alkoxycarbonyl groups are of from 2 to 7 carbons.

The term "alkyl," as used herein, represents a monovalent group derived from a straight or branched chain saturated hydrocarbon of, unless otherwise specified, from 1 to 6 carbons and is exemplified by methyl, ethyl, n- and isopropyl, n-, sec-, iso- and tert-butyl, neopentyl and the like and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight-carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spiroalkyl of three to eight carbon atoms; (20) thioalkoxy of one to six carbon atoms; (21) thiol; (22) —CO$_2$R$^A$, wherein R$^A$ is selected from the group consisting of (a) alkyl, (b) aryl and (c) arylalkyl, wherein the alkylene group is of one to six carbon atoms; (23) —C(O)NR$^B$R$^C$, wherein R$^B$ and R$^C$ are independently selected from the group consisting of (a) hydrogen, (b) alkyl, (c) aryl and (d) arylalkyl, wherein the alkylene group is of one to six carbon atoms; (24) —SO$_2$R$^D$, wherein R$^D$ is selected from the group consisting of (a) alkyl, (b) aryl and (c) arylalkyl, wherein the alkylene group is of one to six carbon atoms; (25) —SO$_2$NR$^E$R$^F$, wherein R$^E$ and R$^F$ are independently selected from the group consisting of (a) hydrogen, (b) alkyl, (c) aryl and (d) arylalkyl, wherein the alkylene group is of one to six carbon atoms; and (26) —NR$^G$R$^H$, wherein R$^G$ and R$^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group.

The term "alkylamino," as used herein, represents an alkyl group attached to the parent molecular group through a nitrogen atom. Exemplary unsubstituted alkylamino groups are of from 1 to 6 carbons.

The term "alkylaminocarbonyl," as used herein, represents an alkylamino group attached to the parent molecular group through a carbonyl group. Exemplary unsubstituted alkylaminocarbonyl groups are of from 2 to 7 carbons.

The term "alkylaminosulfonyl," as used herein, represents an alkylamino group attached to the parent molecular group through an —SO$_2$— group. Exemplary unsubstituted alkylaminosulfonyl groups are of from 1 to 6 carbons.

The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonyl," as used herein, represents an alkyl group attached to the parent molecular group through an —SO$_2$— group. Exemplary unsubstituted alkylsulfonyl groups are of from 1 to 6 carbons.

The term "alkylsulfonylalkyl," as used herein, represents an alkyl group, as defined herein, substituted by a alkylsulfonyl group. Exemplary unsubstituted alkylsulfonylalkyl groups are of from 2 to 12 carbons.

The term "alkylthio," as used herein, represents an alkyl group attached to the parent molecular group through a sulfur atom. Exemplary unsubstituted alkylthio groups are of from 1 to 6 carbons.

The term "alkynyl," as used herein, represents monovalent straight or branched chain groups of from two to six carbon atoms containing a carbon-carbon triple bond and is exemplified by ethynyl, 1-propynyl, and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy, wherein the alkylene group is of one to six carbon atoms; (7) aryloyl; (8) azido; (9) carboxaldehyde; (10) cycloalkyl of three to eight carbon atoms; (11) halo; (12) heterocycle; (13) (heterocycle)oxy; (14) (heterocycle)oyl; (15) hydroxy; (16) N-protected amino; (17) nitro; (18) oxo; (19) spiroalkyl of three to eight carbon atoms; (20) thioalkoxy of one to six carbon atoms; (21) thiol; (22) —CO$_2$R$^A$, wherein R$^A$ is selected from the group consisting of (a) alkyl, (b) aryl and (c) arylalkyl, wherein the alkylene group is of one to six carbon atoms; (23) —C(O)NR$^B$R$^C$, wherein R$^B$ and R$^C$ are independently selected from the group consisting of (a) hydrogen, (b) alkyl, (c) aryl and (d) arylalkyl, wherein the alkylene group is of one to six carbon atoms; (24) —SO$_2$R$^D$, wherein R$^D$ is selected from the group consisting of (a) alkyl, (b) aryl and (c) arylalkyl, wherein the alkylene group is of one to six carbon atoms; (25) —SO$_2$NR$^E$R$^F$, wherein R$^E$ and R$^F$ are independently selected from the group consisting of (a) hydrogen, (b) alkyl, (c) aryl and (d) arylalkyl, wherein the alkylene group is of one to six carbon atoms; and (26) —NR$^G$R$^H$, wherein R$^G$ and R$^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group.

The term "alpha-amino acid residue," as used herein, represents a —N($R^A$)C($R^B$)($R^C$)C(O)— linkage, wherein $R^A$ is selected from the group consisting of (a) hydrogen, (b) alkyl, (c) aryl and (d) arylalkyl, as defined herein; and $R^B$ and $R^C$ are independently selected from the group consisting of: (a) hydrogen, (b) optionally substituted alkyl, (c) optionally substituted cycloalkyl, (d) optionally substituted aryl, (e) optionally substituted arylalkyl, (f) optionally substituted heterocyclyl, and (g) optionally substituted heterocyclylalkyl, each of which is as defined herein. For natural amino acids, $R^B$ is H and $R^C$ corresponds to those side chains of natural amino acids found in nature, or their antipodal configurations. Exemplary natural amino acids include alanine, cysteine, aspartic acid, glutamic acid, phenylalanine, glycine, histidine, isoleucine, lysine, leucine, methionine, aspartamine, ornithine, proline, glutamine, arginine, serine, threonine, valine, tryptophan, and tyrosine, each of which, except glycine, as their D- or L-form. As used herein, for the most part, the names of naturally-occuring amino acids and aminoacyl residues used herein follow the naming conventions suggested by the IUPAC Commission on the Nomenclature of Organic Chemistry and the IUPAC-IUB Commission on Biochemical Nomenclature as set out in Nomenclature of α-Amino Acids (Recommendations, 1974), *Biochemistry* 14 (2), 1975. The present invention also contemplates non-naturally occuring (i.e., unnatural) amino acid residues in their D- or L-form such as, for example, homophenylalanine, phenylglycine, cyclohexylglycine, cyclohexylalanine, cyclopentyl alanine, cyclobutylalanine, cyclopropylalanine, cyclohexylglycine, norvaline, norleucine, thiazoylalanine (2-, 4- and 5-substituted), pyridylalanine (2-, 3- and 4-isomers), naphthalalanine (1- and 2-isomers) and the like. Stereochemistry is as designated by convention, where a bold bond indicates that the substituent is oriented toward the viewer (away from the page) and a dashed bond indicates that the substituent is oriented away from the viewer (into the page). If no stereochemical designation is made, it is to be assumed that the structure definition includes both stereochemical possibilities.

The term "amino," as used herein, represents an —$NH_2$ group.

The term "aminoalkyl," as used herein, represents an alkyl group, as defined herein, substituted by an amino group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, wherein the alkyl and alkylene groups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde)alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_q CO_2 R^A$, wherein q is zero to four and $R^A$ is selected from the group consisting of (a) alkyl, (b) aryl and (c) arylalkyl, wherein the alkylene group is of one to six carbon atoms; (37) —$(CH_2)_q CONR^B R^C$, wherein $R^B$ and $R^C$ are independently selected from the group consisting of (a) hydrogen, (b) alkyl, (c) aryl and (d) arylalkyl, wherein the alkylene group is of one to six carbon atoms; (38) —$(CH_2)_q SO_2 R^D$, wherein $R^D$ is selected from the group consisting of (a) alkyl, (b) aryl and (c) arylalkyl, wherein the alkylene group is of one to six carbon atoms; (39) —$(CH_2)_q SO_2 NR^E R^F$, wherein $R^E$ and $R^F$ are independently selected from the group consisting of (a) hydrogen, (b) alkyl, (c) aryl and (d) arylalkyl, wherein the alkylene group is of one to six carbon atoms; (40) —$(CH_2)_q NR^G R^H$ wherein $R^G$ and $R^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The terms "arylalkenyl" or "aralkenyl," as used interchangeably herein, represent an aryl group attached to the parent molecular group through an alkenyl group. Exemplary unsubstituted arylalkenyl groups are of from 8 to 16 carbons.

The terms "arylalkoxy" or "aralkoxy," as used interchangeably herein, represent an arylalkyl group attached to the parent molecular group through an oxygen atom. Exemplary unsubstituted arylalkoxy groups are of from 7 to 16 carbons.

The terms "arylalkoxycarbonyl" or "aralkoxycarbonyl," as used interchangeably herein, represent an arylalkoxy group attached to the parent molecular group through a carbonyl group. Exemplary unsubstituted arylalkoxycarbonyl groups are of from 8 to 17 carbons.

The terms "arylalkyl" or "aralkyl," as used interchangeably herein, represent an aryl group attached to the parent molecular group through an alkyl group. Exemplary unsubstituted arylalkyl groups are of from 7 to 16 carbons.

The terms "arylalkylamino" or "aralkylamino," as used interchangeably herein, represent an arylalkyl group attached to the parent molecular group through a nitrogen atom. Exemplary unsubstituted arylalkylamino groups are of from 7 to 16 carbons.

The terms "arylalkylaminocarbonyl" or "aralkylaminocarbonyl," as used interchangeably herein, represents an arylalkylamino group attached to the parent molecular group through a carbonyl group. Exemplary unsubstituted arylalkylaminocarbonyl groups are of from 8 to 17 carbons.

The terms "arylalkylsulfinyl" or "aralkylsulfinyl," as used interchangeably herein, represent an arylalkyl group attached to the parent molecular group through an —SO— group. Exemplary unsubstituted arylalkylsulfinyl groups are of from 7 to 16 carbons.

The terms "arylalkylsulfonyl" or "aralkylsulfonyl," as used interchangeably herein, represent an aralkyl group attached to the parent molecular group through an —SO$_2$— group. Exemplary unsubstituted arylalkylsulfonyl groups are of from 7 to 16 carbons.

The term "arylalkylthio" or "aralkylthio," as used interchangeably herein, represents an arylalkyl group attached to the parent molecular group through a sulfur atom. Exemplary unsubstituted arylalkylthio groups are of from 7 to 16 carbons.

The term "arylamino," as used herein, represents an aryl group which is attached to the parent molecular group through a nitrogen atom. Exemplary unsubstituted arylamino groups are of 6 or 10 carbons.

The term "arylaminocarbonyl," as used herein, represents an arylamino group attached to the parent molecular group through a carbonyl group. Exemplary unsubstituted arylaminocarbonyl groups are of from from 7 or 11 carbons.

The term "arylaminosulfonyl," as used herein, represents an arylamino group attached to the parent molecular group through an —SO$_2$— group. Exemplary unsubstituted arylaminosulfonyl groups are of 6 or 10 carbons.

The term "aryloxy," as used herein, represents an aryl group which is attached to the parent molecular group through an oxygen atom. Exemplary unsubstituted aryloxy groups are of 6 or 10 carbons.

The term "aryloxycarbonyl," as used herein, represents an aryloxy group which is attached to the parent molecular group through a carbonyl group. Exemplary unsubstituted aryloxycarbonyl groups are of 7 or 11 carbons.

The terms "aryloyl" or "aroyl," as used interchangeably herein, represent an aryl group which is attached to the parent molecular group through a carbonyl group. Exemplary unsubstituted aryloxycarbonyl groups are of 7 or 11 carbons.

The terms "aryloylamino" or "aroylamino," as used interchangeably herein, represent an aroyl group which is attached to the parent molecular group through a nitrogen atom. Exemplary unsubstituted aryloylamino groups are of 7 or 11 carbons.

The term "arylsulfinyl," as used herein, represens an aryl group attached to the parent molecular group through an —SO— group. Exemplary unsubstituted arylsulfinyl groups are of 6 or 10 carbons.

The term "arylsulfonyl," as used herein, represens an aryl group attached to the parent molecular group through an —SO$_2$— group. Exemplary unsubstituted arylsulfonyl groups are of 6 or 10 carbons.

The term "arylthio," as used herein, represents an aryl group which is attached to the parent molecular group through a sulfur atom. Exemplary unsubstituted arylthio groups are of 6 or 10 carbons.

The term "azido," as used herein, represents an —N$_3$ group.

The term "azidoalkyl," as used herein, represents an alkyl group, as defined herein, substituted by an azido group.

By "blood component" is meant a biological entity normally found in blood, such as, for example cells, such as erythrocytes, leukocytes, and platelets, or proteins such as immunoglobulins, serum albumin, ferritin, steroid binding proteins, such as corticosteroid-binding globulin and sex hormone-binding globulin, transferrin, thyroxin binding protein, and alpha-2-macroglobulin. Blood components also include glycans, including glycosylamino glycans. Preferred blood components are those that have reactive organic functionality, such as thiols or amines.

The terms "carbamate" or "carbamyl," as used interchangeably herein, represent a $R^A OC(O)NR^B$— group, or a —$OC(O)NR^B$— linkage, depending on the chemical context in which this term is used, wherein $R^A$ is selected from the group consisting of (a) alkyl, (b) aryl, and (c) arylalkyl; and $R^B$ is selected from the group consisting of (a) hydrogen, (b) alkyl, (c) aryl and (d) arylalkyl, as defined herein.

The term "carbonate," as used herein represents a —$R^A OC(O)O$— group, or a —$OC(O)O$— linkage, depending on the chemical context in which this term is used, wherein $R^A$ is selected from the group consisting of (a) alkyl, (b) aryl, and (c) arylalkyl, as defined herein.

The term "carbonyl," as used herein, represents a C=O group.

The term "carboxaldehyde," as used herein, represents a —CHO group.

The term "(carboxaldehyde)alkyl," as used herein, represents an alkyl group, as defined herein, substituted by a carboxaldehyde group.

The term "carboxy," as used herein, represents a —CO$_2$H group.

The term "carboxyalkyl," as used herein, represents an alkyl group, as defined herein, substituted by a carboxy group.

The term "cycloalkenyl," as used herein represents a monovalent cyclic hydrocarbon of from three to eight carbons, unless otherwise specified, having at least one carbon-carbon double bond. The cycloalkenyl groups of this invention can be optionally substituted with (1) alkanoyl of one to six carbon atoms; (2) alkyl of one to six carbon atoms; (3) alkoxy of one to six carbon atoms; (4) alkoxyalkyl, wherein die alkyl and alkylene groups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde)alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —(CH$_2$)$_q$CO$_2$R$^A$, wherein q is zero to four and R$^A$ is selected from the group consisting of (a) alkyl, (b) aryl and (c) arylalkyl, wherein the alkylene group is of one to six carbon atoms; (37) —$(CH_2)_qCONR^BR^C$, wherein $R^B$ and $R^C$ are independently selected from the group consisting of (a) hydrogen, (b) alkyl, (c) aryl and (d) arylalkyl, wherein the alkylene group is of one to six carbon atoms; (38) —$(CH_2)_qSO_2R^D$, wherein $R^D$ is selected from the group consisting of (a) alkyl, (b) aryl and (c) arylalkyl, wherein the alkylene group is of one to six carbon atoms; (39) —$(CH_2)_qSO_2NR^ER^F$, wherein $R^E$ and $R^F$ are independently selected from the group consisting of (a) hydrogen, (b) alkyl, (c) aryl and (d) arylalkyl, wherein the alkylene group is of one to six carbon atoms; (40) —$(CH_2)_qNR^GR^H$, wherein $R^G$ and $R^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo [2.2.1.]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, wherein the alkyl and alkylene groups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde)alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_qCO_2R^A$, wherein q is zero to four and $R^A$ is selected from the group consisting of (a) alkyl, (b) aryl and (c) arylalkyl, wherein the alkylene group is of one to six carbon atoms; (37) —$(CH_2)_qCONR^BR^C$, wherein $R^B$ and $R^C$ are independently selected from the group consisting of (a) hydrogen, (b) alkyl, (c) aryl and (d) arylalkyl, wherein the alkylene group is of one to six carbon atoms; (38) —$(CH_2)_qSO_2R^D$, wherein $R^D$ is selected from the group consisting of (a) alkyl, (b) aryl and (c) arylalkyl, wherein the alkylene group is of one to six carbon atoms; (39) —$(CH_2)_qSO_2NR^ER^F$, wherein $R^E$ and $R^F$ are independently selected from the group consisting of (a) hydrogen, (b) alkyl, (c) aryl and (d) arylalkyl, wherein the alkylene group is of one to six carbon atoms; (40) —$(CH_2)_qNR^GR^H$, wherein $R^G$ and $R^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms- and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "cycloalkylamino," as used herein, represents a cycloalkyl group attached to the parent molecular group through a nitrogen atom. Exemplary unsubstituted cycloalkylamino groups are of from 3 to 8 carbons.

The term "cycloalkylaminocarbonyl," as used herein, represents a cycloalkylamino group attached to the parent molecular group through a carbonyl group. Exemplary unsubstituted cycloalkylaminocarbonyl groups are of from 4 to 9 carbons.

The terms "cycloalkyloxy" or "cycloalkoxy," as used interchangeably herein, represent a cycloalkyl group, as defined herein, attached to the parent molecular group through an oxygen atom. Exemplary unsubstituted cycloalkyloxy groups are of from 3 to 8 carbons.

The terms "cycloalkyloxycarbonyl" or "cycloalkoxycarbonyl," as used interchangeably herein, represent a cycloalkyloxy group, as defined herein, attached to the parent molecular group through a carbonyl group. Exemplary unsubstituted cycloalkyloxycarbonyl groups are of from 4 to 9 carbons.

The term "cycloalkylalkoxy," as used herein, represents an alkoxy group, as defined herein, to which is attached a cycloalkyl group. Exemplary unsubstituted cycloalkylalkoxy groups are of from 4 to 14 carbons.

The term "cycloalkylalkyl," as used herein, represents a cycloalkyl group, as defined herein, attached to the parent molecular group through an alkyl group. Exemplary unsubstituted cycloalkylalkyl groups are of from 4 to 14 carbons.

The term "cycloalkylsulfinyl," as used herein, represents a cycloalkyl group attached to the parent molecular group through an —SO— group. Exemplary unsubstituted cycloalkylsulfinyl groups are of from 3 to 8 carbons.

The term "cycloalkylsulfonyl," as used herein, represents a cycloalkyl group attached to the parent molecular group through an —$SO_2$— group. Exemplary unsubstituted cycloalkylsulfonyl groups are of from 3 to 8 carbons.

The term "dialkylamino," as used herein, represents an N,N-dialkylsubstituted amine attached to the parent molecular group through the nitrogen atom. The two alkyl substituents of a dialkylamino group can be the same or different, or can be joined together to form a ring. Exemplary dialkylamino groups are of from 2 to 12 carbons and include dimethylamino, diethylamino, pyrrolidino, and piperidino.

The term "haloalkyl," as used herein, represents an alkyl group, as defined herein, substituted by one, two, or three halogen atoms and is exemplified by chloromethyl, bromoethyl, trifluoromethyl and the like.

The term "halogen," as used herein, represents F, Cl, Br and I.

The term "heteroaryl," as used herein, represents that subset of heterocycles, as defined herein, which are aromatic: i.e., they contain 4n+2 pi electrons within the mono- or multicyclic ring system. Exemplary unsubstituted heteroaryl groups are of from 1 to 9 carbons.

The terms "heteroarylalkenyl" or "heteroaralkenyl," or as used interchangeably herein, represent a heteroaryl group, as defined herein, attached to the parent molecular group through an alkenyl group. Exemplary unsubstituted heteroarylalkenyl groups are of from 3 to 15 carbons.

The terms "heteroarylalkyl" or "heteroaralkyl," as used interchangeably herein, represent a heteroaryl group, as defined herein, attached to the parent molecular group through an alkyl group. Exemplary unsubstituted heteroarylalkyl groups are of from 2 to 15 carbons.

The terms "heteroarylalkylamino" or "heteroaralkylamino," as used interchangeably herein, represent a heteroarylalkyl group, as defined herein, attached to the parent molecular group through a nitrogen atom. Exemplary unsubstituted heteroarylalkylamino groups are of from 2 to 15 carbons.

The terms "heteroarylalkylaminocarbonyl" or "heteroaralkylaminocarbonyl," or as used interchangeably herein, represent a heteroarylalkylamino group, as defined herein, attached to the parent molecular group through a carbonyl group. Exemplary unsubstituted heteroarylalkylaminocarbonyl groups are of from 3 to 16 carbons.

The terms "heteroaryloyl" or "heteroaroyl," or as used interchangeably herein, represent a heteroaryl group, as defined herein, attached to the parent molecular group through a carbonyl group. Exemplary unsubstituted heteroaryloyl groups are of from 2 to 10 carbons.

The terms "heteroarylalkyloxy" or "heteroaralkoxy," or as used interchangeably herein, represent a heteroarylalkyl group, as defined herein, attached to the parent molecular group through an oxygen atom. Exemplary unsubstituted heteroarylalkyloxy groups are of from 2 to 15 carbons.

The terms "heteroarylalkyloxycarbonyl" or "heteroaralkoxycarbonyl," as used interchangeably herein, represent a heteroaralkoxy group, as defined herein, attached to the parent molecular group through a carbonyl group. Exemplary unsubstituted heteroarylalkyloxycarbonyl groups are of from 3 to 16 carbons.

The terms "heteroarylalkylsulfonyl" or "heteroaralkylsulfonyl," as used interchangeably herein, represent a heteroarylalkyl group attached to the parent molecular group through an —SO$_2$— group. Exemplary unsubstituted heteroarylalkylsulfonyl groups are of from 2 to 15 carbons.

The term "heteroarylamino," as used herein, represents a heteroaryl group attached to the parent molecular group through a nitrogen atom. Exemplary unsubstituted heteroarylamino groups are of from 1 to 9 carbons.

The term "heteroarylaminocarbonyl," as used herein, represents a heteroarylamino group attached to the parent molecular group through a carbonyl group. Exemplary unsubstituted heteroarylaminocarbonyl groups are of from 2 to 10 carbons.

The term "heteroarylaminosulfonyl," as used herein, represents a heteroarylamino group attached to the parent molecular group through an —SO$_2$— group. Exemplary unsubstituted heteroarylaminosulfdnyl groups are of from 1 to 9 carbons.

The term "heteroaryloxy," as used herein, represents a heteroaryl group attached to the parent molecular group through an oxygen atom. Exemplary unsubstituted heteroaryloxy groups are of from 1 to 9 carbons.

The term "heterdaryloxycarbonyl," as used herein, represents a heteroaryloxy group attached to the parent molecular group through a carbonyl group. Exemplary unsubstituted heteroaryloxycarbonyl groups are of from 1 to 9 carbons.

The term "heteroarylsulfonyl," as used herein, represents a heteroaryl group attached to the parent molecular group through an —SO$_2$— group. Exemplary unsubstituted heteroarylsulfonyl groups are of from 1 to 9 carbons.

The term "heteroarylthio," as used herein, represents a heteroaryl group attached to the parent molecular group through a sulfur atom. Exemplary unsubstituted heteroaryloxy groups are of from 1 to 9 carbons.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring such as indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroinidolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

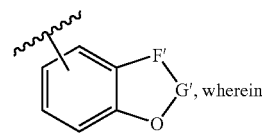

F' is selected from the group consisting of —CH$_2$—, —CH$_2$O— and —O—, and G' is selected from the group consisting of —C(O)— and —(C(R')(R''))$_v$—, wherein R' and R'' are independently selected from the group consisting of hydrogen or alkyl of one to four carbon atoms, and v is one to three and includes groups such as 1,3-benzodioxolyl, 1,4-benzodioxanyl and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, wherein the alkyl and alkylene groups are independently of one to six carbon atoms; (5) alkylsulfinyl of one to six carbon atoms; (6) alkylsulfinylalkyl, wherein the alkyl and alkylene groups are independently of one to six carbon atoms; (7) alkylsulfonyl of one to six carbon atoms; (8) alkylsulfonylalkyl, wherein the alkyl and alkylene groups are independently of one to six carbon atoms; (9) aryl; (10) arylalkyl, wherein the alkyl group is of one to six carbon atoms; (11) amino; (12) aminoalkyl of one to six carbon atoms; (13) aryl; (14) arylalkyl, wherein the alkylene group is of one to six carbon atoms; (15) aryloyl; (16) azido; (17) azidoalkyl of one to six carbon atoms; (18) carboxaldehyde; (19) (carboxaldehyde)alkyl, wherein the alkylene group is of one to six carbon atoms; (20) cycloalkyl of three to eight carbon atoms; (21) cycloalkylalkyl, wherein the cycloalkyl group is of three to eight carbon atoms and the alkylene group is of one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, wherein the alkylene group is of one to six carbon atoms; (33) oxo; (34) thioalkoxy of one to six carbon atoms; (35) thioalkoxyalkyl, wherein the alkyl and alkylene groups are independently of one to six carbon atoms; (36) —$(CH_2)_q$CO$_2$R$^A$, wherein q is zero to four and R$^A$ is selected from the group consisting of (a) alkyl, (b) aryl and (c) arylalkyl, wherein the alkylene group is of one to six carbon atoms; (37) —$(CH_2)_q$CONR$^B$R$^C$, wherein R$^B$ and R$^C$ are independently selected from the group consisting of (a) hydrogen, (b) alkyl, (c) aryl and (d) arylalkyl, wherein the alkylene group is of one to six carbon atoms; (38) —$(CH_2)_q$SO$_2$R$^D$, wherein R$^D$ is selected from the group consisting of (a) alkyl, (b) aryl and (c) arylalkyl, wherein the alkylene group is of one to six carbon atoms; (39) —$(CH_2)_q$SO$_2$NR$^E$R$^F$, wherein R$^E$ and R$^F$ are independently selected from the group consisting of (a) hydrogen, (b) alkyl, (c) aryl and (d) arylalkyl, wherein the alkylene group is of one to six carbon atoms; (40) —$(CH_2)_q$NR$^G$R$^H$ wherein R$^G$ and R$^H$ are independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, wherein the alkylene group is of one to six carbon atoms; (h) cycloalkyl of three to eight carbon atoms and (i) cycloalkylalkyl, wherein the cycloalkyl group is of three to eight carbon atoms, and the alkylene group is of one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "heterocyclylalkyl" represents a heterocyclyl group attached to the parent molecular group through an alkyl group. Exemplary unsubstituted heterocyclylalkyl groups are of from 2 to 15 carbons.

The terms "heterocyclylamino" or "(heterocycle)amino," as used interchangeably herein, represents a heterocycle group, as defined herein, attached to the parent molecular group through nitrogen. Exemplary unsubstituted heterocylylamino groups are of from 1 to 9 carbons.

The terms "heterocyclyloxy" or "(heterocycle)oxy," as used interchangeably herein, represents a heterocycle group, as defined herein, attached to the parent molecular group through an oxygen atom. Exemplary unsubstituted heterocyclyloxy groups are of from 1 to 9 carbons.

The terms "heterocyclyloxycarbonyl" or "(heterocycle)oxycarbonyl," as used interchangeably herein, represents a heterocycloxy group, as defined herein, attached to the parent molecular group through a carbonyl group. Exemplary unsubstituted heterocyclyloxycarbonyl groups are of from 2 to 10 carbons.

The term "heterocyclyloyl" or "(heterocycle)oyl," as used interchangeably herein, represents a heterocycle group, as defined herein, attached to the parent molecular group through a carbonyl group. Exemplary unsubstituted heterocylyloyl groups are of from 2 to 10 carbons.

The term "heterocyclylsulfonyl," as used herein, represents a heterocyclyl group attached to the parent molecular group through an —SO$_2$— group. Exemplary unsubstituted heterocyclylsulfonyl groups are of from 1 to 9 carbons.

The term "heterocyclylthio," as used herein, represents a heterocyclyl group attached to the parent molecular group through a sulfur atom. Exemplary unsubstituted heteroaryloxy groups are of from 1 to 9 carbons.

The term "hydroxy" as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl and the like.

The term "methine" as used herein, represents a =C(H)— group.

The term "N-protected amino," as used herein, refers to an amino group, as defined herein, to which is attached an N-protecting or nitrogen-protecting group, as defined herein.

The term "N-protected aminoalkyl," as used herein, refers to an alkyl group, as defined herein, which is substituted by an N-protecting or nitrogen-protecting group, as defined herein.

The terms "N-protecting group" or "nitrogen protecting group" as used herein, represent those groups intended to protect an amino group against undesirable reactions during synthetic procedures. Commonly used N-protecting groups are disclosed in Greene, "Protective Groups In Organic Synthesis, 3$^{rd}$ Edition" (John Wiley & Sons, New York, 1999), which is incorporated herein by reference. N-protecting groups comprise acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "nitro," as used herein, represents an —NO$_2$ group.

The term "nitroalkyl," as used herein, represents an alkyl group substituted by an —NO$_2$ group.

The term "oxo," as used herein, represents =O.

The term "perfluoroalkyl," as used herein, represents an alkyl group, as defined herein, wherein each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, refers to a perfluoroalkyl group, as defined herein, attached to the parent molecular group through an oxygen atom.

The term "pharmaceutically acceptable salt," as use herein, represents those salts which are, within the scope of sound medical judgement, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in *J. Pharmaceutical Sciences* 66: 1–19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like. The term "pharmaceutically acceptable ester," as used herein, represents esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl group preferably has not more than 6 carbon atoms. Examples of particular esters includes formates, acetates, propionates, butyates, acrylates and ethylsuccinates.

The term "pharmaceutically acceptable prodrugs" as used herein, represents those prodrugs of the compounds of the present invention which are, within the scope of sound medical judgement, suitable for use in contact with with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351–4367, 1996), each of which is incorporated herein by reference.

By "ring system substituent" is meant a substituent attached to an aromatic or non-aromatic ring system. When a ring system is saturated or partially saturated the "ring system substituent" further includes methylene (double bonded carbon), oxo (double bonded oxygen) or thioxo (double bonded sulfur).

The term "spiroalkyl," as used herein, represents an alkylene diradical, both ends of which are bonded to the same carbon atom of the parent group to form a spirocyclic group.

The term "sulfonyl," as used herein, represents an —SO$_2$— group.

The term "thioalkoxy," as used herein, represents represents an alkyl group attached to the parent molecular group through a sulfur atom. Exemplary unsubstituted thioalkoxy groups are of from 1 to 6 carbons.

The term "thioalkoxyalkyl," as used herein, represents an alkyl group substituted by a thioalkoxy group. Exemplary unsubstituted thioalkoxyalkyl groups are of from 2 to 12 carbons.

By "thiocarbonyl" is meant a —C(S)— group.

By "thiol" is meant an —SH group.

Asymmetric or chiral centers may exist in the compounds of the present invention. The present invention contemplates the various stereoisomers and mixtures thereof. Individual stereoisomers of compounds or the present invention are prepared synthetically from commercially available starting materials which contain asymmetric or chiral centers or by preparation of mixtures of enantiometic compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R" or "S," depending on the configuration of substituents around the chiral carbon atom.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified. For example, amidine structures of the formula —C(=NR$^Q$)NHR$^T$ and —C(NHR$^Q$)=NR$^T$, where R$^T$ and R$^Q$ are different, are equivalent tautomeric structures and the description of one inherently includes the other.

BRIEF DESCRIPTION OF THE DRAWINGS

FIG. 2 is a table that lists the conversion between the amino acid numbering of FXIcat in the native zymogen found in the bloodstream and trypsin. Residue numbers greater than 999 under "trypsin" denote amino acid insersions in FXIcat relative to trypsin, while missing numbers under "trypsin" denote amino acid deletions in FXIcat relative to trypsin.

FIG. 3 is a table describing the Protein Data Bank (PDB) format used to list the atomic coordinates of the various structures of this invention shown in the files listed in FIG. 16).

FIG. 4A is a table that lists the residues of human Factor XIa that are altered to other amino acids or removed by mutagenesis/engineering strategies. Relative enzymatic activity and crystallization results for the different recombinant FXIcat proteins are listed. The numbering system is that of Factor XI native zymogen found in the bloodstream. The AVC-terminal truncation mutation is the removal of the C-terminal Ala606 and Val607 residues, such that the last residue of the mutant is Gln605. By "N.D." is meant that the enzymatic activity of the mutant has not been determined or that crystalization of the mutant has not been undertaken or has not produced crystals of sufficient quality to determine the three-dimensional structure.

FIG. 4B is a table that lists relevant crystallographic data derived from crystals of the invention. Crystallization conditions are also listed.

FIG. 5C is a stereoview of the active site of human FXIcat, as derived from its crystal structure with ecotin. For clarity, no hydrogen atoms or water molecules are shown.

FIG. 5D is a stereoview of the active site of human FXIcat, as derived from its crystal structure with benzamidine. For clarity, no hydrogen atoms or water molecules are shown.

FIG. 6 shows the position of the oligonucleotides chosen for the PCR approach to isolate rat FXIcat and the rat FXIcat nucleotide sequence that was derived.

FIG. 7 is an alignment of amino acid sequences of FXIcat proteins from human, mouse, rabbit and rat.

FIG. 9 lists the signal peptide cleavage site of pPICZα FXIcat.

FIG. 10 shows the effect of continuous intravenous administration of compound 22 in a rat model of venous thrombosis. In anesthetized male Sprague-Dawley rats venous thrombosis was induced by incorporating stenosis of the inferior vena cava with rapid infusion of hypotonic saline followed by partial stenosis. Compound 22 was administered as a continuous intravenous infusion via the femoral vein commenced 15 minutes prior to the thrombotic challenge. Thrombus mass was assessed at 60 minutes following challenge. Results are expressed as the percentage of the vehicle mean.

FIG. 12 is a table containing data on the superposition of the three-dimensional structure of FXIcat complexed with compound 144 and that of complexes with other ligands. The first row, labeled "rms/loop," is the root mean squared (rms) deviation of just the 48 backbone atoms constituting the loop when backbone atoms (number of atoms are listed on second row) of the two structures are superimposed. The second row, labeled "rms/fit," is the rms deviation and number of backbone atoms used for superposition. The third row, labeled "rms/loop," is the rms deviation of just the 48 backbone atoms constituting the loop using a best fit of all backbone atoms that do not deviate by more than 3.8 Å between the two structures. The fourth row, labeled "rms/fit," is the rms deviation of all backbone atom pairs that do not deviate by more than 3.8 Å.

FIG. 13 is a table of the rms deviation (values to the right of the diagonal) of the superposition of FXIcat structures solved in the presence of the indicated compounds. Values to the left are the number of backbone atom pairs used in the superposition. Rms values are calculated only for pairs of atoms that do not deviate from each others by more than 3.8 Å.

FIG. 14 is the same as FIG. 13 except that all backbone atom pairs are used in the superposition.

FIG. 15 is a table of the rms deviation between Ser195, His 57, and Asp102 in FXIcat structures solved in the presence of the indicated compounds using a best fit of backbone atoms (values to the right) and all backbone atoms (values to the left).

FIG. 16 is a list of an electronic file contained on 2 identical compact discs (Copy 1 and Copy 2) as "Table of FIG. 16 listings", which is hereby incorporated by reference. "Listing 4" contains the file atomic coordinates of the complex between two molecules of human FXIcat and two molecules of ecotin M84R. "Listing 5" contains the coordinates of the complex between two molecules of human FXIcat and two molecules of wild type ecotin. "Listing 6" contains the coordinates of the complex between two molecules of human FXIcat and two molecules of ecotin IX-D. "Listing 7" contains the atomic coordinates of the complex between human FXIcat and benzamidine. "Listing 8" contains the atomic coordinates of the complex between human FXIcat and compound 77. "Listing 9" contains the atomic coordinates of the complex between human FXIcat and compound 85. "Listing 10" contains the atomic coordinates of the complex between human FXIcat and compound 25. "Listing 11" contains the atomic coordinates of the complex between human FXIcat and compound 79. "Listing 12" contains the atomic coordinates of the complex between human FXIcat and compound 86. "Listing 13" contains the atomic coordinates of the complex between human FXIcat and compound 144. "Listing 14" contains the atomic coordinates of the complex between human FXIcat and compound 141. "Listing 15" contains the atomic coordinates of the complex between human FXIcat and compound 145. The numbering system is based upon structural homology to trypsin (see FIG. 2 for conversion between Factor XI numbering system and trypsin). The format is as described in FIG. 3.

DETAILED DESCRIPTION

Figure 1:
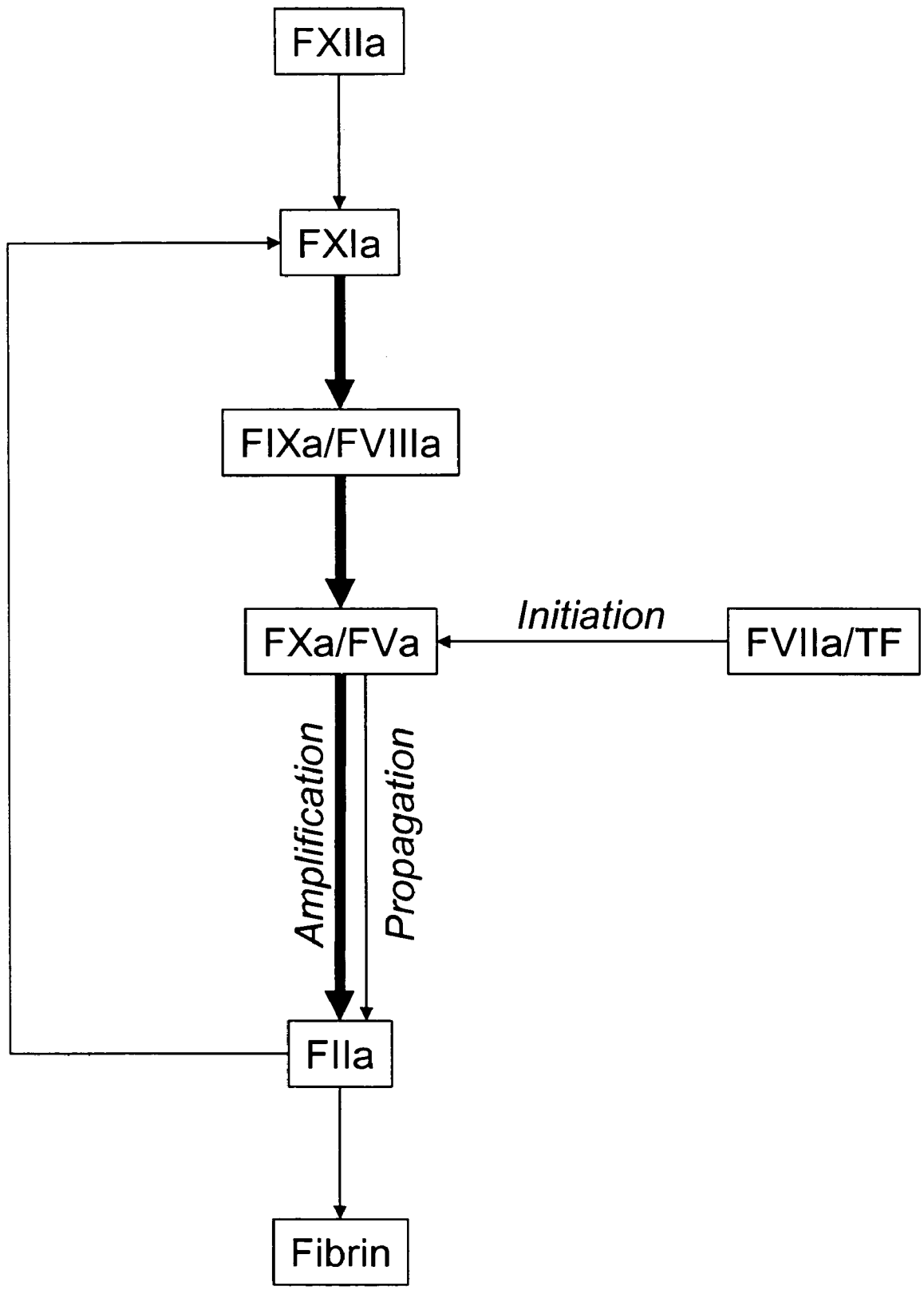
FIG. 1 is a simplified diagrammatic representation of the coagulation cascade showing the role of Factor XI in this pathway. All three thick arrows represent the amplification phase. The initiation and propagation phases are also labled. FIIa is also known as thrombin. The arrow from FIIa to FXIa indicates that FXI is activated by FIIa and FXIIa.
Figure 5A:
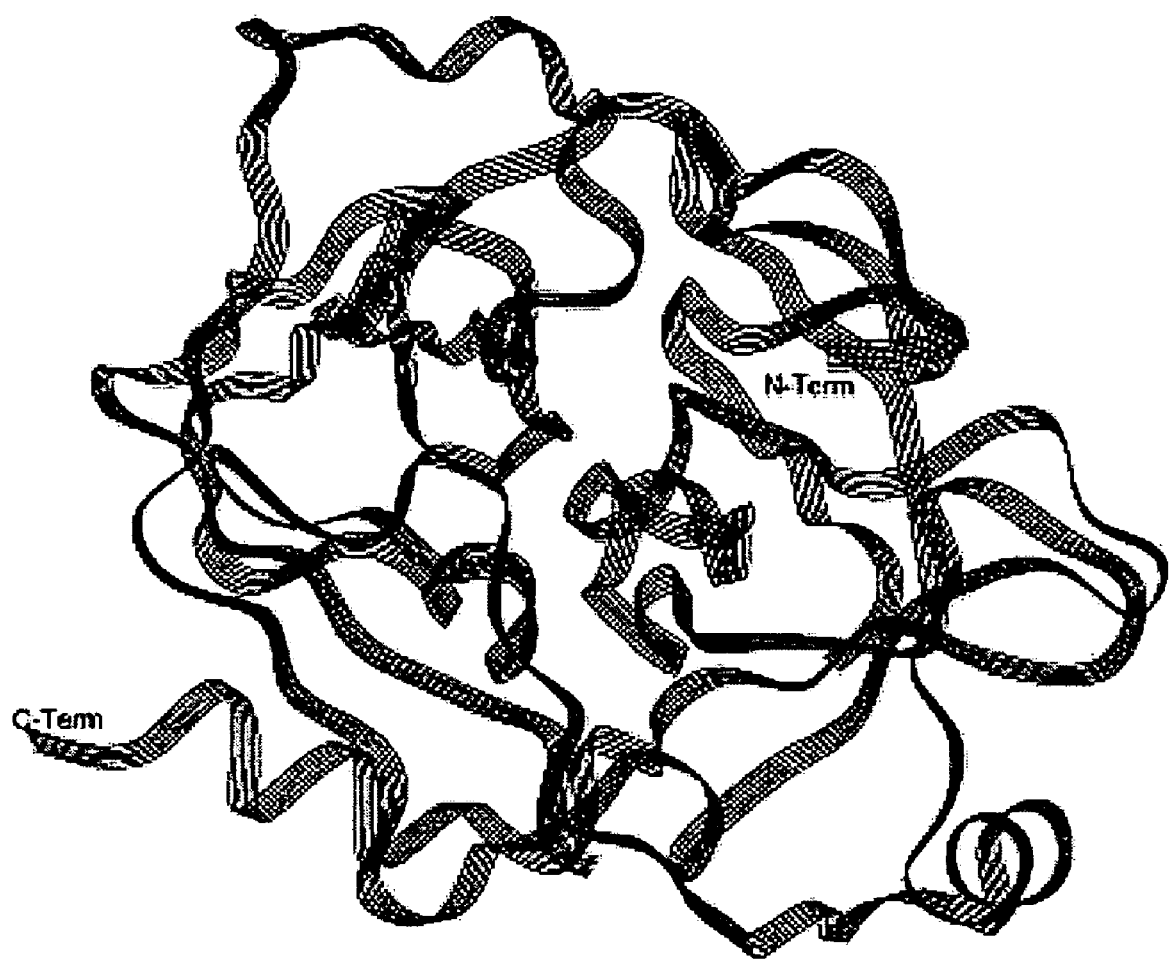
FIG. 5A is a ribbon diagram of human FXIcat, as derived from its crystal structure with ecotin. The amino- and carboxy-termini are indicated by N and C. The drawing was produced using the program Insight II.
Figure 5B:
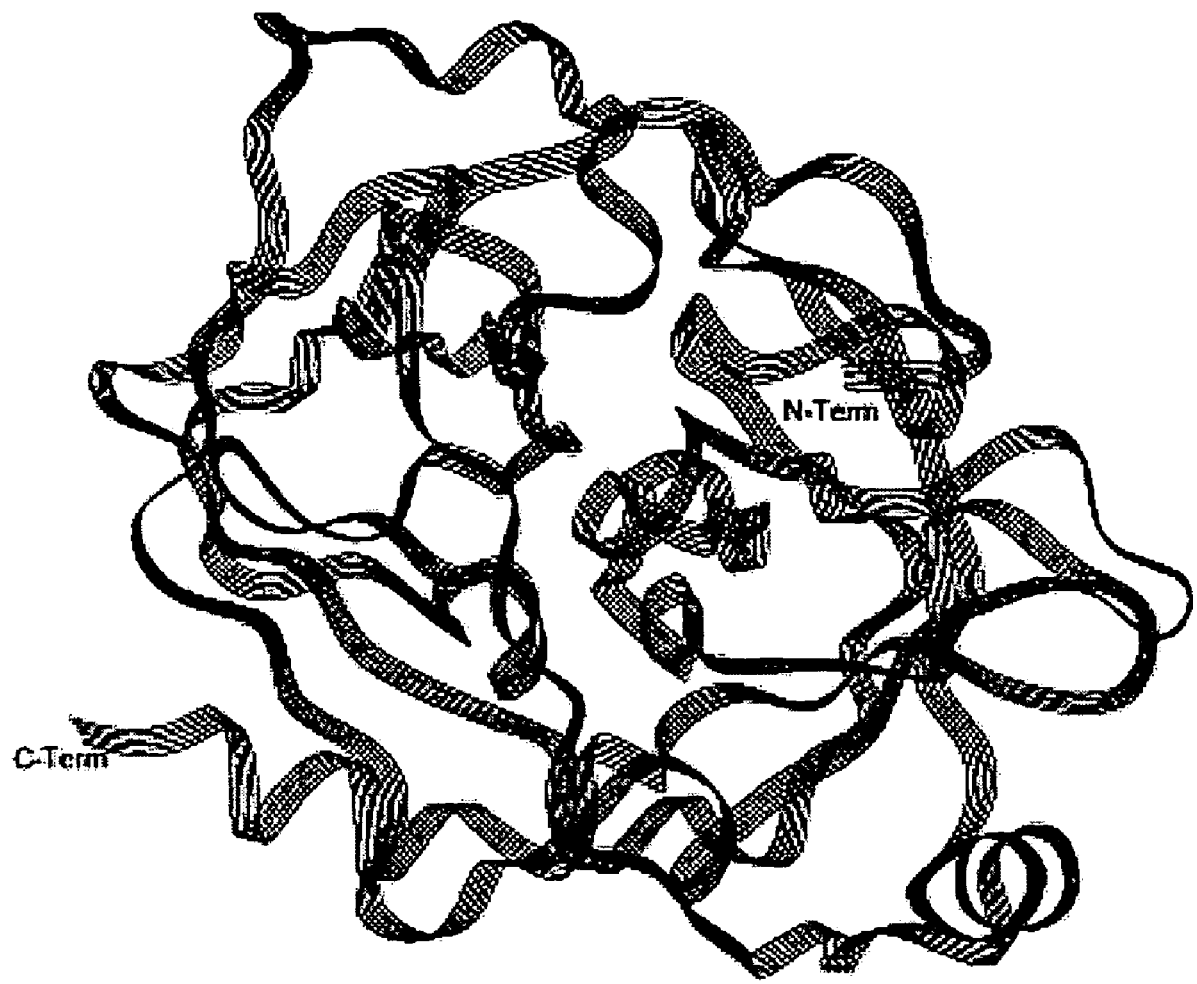
FIG. 5B is a ribbon diagram of human FXIcat, as derived from its crystal structure with benzamidine. The amino- and carboxy-termini are indicated by N and C. The drawing was produced using the program Insight II.

Human coagulation Factor XIa is a serine protease that results from activation of Factor XI by thrombin, Factor XIIa, or autoactivation. Factor XI is an upstream serine protease in the amplification phase of the intrinsic anticoagulant cascade that circulates in blood plasma as a homodimeric zymogen (FIG. 1). Although the protease domain exhibits homology with other coagulation serine proteases, the remaining domains are not shared. Factor XI is not gamma carboxylated (i.e., not vitamin K-dependent) and does not have EGF domains, but possesses an N-terminal series of 'apple' domains and a C-terminal catalytic domain.

Inhibiting enzymes of the amplification phase of the clotting cascade represents an attractive strategy for novel antithrombotic agents. On the one hand this approach may allow for sufficient anticoagulant activity to prevent unwanted thrombotic episodes, but also allow enough clotting to occur so as to prevent or minimize bleeding. Although complete deficiency of factors involved in the amplification phase of the coagulation cascade can result in bleeding (e.g., hemophilia A and B are caused by deficiencies in Factors VIII and IX, respectively), low levels of activity, generally in the range of 5% of normal, are sufficient to minimize any bleeding diathesis and confer a low probability of suffering acute thrombotic disorders such as AMI or stroke. Furthermore, Factor XI deficiency results in a mild-to-moderate bleeding disorder, especially in tissues with high levels of local fibrinolytic activity, such as the urinary tract, nose, oral cavity, and tonsils. The important role of Factor XI in coagulation is also indicated by the recent observation that high levels of Factor XI are associated with increased venous thrombosis (Meijers et al., *N. Engl. J. Med.* 342:696, 2000).

To facilitate the identification and/or design of high affinity inhibitors for Factor XIa, several three-dimensional structures of the human Factor XI catalytic domain (FXIcat) bound to a ligand have been determined (FIGS. 3, 4A, 4B, 5A, 5B, 5C, 5D, and 12–16). These structures can be used to homology model the structure of other candidate inhibitors with FXIcat. In addition, the methods described herein for the crystallization and structural determination of complexes of FXIcat with a ligand can be used to experimentally determine the structure of other ligands bound to FXIcat. This structural information can be used to identify functional groups within a ligand that can be modified to increase the affinity and selectivity of the ligand for Factor XIa or to identify functional groups within the ligand that can be modified to increase the bioavailability of the ligand without adversely affecting its affinity for Factor XIa.

Compounds that may be tested for their ability to decrease Factor XIa activity include, but are not limited to, synthetic organic molecules, naturally occurring organic molecules and their semi-synthetic derivatives, nucleic acid molecules, biosynthetic proteins or peptides, naturally occurring peptides or proteins, or antibodies. In various embodiments of any of the aspects of the invention, the organic compound has a molecular weight contained in one of the following ranges: 100–3,000 daltons; 100–2,000 daltons; 100–1,000 daltons; 100–750 daltons; 250–3,000 daltons; 250–2,000 daltons; 250–1,000 daltons; 250–750 daltons; 400–3,000 daltons; 400–2,000 daltons; 400–1,000 daltons; or 400–750 daltons, inclusive.

Accordingly, in addition to providing compounds designed based on the structure of FXIcat, the present invention includes a class of peptidomimetics and non-peptides that inhibit the activity of Factor XIa (e.g., the compounds of formula I or formula II, as described herein). Any of the compounds of the invention are useful for treating or preventing diseases for which inhibition of Factor XIa is desirable, such as, but not limited to, arterial (e.g., unstable angina, acute myocardial infarction, percutaneous coronary interventions, or peripheral arterial occlusions), venous (e.g., deep venous thrombosis) and cardiac (e.g., atrial fibrillation) conditions and resulting ischemic conditions (e.g., acute myocardial infarction, pulmonary embolism, or stroke), and heparin induced complications (e.g., heparin induced thromobocytopenia).

The following non-limiting examples are provided to further describe various aspects and embodiments of the present invention.

Factor XIa Proteins and Nucleic Acids

In one aspect, the invention provides a purified, less than full-length protein fragment of Factor XI, such as a protein consisting essentially of the catalytic domain of Factor XI. The catalytic domain is identified as the residues carboxyl to the activating protease cleavage site designated as KPR↓IVG (where the arrow denotes the proteolytic cleavage). The residues that make up this domain are 370–607 for the human, 372–606 for the mouse and 369–606 for the rabbit. The sequence for entire Factor XI rat gene is not yet known, but the catalytic domain comprises residues 1–234. In some embodiments, the human protein fragment consists of residues 370–607 of SEQ ID NO: 1 (GenBank Accession No. $P_{03951}$). For the rabbit, the protein fragment consists of residues 369–606 of SEQ ID NO: 2 (GenBank Accession No. AF395821). For the mouse, the protein fragment consists of residues 372–606 of SEQ ID NO: 3 (GenBank Accession No. AF356627). For the rat, the protein fragment consists of residues 1–234 of SEQ ID NO: 4.

In another aspect, the invention features a purified Factor XI protein or fragment thereof including (a) a mutation of a residue that is otherwise post-translationally modified either naturally or in an organism used for recombinant expression, (b) a mutation that alters the charge of Factor XI, (c) a mutation that eliminates a free, reactive sulfhydryl group of a cysteine, (d) a combination of mutations that together alter the distribution of charge density without altering the overall charge of Factor XI, (e) a mutation of the $NH_2$— or COOH-terminal residue of Factor XI, and/or (f) a mutation that alters the folding and/or crystal packing of Factor XI. In certain embodiments, the protein is enzymatically de-glycosylated. In other embodiments, one or more residues that would otherwise lead to glycosylation are mutated to another residue that results in no glycosylation. In some embodiments, the protein has at least 2, 3, 4, 5, 6, 7, 8, or 9 residues that are mutated compared to a naturally occurring Factor XI protein or the catalytic domain of a naturally-occurring Factor XI protein. In desirable embodiments, the mutation(s) allow crystallization or increase the resolution of the corresponding three-dimensional structure of the mutant protein compared to the structure of Factor XI without the mutation(s). For example, the mutations may increase the size or order of the resulting crystals, resulting in a higher resolution structure. Desirable mutant Factor XI proteins or fragments are at least 80, 85, 90, 92, 94, 96, 98, or 99% identical to any one of SEQ ID NOs: 1–4.

In another aspect, the invention provides a purified protein including a region that is at least 92, 94, 96, 98, or 100% identical to the amino acid sequence of SEQ ID NO: 1 (human Factor XI) or SEQ ID NO: 3 (rat Factor XI). In some embodiments, the protein has an amino acid sequence at least 92, 94, 96, 98, or 100% identical to the amino acid sequence of SEQ ID NO: 1, over the entire length of SEQ ID NO: 1 or 3.

In another aspect, the invention features a purified nucleic acid encoding one or more of the proteins or protein fragments of the invention. Desirably, the nucleic acid is contained within a vector and operably linked to a promoter that regulates transcription of the nucleic acid. GTGTTCG-GAGGA.

EXAMPLE 1

Expression of Human Coagulation FXIcat

FXIcat was expressed in a heterologous organism and purified for three-dimensional structural determination. The ability of individual residues or combinations of residues to influence the folding and packing of FXIcat into protein crystals was also evaluated.

Figure 8:
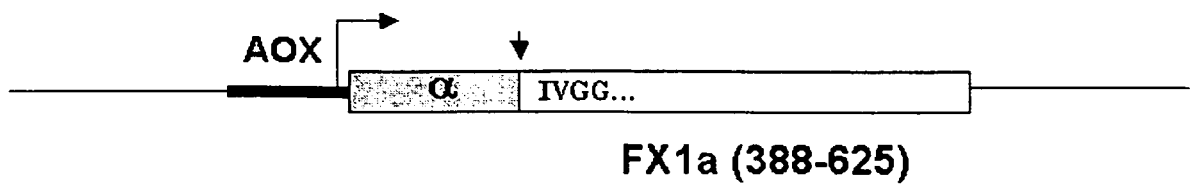
FIG. 8 is a schematic diagram of an expression plasmid for FXIcat in *Pichia pastoris*. A fusion between the α-factor secretion signal sequence and FXIcat was constructed in order to create a fusion protein with an N-terminal α-factor, signal peptide, and FXIcat. This gene is expressed from the methanol-regulated AOX promoter.
Figure 11:
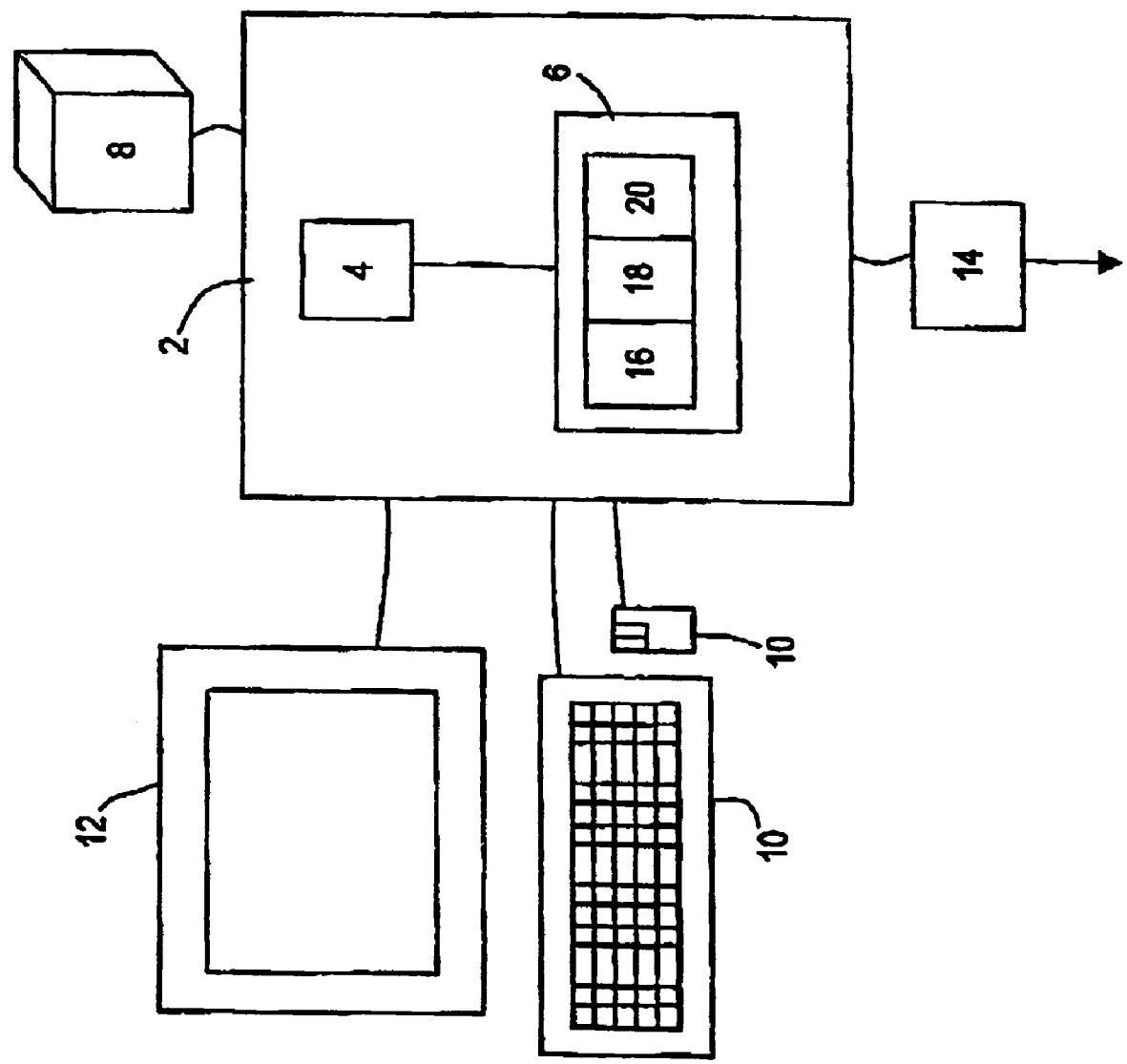
FIG. 11 is a schematic illustration of an exemplary computer.

The light chain segment of Factor XIa was expressed as a recombinant protein in the absence of Factor XIa heavy chain. A human FXI cDNA fragment encompassing amino acids 370–607 of SEQ ID NO. 1 was derived by PCR amplification from a cDNA encoding the full length protein, and subcloned into pPICZαA (Invitrogen, Cat. No. V195-20). The resulting plasmid was designated pPICZα FXIcat (FIG. 8). During PCR cloning, the coding sequence of FXIcat was arranged so that a fusion protein with the S. cerevisiae α-factor was generated. After translation of this fusion protein, a single KEX-2 signal peptide cleavage site was present, allowing post-translational proteolytic cleavage at this site during the process of secretion. The cleavage site was placed so that cleavage generates the same light chain segment as is found for human Factor XIa protein. The pPICZα FXIcat plasmid was transformed into the methanolotrophic yeast Pichia pastoris Mut+ strain, X33 (Invitrogen, Cat. No. C180-00) by standard methods, and transformants selected on Zeocin-containing selection plates. Methanol induction of recombinant protein expression was screened by expanding 10–20 colonies each in 30 mL cultures of buffered methanol complex (BMMY) medium by standard growth conditions (Invitrogen). Methanol was added to 0.5% at 12 hour intervals for 72 hours.

Cell supernatants were analyzed for FXIcat expression by several methods. First, enzymatic activity was measured at defined culture intervals in a Factor XIa peptidolysis assay as described below. Second, Western blot analysis with anti-human Factor XIa-specific antisera identified transfonmants with the highest expression of FXIcat. N-terminal sequence analysis of the purified protein yielded the sequence IVGGTA(S)VxGExP, consistent with cleavage at the expected signal peptide processing site resulting in a protein with the authentic amino terminus of Factor XIa light chain.

Large-scale preparation of FXIcat was conducted in a 10 L fermentor using 1% glycerol to achieve high cell density, followed by continuous infusion of methanol (0.5–0.7%) for 100 hours. Conditioned medium was collected at intervals throughout the methanol induction phase. Alternatively, cells harboring the FXIcat vector were grown in flasks in a shaking incubator, and FXIcat expression was induced by the addition of methanol to a final concentration of 0.5% every 12 hours. Conditioned medium was collected by centrifugation after 72 hours of induction.

EXAMPLE 2

Expression and Purification of Ecotin

For expression and purification of ecotin for structural studies with FXIcat, the bacterial ecotin gene and mutants thereof were expressed as recombinant proteins in the plasmid, pTacTac (see Yang, et al., J. Mol. Biol. 279:945–957, 1998). Two liters of E. coli, transformed with the appropriate plasmid, were grown at 37° C. to $OD_{600}$=0.7 and then induced with 0.25 mM IPTG for 12 hours. Cells were harvested by centrifugation, and cell pellets were suspended in 100 mL of 25% sucrose, 10 mM Tris, pH 8, 6.8 mM EDTA, and 20 μg/mL lysozyme. The periplasmic fraction was isolated by centrifugation. Ecotin was purified by heating the lysate to 100° C. for ten minutes and centrifuging to remove precipitated denatured protein. The supernatant was fractionated by reversed-phase HPLC. The protein peak corresponding to ecotin was analyzed by SDS-PAGE, and fractions containing pure ecotin were concentrated by centrifugal filtration with a Centriprep-10.

Ecotin was further purified using a POROS® HQ column (Applied Biosystems) on a BIOCAD® 700E in buffer containing 5 mM $MgCl_2$ in 10 mM Tris-HCl, pH 7.8. Ecotin did not bind to the matrix under these conditions, while impurities were retained on the column.

EXAMPLE 3

Purification of Human Coagulation FXIcat

Recombinant FXIcat for use in crystallography was purified from Pichia pastoris conditioned medium by one of two methods. In one method, the recombinant enzyme was collected from conditioned medium by animonium sulfate precipitation. The medium was first brought to 50% of saturation by the addition of crystalline $(NH_4)_2SO_4$. The resulting slurry was mixed at room temperature for 30 minutes, and the precipitated proteins removed by centrifugation at 20,000×g from 20 minutes. The supernatant solution was isolated and brought to 80% of saturation by the addition of $(NH_4)_2SO_4$. The slurry was again mixed at room temperature for 30 minutes, and the precipitated protein was collected by centrifugation as described above. The supernatant solution was discarded, and the precipitate was redissolved in a minimal amount of 20 mM Tris-HCl, pH 7.4. The redissolved protein was dialyzed against two changes (at least 50 volumes each) of the same buffer at 4° C. The dialyzed protein was applied to a 2.6×8 cm Chelating SEPHAROSE™ Fast Flow column (Amersham Bioscience, P/N 17-0575-01) charged with $Zn^{+2}$. The column was run at room temperature at a flow rate of ~8 mL/minutes. Following loading, the column was washed with additional 20 mM Tris-HCl, pH 7.4 until the $A_{280}$ of the effluent returned to baseline. The column was eluted with a 250 mL gradient from 0 to 50 mM imidazole in 20 mM Tris-HCl, pH 7.4. The pH of the fraction containing eluted, recombinant FXIcat was adjusted to pH~6 by the addition of 1/200 volume of 20% $CH_3COOH$. The protein was then enzymatically deglycosylated by the addition of Endoglycosidase H (New England Biolabs, Cat. No. P0703S) to a final concentration of 500–1000 mU/mL. Digestion was carried out at room temperature for 1.5–2 hours. The pH of the solution was brought up to pH~7.4 by the addition of 1/200 volume of 2 M Tris, and the fraction was applied to a 1.6×8 cm SP-SEPHAROSE™ Fast Flow column (Amersham Bioscience, P/N 17-0729-01) equilibrated in 20 mM Tris-HCl, pH 7.4 at a flow rate of 8 mL/minutes. After the column was loaded, it was washed with additional 20 mM Tris-HCl, pH 7.4 buffer. The column was then washed with 0.1 M NaCl in the same buffer to remove minor contaminants. Recombinant FXIcat was eluted from the column with a step to 0.2 M NaCl in 20 mM Tris-HCl, pH 7.4.

Alternatively, various mutant forms of FXIcat were purified from concentrated, diafiltered *P. pastoris* conditioned medium. Cells and cell debris were removed by centrifugation followed by filtration through 0.8 µm mixed ester cellulose nitrate filters. The filtered medium (7–15 L) was concentrated to ~1 L using a CENTRAMATE™ PE apparatus equipped with a 10K NMWCO membrane cassette (Pall-Gelman, P/N OS010C10). The concentrate was diluted with 4 L of 20 mM Tris-HCl, pH 7.4 and reconcentrated to ~1 L. The dilution and concentration were repeated once more to yield the final concentrated, diafiltered medium. Recombinant FXIcat was purified by a combination of cation exchange and heparin-affinity chromatography. The concentrated, diafiltered medium was applied directly to a 1.6×8 cm SP-SEPHAROSE™ Fast Flow colunm equilibrated in 20 mM Tris-HCl, pH 7.4 at a flow rate of 8–10 mL/minutes. After the column was loaded, it was washed with additional 20 mM Tris-HCl, pH 7.4 buffer. The column was then washed with 0.1 M NaCl in the same buffer to remove minor contaminants. Recombinant FXIcat was eluted from the column with a step to 0.2 M NaCl in 20 mM Tris-HCl, pH 7.4. Recombinant FXIcat eluted from the SP-column was diluted 1:1 with 20 mM Tris-HCl, pH 7.4 and applied to a 5 mL HITRAP™ Heparin column (Amersham Bioscience, P/N 17-0407-01) equilibrated in 0.1 M NaCl; 20 mM Tris-HCl, pH 7.4 at a flow rate of 3–4 mLl/minutes. The protein was eluted from this column with a 50 mL gradient from 0.1 to 1 M NaCl in the same buffer. The purity and concentration of the enzyme was determined by RP-HPLC and SDS-PAGE. Typically, the concentration was ~1 mg/mL, and the purity was at least 95%. In some instances, a third purifcation step was included. The heparin column eluate was applied to a 2.6×90 cm SUPERDEX™ 75 column equilibrated in 20 mM Tris-HCl, pH 7.4; 0.2 M NaCl at a flow rate of 4–5 mL/minutes. The enzyme eluted between 70 and 90 minutes, consistent with an apparent molecular weight of 30,000.

EXAMPLE 4

Expression of FXIcat of Other Mammalian Species in Non-Glycosylated Forms

In another strategy for producing alternative forms of FXIcat monomers, a comparison was made between the Factor XIa light chain domains of other organisms, either from databases publicly available or by discovery. Utilizing the cDNA sequence of human Factor XI in the regions A, B, C, and D shown in FIG. 7, oligonucleotides composing these sequences were prepared. Using standard PCR approaches, genes encoding the putative Factor XI catalytic domains from rat, mouse, and rabbit were derived from liver cDNA libraries, and subsequently cloned into the yeast *Pichia pastoris* expression vector, pPICZα, according to the procedure described above (FIG. 9). The regions of homology corresponding to human FXIcat were cloned and identified (FIG. 7). For example, for the Rat FXIcat, a 5' oligonucleotide consisting of the sequence GTGTTCGGAGGAGCT-GCGTCTGTTCACGGCGAG (SEQ ID NO. 5) and a 3' oligonucleotide consisting of the sequence GTGGACTG-GATTTTGGAGAAAACTCAGTCGGAATGA (SEQ ID NO. 6) were chosen (FIG. 6). Alternatively, by choosing a position of the oligonucleotides that was spaced further towards the N-terminus of the gene for the 5' oligonucleotide ATGGATAATGTGTGCACAACTAAAATC (SEQ ID NO. 7), and spaced into the 3' LTR for the 3' oligonucleotide TCCAGGGCCACAAAGTGATACCAGTTGAAC (SEQ ID NO. 8), a larger portion of the rat Factor XI cDNA was derived. Using DNA sequencing approaches to determine the ends of this cloned DNA, the rat cDNA sequence was determined to be located in the vicinity of the residues corresponding to the boundaries of the light chain protein, conserved between human, rat, mouse, and rabbit proteins. Expression studies were continued as described above. DNA sequence analysis revealed that there was a significant percentage of identity between species for rat and human (79%), mouse and human (79%), and rabbit and human (91%) FXIcat. Importantly, this information also demonstrated variation between FXIcat structures that was concentrated to surface regions of the proteins, based on homology models. Therefore, examination of the crystallographic properties of these additional FXIcat proteins is a means to investigate further the role of surface variations in controlling crystal integrity.

Mutational analysis of rat, mouse, and rabbit Factor XI was utilized to alter residues potentially governing N-linked glycosylation of these proteins when they are expressed in *Pichia pastoris*. In rat FXIcat, there are two potential N-linked glycosylation sites at residues Asn60 and Asn101. PCR based mutational substitution of Ala for residues in the glycosylation consensus sequence (i.e., Ser62 and Thr103) in tandem created a non-glycosylated version of the rat FXIcat protein.

EXAMPLE 5

Mutations to FXIcat to Improve Crystallization Quality

If desired, modification of the protein structure of human FXIcat can be achieved by mutational change of the DNA plasmid prior to the introduction into the organism for gene expression. In one such method, the pPICZα FXIcat plasmid was altered at a single codon using PCR-based mutagenesis with synthesized oligonucleotides bearing the changes. In another approach, one or more additional residues were altered by the same methodology in a sequential fashion. Following mutagenesis and DNA sequencing to determine the sequence integrity of the plasmid, pPICZα FXIcat mutant plasmids were then transformed into the methanolotrophic yeast *Pichia pastoris* Mut+ strain, X33 (Invitrogen) by standard methods. The mutant proteins were purified as described above and characterized in terms of their purity, activity, and crystallographic properties.

A series of amino acid substitution mutants that alter the ability of recombinant human FXIcat to be glycosylated in the host used for expression of the recombinant protein were generated. Expression of recombinant FXIcat in *Pichia pastoris* leads to production of a protein that is glycosylated by an N-linked glycosylation pathway. By altering residues in the consensus epitope for N-linked glycosylation (Asn-Xaa-(Ser/Thr) where Xaa is any amino acid except Pro), the protein would not be glycosylated. As expressed in *Pichia*

*pastoris*, FXIcat has two potential N-linked glycosylation sites based on the N—X—S/T motif. In one example, the substitution of an Ala for Ser434 was accomplished by the above PCR methodologies. Following the transformation and expression of the S434A mutant protein in *Pichia pastoris*, the migration-of the protein was analyzed using a standard gel assay. The mobility of the S434A protein differed from that of the fully glycosylated (wild-type, WT) protein and that of the protein resulting from endoglycosidase H treatment of the expressed recombinant protein.

Additionally, multiple mutations that more profoundly reduced the ability of FXIcat to be glycosylated were generated. In this method, S434A and T475A mutations were prepared by serial mutagenesis of the *Pichia pastoris* expression plasmid, pPICZα FXIcat. Individual mutagenesis of either S434A or T475A reduced glycosylation of the mutant protein as evidenced by a lower apparent molecular weight by SDS-PAGE analysis. The ability of the double mutations to dramatically reduce the extent of glycosylation was demonstrated by SDS-PAGE and Western blot analysis. The increased mobility of the protein in SDS-PAGE was indicative of a lack of glycosylation. The single mutants had mobility intermediate to wild-type and the double mutant which migrated with an apparent molecular weight slightly lower than that of the Endoglycosidase H treated, wild-type FXIcat. In addition, wild-type FXIcat yielded four distinct peaks on RP-HPLC analysis. These peaks collapsed into two major peaks following Endoglycosidase H treatment. These peaks had significantly longer retention times than the wild-type peaks. The double glycosylation mutant showed a single major peak with a longer retention time than any of the enzymatically deglycosylated forms. This increased hydrophobicity is consistent with the loss of surface-exposed, hydrophilic carbohydrate moieties. Taken together with the observed absence of carbohydrate moieties in the solved structures for FXIcat, these observation suggest strongly that the mutations resulted in the complete elimination of glycosylation on this form of the protein.

Additionally, one or more mutants were generated to eliminate free sulfhydryls within FXIcat. Unpaired cysteine residues may impact folding and crystal formation. Alternatively, by covalent association with reactive proteins or small molecules, the free sulfhydryl group may change the nature of the FXIcat. The presence of free sulfhydryl groups on FXIcat monomers may also influence solubility, aggregation, and crystallization properties. For example, FXIcat has a single cysteine residue (Cys482) that is not involved in a disulfide bond. Cys482 forms a disulfide bond with Cys362 in intact Factor XI and thus is unpaired in the FXIcat. Thus, FXIcat-C482S was generated to replace the free sulfhydryl group with an isosteric serine residue.

In an additional strategy to enhance crystallization, a series of mutants that alter individual charged residues on the surface of FXIcat were generated by alanine substitution mutagenesis. The methodologies are technically parallel to those described above. Surface charged residues were identified by the inspection of the FXIcat/ecotin structure. In one particular example, a K437A substitution was generated in FXIcat. The neutral alanine substitution replaces the positively charged lysine residue leading to a net loss of charge in that location. Additional modifications leading to a change in charge on the surface of FXIcat can be used to further characterize the influence of Lys437 on the structure and packing of FXIcat. A D476A substitution was also created using the methodology described above. The alanine substitution replaces the negatively charged aspartic acid, leading to a local change of charge; however, the charge change is opposite to that of K437A.

In another variation of this method, a series of substitution mutations that do not alter the net surface charge of the FXIcat monomer, but change the charge distribution were generated. If a localized region of FXIa monomers is important to the packing of crystals, changes in the charge distribution is expected to impact crystal integrity. For example, the double mutation N571D, E572Q may change the charge distribution in one local region of the protein monomer. This alteration of the charge distribution may impact packing of crystals.

A related strategy involved the generation of a series of substitution mutants that affect the packing of FXIcat monomers in crystals by influencing van der Waals interactions between hydrophobic residues and the protein backbone of another monomer in the crystal. For example, the residue Tyr416 is oriented such that the active site is at least partially occluded, and such that this residue interacts with the peptide backbone of another FXIcat monomer in the crystal packing. Since this position is a serine residue in the mouse and rat FXI proteins, substitution of Y416S was expected to retain the activity of the protein. The Y416S substitution disrupts the interaction of the tyrosine residue with the peptide backbone of another monomer.

In an additional strategy, a series of substitution mutations that combine the different features of the strategies described above are examined to yield a different outcome than any of the substitution mutations by itself. For example, mutations that alter the charge distribution of the protein surface can be combined with mutations that block glycosylation of the protein and the availability of free sulfhydryl groups on the surface. Therefore, the FXIcat-S434A, T475A, C482S triple mutant was made. In another method, mutations with the same functional effects on protein folding and/or packing were examined in different combinations. For example, a serial substitution at K437A and K505A is a means to combine the effects of eliminating positively charged lysine residues at two different locations on the surface of FXIcat. The quadruple mutant S434A, T475A, K437A, C482S has proven quite robust for obtaining useful crystals of various inhibitors as exemplified in the examples that follow.

EXAMPLE 6

Formation of FXIcat-Ecotin Complexes

FXIcat-ecotin complex was formed by incubating a stoichiometric quantity of each component at 4° C. overnight and subsequently isolated by chromatography on a SUPEROSE™ 12 column (Amersham Bioscience) in 20 mM Tris-HCl, pH7.8 and 0.1 M NaCl on BIOCAD™ 700E.

EXAMPLE 7

Crystallization of FXIcat-Ecotin M84R Complex

The FXIcat-ecotin M84R complex was crystallized at room temperature by the hanging drop vapor diffusion method (McPherson, *Methods Biochem. Anal.* 23:249, 1976) from 0.2 M NaCl, 20% (w/v) PEG-1000 and 0.1 M Na/K phosphate, pH 6.2. The crystals belong to the space group $P2_12_12_1$ with unit cell parameters of a=44.6 Å, b=92.7 Å, and c=186.9 Å. There are two FXIcat and two ecotin molecules forming a tetramer in the asymmetric unit, and the diffraction data extends to 2.2 Å.

EXAMPLE 8

Structure Determination, Model Building, and Refinement

The structure of FXJcat-ecotin M84R was solved by molecular replacement using AMoRe. The search model was created from the coordinates of the tetramenc rat granzyme B [N66Q]—ecotin [81–84 IEPD] with PDB code 1FI8 (Waugh et al., *Nat. Struct. Biol.* 7:762, 2000). The conserved core structure of serine proteases was identified first by structure alignment of several serine proteases. All the side chain atoms beyond $C_\beta$, all surface loops in granzyme B, and all water molecules were deleted from the model. A clear solution was obtained using data of 20–5 Å with correlation coefficient of 52.4 and R factor of 48.9%. This solution also persisted in calculations performed using data in different resolution ranges. Structure refinement was carried out using CNX™ (Accelrys Inc., San Diego, Calif.) and model building was performed in QUANTA® (Accelrys Inc., San Diego, Calif.).

EXAMPLE 9

Design of Factor XIa Inhibitors

The three-dimensional atomic structures reported herein can be readily used as a template for selecting potent inhibitors. Various computer programs and databases can be used for this purpose. Desirable inhibitors have excellent steric and electrostatic complementarity to Factor XIa, a fair amount of buried hydrophobic surface, and sufficient conformational rigidity to minimize entropy loss upon binding (see, for example, Babine and Bender, *Chem. Rev.*, 97:1359–1472, 1997).

The approach usually comprises the following steps. First, a target site in FXIcat is defined. This region can be any place important or essential for the protease activity such as, but not limited to, the active site cavity of Factor XIa. Because the FXIcat crystal structure was first determined in the presence of ecotin, a protein inhibitor, the spatial and chemical properties of the active site cavity of Factor XIa were clearly delineated and maped. Alternatively, the target site can be a region other than the active site, such as a region that when bound by an inhibitor prevents a substrate from binding Factor XIa or prevents Factor XIa from adopting a three-dimensional structure that enables full catalytic activity. Second, a small molecule or other candidate molecule is docked onto the target site of Factor XIa. Many methods can be used for this purpose such as, but not limited to, fast shape matching (Dock [Kuntz et al., *J. Mol. Biol.*, 161:269–288, 1982]; Eudock [Perola et al., *J. Med. Chem.*, 43:401–408, 2000]); incremental construction (FlexX [Rarey et al., *J. Mol. Biol.*, 261:470–89, 1996]; Hammerhead [Welch et al., *Chem. Biol.*, 3:449–462, 1996]), Tabu search (Pro_Leads [Baxter et al., *Proteins*, 33:367–382, 1998]; SFDock [Hou et al., *Protein Eng.*, 12:639–647, 1999]), genetic algorithms (GOLD [Gold et al., *J. Mol. Biol.*, 267:727–748, 1997]; AutoDock 3.0 [Morris et al., *J. Comput. Chem.*, 19:1639–1662, 1998]; Gambler [Charifson et al., *J. Med. Chem.*, 42:5100–5109, 1999]), evolutionary programming [Gehlhaar et al., *Chem. Biol.*, 2:317–324, 1995], simulated annealing (AutoDock 2.4 [Goodsell et al., *Proteins*, 8:195–202, 1990]), Monte Carlo simulations (MCDock [Liu et al., *J. Comput.-Aided Mol. Des.*, 13:435–451, 1999]; QXP [McMartin et al., *J. Comput.-Aided Mol. Des.*, 11:333–344, 1997]), and distance geometry (Dockit [Metaphorics LLC, Piemont, Calif., USA]). The profiles of hydrogen bond donor-acceptor and lipophilic points of the candidate compounds can also be used to complement those of the target site in FXIcat. Those skilled in the art can readily identify many small molecules or fragments as hits. If desired, one can link the different functional groups or small molecules identified by the above procedure into a single, larger molecule. The resulting molecule is likely to be more potent and have higher specificity. The affinity and/or specificity of a hit can also be improved by adding more atoms or fragments that will interact with the target protein. The originally defined target site can be readily expanded to allow further necessary extension.

The differences in three-dimensional structure between FXIcat and related proteins with known structure can be used to optimize selectivity of an inhibitor for Factor XIa. In addition to the structural differences described herein, other differences between FXIcat and other proteins can also be identified by a skilled artisan.

Promising compounds can be selected through the process. They can then be synthesized and assayed for their inhibitory properties. The success rate can sometimes be as high as 20% and may be even higher due to the rapid progress in standard computing methods.

EXAMPLE 10

Inhibition of Factor XIa

The peptidolytic activity of recombinant FXIcat was measured using the chromogenic substrate pyroGlu-Pro-Arg-p-nitroanaline (DiaPharma, Cat. No. S-2366). The substrate was diluted to 1 mM in 20 mM Tris-HCl, pH 7.4, 150 mM NaCl, 0.02% Tween20 (assay buffer) and mixed with an equal volume of diluted enzyme in a microtiter plate (Wallac Isoplate, P/N 1450-514). The final volume in the wells was 100 ul. The plate was placed immediately into a ThermoMax plate reader (Molecular Devices), and the time course of hydrolysis was monitored for 10 minutes at 405 nm. The progress curves were visually inspected and the linear portion of the curves was used to determine the activity of the enzyme.

Potential inhibitors of Factor XIa were evaluated using a modification of the above assay. Briefly, the inhibitors were tested against native Factor XIa (Haematological Associates, P/N FXIA01) using a custom made analog of S-2366. This substrate had the p-nitroanaline group replaced with 7-methylaminocoumarin (AMC). The final concentration of the substrate in the assay was 100 μM, and the final concentration of the enzyme was 0.25 nM. Inhibitors were tested by serial dilution over an appropriate range to yield a dose response curve for determination of the inhibitors' $IC_{50}$ values. The assay mixture was incubated for 30 minutes at 30° C., and the fluorescent yield was measured using a PE-Wallac Victor 2 Plate Reader. Dose response curves were fit to Equation 1 in which A is the maximum inhibition, B is the minimum inhibition, C is the $IC_{50}$, and D is the Hill coefficient.

$$\left[(A - B) \bigg/ \left(1 + \left(\frac{X}{C}\right)^D\right)\right] + B \qquad \text{(Equation 1)}$$

Desirably, the compounds have an $IC_{50}$ value better than 1.0 micromolar, 0.1 micromolar, 0.01 micromolar or 0.001 micromolar (in order of increasing preference).

EXAMPLE 11

Crystallization of FXIcat-Wild Type Ecotin Complex

The FXIcat-wild type ecotin complex was crystallized at room temperature by the hanging drop vapor diffusion method (McPherson, *Methods Biochem. Anal.* 23:249–345, 1976) from 0.1 M $(NR_4)_2SO_4$, 22% (w/v) PEGMME-2000 and 0.1 M Na cacodylate, pH 6.2. The crystals belong to the space group $P2_12_12_1$ with unit cell parameters of a=44.3 Å, b=91.9 Å, and c=186.2 Å. There are two FXIcat and two ecotin molecules forming a tetramer in the asymmetric unit, and the diffraction data extends to 2.6 Å. The coordinates of FXIcat-ecotin M84R were used for the calculation of the difference electron density map by the program CNX™ (Accelrys Inc., San Diego, Calif.) for FXIcat-wild type ecotin. Subsequent model building was carried out in the program QUANTA®2000 (Accelrys Inc., San Diego, Calif.) and refinement was done by CNX™.

EXAMPLE 12

Crystallization of FXJcat-Ecotin IX-D Complex

The FXIcat-ecotin IX-D complexe was crystallized at 10° C. by the hanging drop vapor diffusion method (McPherson, *Methods Biochem. Anal.* 23:249–345, 1976) from 0.1 M $(NH_4)_2SO_4$, 22% (w/v) PEGMME-2000 and 0.1 M Na cacodylate, pH 6.2. The crystals belong to the space group $P2_12_12_1$ with unit cell parameters of a=45.4 Å, b=91.4 Å, and c=188.6 Å. There are two FXIcat and two ecotin molecules forming a tetramer in the asymmetric unit, and the diffraction data extends to 3.0 Å. The coordinates of FXIcat-ecotin M84R were used for the calculation of the difference electron density map by the program CNX™ (Accelrys Inc., San Diego, Calif.) for FXIcat-ecotin IX-D. Subsequent model building was carried out in the program QUANTA®2000 (Accelrys Inc., San Diego, Calif.) and refinement was done by CNX™.

EXAMPLE 13

Crystallization of FXIcat-S434A, T475A, K437A with Benzamidine

The FXIcat triple mutant S434A, T475A, K437A was cloned and purified as described above. Benzamidine was added to the protein to a concentration of 1 mM and the complex was concentrated to about 18–20 mg/mL. Cubic crystals were obtained in 2.0 M ammonium sulfate and 0.1 M Tris-HCl, pH 7.5–9 at 20° C. The crystals belong to the cubic space group I23 with unit cell parameters of a=b=c=120.1 Å. There is one FXIcat molecule in the asymmetric unit, and the X-ray diffraction data extends to 1.96 Å.

The initial solution of this structure was found by molecular replacement using an automated package for molecular replacement (AmoRe,: Navaza J, *Acta Cryst.* A50: 157–163, 1994). The search model was one FXIcat molecule from the tetramer structure of FXJcat-ecotin M84R complex. To avoid model bias, all the surface loops, the side chain atoms beyond $C_\beta$, and water molecules were removed from the model. A clear solution was obtained using data of 20–5 Å with correlation coefficient of 50.6 and R factor of 34.8%. Structure refinement was performed using CNX™ (Accelrys Inc., San Diego, Calif.), and model building was performed using QUANTA® (Accelrys Inc., San Diego, Calif.)).

EXAMPLE 14

Crystallization of FXIcat with SPRL-122599

A ten-fold molar excess of 10 mM SPRL-122599 in DMSO was added to the FXIcat quadruple mutant S434A, T475A, C482S, K437A, incubated at 4° C. and then concentrated to 15 mg/mL. Cubic crystals were obtained using the hanging drop method (McPherson, *Methods Biochem. Anal.* 23:249–345, 1976) with 23% (w/v) PEG 4000, 0.2 M $Li_2SO_4$, 0.1 M Tris-HCl, pH 8.5 at 10° C. The crystals belong to the space group I23 with unit cell parameters of a=b=c=121.5 Å. Diffraction data were measured to 2.8 Å resolution and processed by HKL2000. Phases were calculated using the structure described in Example 13 as the model, and CNX™ (Accelrys Inc., San Diego, Calif.) was used for calculating the difference electron density map.

EXAMPLE 15

Crystallization of FXIcat with SPRL-121995

A ten-fold molar excess of 10 mM SPRL-121995 in DMSO was added to diluted FXJcat-S434A,T475A,C482S, K437A, incubated at 4° C., and then concentrated to 15 mg/mL. Cubic crystals were obtained using the hanging drop method (McPherson, *Methods Biochem. Anal.* 23:249–345, 1976) with 24% w/v polyethylene glycol 4000, 0.16 M lithium sulfate, and 0.08 M Tris-HCl, pH 8.5 at 10° C. The crystals belong to space group I23 with unit cell parameters of a=b=c=121.7 Å. Diffraction data were measured to 2.1 Å resolution and processed by HKL2000. Phases were calculated using the structure described in Example 13 as the model, and CNX™ (Accelrys Inc., San Diego, Calif.) was used for calculating the difference electron density map.

EXAMPLE 16

Crystallization of FXIcat with SPRL-124336

A ten-fold molar excess of 10 mM SPRL-121995 in DMSO was added to diluted FXIcat-S434A,T475A,C482S, K437A, incubated at 4° C., and then concentrated to 20 mg/mL. Cubic crystals were obtained using the hanging drop method (McPherson, *Methods Biochem. Anal.* 23:249–345, 1976) with 30% PEGMME 5000, 0.1 M Tris pH 7.9, 0.2 M $(NH_4)_2SO_4$, pH 8.5 at 10° C. The crystals belong to space group P32 with unit cell parameters of a=b=41.9, c=103.8 Å. Diffraction data were measured to 3.0 Å resolution and processed by HKL2000. Phases were calculated using the structure described in Example 13 as the model, and CNX™ (Accelrys Inc., San Diego, Calif.) was used for calculating the difference electron density map.

EXAMPLE 17

Crystallization of FXIcat with SPRL-123682

A ten-fold molar excess of 10 mM SPRL-123682 in DMSO was added to diluted FXIcat-S434A,T475A,C482S, K437A, incubated at 4° C., and then concentrated to 15 mg/mL. Cubic crystals were obtained using the hanging drop method (McPherson, *Methods Biochem. Anal.* 23:249–345, 1976) with 18% (w/v) PEG 4000, 0.2 M $Li_2SO_4$, 0.1 M Tris-HCl, pH 8.5 at 10° C. The crystals belong to space group I23 with unit cell parameters of a=b=c=121.3 Å. The diffraction data were measured to 2.0 Å resolution and processed by HKL2000. Phases were calculated using the structure described in Example 13 as the model, and CNX™ (Accelrys Inc., San Diego, Calif.) was used for calculating the difference electron density map.

EXAMPLE 18

Crystallization of FXIcat with SPRL-123672

A ten-fold molar excess of 10 mM SPRL-123672 in DMSO was added to diluted FXIcat-S434A,T475A,C482S, K437A, incubated at 4° C., and then concentrated to 15 mg/mL. Cubic crystals were obtained using the hanging drop method (McPherson, *Methods Biochem. Anal.* 23:249, 1976) with 2.0 M ammonium sulfate, 0.1 M Tris-HCl, pH 8.5 at 10° C. The crystals belong to space group I23 with unit cell parameters of a=b=c=121.4 Å. Diffraction data were measured to 2.2 Å resolution and processed by HKL2000. Phases were calculated using the structure described in Example 13 as the model, and CNX™ (Accelrys Inc., San Diego, Calif.) was used for calculating the difference electron density map.

EXAMPLE 19

Crystallization of FXIcat with SPRL-123545

A ten-fold molar excess of 10 mM SPRL-123545 in DMSO was added to diluted FXJcat-S434A,T475A,C482S, K437A, incubated at 4° C., and then concentrated to 15 mg/mL. Cubic crystals were obtained using the hanging drop method (McPherson, *Methods Biochem. Anal.* 23:249, 1976) with 30% (w/v) PEG 4000, 0.2 M Li$_2$SO$_4$, 0.1 M Tris-HCl, pH 8.5. at 10° C. The crystals belong to space group I23 with unit cell parameters of a=b=c=120.7 Å. Diffraction data were measured to 2.05 Å and processed by HKL2000. Phases were calculated using the structure described in Example 13 as the model, and CNX™ (Accelrys Inc., San Diego, Calif.) was used for calculating the difference electron density map.

EXAMPLE 20

Crystallization of FXIcat with SPRL-122624

A ten-fold molar excess of 10 mM SPRL-122624 in DMSO was added to the FXJcat-S434A,T475A,C482S, K437A, incubated 30 minutes at 20° C. and then concentrated to 20 mg/mL. Cubic crystals were obtained using the hanging drop method (McPherson, *Methods Biochem. Anal.* 23:249–345, 1976) with 20% (w/v) PEG monomethyl ether 5000, 0.1 M ammonium sulfate, and 0.1 M Tris-HCl, pH 7.6 at 10° C. The crystals belong to the space group I23 with unit cell parameters of a=b=c=122.4 Å. Diffraction data were measured to 2.05 Å and processed by HKL2000. Phases were calculated using the structure described in Example 13 as the model, and CNX™ (Accelrys Inc., San Diego, Calif.) was used for calculating the difference electron density map.

EXAMPLE 21

Crystallization of FXIcat with SPRL-123586

A ten-fold molar excess of 10 mM SPRL-123586 in DMSO was added to the FXIcat-S434A,T475A,C482S, K437A, incubated 30 minutes at 4° C. and then concentrated to 20 mg/mL. Needle-like crystals were obtained using the hanging drop method (McPherson, *Methods Biochem. Anal.* 23:249–345, 1976) with 1.4 M tri-sodium citrate, 0.1 M HEPES, pH 7.5 at 10° C. The crystals belong to the space group P21 with unit cell parameters of a=55.8 Å, b=70.3 Å, c=62.1 Å, α=γ=90° and β=102.2°. Diffraction data were measured to 2.7 Å and processed by HKL2000. There are two FXIcat molecules in the asymmetric unit. The orientations of the two monomers were determined by AMoRe using the structure described in Example 13 as model. The solutions were refined in CNX™ (Accelrys Inc., San Diego, Calif.). The difference electron density map was also calculated in CNX.

EXAMPLE 22

Soaking SPRL-130421 into Preformed FXIcat-Benzamidine Crystal

The preformed FXIcat-benzamidine crystals were obtained in a condition similar to Example 13. Benzamidine was added to the FXIcat-S434A,T475A,C4825,K437A protein to a concentration of 1 mM and the complex was concentrated to 20 mg/mL. Cubic crystals were obtained by the hanging-drop method in 2.0 M ammonium sulfate and 0.1 M Tris-HCl, pH 8.5 at 10° C. A preformed FXIcat-benzamidine crystal was transferred into a drop containing its mother liquor with 5 mM of SPRL-130421 and incubated at 10° C. overnight. The crystal is in the space group I23 with unit cell parameters of a=b=c=121.0 Å. Diffraction data were measured to 1.9 Å and processed by HKL2000. Phases were calculated using the structure of FXIcat-SPRL-123545 described in Example 19 as the model, and CNX™ (Accelrys Inc., San Diego, Calif.) was used for calculating the difference electron density map. Model building was performed using QUANTA® (Accelrys Inc., San Diego, Calif.).

EXAMPLE 23

General Synthetic Methods for the Compounds of the Present Invention

Preparation of Compounds of Formula I

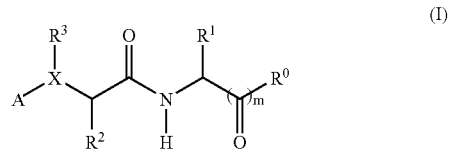

The compounds of formula I may be synthesized by either solid or liquid phase methods described and referenced in standard textbooks, or by a combination of both methods. These methods are well known to those skilled in the art, (see, for example, Bodanszky, In "The Principles of Peptide Synthesis", Hafner, Rees, Trost, Lehn, Schleyer, Zahradnik, Eds., Springer-Verlag, Berlin, 1984; Stewart and Young, Solid Phase Peptide Synthesis, Pierce Chemical Co., Rockford, Ill. (1984); and U.S. Pat. Nos. 4,105,603; 3,972,859; 3,842,067; and 3,862,925).

As described herein, compounds of formula I can be prepared by standard amide bond forming reactions, including fragment condensation when compounds of formula Ia are coupled to compounds of formula Ib, wherein A, $R^0$, $R^1$, $R^2$, and $R^3$ are as previously defined herein.

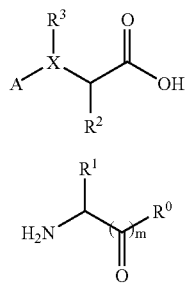

(Ia)

(Ib)

Peptide alpha-keto acids, esters, thio esters, and amides can be prepared as described by Medhi et al., *Biochem. Biophys. Res. Commun.* 166:595–600, 1990; Angelastro et al., *J. Med. Chem.* 33:11–13, 1990; Wipf et al., *J. Org. Chem.* 58:5592–5594, 1993; or Webb et al., PCT Publication WO 9408941. Ketothiazoles can be prepared by solid-phase synthesis as described by Parlow et al., *J. Med. Chem.* 46:4043–9, 2003. The pyrimidinones of formula I can be prepared as described by Veale et al., *J. Med. Chem.* 38:98–108, 1995; Tamura et al., PCT Publication WO 9618644, South et al., PCT Publication WO 0069832; Ewin, et al., PCT Publication WO 0032590; and Akahoshi et al., *J. Med Chem.* 44:1286–96, 2000.

During the synthesis of the compounds of the present invention, the functional groups of the amino acid derivatives used in these methods are protected by blocking groups to prevent cross reaction during the amide bond-forming procedure. Examples of suitable blocking groups and their use are described in "The Peptides: Analysis, Synthesis, Biology," Academic Press, Gross & Meienhofer, Eds., Vol. 3 (1981) and Vol. 9 (1987). The reaction products are isolated and purified by conventional methods, typically by solvent extraction into a compatible solvent, or by using a washing protocol for resin bound intermediates. The products may be further purified by column chromatography or other appropriate methods, including medium pressure or high pressure liquid chromatography.

In one example, compounds of the invention can be conveniently prepared using solid phase synthesis methodology (Merrifield J. Am. Chem. Soc., 85:2149, 1964; Houghten, Proc. Natl. Acad. Sci. USA, 82:5132, 1985). Solid phase synthesis begins at the carboxy terminus of the putative compound by forming a bond (e.g., an amide or ester bond) between a protected amino acid, or other carboxylic acid-containing compound, and an inert solid support. The inert solid support can be any macromolecule capable of serving as an anchor for the C-terminus of the initial amino acid. Typically, the macromolecular support is a cross-linked polymeric resin (e.g. a polyamide or polystyrene resin). In one embodiment, the C-terminal amino acid is coupled to a polystyrene resin to form a benzyl ester. Particularly useful benzyl-type resins, such as trityl resin, chlorotrityl resin, and Wang resin, are those in which the linkage of the carboxy group (or carboxamide) to the resing is acid-lable. A macromolecular support is selected such that the peptide anchor link is stable under the conditions used to deprotect the α-amino group of the blocked amino acids in peptide synthesis. If a base-labile α-protecting group is used, then it is desirable to use an acid-labile link between the peptide and the solid support. For example, an acid-labile ether resin is effective for base-labile Fmoc-amino acid peptide synthesis as described by Stewart and Young, vide supra. Alternatively, a peptide anchor link and α-protecting group that are differentially labile to acidolysis can be used. For example, an aminomethyl resin such as the phenylacetamidomethyl (Pam) resin works well in conjunction with Boc-amino acid peptide synthesis.

After the initial amino acid is coupled to an inert solid support, the α-amino protecting group of the initial amino acid is removed with, for example, trifluoroacetic acid (TFA) in methylene chloride and neutralizing in, for example, triethylamine (TEA). Following deprotection of the initial amino acid's α-amino group, the next α-amino and side chain protected amino acid in the synthesis is added. The remaining α-amino protected and, if necessary, side chain protected amino acids are then coupled sequentially in the desired order by condensation to obtain an intermediate compound connected to the solid support. Alternatively, some amino acids may be coupled to one another in solution to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the azide method, acyl halide method (preferably acyl fluoride), mixed acid anhydride method, DCC(N,N'-dicyclohexylcarbodiimide) or DIC (N,N'-diisopropylcarbodiimide) methods, active ester method, p-nitrophenyl ester method, BOP (benzotriazole-1-yl-oxy-tris[dimethylamino] phosphonium hexafluorophosphate)method, N-hydroxysuccinicacid imido ester method, O-benzotriazolyl-N,N,N',N'-tetramethyluronium hexafluorophosphate (HBTU) or O-(7-azabenzotriazol-1-yl)-N,N,N', N'-tetramethyluronium hexafluorophosphate (HATU), and Woodward reagent K method.

Alternatively, other functional groups, can be introduced on the liberated N-terminus of the resin. For example, reaction with commercially available carboxylic acids or acid chlorides, sulfonyl chlorides, or isocyanates under standard conditions known in the art produce compounds of the invention containing an amide, sulfonamide, or urea bond, respectively. An alternative to using isocyanates in preparing urea-containing compounds is to activate the deprotected amine terminus with, for example, phosgene, triphosgene, carbonyl di-imidazole, or p-$NO_2$ phenylchloroformate followed by reaction with primary or secondary amines employed in excess.

It is common in both solid-phase and solution-phase synthesis to protect any reactive side-chain groups of the amino acid with suitable protecting groups. Ultimately, these protecting groups are removed after the desired compounds have been sequentially assembled. Also common is the protection of the α-amino group on an amino acid or a fragment while that entity reacts at the carboxy group followed by the selective removal of the α-amino protecting group to allow subsequent reaction to take place at that location. Accordingly, it is common that an intermediate compound is produced which contains each of the amino acid residues located in the desired sequence in the peptide chain with various of these residues having side chain protecting groups attached. These protecting groups are then commonly removed at substantially the same time so as to produce the desired product following cleavage from the resin. Protecting groups and procedure for their use in peptide synthesis are reviewed in Protective Groups in Organic Synthesis, 3d ed., Greene, T. W. and Wuts, P. G. M., Wiley & Sons (New York: 1999).

Suitable protecting groups for α-amino and side chain amino groups are exemplified by benzyloxycarbonyl (abbreviated Z), isonicotinyloxycarbonyl (iNOC), o-chlorobenzyloxycarbonyl [Z(2Cl)], p-nitrobezyloxycarbonyl [Z(NO$_2$)], p-methoxybenzyloxycarbonyl [Z(OMe)], t-butoxycarbonyl (Boc), t-amyloxycarbonyl(Aoc), isobornyloxycarbonyl, adamantyloxycarbonyl, 2-(4-biphenyl)-2-propyloxycarbonyl (Bpoc), 9-fluorenylmethoxycarbonyl(Fmoc), methylsulfonyethoxycarbonyl (Msc), trifluoroacetyl, phthalyl, formyl, 2-nitrophenylsulfenyl (NPS), diphenylphosphinothioyl (Ppt), and dimethylphosphinothioyl (Mpt) groups, and the like.

Protective groups for the carboxy functional group are exemplified by benzyl ester, (OBz), cyclohexyl ester (Chx), 4-nitrobenzyl ester (ONb), t-butyl ester (OtBu), 4-pyridylmethyl ester (OPic), and the like. It is often desirable that amino acids possessing a functional group other than amino and carboxy groups, such as, for example, arginine, cysteine, histidine, asparagine, glutamine, threonine, tyrosine, tryptophan and serine, be protected by a suitable protecting group. For example, the guanidino group may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Nds), 1,3,5-trimethylphenysulfonyl (Mts), and 2,3,6-trimethyl-4-methoxyphenylsulfonyl (Mtr), and the like. The thiol group can be protected with p-methoxybenzyl, trityl, and the like. Other suitable protecting groups for hydroxy, phenoxy, the indole amine, carboxamide, the imidazole nitrogen can be found in Greene, vide supra.

In one embodiment, the compounds of the invention are synthesized with the help of blocking groups that protect the side chain amide bond-forming substituents of the N-terminal and C-terminal flanking residues. The protecting group or groups used for the side chain amide bond-forming substituents of the N-terminal and C-terminal flanking residues can be the same or different than the protecting group or groups used to block the side chain functional groups of other residues in the peptide. In a preferred embodiment, the protecting group or groups used to block the side chain amide bond-forming substituents is (are) differentially removable with respect to the protecting groups used for other side chain functional groups, i.e. the side chain amide bond-forming substituents can be deprotected without deprotecting the other side chain functional groups, in addition to being differentially removable with respect to the α-amino protecting group used in peptide synthesis. In another preferred embodiment, the side chain amide bond-forming substituents of the flanking residues are orthogonally protected with respect to each other such that the side chain amide bond-forming substituent of one flanking residue can be deprotected without deprotecting the side chain amide bond-forming substituent of the other flanking residue.

Suitable protecting groups for use in orthogonally protecting the side chain amide bond-forming substituents of the flanking residues with respect to other functional groups and/or with respect to each other include pairs of differentially removable carboxy protective groups, such as a reduction-labile carboxy protective group, e.g. allyl or benzyl esters, paired with a base-labile carboxy protective group, e.g. fluorenylmethylesters, methyl or other primary alkyl esters. Fluorenylmethyl, methyl or other primary alkyl groups or other base-labile carboxy protective groups can be removed from their corresponding esters to yield a free carboxy group (without deprotecting allyl or benzyl esters or other reduction-labile esters) by saponification of the esters with a suitable base such as piperidine and sodium hydroxide in a suitable solvent such as dimethylacetamide, or methanol and water, for a period of 10 to 120 minutes, and preferably 20 minutes, 0° C. to 50° C. The allyl or benzyl or other reduction-labile esters can be removed when desired by reduction in the presence of a suitable transition metal catalyst, such as Pd(PPh$_3$)$_4$, Pd(PPh$_3$)$_2$Cl$_2$, Pd(OAc)$_2$ or Pd on carbon with a source of hydrogen, e.g. H$_2$ gas, in a suitable solvent such as dimethylacetamide, dimethylformamide, N-methylpyrrolidinoneor methanol for a period of 10 to 500 minutes, and preferably 100 minutes, at 0° C. to 50° C. For the sake of simplicity and convenience, all carboxy protective groups that are removable by Pd-catalyzed methods which result in the reduction of the protected carboxy substitutent are included n the term "reduction-labile protective groups" as used herein, even though such Pd-catalyzed deprotection methods may not result in the reduction of the protective group in question.

In embodiments wherein Pd catalysis involves the formation of intermediates of Pd derivatized with reduction-labile protecting groups, e.g. Pd-allyl derivatives, the Pd catalyst can be restored by reaction with a suitable nucleophile, such as piperidine or tributyltin hydride. When such reduction-labile groups are used to provide orthogonal protection in combination with base-labile protecting groups, it is preferable to either (1) utilize a synthetic scheme that calls for the removal of the base-labile protecting groups before the removal of the reduction-labile protecting groups or (2) restore the Pd catalyst with a nucleophile that does not deprotect the base-labile protecting groups.

Alternatively, the carboxy substituents of the flanking residues can be orthogonally protected with respect the other functional groups and/or with respect to each other by using an acid-labile protecting group, such as a tertiary alkyl ester, e.g. t-butyl ester, in combination with a reduction-labile protecting group, such as the allyl or benzyl esters described above. The tertiary alkyl or other acid-labile ester group can be removed by acidolysis, e.g. with trifluoroacetic acid in methylene chloride, and the allyl or benzyl or other reduction-labile esters can be removed by reduction in the presence of a transition metal catalyst as described above.

In another embodiment, the carboxy substituents of the flanking residues can be orthogonally protected with respect to other functional groups and/or with respect to each other by using a fluoride ion-labile protecting group, such as 2-(trimethylsilyl)ethyl and silyl esters, in combination-with a reduction-labile protecting group, such as the allyl or benzyl esters described above, or in combination with a base-labile protecting group, such as the fluorenylmethyl, methyl or other primary alkyl esters described above, without deprotecing the reduction-labile or base-labile esters. The 2-(trimethylsilyl)ethyl, silyl or other fluoride-labile ester group can be removed by reaction with a suitable fluoride ion source, such as tetrabutylammonium fluoride in the presence of a suitable solvent, such as dimethylacetamide (DMA), dimethylformamide (DMF), tetrahydrofuran (THF), or acetonitrile.

Suitable protecting groups for use in orthogonally protecting the side chain amide bond-forming substituents of the flanking residues with respect to other functional groups and/or with respect to each other also include pairs of differentially removable amino protective groups, such as an allyloxycarbonyl or other reduction-labile amino protective group paired with a t-butoxycarbonyl (Boc) or other acid-labile amino protective group, and a reduction-labile amino protective group paired with a fluorenylmethoxycarbonyl (Fmoc) or other base-labile amino protective group. An allyloxycarbonyl (or other reduction-labile blocking group) protected amino group can be deprotected by reduction using a transition metal catalyst as in the procedure for removing reduction-labile carboxy protective groups described above, without deprotecting a Boc or Fmoc protected amino group. Likewise, an acid-labile amino protective group and a base-labile amino protective group can be removed by acidolysis and base saponification, respectively, without removing a reduction-labile amino protective group. For the sake of simplicity and convenience, all amino protective groups that are removable by Pd-catalyzed methods which result in the reduction of the protected amino substituent are included in the term "reduction-labile protective groups" as used herein, even though such Pd-catalyzed deprotection methods may not result in the reduction of the protective group in question.

In another embodiment, the amino substituents of the flanking residues can be orthogonally protected with respect to other functional groups and/or with respect to each other by using a fluoride-labile protecting group, such as 2-trimethylsilylethylcarbamate (Teoc), in combination with a reduction-labile protecting group, such as allyloxylcarbonyl, or in combination with a base-labile protecting group, such as fluorenylmethoxycarbonyl, as described above. The Teoc or other fluoride-labile group can be removed by reaction a with a suitable fluoride ion source, such as tetrabutylammonium fluoride, as in the procedures for removal of fluoride-labile carboxy protective groups described above, without deprotecting an allyloxycarbonyl or fluorenylmethoxycarbonyl protected amino group. Likewise, a reduction-labile amino protective group and a base-labile amino protective group can be removed by reduction and base saponification, respectively, without removing a fluoride-labile amino protective group.

In embodiments that use a carboxy substituent as the side chain amide bond-forming substituent of one flanking residue and that use an amino substituent as the side chain amide bond-forming substituent of the other flanking residue, the carboxy substituent and the amino substituent can be orthogonally protected with respect to each other by using a reduction-labile protecting group to block one substituent, e.g. allyl ester or allyloxycarbonyl, and a fluoride-labile, acid-labile or base-labile protecting group to block other substituent, e.g. silyl ester, t-butyl ester, fluorenylmethyl ester, Teoc, Boc, or Fmoc.

In a preferred embodiment, a reduction-labile protecting group is used to block the side chain amide bond-forming substituent of one flanking residue and the protecting group for the side chain amide bond-forming substituent of the other flanking residue is selected such that it provides orthogonal protection with respect to both the reduction-labile protecting group and the α-amino protecting group used in the synthesis. For example, in an embodiment using Fmoc chemistry for peptide synthesis, orthogonal protection of the side chain amide bond-forming substituents would be provided by a reduction-labile protecting group and an acid-labile protecting group. Likewise, in an embodiment using Boc chemistry for peptide synthesis, orthogonal protection of the side chain amide bond-forming substituents would be provided by a reduction-labile protecting group and a base-labile protecting group.

In yet another preferred embodiment, the side chain amide bond-forming substituents of the flanking residues are orthogonally protected with respect to each other, with respect to α-amino protecting group used in the synthesis, and with respect to the protecting groups used to block other side chain functional groups in the peptide chain.

In still another preferred embodiment, the side chain amide bond-forming substituents of the flanking residues are orthogonally protected with respect to each other, and with respect to α-amino protecting group, but only one of the side chain amide bond-forming substituents is orthogonally protected with respect to the protecting groups used to block other side chain functional groups. In this embodiment, it is preferable to use the side chain amide bond-forming substituent with fully orthogonal protection as the target for initial attachment of the compound to the difunctional linker. Since the side chain amide bond-forming substituent with fully orthogonal protection can be deprotected without deprotecting other functional groups, the amide bond-forming reaction will be specific to the desired side chain amide bond-forming substituent, and will reduce the production of unwanted difunctional linker derivatives. Although cyclization will require the deprotection of the side chain amide bond-forming substituent of the other flanking residue, and may cause concomitant deprotection of other side chain functional groups, unwanted derivatives are less likely to form given that the peptide chains are anchored to a solid support and that the linker length will regioselectively favor a amide bond-forming reaction between the unbound functional group of the linker and the side chain amide bond-forming substituent of the other flanking residue. If further peptide chain synthesis is desired after cyclization, any side chain functional groups on other amino acid residues left unprotected by the cyclization reactions can be reprotected before chain synthesis is resumed.

Many of the blocked amino acids described above can be obtained from commercial sources such as Novabiochem (San Diego, Calif.), Bachem Calif. (Torrence, Calif.) or Peninsula Labs (Belmont, Calif.). Alternatively, functionalized or protected amino acids, including unnatural amino acids, can be prepared by methods known in the art.

In addition, the compounds of the invention can be prepared by, or in conjunction with, solution phase peptide synthesis, for example, the solution phase peptide synthesis methods described in Principles of Peptide Synthesis, 2d ed, M. Bodanszky, Springer-Verlag (1993) or in The Practice of Peptide Synthesis, 2d ed, M. Bodanszky and A. Bodanszky, Springer-Verlag (1994). It will be appreciated that solution phase peptide synthesis methods can be easily modified to incorporate the desired flanking residues, with or without orthogonally-protected side chain amide bond-forming substituents, into the compound of interest, using procedures similar to those used in the solid phase synthesis methods described herein. It will be further appreciated that all references to amide bond-forming reactions herein encompass both solid phase and solution (or liquid) phase peptide synthesis methods, unless otherwise indicated.

The preparation of ketone derivatives of the formula I (for example, m is 1, $R^0$ is an optionally substituted alkyl, alkenyl, cycloalkyl, aralkyl, aralkenyl, aryl, heterocyclyl, heteroaralkyl, or heteroaralkenyl, or $C(O)R^9$, where $R^9$ is as previously defined herein) can be prepared by reacting appropriately protected amino acid derivatives having a free carboxyl group (e.g., an appropriately alpha-amine protected analog of formula Ib, where m is 1 and $R^0$ is OH) with an alkoxyamine under amide bond-forming conditions, as described herein, to form Weinreb amides of formula III, where P is a nitrogen protecting group. The Weinreb amide can be reacted with alkyl, alkenyl, cycloalkyl, aralkyl, aralkenyl, aryl, heterocyclyl, heteroaralkyl, heteroaralkenyl, or heteroaryl carbanions such as lithium salts or Grignard reagents to form ketones of formula IV, which can be subsequently deprotected at the alpha-amine position to form compounds of formula Ib, where m is 1 and $R^0$ is alkyl, alkenyl, cycloalkyl, aralkyl, aralkenyl, aryl, heterocyclyl, heteroaralkyl, heteroaralkenyl, or heteroaryl. These ketone compounds can then be coupled to the carboxyl-containing compounds of formula Ia to produce the corresponding compounds of formula I.

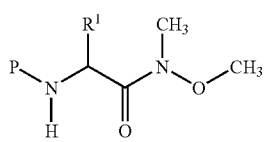
(III)

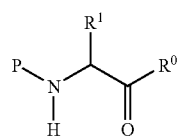
(IV)

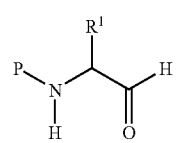
(V)

Alternatively, ketone derivatives of the formula I can be prepared from Weinreb amide III by reduction of this amide to the corresponding aldehyde with a hydride reagent, such as DIBAL-H or LAH, to produce compounds of formula V, to which an $R^0$ group can be introduced by the addition of a nucleophile, such as the carbanions, organolithio reagents, or Grignard reagents described before in the nucleophilic addition to Weinreb amides. The resulting compound can then be reacted with compounds of formula Ia, as previously described, followed by oxidation of the secondary alcohol, such as with Dess-Martin reagent, to yield a compound of formula IV. In one example, compounds of formula I, where m is 1 and $R^0$ is 2-thiazole, are prepared by reacting aldehydes of formula V with 2-trimethylsilyl (TMS) thiazole. The resulting TMS ether is deprotected with fluoride and subsequent oxidation of the resulting secondary alchohol, followed by removal of the amine protecting group and reaction with compounds of formula Ia, provides thiazole ketones of formula I (i.e., m is 1 and $R^0$ is 2-thiazole).

When an appropriately protected Weinreb amide of formula III is reacted with 2-lithiofuran, compounds of formula IV are produced, wherein m is 1 and $R^0$ is a 2-furyl moiety. Subsequent reduction of this ketone with sodium borohydride provides a mixture of antipodal alcohols. Acetylation of the alcohol, followed by oxidative degradation of the furan with $RuCl_3$ and $NaIO_4$, produces a compound of formula VI, where $R^9$ is OH. Condensation of this carboxylic acid with amines, alcohols, or thiols, provides the alpha-acetoxy amides, esters, or thioesters, respectively, of formula VI, where $R^9$ is, for example, an optionally substituted alkyloxy, aryloxy, heteroaryloxy, aralkyloxy, alkylthio, cycloalkylthio, arylthio, aralkylthio, alkylamino, alkylamino, dialkylamino, aralkylamino, arylamino, heterocyclylamino, or heterocyclylakylamino.

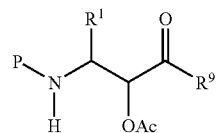
(VI)

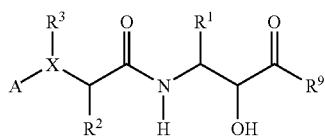
(VII)

The acetoxy and amine protecting groups of the compounds of formula VI can be removed and the amine coupled to compounds of formula Ia to form the corresponding compounds of formula VII, which can be further transformed by oxidation, with oxidants such as Dess-Martin reagent, to provide ketones of formula I, wherein m is 1 and $R^0$ is, for example, an alkylaminocarbonyl, aralkylaminocarbonyl, arylaminocarbonyl, heteroarylaminocarbonyl, alkoxycarbonyl, aryloxycarbonyl, or aralkoxycarbonyl. Alternatively, the acetoxy protecting group can be retained and carried through the coupling step and removed later.

Compounds of the formula I, wherein m is 0 and $R^0$ is H, can be prepared through condensation of compounds of the formula Ia with amine derivatives of formula $H_2NCH_2—R^1$. In one example, appropriately protected compounds of the formula Ia are reacted with appropriately protected amines of the formula VIII, using amide-bond-forming conditions as described herein. Subsequent removal of any protecting groups provides compounds of formula IX, wherein Z, A, $R^2$, $R^3$, $R^4$, and $R^7$ are as previously defined herein.

(VIII)

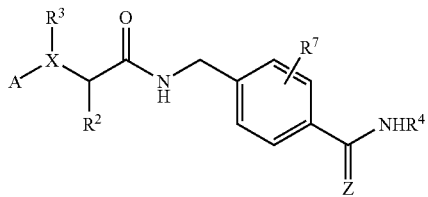
(IX)

Compounds of formula I, where $R^3$ together with A forms a ring having formula (X) are prepared as exemplified by the synthesis of pyrimidinones, where W is N.

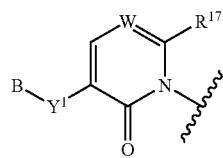
(X)

Accordingly, thiouracil is methylated (methyl iodide) then halogenated (e.g., with $I_2$ or $Br_2$), and the resulting halopyrimidinone XI is alkylated with electrophile XII, where $Y^1$ is Br, I, or OTf and $P^1$ is a carboxylic acid protecting group, to produce compounds of the formula XIII. Various amine groups, including primary and secondary amines of the formula B—N($R^{18}$)H, where $R^{18}$ is H or alkyl and B is an optionally substituted alkyl, alkenyl, cycloalkyl, aralkyl, aryl, heterocyclyl, heterocyclylalkyl, or a suitable nitrogen protecting group, can be incorporated into the pyrimidinone scaffold utilizing, for example, the palladium-mediated amide bond-forming method of Buchwald, et al., *J. Org. Chem.* 65:1144–1157, 2000, to produce compounds of the formula XIVa. If B is a nitrogen protecting group, it can be removed and the free amine thus generated further functionalized such that B can be an acyl, aroyl, heteroaroyl, alkoxycarbonyl, cycloalkoxycarbonyl, aralkoxycarbonyl, aryloxycarbonyl, heterocyclyloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, alkylthiocarbonyl, arylthiocarbonyl, heteroarylthiocarbonyl, alkoxythiocarbonyl, cycloalkoxythiocarbonyl, aralkoxythiocarbonyl, aryloxythiocarbonyl, aminothiocarbonyl, alkylaminothiocarbonyl, dialkylaminothiocarbonyl, cycloalkylaminothiocarbonyl, aralkylaminothiocarbonyl, arylaminothiocarbonyl, heterocyclylaminothiocarbonyl, heteroaralkylaminothiocarbonyl, alkylsulfonyl, cycloalkylsulfonyl, aralkylsulfonyl, arylsulfonyl, heterocyclylsulfonyl, or a heterocyclylalkylsulfonyl group. The free amine can also be condensed with the carboxyl group of amino acid derivatives.

Substituents $R^{17}$, which includes, but is not limited to, substituted aromatic rings, can be introduced at the 2-position of the pyrimidinone scaffold of compound XIVa by utilizing, for example, C—C palladium-mediated bond forming conditions (see, for example, Lindley, *Tetrahedron* 40:1433, 1984) to produce compounds of the formula XIVb after removal of the carboxyl protecting group, $P^1$. Other intermediates of formula XIVb can be prepared by alkylating thiouracil with another appropriately activated compound other than methyl iodide to produce compounds in which $R^{17}$ is alkylthio, cycloalkylthio, arylthio, aralkylthio, heterocyclylthio, or heteroaralkylthio. Alternatively, the thiomethyl group, or the methyl sulfoxide or methyl sulfone derived therefrom, of compounds of formula XIVa can be displaced with other nucleophilic groups, such as, for example, the $NH_2$ group of various amines, to produce compounds for formula XIVb where R17 is alkylamino, cycloalkylamino, aralkylamino, arylamino, or heterocyclylamino.

Subsequent amide bond formation by the condensation of compounds of formula XIVb with the alpha amine of amino acid derivatives, including Weinreb amides, with subsequent functional group manipulation, as described herein, and removal of any protecting groups used, provides pyrimidinone compounds of formula I (e.g., compounds of formula XV). Alternatively, subsequent amide bond formation by the condensation of compounds of the formula XIVb with amine derivatives of formula $H_2NCH_2$—$R^1$, provides pyrimidinone compounds of the formula I (m is 0, $R^0$ is H).

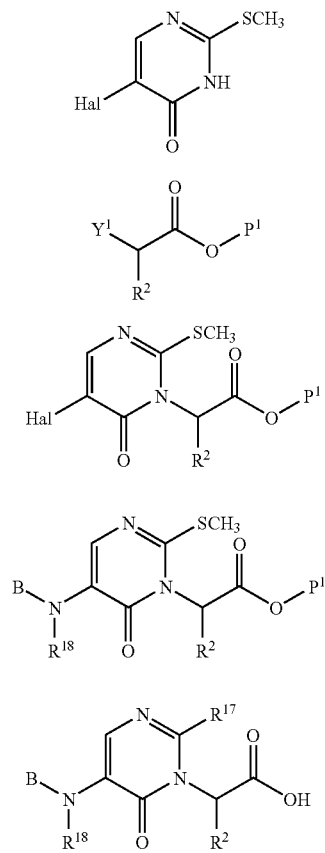

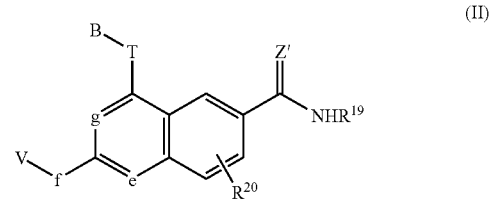

Preparation of Compounds of Formula II

For compounds of the formula II, naphthyl amidines or amines (i.e., each of e and g is C—H) can be prepared, at least in part, as described by Geye et al., U.S. Pat. No. 6,258,822 and U.S. Pat. No. 6,284,796 B1; Klinghofer et al., *Biochemistry* 40:9125–9131, 2001; and Atwell et al., EP Patent 0206802 and U.S. Pat. No. 4,904,659. Quinazoline amidines or amines (i.e., each of e and g is N) can be prepared according to procedures detailed by Mederski et al., WO 0224667 and Ahn et al., U.S. Pat. No. 5,658,902.

In one example, compounds of formula II, where each of e and g is C—H; T is NH, B is an alkyl, substituted carbonyl or substituted sulfonyl group, f is a bond, V is H, $R^{19}$ is H, and $Z^1$ is NH (i.e., 8-substituted naphthalene-2-carboxamidines), can be prepared starting from 8-amino-naphthalen-2-ol, which is first N-protected, such as with the carbonylbenzyloxy group (Cbz), and then activated at the 2-position, such as by conversion of the hydroxyl group to a triflate. The triflate can be cyanated under Pd-mediated C—C bond forming conditions (see (a) Takagi et al., *Chem. Lett.* 1973: 471; (b) Sekiya et al., Chem. Lett. 1975:277; (c) Tschaen et al., *Synth. Commun.* 24:887, 1994; and (d) Sundermeier et al., *Tetrahedron Lett.* 42:6707, 2001). After removal of the N-protecting group, the naphthylamine can be derivatized with acid halides, sulfonyl chlorides, chloroformates, isocyanates, isothiocyanates, alkyl halides, or coupled to amino acid derivatives to provide compounds of the formula XVI where T is NH and B is a natural or unnatural alpha-amino acid residue of D- or L-configuration, or an optionally substituted alkyl, cycloalkyl, alkenyl, aralkyl, aralkylcarbonyl, aralkenyl, aryl, heteroaralkyl, heteroaralkylcarbonyl, heteroaralkenyl, acyl, cycloalkylcarbonyl, aroyl, heterocyclyloyl, cycloalkoxycarbonyl, aryloxycarbonyl, heterocyclyloxycarbonyl, heteroaralkyloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, heteroaralkylaminocarbonyl, alkylthiocarbonyl, cycloalkylthiocarbonyl, arylthiocarbonyl, aralkylthiocarbonyl, heterocyclylthiocarbonyl, heteroaralkylthiocarbonyl, aminothiocarbonyl, alkylaminothiocarbonyl, dialkylaminothiocarbonyl, cycloalkylaminothiocarbonyl, aralkylaminothiocarbonyl, arylaminothiocarbonyl, heterocyclylaminothiocarbonyl, heteroaralkylaminothiocarbonyl, alkylsulfonyl, cycloalkylsulfonyl, aralkylsulfonyl, arylsulfonyl, heterocyclylsulfonyl, or heteroaralkylsulfonyl. In those cases where B is aryl, the use of organometallic chemistry coupling techniques involving a palladium catalyst in the reaction of an amine (e.g., an amine on a naphthyl ring of formula II) with an aryl triflate is recommended.

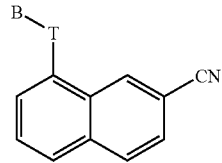

(XVI)

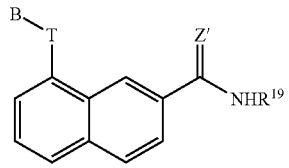

(XVII)

The nitrile group can then be transformed to an amidine group under a variety of conditions, including acidic conditions in alcohol (e.g., Pinner conditions followed by aminolysis as described by (a) Pinner, Die Iminoäther und ihre Derivate, Verlag, R. Oppenheim: Berlin, 1892; (b) Roger et al., *Chem. Rev.* 61:179, 1961; (c) Schaefer et al., *J. Org. Chem.* 26:412, 1961), or treatment with hydroxylamine followed by acetylation of the N—OH amidine group and subsequent reduction under hydrogenation conditions (see Judkins et al., *Synth. Commun.* 26:4351, 1996), to provide compounds of the formula XVII, where Z' is NH and $R^{19}$ is H. For those compounds of formula II where Z' is $NR^{22}$, where $R^{22}$ is alkyl, OH, or $NH_2$, the nitrile is treated with an alkyl amine, hydroxylamine or hydrazine, respectively. Carbamoylation of the amidine group with a suitable chloroformate reagent under basic conditions provides compounds of the formula II where $R^{22}$ is $CO_2$—R. Other syntheses of amidines from nitriles are described by Garigipati et al., *Tetrahedron Lett.* 31:1969, 1990; Moss et al., *Tetrahedron Lett.* 36:8761, 1995; Rousselet et al., *Tetrahedron Lett.* 34: 6395, 1993; and Fosberg et al., *J. Org. Chem.* 52:1017, 1987.

Compounds of formula II, where T is a bond, B is H, each of e and g is C—H, f is O, and Z' is NH can be prepared from 2-cyano-6-hydroxynaphthalene, which is first O-alkylated with an alkyl halide, aralkyl halide, or heteroaralkyl halide, where the halide group is chloro, bromo, or iodo, to give compounds of the formula XVIII. Alternatively, O-alkylation can be achieved with alkyl alcohols, aralkyl alcohols, or heteroaralkyl alcohols under Mitsunobu conditions using diisopropylazodicarboxylate and triphenylphosphine. The amidine, hydroxyamidine, or aminoamidine groups can be obtained from the nitrile, as previously described herein, to afford compounds of the formula XIX, where $R^{19}$ is H, and $R^{22}$ is H, alkyl, OH, or $NH_2$, and V is an alkyl, aralkyl, or heteroaralkyl group.

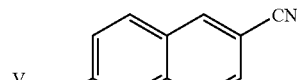

(XVIII)

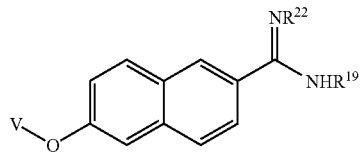

(XIX)

Compounds of formula II, where T is a bond, B is H, each of e and g is C—H, f is a bond, V is a substituted carbonyl group, and Z' is NH can be prepared as follows. Hydrolysis of naphthalene-2,6 dicarboxylic acid dimethyl ester with one equivalent of a base such as KOH, followed by acidification of the product with an acid such as HCl, affords the naphthalene mono carboxylic acid. After conversion of the carboxylic acid to an acid chloride with a reagent such as thionyl chloride and subsequent reaction with ammonia in methylene chloride, the resulting 6-carbamoyl-naphthalene-2-carboxylic acid methyl ester is reacted with triphosgene in trimethylphosphate to provide 6-cyano-naphthalene-2-carboxylic acid methyl ester. Hydrolysis of the ester with LiOH in aqueous THF solution, followed by reaction with thionyl chloride, affords 6-cyano-naphthalene-2-carbonyl chloride, which can then be coupled with alcohols or amines to provide compounds of the formula XX. The amidine, hydroxyamidine, or aminoamidine groups can be obtained from the nitrile as described previously to afford compounds the formula XXI, where $R^{19}$ is H, and $R^{22}$ is H, alkyl, OH, or $NH_2$, and V is an alkylaminocarbonyl, dialkylaminocarbonyl, cycloalkylaminocarbonyl, aralkylaminocarbonyl, arylaminocarbonyl, heterocyclylaminocarbonyl, alkoxycarbonyl, cycloalkoxycarbonyl, aralkoxycarbonyl, aryloxycarbonyl, heterocyclyloxycarbonyl, or heteroaralkyloxycarbonyl.

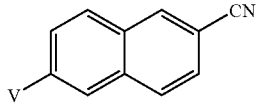

(XX)

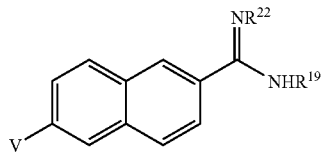
(XXI)

Compounds of formula II, where each of e and g is C—H; T is NH, B is an alkyl, substituted carbonyl or substituted sulfonyl group, f is a bond, V is a substituted carbonyl group, and Z' is NH can be prepared as follows. Nitration of 6-cyano-naphthalene-2-carboxylic acid methyl ester with $KNO_3/H_2SO_4$ gives of 6-cyano-4-nitro-naphthalene-2-carboxylic acid methyl ester. Hydrolysis of the ester with LiOH in aqueous THF solution, followed by treatment with thionyl chloride, gives 6-cyano-4-nitro-naphthalene-2-carbonyl chloride, which is coupled with a primary or secondary amine to give amides of the formula XXII, where V is an alkylaminocarbonyl, dialkylaminocarbonyl, cycloalkylaminocarbonyl, aralkylaminocarbonyl, arylaminocarbonyl, or heterocyclylaminocarbonyl group. Hydrogenation of compounds of the formula XXII in the presence of Pd/C (10%) in methanol affords amines of the formula XXIII. Compounds of the formula XIII in the presence of a base, such as, for example, diisopropylethylamine or $K_2CO_3$ in THF, are treated with acid chlorides, chloroformates, isocyanates, or sulfonyl chlorides, or coupled with carboxylic acids as described herein, to afford compounds of the formula XXIV, where T is $NR^{23}$, where $R^{23}$ is H, OH, or optionally substituted alkyl, alkenyl, aralkyl, aralkenyl, heteroaralkyl, or heteroaralkenyl, and B is acyl, aroyl, heterocyclylcarbonyl, alkoxycarbonyl, cycloalkoxycarbonyl, aralkoxycarbonyl, alkylaminocarbonyl, cycloalkylaminocarbonyl, aralkylaminocarbonyl, alkylaminosulfonyl, cycloalkylaminosulfonyl, aralkylaminosulfonyl, or B is a protected natural or unnatural alpha-amino acid residue of D- or L-configuration.

Alternatively, the primary amine of compounds of formula XXIII can be monoalkylated via reaction with an alkyl halide or via reductive amination procedures, followed by treatment with an activated carboxylic acid, to produce compounds of formula XXIV, where T is $NR^{23}$, where $R^{23}$ is alkyl. Amidine, hydroxyamidine, or aminoamidine groups can be obtained from the nitrile as described previously to afford compounds of the formula XXV, where $R^{19}$ is H and $R^{22}$ is H, alkyl, OH, or $NH_2$, and V is an alkylaminocarbonyl, dialkylaminocarbonyl, cycloalkylaminocarbonyl, aralkylaminocarbonyl, arylaminocarbonyl, or heterocyclylaminocarbonyl group.

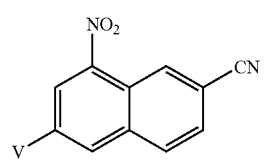
(XXII)

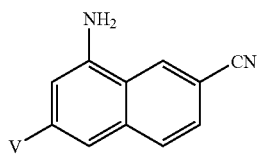
(XXIII)

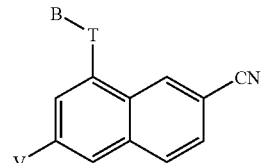
(XXIV)

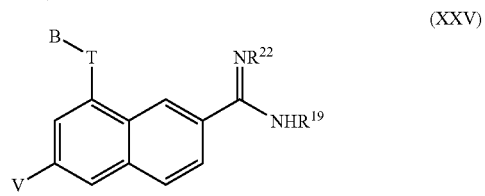
(XXV)

Similarly, the compounds of formula XXV in which T is a bond, B is $NO_2$, V is methoxycarbonyl, $R^{22}$ is H, and $R^{19}$ is H, alkyl, OH, $CO_2$-alkyl or $NH_2$ can be obtained directly from 6-cyano-4-nitro-naphthalene-2-carboxylic acid methyl ester from the nitrile as described herein or the methoxycarbonyl group can be transformed to compounds of formula XXV in which T is a bond, B is $NO_2$, V is an alkylaminocarbonyl, dialkylaminocarbonyl, cycloalkylaminocarbonyl, aralkylaminocarbonyl, arylaminocarbonyl, or heterocyclylaminocarbonyl group, followed by transformation of the cyano moiety to an amidine, hydroxyamidine, or aminoamidine group.

Alternatively, the nitro group of 6-cyano-4-nitro-naphthalene-2-carboxylic acid methyl ester can be reduced and optionally acylated as described herein to produce compounds of formula XXV, wherein V is methoxycarbonyl. Those compounds of formula XXII in which V is an alkoxycarbonyl can be further saponified and reduced with borane or $LiBH_4$ to provide, after the cyano is converted to an amidine, compounds of the formula XXV is which V is hydroxylmethyl, or derivative thereof.

Compounds of formula II in which T is O can be prepared in a modification of the procedure of Fuganti et al., *J. Chem. Res. Miniprint* 10:2769–2782, 1998. Emmons-Horner reaction of 4-cyanobenzaldehyde with compound XXVI to produce compound XXVII, and subsequent cyclization by treatment with acetic acid in acetic anhydride yields compound XXVIII. Compound XXVIII carried forward to compounds of formula XXV, where T is O and B is alkyl, alkenyl, cycloalkyl, aralkyl, aralkenyl, heteroaralkyl, heteroaralkenyl, acyl, aroyl, heteroaroyl, alkoxycarbonyl, cycloalkoxycarbonyl, aralkoxycarbonyl, aryloxycarbonyl, heterocyclyloxycarbonyl, heteroaralkyloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, heteroaralkylaminocarbonyl, alkylsulfonyl, cycloalkylsulfonyl, aralkylsulfonyl, arylsulfonyl, heterocyclylsulfonyl, or heteroaralkylsulfonyl by saponification of the acetyl group, refunctionalization of the resulting hydroxyl group by methods known in the art or those described herein, and tranformation of the nitrile moiety to an amidine, hydroxyamidine, or aminoamidine group as described herein.

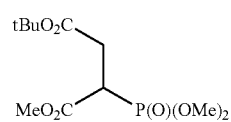
(XXVI)

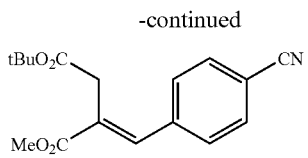

(XXVII)

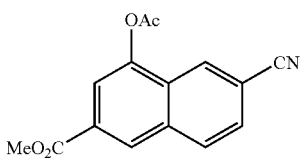

(XXVIII)

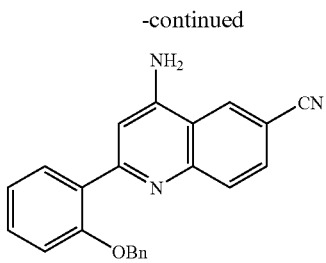

(XXX)

Quinoline compounds of formula II, where e is N and g is C—H can be prepared via the condensation product XXIX derived from 4-iodoaniline, pyruvic acid, and O-benzyl protected salicylaldehyde (Doebner-Miller protocol, see M. Matsugi et al., *Tet. Lett.* 41:8523–8525, 2000). The resulting quinoline carboxylic acid is reacted with CuCN to displace the iodo group with a cyano group after the carboxyl group is converted by a Curtius rearrangement to a carbamoylated amine. After deprotecting this amine, the cyano-aminoquinoline intermediate, XXX can be acylated (or otherwise derivatized), followed by subsequent conversion of the nitrile group to an amidine group as previously described to provide quinoline compounds of the formula II, where T is $NR^{23}$; B is acyl, cycloalkylcarbonyl, aroyl, heterocyclyloyl, cycloalkoxycarbonyl, aryloxycarbonyl, heterocyclyloxycarbonyl, heteroaralkyloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, heteroaralkylaminocarbonyl, alkylthiocarbonyl, cycloalkylthiocarbonyl, arylthiocarbonyl, aralkylthiocarbonyl, heterocyclylthiocarbonyl, heteroaralkylthiocarbonyl, aminothiocarbonyl, alkylaminothiocarbonyl, dialkylaminothiocarbonyl, cycloalkylaminothiocarbonyl, aralkylaminothiocarbonyl, arylaminothiocarbonyl, heterocyclylaminothiocarbonyl, heteroaralkylaminothiocarbonyl, alkylsulfonyl, cycloalkylsulfonyl, aralkylsulfonyl, arylsulfonyl, heterocyclylsulfonyl, or heteroaralkylsulfonyl; f is a bond; and V is aryl.

Compounds of formula II in which e is N, f is a bond, and V is an optionally substituted alkyl, cycloalkyl, alkenyl, aralkyl, aralkenyl, heteroaralkyl, heteroaralkenyl, aryl, or heterocyclyl can be prepared by using the appropriate aldehyde. A particularly useful aldehyde is 2-furaldehyde, as the furyl group can be subsequently oxidized with $RuCl_3/NaIO_4$ and the resulting carboxyl group transformed to amides, esters, or thioesters, as described herein.

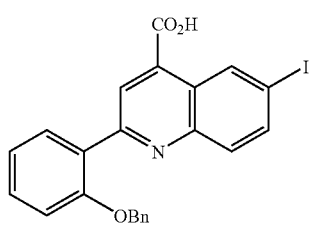

(XXIX)

Alternatively, 4-aminobenzonitrile can be converted to 6-cyano-4-hydroxyquinoline-2-carboxylic acid, methyl ester, by Michael addition to dimethylacetylene dicarboxylate, followed by thermal cycloaddition (see Jaen et al., *J. Med. Chem.* 38:4439–45, 1995). The resulting hydroxyquinoline is converted to 4-amino-6-cyanoquinoline-2-carboxylic acid, methyl ester by bromination with tetrabutylammonium bromide/phosphorus pentoxide (see Kato et al., *Tetrahedron Lett.* 42:4849–52, 2001), azide displacement of the bromo group (see Sashida et al., *Chem. Pharm. Bull.* 38:2919–2925, 1990), and sodium borohydride reduction of the azide to the amine (see Outt et al., *J. Org. Chem.* 63:5762–68, 1998). The amine can be acylated (or otherwise derivatized, such as, for example, to an amide), followed by subsequent conversion of the nitrile group to an amidine group as previously described for compounds of formula XXX to provide quinoline compounds of formula II, where V-f- is, for example, aminocarbonyl, alkylaminocarbonyl, dialkylaminocarbonyl, cycloalkylaminocarbonyl, aralkylaminocarbonyl, arylaminocarbonyl, heterocyclylaminocarbonyl, or heteroaralkylaminocarbonyl.

Quinazoline compounds of the formula II, where each of e and g is N, can be prepared via iodination of 2-aminobenzonitrile with N-iodosuccinimide, followed by acylation with 2-acetoxybenzoyl chloride to form compound XXXI. Cyclization of XXXI can be mediated with a variety of primary amines, followed by conversion of the quinazolyl iodide to the quinazolyl cyanide, under cross coupling conditions with a cyanide source. In one example, aminoquinazoline XXXII can be obtained by reacting compound XXXI with 4-methoxybenzylamine and subsequent conversion to the quinazolyl cyanide. After orthogonal protection of the phenol, benzylic cleavage can be affected under oxidative or acidic conditions and the resulting aminoquinazolines can be derivatized, for example, with electrophilic reagents to prepare amides, ureas, carbamates, or sulfonamides after phenol deprotection. Subsequent conversion of the nitrile group to an amidine group as previously described provides compounds of the formula II, where each of e and g is N, and T is $NR^{23}$; and B is acyl, cycloalkylcarbonyl, aroyl, heterocyclyloyl, cycloalkoxycarbonyl, aryloxycarbonyl, heterocyclyloxycarbonyl, heteroaralkyloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, heteroaralkylaminocarbonyl, alkylthiocarbonyl, cycloalkylthiocarbonyl, arylthiocarbonyl, aralkylthiocarbonyl, heterocyclylthiocarbonyl, heteroaralkylthiocarbonyl, aminothiocarbonyl, alkylaminothiocarbonyl, dialkylaminothiocarbonyl, cycloalkylaminothiocarbonyl, aralkylaminothiocarbonyl, arylaminothiocarbonyl, heterocyclylaminothiocarbonyl, heteroaralkylaminothiocarbonyl, alkylsulfonyl, cycloalkylsulfonyl, aralkylsulfonyl, arylsulfonyl, heterocyclylsulfonyl, or heteroaralkylsulfonyl; t is a bond; and V is 2-hydroxyphenyl. Compounds in which V is as described above can be prepared by the replacement in the synthesis of 2-acetoxybenzoyl chloride with other carbonyl chloride moieties.

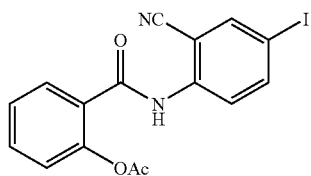

(XXXI)

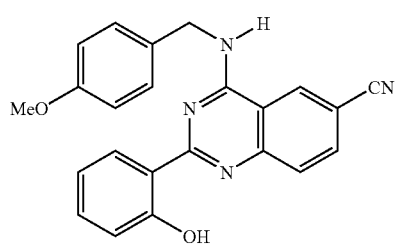

(XXXII)

For the quinazolines just described, it may be necessary to covert the nitrile to an appropriately protected amidine earlier in the synthesis, as Pinner conditions used for its conversion can result in partial hydrolysis of a B-T- substituent amide bond.

REPRESENTATIVE EXAMPLES

EXAMPLE 24

Synthesis of compounds of formula Ib,

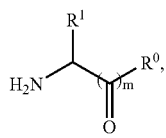

(Ib)

where m is 1, $R^0$ is 2-thiazole, and $R^1$ is 3-$N_g$-Mtr-guanidinopropyl.

(L)-Boc-NH-Arg(Mtr)OH (1.14 g, 2.34 mmol, 1.0 equiv), N,O-dimethylhydroxylamine hydrochloride (460 mg, 4.72 mmol, 2.0 equiv), and 1-hydroxybenzotriazole (HOBt, 350 mg, 2.59 mmol, 1.1 equiv) were dissolved in 25 mL THF at room temperature. N,N-Diisopropylethylamine (DIEA, 1.22 mL, 7.00 mmol, 3 equiv) was added via syringe, and the solution was stirred until it was homogeneous. 1-(3-Dimethylaminopropyl)-3-ethylcarbodiimide hydrochloride (EDCI, 470 mg, 2.45 mmol, 1.05 equiv) was added in one portion, and the reaction was allowed to stir at room temperature overnight. The reaction was diluted with ethyl acetate (150 mL), washed with 5% aqueous acetic acid (1×75 mL), sat. aq. NaHCO$_3$ (2×75 mL), water (1×75 mL), and brine (1×75 mL). The organic layer was dried with Na$_2$SO$_4$, filtered, and concentrated. The yield was 1.14 g (92%) for the desired Weinreb amide (XXXIII) as a white powder (MS: m/z 530.1, M+1, calculated mass: 529.3).

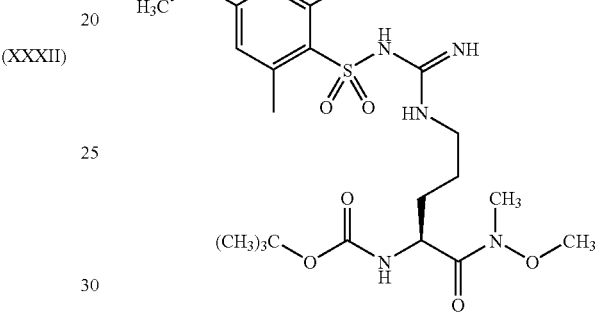

(XXXIII)

To thiazole (5.85 mL, 82.5 mmol) and TMEDA (11.4 mL, 75.6 mmol) in THF (180 mL) at −78° C. was added nBuLi in hexane (30 mL, 75 mmol, 2.5 M) at a rate that raised the internal temperature to −50° C. The reaction flask was placed in a dry ice/acetonitrile bath to give an internal temperature of −41° C. The reaction was stirred for 25 minutes and then cooled to −78° C. Compound XXXIII (9.54 g, 18 mmol) in THF (100 mL) was added to the reaction mixture and stirred for 45 minutes. The reaction was poured over a saturated aqueous ammonium chloride solution (600 mL), shaken vigorously, and then extracted with ethyl acetate (2×500 mL). The combined organic phases were washed with water (200 mL) and brine (200 mL), dried with sodium sulfate, filtered, and concentrated in vacuo. The residue was purified on a silica gel column, eluting with 75% ethyl acetate in hexane to 100% ethyl acetate to afford ketothiazole XXXIV (7.5 g, 75%) as a white foam (MS: m/z 554.1, M+1, calculated mass: 553.7).

The Boc-protected ketothiazole (4.0 g) was stirred in CH$_2$Cl$_2$ (30 mL) at 0° C., and trifluoroacetic acid (TFA, 10 mL) was added slowly. The ice bath was immediately removed after the addition of TFA. The resulting solution was stirred at room temperature for 1.5 hours, then a small amount of isopropyl alcohol (2 mL) was added. Concentration of the solution under reduced pressure gave the trifluoroacetic acid salt as a brown gum. The brown gum was triturated with diethyl ether. The ether supernatant was decanted, and the remaining solid was dried under vacuum to yield compound XXXV as a light yellow solid (4.01 g; 98% recovered yield, MS: m/z 454, M+1, calculated mass: 453.2).

(XXXIV)

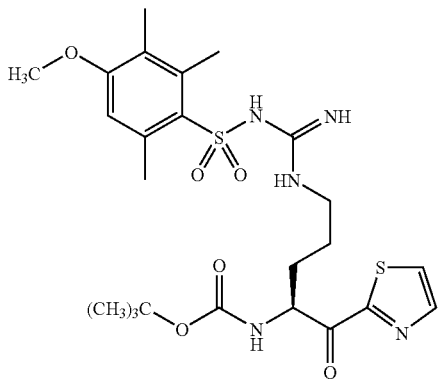

(XXXV)

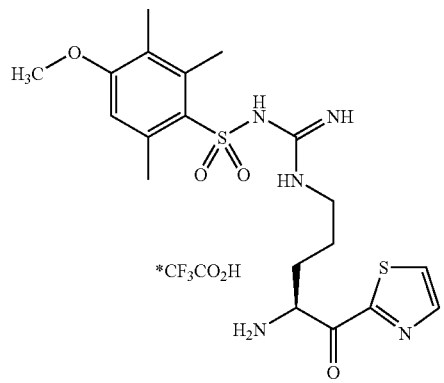

Alternatively, compounds of formula Ib, where m is 1, R[1] is 3-N$_g$-Mtr-guanidinopropyl, and R$^0$ is

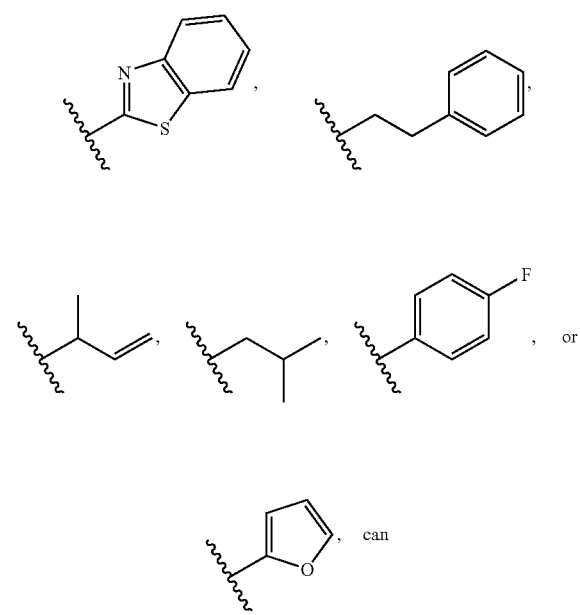

can also be prepared by reaction of compound XXXIII with the appropriate organometallic reagent. As described elsewhere herein, the furyl group can be further synthetically manipulated by an oxidation procedure to produce an alpha-keto moiety.

EXAMPLE 25

Solid-Phase Synthesis of Compounds of Formula Ia

The following representative procedure is for compounds of formula Ia in which R$^2$ is 2-butyl (i.e., the side chain of isoleucine), X is N, R$^3$ is H and A is 3,4-dichlorobenzylleucine. This procedure can be readily adapted for the synthesis of related compounds of the invention. Commercially available Fmoc-(L)-Ile Wang resin (100–200 mesh, 200 mg, 0.6 mmol/g, 0.12 mmol) was placed in a peptide synthesis vessel. N,N-Dimethylformamide (DMF, 2.0 mL) and then piperidine (500 ul) were added. The reaction mixture was shaken at room temperature for 2 hours. The resin was then filtered and washed four times with dry DMF.

A solution of Fmoc-Leu-OH (250 mg, 0.72 mmol, 6.0 equiv), 1-hydroxybenzotriazole (HOBt, 100 mg, 0.74 mmol, 6 equiv), and diisopropylcarbodiimide (DIC, 115 ul, 0.72 mmol, 6 equiv) in THF (2 mL) or DMF or DMF/CH$_2$Cl$_2$ (2/1, v/v) was added to the resin. The reaction mixture was shaken at room temperature overnight, filtered, and washed sequentially with CH$_2$Cl$_2$, DMF, CH$_3$OH, CH$_2$Cl$_2$, DMF, and CH$_2$Cl$_2$, and pumped to dryness under a high vacuum.

The resin was subjected to DMF (2 mL) and piperidine (500 ul) for 2 hours at room temperature, filtered, and washed four times with DMF to remove the N-terminal Fmoc-protecting group. In one example, the resin was treated with methylene chloride (2.25 mL) and 3,4-dichlorobenzylisocyanate (105 ul, 0.72 mmol, 6.0 equiv), and the reaction mixture was shaken overnight at room temperature to produce resin-supported 3,4-dichlorobenzylaminocarbonyl-Leu-Ile. As an alternative to the isocyanate approach, N-terminal ureas can be synthesized by reaction of the amine terminus of the resin with p-nitrophenylchloroformate (5–10 equiv) in the presence of diisopropylethylamine, followed by the addition of excess (5 equiv) of a primary or secondary amine. In one example, the resin supported Leu-Ile dipeptide was so treated with 4-Br-α-methyl benzylamine to provide resin-supported compound XXXVI.

(XXXVI)

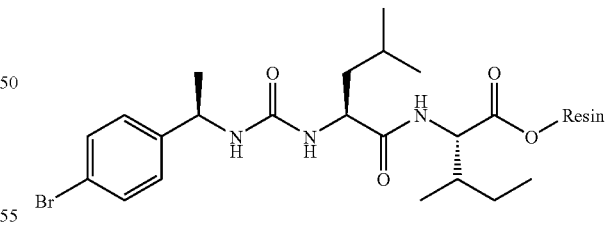

The resin was filtered and washed sequentially with CH$_2$Cl$_2$, DMF, CH$_3$OH, CH$_2$Cl$_2$, DMF, and CH$_2$Cl$_2$, and taken to dryness under a high vacuum. To the dry resin was added 50% trifluoroacetic acid/50% methylene chloride (3 mL total volume), and the reaction mixture was shaken at room temperature for 1.5 hours. The resin was filtered, washed with methylene chloride once, and the filtrate was concentrated in vacuo. Representative compounds of formula Ia, where X is N, R$^3$ is H, A is an α-amino acid AA$_2$, and R$^8$ is an aminocarbonyl substituent on the α-nitrogen of AA$_2$, are provided in Table 1 below.

TABLE 1

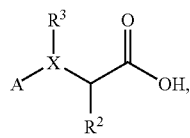

(Ia)

Compounds of formula Ia (X is N, $R^3$ is H, A is an α-amino acid $AA_2$, and $R^8$ is an aminocarbonyl substituent on the α-nitrogen of $AA_2$)

| $R^8$ | $AA_2$ | $R^2$ | Purity[a] | m/z | Calc MW |
|---|---|---|---|---|---|
| 3,4-dichlorobenzylaminocarbonyl | D-Leu | | 60.4 | 432.2 | 431.1 |
| 3,4-dichlorobenzylaminocarbonyl | Chg | | 13.9 | 458.2 | 457.2 |
| 3,4-dichlorobenzylaminocarbonyl | 3-Pal | | 92.1 | 467.3 | 466.1 |
| 3,4-dichlorobenzylaminocarbonyl | Ile | | 50.7 | 432.2 | 431.1 |
| 2,4-dichlorobenzylaminocarbonyl | 3-Pal | | 88.2 | 467.3 | 466.1 |
| 2,4-dichlorobenzylaminocarbonyl | Ile | | 40.6 | 432.2 | 431.1 |
| α-methyl-4-bromobenzylaminocarbonyl | D-Leu | | 78.3[b] | 456.2 | 455.1 |
| α-methyl-4-bromobenzylaminocarbonyl | Chg | | 76.3[b] | 482.2 | 481.2 |
| α-methyl-4-bromobenzylaminocarbonyl | 3-Pal | | 95.2[b] | 491.3 | 490.1 |
| α-methyl-4-bromobenzylaminocarbonyl | Ile | | 60.8[b] | 456.2 | 455.1 |
| (R)-α-methyl-4-bromobenzylaminocarbonyl | 3-Pal | | 84.0 | 491.3 | 490.1 |
| (S)-α-methyl-4-bromobenzylaminocarbonyl | 3-Pal | | 77.9 | 491.3 | 490.1 |
| 3,4-dichlorobenzylaminocarbonyl | Leu | | 18.5 | 446.1 | 445.2 |

TABLE 1-continued (Ia)

Compounds of formula Ia (X is N, $R^3$ is H, A is an α-amino acid $AA_2$, and $R^8$ is an aminocarbonyl substituent on the α-nitrogen of $AA_2$)

| $R^8$ | $AA_2$ | $R^2$ | Purity[a] | m/z | Calc MW |
|---|---|---|---|---|---|
| 3,4-dichlorobenzylaminocarbonyl | Leu | benzyl | 56.0 | 480.1 | 479.1 |
| 3,4-dichlorobenzylaminocarbonyl | Leu | isopropyl | 42.9 | 432.2 | 431.1 |
| indanylaminocarbonyl | Leu | isopropyl | 58.6 | 390.2 | 389.2 |
| (R)-α-methyl-4-bromobenzylaminocarbonyl | Tyr | isopropyl | 72.5 | 506.3 | 505.1 |
| (R)-α-methyl-4-bromobenzylaminocarbonyl | Cit | isopropyl | 30.0 | 500.2 | 499.1 |
| (R)-α-methyl-4-bromobenzylaminocarbonyl | Asn | isopropyl | 35.0 | 457.0 | 456.1 |

[a]The purity percentage was determined by HPLC analysis using a C18 (3 × 30 mm, 3 μ) column with AcCN:$H_2O$ (0.1 %TFA) as mobile phase.
[b]The combined purity percentages of the two α-methyl diastereomeric isomers which were not separated for subsequent amide bond-formation.

Additional compounds of formula Ia can be prepared in which X is N, $R^3$ is H, A is an α-amino acid $AA_2$, and $R^8$ is an aminocarbonyl substituent acyl, aroyl, heteroaroyl, or alkoxycarbonyl moiety on the α-nitrogen of $AA_2$. These compounds can be prepared by reaction of the N-terminal amine of the resin-supported amino acid as described previously when $R^8$ is an aminocarbonyl substituent, or with the appropriate carbonyl chloride compounds, chloroformates, or by reacting the N-terminal amine with the appropriate carboxylic acid in a coupling step. Compounds prepared in this manner include, but are not limited to, compounds of formula Ia wherein X is N, $R^3$ is H, $AA_2$ is Leu, Phe, Val, Ala, cyclohexylglycine (Chg), Arg, Asn, 3-pyridylalanine (3-Pal), 4-pyridylalanine (4-Pal), Trp, Ile, Lys, Glu, His, or Gln, and $R^8$ is a substituent on the α-nitrogen of $AA_2$ and can be

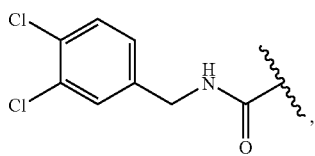

-continued

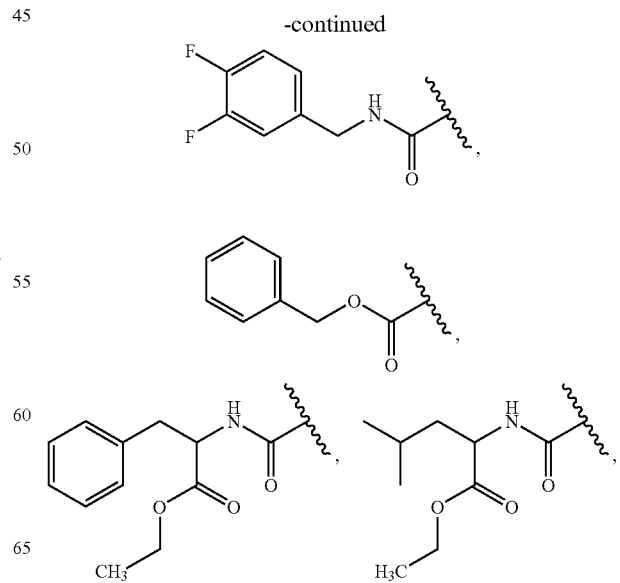

-continued

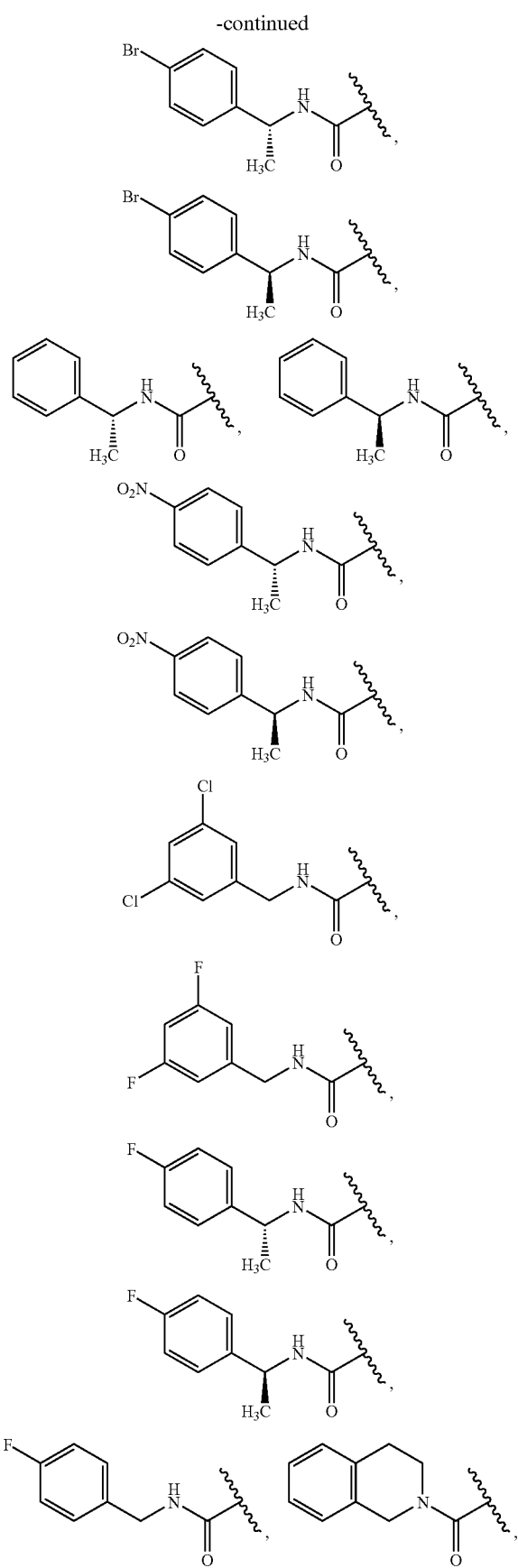

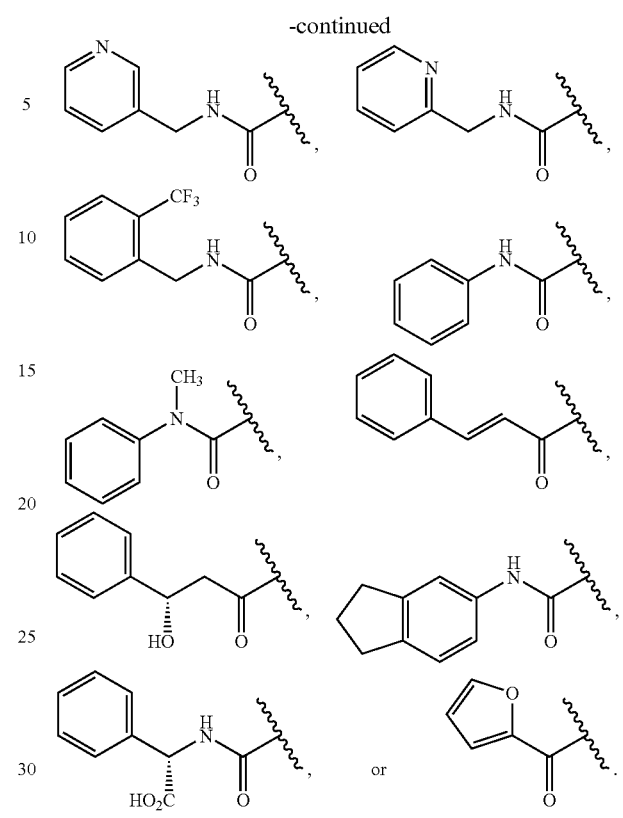

Compounds of formula Ia can be prepared in which A is an aminocarbonyl substituent (i.e., the step in which $AA_2$ is coupled to the resin-supported amino acid is omitted and an N-terminal urea is formed directly to the alpha amine of the amino acid bearing the $R^2$ side-chain by methods previously described herein). Compounds prepared in this manner include compounds of formula Ia in which X is N, $R^2$ is isopropyl, $R^3$ is H, and A is

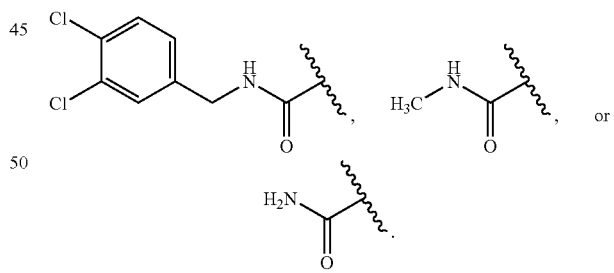

Compounds of formula Ia can also be prepared in which A is an acyl, such as the substituents selected from the following group:

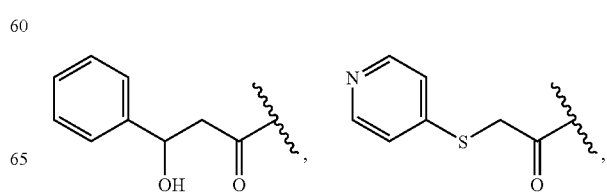

-continued

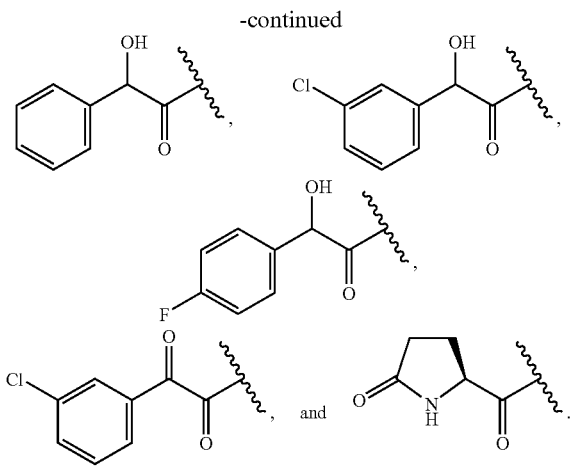

Compounds of formula Ia, where X is N, $R^3$ is H, A is α-amino acid $AA_2$, and $R^8$ is a sulfonyl substituent on the α-nitrogen of $AA_2$ are prepared in a similar fashion, except the penultimate step before removal of the peptide from the resin with TFA involves treatment of the N-terminal amine with a sulfonyl chloride in the presence of a base. In one example, resin-supported D-cyclohexylglycine-leucine (0.20 mmol) was treated with (methyl-3-benzoate)methanesulfonyl chloride (304 mg, 1.2 mmol) in 3 mL of 2,6-lutidine/$CH_2Cl_2$ (1:9). The resulting slurry was agitated for 3 h at room temperature. The resin was filtered and washed with DMF/MeOH (4×), $CH_2Cl_2$ (2×), and then dried under vacuum overnight. After swelling in 3 mL of $CH_2Cl_2$, the solvent was drained and the resin treated with 50% TFA/DCM (5 mL) at room temperature for 2 hrs. The resin was filtered and washed with $CH_2Cl_2$ (2×). The collected cleavage product was combined with washes and mixed with 0.3 mL of isopropanol. After concentration of solvents in vacuo, 0.89 g of a yellow residue was collected (LCMS: m/z=483.1, M+1). Representative compounds of formula Ia, where X is N, $R^3$ is H, A is α-amino acid $AA_2$, and $R^8$ is a sulfonyl substituent on the α-nitrogen of $AA_2$, are provided in Table 2.

TABLE 2

Compounds of formula Ia (X is N, $R^3$ is H, A is α-amino acid $AA_2$, and R is a sulfonyl substituent on the α-nitrogen of $AA_2$)

| $R^8$ | $AA_2$ | $R^2$ | Purity[a] | m/z | Calc MW |
|---|---|---|---|---|---|
| α-toluenesulfonyl | D-Chg | isopropyl | 52.5 | 425.1 | 424.6 |
| α-toluenesulfonyl | Chg | isopropyl | 21.5 | 425.1 | 424.6 |
| α-toluenesulfonyl | D-3-Pal | isopropyl | 54.7 | 434.3 | 433.5 |
| α-toluenesulfonyl | 3-Pal | isopropyl | 62.4 | 434.3 | 433.5 |
| (methyl-3-benzoate)methanesulfonyl | D-Chg | isopropyl | 70.9 | 483.1 | 482.6 |
| (methyl-3-benzoate)methanesulfonyl | Chg | isopropyl | 57.2 | 483.1 | 482.6 |
| 2-nitro-α-toluenesulfonyl | D-Chg | isopropyl | 73.6 | 470.1 | 469.6 |
| 1-propanesulfonyl | D-Chg | isopropyl | 72.9 | 377.1 | 376.5 |
| 3-chloropropanesulfonyl | D-Chg | isopropyl | 68.8 | 411.1 | 411.0 |
| (methyl-3-benzoate)methanesulfonyl | D-Phg | isopropyl | 37.6 | 477.1 | 476.5 |

[a]The purity was determined by HPLC analysis without purification

EXAMPLE 26

Exemplary Coupling Reactions of Compounds of Formula Ia to Compounds of Formula Ib The following procedure is reprensentative of the condensation of carboxylic acids of formula Ia with amine compounds of formula Ib.

3,4-dichlorobenzylcarbamyl-Leu-Phe-OH (17 mg, 0.036 mmol, 1.0 equiv) and HOBt (10.5 mg, 0.078 mmol, 1.1 equiv) were dissolved in 1.0 mL THF at room temperature. DIEA (37 ul, 0.213 mmol, 3 equiv) was added via syringe, and the solution was stirred until it was homogeneous. 1-(3-Dimethylaminopropyl)-3-ethylcarbodiimide hydrochloride (EDCI, 14.5 mg, 0.075 mmol, 1.05 equiv) was then added in one portion, and the reaction was allowed to stir at room temperature. The Mtr-protected Arg monomer amine prepared in Example 24 (compound XXXV, 1.0–2.0 equiv.) was added and the reaction stirred for 3 hours. The reaction mixture was diluted with ethyl acetate (2 mL), washed with 5% aqueous acetic acid (1 mL), saturated aqueous NaHCO$_3$ (2×1 mL), water (1 mL), and brine (1 mL). The organic layer was dried over Na$_2$SO$_4$, filtered, and concentrated and the resulting residue (compound XXXVII) used in the following deprotection reaction (Example 27) without further purification.

(XXXVII)

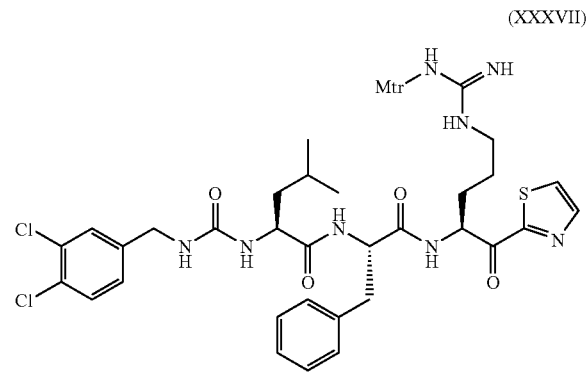

EXAMPLE 27

Synthesis of Exemplary Compounds of the Formula I (m=1)

The following procedure is representative of the Mtr-deprotection of compounds produced by the procedure of Example 26. Compound XXXVII (10 mg, 0.011 mmol) was dissolved in thioanisole (25 ul) and trifluoroacetic acid (475 ul). The reaction was shaken at room temperature in a sealed vial for 4 hours. The liquid was removed in vacuo overnight, and the residue was triturated with Et$_2$O (2×), then dissolved in 50% acetonitrile/50% water and the product purified by reverse phase preparative HPLC. Representative compounds of formula I, where X is N, R$^3$ is H, R$^1$ is 3-guanidinopropyl, R$^0$ is 2-thiazole, and A is α-amino acid AA$_2$, wherein R$^8$ is a substituent on the α-nitrogen of AA$_2$, are provided in Table 3a.

TABLE 3a

Compounds of formula I (X is N, R$^3$ is H, R$^1$ is 3-guanidinopropyl, R$^0$ is 2-thiazole, and A is α-amino acid AA$_2$, wherein R$^8$ is a substituent on the α-nitrogen of AA$_2$)

| Cmpd. No. | R$^8$ | AA$_2$ | R$^2$ | Purity[a] | m/z | Calc MW |
|---|---|---|---|---|---|---|
| 1 | 3,4-dichlorobenzylaminocarbonyl | D-Leu | | 97.7 | 655.3 | 654.2 |
| 2 | 3,4-dichlorobenzylaminocarbonyl | Chg | | 93.3 | 681.2 | 680.2 |
| 3 | 3,4-dichlorobenzylaminocarbonyl | 3-Pal | | 90.0 | 690.2 | 689.2 |
| 4 | 3,4-dichlorobenzylaminocarbonyl | Ile | | 100.0 | 655.2 | 654.2 |
| 5 | 3,4-dichlorobenzylaminocarbonyl | Phe | | — | — | — |
| 6 | 3,4-dichlorobenzylaminocarbonyl | Val | | — | — | — |
| 7 | 3,4-dichlorobenzylaminocarbonyl | Leu | | 18.5 | 669.6 | 668.2 |
| 8 | 3,4-dichlorobenzylaminocarbonyl | Leu | | 56.0 | 703.5 | 702.2 |

TABLE 3a-continued

Compounds of formula I (X is N, $R^3$ is H, $R^1$ is 3-guanidinopropyl, $R^0$ is 2-thiazole, and A is α-amino acid $AA_2$, wherein $R^8$ is a substituent on the α-nitrogen of $AA_2$)

| Cmpd. No. | $R^8$ | $AA_2$ | $R^2$ | Purity[a] | m/z | Calc MW |
|---|---|---|---|---|---|---|
| 9 | 3,4-dichlorobenzylaminocarbonyl | Leu | 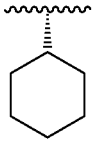 | — | — | — |
| 10 | 3,4-dichlorobenzylaminocarbonyl | Leu |  | 42.9 | — | 654.2 |
| 11 | 3,4-dichlorobenzylaminocarbonyl | Leu |  | — | — | — |
| 12 | 3,4-dichlorobenzylaminocarbonyl | Asn | 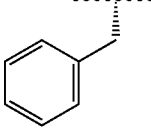 | — | — | — |
| 13 | 3,4-dichlorobenzylaminocarbonyl | Leu | 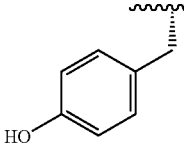 | — | — | — |
| 14 | 2,4-dichlorobenzylaminocarbonyl | 3-Pal |  | 95.7 | 690.4 | 689.2 |
| 15 | 2,4-dichlorobenzylaminocarbonyl | Ile |  | 94.0 | 655.2 | 654.2 |
| 16 | 2,4-dichlorobenzylaminocarbonyl | Ala |  | — | — | — |
| 17 | 2,4-dichlorobenzylaminocarbonyl | Leu |  | — | — | — |
| 18 | α-methyl-4-bromobenzylaminocarbonyl | D-Leu |  | 94.8[b] | 679.2 | 678.2 |
| 19 | α-methyl-4-bromobenzylaminocarbonyl | Chg |  | 98.4[b] | 705.2 | 704.3 |
| 20 | α-methyl-4-bromobenzylaminocarbonyl | 3-Pal |  | 93.4[b] | 714.2 | 713.2 |
| 21 | α-methyl-4-bromobenzylaminocarbonyl | Ile |  | 94.6[b] | 679.2 | 678.2 |

TABLE 3a-continued

Compounds of formula I (X is N, R$^3$ is H, R$^1$ is 3-guanidinopropyl, R$^0$ is 2-thiazole, and A is α-amino acid AA$_2$, wherein R$^8$ is a substituent on the α-nitrogen of AA$_2$)

| Cmpd. No. | R$^8$ | AA$_2$ | R$^2$ | Purity$^a$ | m/z | Calc MW |
|---|---|---|---|---|---|---|
| 22 | (R)-α-methyl-4-bromobenzylaminocarbonyl | 3-Pal |  | 96.5 | 714.5 | 713.2 |
| 23 | (R)-α-methyl-4-bromobenzylaminocarbonyl | Tyr |  | 97.3 | 655.3 | 654.2 |
| 24 | (R)-α-methyl-4-bromobenzylaminocarbonyl | Cit |  | 96.6 | 681.2 | 680.2 |
| 25 | (R)-α-methyl-4-bromobenzylaminocarbonyl | Asn |  | 95.0 | 690.2 | 689.2 |
| 26 | (R)-α-methyl-4-bromobenzylaminocarbonyl | 4-Pal |  | — | — | — |
| 27 | (R)-α-methyl-4-bromobenzylaminocarbonyl | 4-Pal-N-oxide |  | — | — | — |
| 28 | (R)-α-methyl-4-bromobenzylaminocarbonyl | Chg |  | — | — | — |
| 29 | (R)-α-methyl-4-bromobenzylaminocarbonyl | Leu |  | — | — | — |
| 30 | (R)-α-methyl-4-bromobenzylaminocarbonyl | Arg |  | — | — | — |
| 31 | (R)-α-methyl-4-bromobenzylaminocarbonyl | Trp |  | — | — | — |
| 32 | (R)-α-methyl-4-bromobenzylaminocarbonyl | Ile |  | — | — | — |
| 33 | (R)-α-methyl-4-bromobenzylaminocarbonyl | Val |  | — | — | — |
| 34 | (R)-α-methyl-4-bromobenzylaminocarbonyl | Lys |  | — | — | — |
| 35 | (R)-α-methyl-4-bromobenzylaminocarbonyl | Glu |  | — | — | — |
| 36 | (R)-α-methyl-4-bromobenzylaminocarbonyl | His |  | — | — | — |

TABLE 3a-continued

Compounds of formula I (X is N, R³ is H, R¹ is 3-guanidinopropyl, R⁰ is 2-thiazole, and A is α-amino acid AA₂, wherein R⁸ is a substituent on the α-nitrogen of AA₂)

| Cmpd. No. | R⁸ | AA₂ | R² | Purity[a] | m/z | Calc MW |
|---|---|---|---|---|---|---|
| 37 | (R)-α-methyl-4-bromobenzylaminocarbonyl | Gln |  | — | — | — |
| 38 | (R)-α-methyl-4-bromobenzylaminocarbonyl | Phe |  | — | — | — |
| 39 | (R)-α-methyl-4-bromobenzylaminocarbonyl | Phe |  | — | — | — |
| 40 | (R)-α-methyl-4-bromobenzylaminocarbonyl | Chg |  | — | — | — |
| 41 | (S)-α-methyl-4-bromobenzylaminocarbonyl | 3-Pal |  | 97.4 | 714.5 | 713.2 |
| 42 | (S)-α-methyl-4-bromobenzylaminocarbonyl | Leu |  | — | — | — |
| 43 | (S)-α-methyl-4-bromobenzylaminocarbonyl | Chg |  | — | — | — |
| 44 | (S)-α-methylbenzylaminocarbonyl | Leu |  | — | — | — |
| 45 | (R)-α-methylbenzylaminocarbonyl | Leu |  | — | — | — |
| 46 | (R)-α-methyl-4-nitrobenzylaminocarbonyl | Leu |  | — | — | — |
| 47 | (S)-α-methyl-4-nitrobenzylaminocarbonyl | Leu |  | — | — | — |
| 48 | indanylaminocarbonyl | Leu |  | 58.6 | — | 612.3 |
| 49 | (R)-α-methyl-4-fluorobenzylaminocarbonyl | Leu | — | — | — | |

TABLE 3a-continued

Compounds of formula I (X is N, R³ is H, R¹ is 3-guanidinopropyl, R⁰ is 2-thiazole, and A is α-amino acid AA₂, wherein R⁸ is a substituent on the α-nitrogen of AA₂)

| Cmpd. No. | R⁸ | AA₂ | R² | Purity[a] | m/z | Calc MW |
|---|---|---|---|---|---|---|
| 50 | 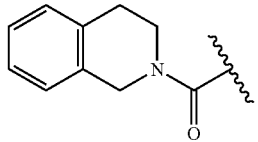 | 3-Pal |  | — | — | — |
| 51 | 3,4-difluorobenzylaminocarbonyl | 3-Pal |  | — | — | — |
| 52 | 3,5-difluorobenzylaminocarbonyl | Leu | 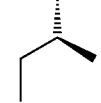 | — | — | — |
| 53 | 2-trifluoromethyl-benzylaminocarbonyl | Leu | 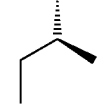 | — | — | — |
| 54 | 4-fluorobenzylaminocarbonyl | Leu |  | — | — | — |
| 55 | indanylaminocarbonyl | Leu |  | — | — | — |
| 56 | benzyloxycarbonyl | Leu |  | — | — | — |
| 57 | 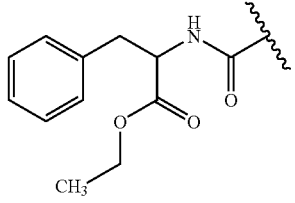 | Phe |  | — | — | — |
| 58 | 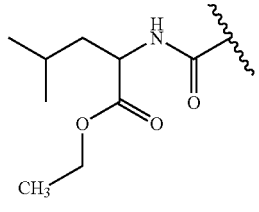 | Phe |  | — | — | — |
| 59 | phenylaminocarbonyl | Phe |  | — | — | — |
| 60 | N-phenyl-N-methylaminocarbonyl | Leu |  | — | — | — |

TABLE 3a-continued

Compounds of formula I (X is N, $R^3$ is H, $R^1$ is 3-guanidinopropyl, $R^0$ is 2-thiazole, and A is α-amino acid $AA_2$, wherein $R^8$ is a substituent on the α-nitrogen of $AA_2$)

| Cmpd. No. | $R^8$ | $AA_2$ | $R^2$ | Purity[a] | m/z | Calc MW |
|---|---|---|---|---|---|---|
| 61 | (phenylglycine amide structure with HO2C) | Leu | (isopropyl) | — | — | — |
| 62 | (cinnamoyl structure) | Leu | (isopropyl) | — | — | — |
| 63 | (3-hydroxy-3-phenylpropanoyl structure) | 3-Pal | (isopropyl) | — | — | — |
| 64 | (3-pyridylmethylcarbamoyl structure) | 3-Pal | (isopropyl) | — | — | — |
| 65 | (2-pyridylmethylacetamide structure) | 3-Pal | (isopropyl) | — | — | — |
| 66 | (2-furoyl structure) | Phe | (isopropyl) | — | — | — |
| 67 | α-toluenesulfonyl | D-Chg | (isobutyl) | 90.1 | 648.5 | 647.9 |
| 68 | (methyl-3-benzoate)methanesulfonyl | D-Chg | (isobutyl) | 92.3 | 706.5 | 705.9 |
| 69 | (methyl-3-benzoate)methanesulfonyl | Chg | (isobutyl) | 71.1 | 706.5 | 705.9 |

TABLE 3a-continued

Compounds of formula I (X is N, $R^3$ is H, $R^1$ is 3-guanidinopropyl, $R^0$ is 2-thiazole, and A is α-amino acid $AA_2$, wherein $R^8$ is a substituent on the α-nitrogen of $AA_2$)

| Cmpd. No. | $R^8$ | $AA_2$ | $R^2$ | Purity[a] | m/z | Calc MW |
|---|---|---|---|---|---|---|
| 70 | 3-carboxyl-α-toluenesulfonyl[c] | D-Chg | | 85.3 | 692.6 | 691.9 |
| 71 | 2-nitro-α-toluenesulfonyl | D-Chg | | 96.9 | 693.4 | 692.9 |
| 72 | 1-propanesulfonyl | D-Chg | | 91.5 | 600.5 | 599.8 |
| 73 | 3-chloropropanesulfonyl | D-Chg | | 91.1 | 634.5 | 634.3 |
| 74 | (methyl-3-benzoate)methanesulfonyl | D-Phg | | 95.0 | 700.4 | 699.8 |
| 75 | 3-carboxyl-α-toluenesulfonyl[c] | D-Phg | | 82.6 | 686.4 | 685.8 |
| 76 | 2,4,5-trichlorobenzylsulfonyl | Phe | | — | — | — |
| 77 | 2,6-difluorobenzylaminocarbonyl | Leu | | — | — | — |

[a] The purity percentage was determined by HPLC analysis using a C18 (3 × 30 mm, 3 μ) column with AcCN:H$_2$O (0.1% TFA) as mobile phase.
[b] The purity of a single α-methyl isomer of unknown configuration.
[c] Prior to the Mtr deprotection step, the benzoate ester was saponified (NaOH, THF/water).

Additional compounds of the invention formed from the reaction of compounds of formula Ia with those of formula Ib, followed by deprotection, include those of formula I where m is 1, $R^0$ is 2-thiazole, $R^1$ is 3-guanidinopropyl, X is N, $R^2$ is isopropyl, $R^3$ is H, and A is selected from the following group:

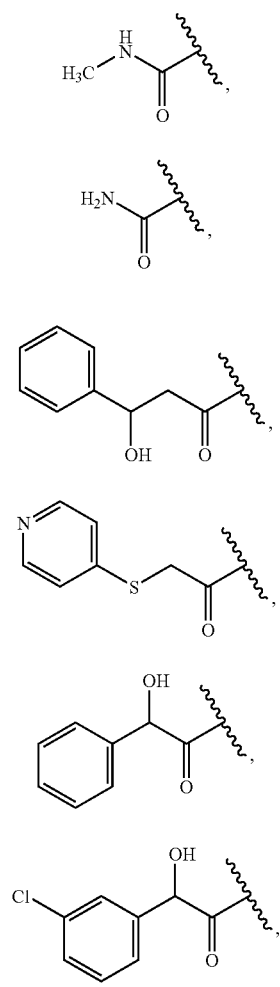
(78), (79), (80), (81), (82), (83)

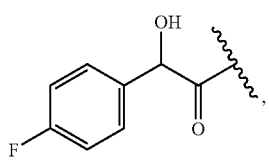
(84)

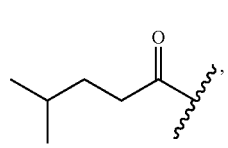
(85)

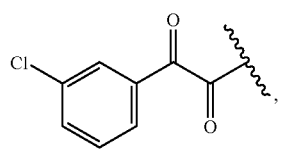
(86)

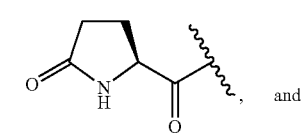
(87), and

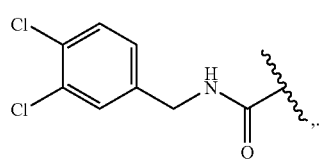
(88)

Other compounds of the invention formed from the reaction of compounds of formula Ia with those of formula Ib, followed by further-functional group synthetic manipulation and/or deprotection include those of formula I, where X is N, $R^3$ is H, m is 1, $R^1$ is 3-guanidinopropyl, and A is α-amino acid $AA_2$, wherein $R^8$ is a substituent on the α-nitrogen of $AA_2$, where $R^8$ $AA_2$, $R^2$, and $R^0$ are as shown in Table 3b.

TABLE 3b

Compounds of formula I (X is N, $R^3$ is H, m is 1, $R^1$ is 3-guanidinopropyl, and A is α-amino acid $AA_2$, $R^8$ is a substituent on the α-nitrogen of $AA_2$)

| Cmpd. No. | $R^8$ | $AA_2$ | $R^2$ | $R^0$ |
|---|---|---|---|---|
| 89 | (R)-α-methyl-4-bromobenzylaminocarbonyl | 3-Pal | isopropyl | —$CONH_2$ |
| 90 | (R)-α-methyl-4-bromobenzylaminocarbonyl | Phe | isopropyl | —$CONH_2$ |

TABLE 3b-continued

Compounds of formula I (X is N, $R^3$ is H, m is 1, $R^1$ is 3-guanidinopropyl, and A is α-amino acid $AA_2$, $R^8$ is a substituent on the α-nitrogen of $AA_2$)

| Cmpd. No. | $R^8$ | $AA_2$ | $R^2$ | $R^0$ |
|---|---|---|---|---|
| 91 | (R)-α-methyl-4-bromobenzylaminocarbonyl | 3-Pal | | |
| 92 | (R)-α-methyl-4-bromobenzylaminocarbonyl | Phe | | |
| 93 | (R)-α-methyl-4-bromobenzylaminocarbonyl | Leu | | |
| 94 | (R)-α-methyl-4-bromobenzylaminocarbonyl | 3-Pal | | |
| 95 | (R)-α-methyl-4-bromobenzylaminocarbonyl | Leu | | |
| 96 | (R)-α-methyl-4-bromobenzylaminocarbonyl | 3-Pal | | |
| 97 | (R)-α-methyl-4-bromobenzylaminocarbonyl | 3-Pal | | |
| 98 | (R)-α-methyl-4-bromobenzylaminocarbonyl | Leu | | |
| 99 | (R)-α-methyl-4-bromobenzylaminocarbonyl | Leu | | |
| 100 | (R)-α-methyl-4-bromobenzylaminocarbonyl | Leu | | |

TABLE 3b-continued

Compounds of formula I (X is N, R³ is H, m is 1, R¹ is 3-guanidinopropyl, and A is α-amino acid AA₂, R⁸ is a substituent on the α-nitrogen of AA₂)

| Cmpd. No. | R⁸ | AA₂ | R² | R⁰ |
|---|---|---|---|---|
| 101 | (R)-α-methyl-4-bromobenzylaminocarbonyl | Leu | isopropyl | 1,3-benzothiazol-2-yl |
| 102 | (R)-α-methyl-4-bromobenzylaminocarbonyl | 3-Pal | isopropyl | 1,3-benzothiazol-2-yl |
| 103 | (R)-α-methyl-4-bromobenzylaminocarbonyl | Leu | isopropyl | 4-methyl-5-(2-hydroxyethyl)thiazol-2-yl |
| 104 | (R)-α-methyl-4-bromobenzylaminocarbonyl | 3-Pal | isopropyl | 4-methyl-5-(2-hydroxyethyl)thiazol-2-yl |
| 105 | (R)-α-methyl-4-bromobenzylaminocarbonyl | Leu | isopropyl | 5-methylthiazol-2-yl |
| 106 | (R)-α-methyl-4-bromobenzylaminocarbonyl | 3-Pal | isopropyl | 5-methylthiazol-2-yl |
| 107 | (R)-α-methyl-4-bromobenzylaminocarbonyl | Leu | isopropyl | 4-methylthiazol-2-yl |
| 108 | (R)-α-methyl-4-bromobenzylaminocarbonyl | 3-Pal | isopropyl | 4-methylthiazol-2-yl |
| 109 | (R)-α-methyl-4-bromobenzylaminocarbonyl | Leu | isopropyl | 1-methylimidazol-2-yl |

TABLE 3b-continued

Compounds of formula I (X is N, $R^3$ is H, m is 1, $R^1$ is 3-guanidinopropyl, and A is α-amino acid $AA_2$, $R^8$ is a substituent on the α-nitrogen of $AA_2$)

| Cmpd. No. | $R^8$ | $AA_2$ | $R^2$ | $R^0$ |
|---|---|---|---|---|
| 110 | (R)-α-methyl-4-bromobenzylaminocarbonyl | 3-Pal | 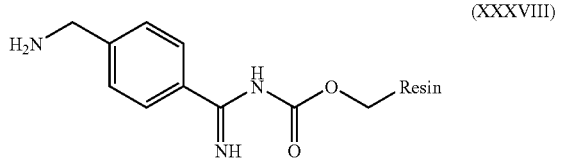 | 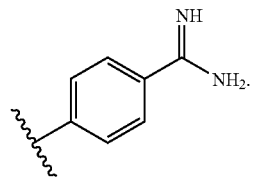 |

EXAMPLE 28

Synthesis of Exemplary Compounds of the Formula I (m=0)

The compounds of formula I where m is 0 can also be prepared by either using solid-phase approaches or solution phase approaches. In one example, resin supported amine XXXVIII, is prepared by treating x-bromo-p-tolunitrile with $NaN_3$ and $Bu_4NCl$ to form the corresponding α-azido-p-tolunitrile, followed by conversion of the nitrile group to the amidine group employing typical Pinner and aminolysis conditions, as described herein. The p-azidomethyl benzamidine thus produced is attached to an activated p-nitrophenylcarbonate Wang resin, followed by reduction of the azide group to an amine by $SnCl_2$ to provide compound XXXVIII.

(XXXVIII)

Reaction of this amine with a compound of formula Ia under amide bond forming conditions, as described herein, produces compounds of formula I, where m is 0, $R^1$ is H, and $R^0$ is Alternatively, compounds of formula I where m is 0 and $R^1$ is H can be prepared in solution by condensing an amine, such as 4-cyanobenzylamine, to compounds of the formula Ia, followed by conversion of the cyano group to an amidine moiety, as described herein. Representative compounds of formula I, where m is 0, $R^1$ is H, X is N, $R^3$ is H, A is α-amino acid $AA_2$, and $R^8$ is a substituent on the α-nitrogen of $AA_2$, are given in Table 5.

TABLE 5

Compounds of the formula I (m is 0, $R^1$ is H, X is N, $R^3$ is H, A is α-amino acid $AA_2$, and $R^8$ is a substituent on the α-nitrogen of $AA_2$)

| Cmpd. No. | $R^8$ | $AA_2$ | $R^2$ | Purity[a] | m/z | Calc MW |
|---|---|---|---|---|---|---|
| 111 | α-toluenesulfonyl | D-Chg | | 94.6 | 556.4 | 555.7 |
| 112 | α-toluenesulfonyl | Chg | | 97.8 | 556.4 | 555.7 |
| 113 | α-toluenesulfonyl | D-3-Pal | | 81.9 | 565.4 | 564.7 |

TABLE 5-continued

Compounds of the formula I (m is 0, $R^1$ is H, X is N, $R^3$ is H, A is α-amino acid $AA_2$, and $R^8$ is a substituent on the α-nitrogen of $AA_2$)

| Cmpd. No. | $R^8$ | $AA_2$ | $R^2$ | Purity[a] | m/z | Calc MW |
|---|---|---|---|---|---|---|
| 114 | α-toluenesulfonyl | 3-Pal | isopropyl | 96.9 | 565.4 | 564.7 |
| 115 | 3-carboxyl-α-toluenesulfonyl[b] | D-Chg | isopropyl | 94.5 | 600.5 | 599.7 |
| 116 | 3-carboxyl-α-toluenesulfonyl[b] | Chg | isopropyl | 96.7 | 600.5 | 599.7 |
| 117 | (methyl-3-benzoate)methanesulfonyl | D-Chg | isopropyl | 95.7 | 614.5 | 613.8 |

[a] The purity was determined by HPLC analysis after reverse phase HPLC purification.
[b] The benzoate ester can be saponified on the resin prior to cleavage, or as a final step after amide bond formation (NaOH, THF/water).

EXAMPLE 29

Synthesis of Exemplary Compounds of Formula I (m is 1, A is Acyl)

The following procedure is representative of the preparation of compounds of formula I where m is 1, X is N, $R^3$ is H, and A is acyl. Valine methyl ester (HCl salt) (176 mg, 1.05 mmol) was dissolved in 6 mL of methylene chloride at room temperature. (R)-m-chloro mandelic acid (187 mg, 1.00 mmol), 261 ul of diisopropylethylamine (1.50 mmol), 162 mg of hydroxybenzotriazole hydrate (1.20 mmol), and 231 mg of the amide bond-forming reagent, EDC (1.20 mmol) were added sequentially. The mixture was maintained at room temperature for 6 hours and diluted with water (10 mL) and ethyl acetate (10 mL). The water layer was extracted with 2×10 mL portions of ethyl acetate. The combined organic layers were washed with 0.1N HCl and brine. Concentration of the organic layer in vacuo and flash chromatographic purification of the residue on silica gel using a gradient (1:2 ethyl acetate/hexane, up to 100% ethyl acetate) gave compound XXXIX (255 mg, 85% yld., MS: m/z 300, M+1).

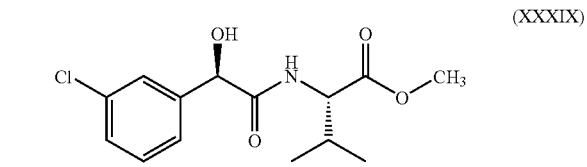

(XXXIX)

A portion of this ester (121 mg, 0.42 mmol) was dissolved in 3 mL of a 1:1:1 mixture of tetrahydrofuran/methanol/water. Lithium hydroxide (101 mg, 4.2 mmol) was added. After 2 hours at room temperature, 10 mL of 0.5N HCl was added dropwise, followed by 10 mL of ethyl acetate. The aqueous layer was separated and washed with 2×10 mL portions of ethyl acetate. The combined organic layers were washed with brine, dried over sodium sulfate, and concentrated in vacuo to give the pure crude carboxylic acid which was used without further purification (98 mg, 95% yld., MS: m/z 286, M+1).

This carboxylic acid (a compound of formula Ia) was converted to an arginine-ketothiazole (a compound of formula I) by amide bond-forming to compound XXXV and subsequent Mtr-deprotection as previously described herein (product MS: m/z 509, M+1). Representative compounds of formula I, where m is 1, X is N, $R^3$ is H, $R^2$ is isopropyl, $R^1$ is 3-guanidinopropyl, $R^0$ is 2-thiazole, A is $R^8$ ($R^8$-$AA_2$, where $AA_2$ is a covalent bond and $R^8$ is acyl) are given in Table 6.

TABLE 6

Compounds of formula I (X is N, $R^3$ is H, R is isopropyl, $R^1$ is 3-guanidinopropyl, $R^0$ is 2-thiazole, and A is $R^8$)

| Cmpd. No. | $R^8$ | Purity[a] | m/z | Calc MW |
|---|---|---|---|---|
| 118 | (R)-2-(3-Chlorophenyl)-2-hydroxy-acetyl | 90 | 509.2 | 508.2 |
| 119 | (R)-2-(2-Chlorophenyl)-2-hydroxy-acetyl | 95 | 509.4 | 508.2 |
| 120 | (R)-2-Hydroxy-2-phenyl-acetyl | 95 | 475.3 | 474.2 |
| 121 | (S)-2-Hydroxy-2-phenyl-acetyl | 95 | 475.2 | 474.2 |
| 122 | 2-(3-Chlorophenyl)-2-keto-acetyl | 70 | 525.2 | 506.2 |
| 123 | (R)-2-Hydroxy-3-phenyl-propionyl | 90 | 489.4 | 488.2 |
| 124 | (S)-2-Hydroxy-3-phenyl-propionyl | 85 | 489.3 | 488.2 |
| 125 | 2,4-Dihydroxy-pyrimidine-5-acyl | 88 | 480.1 | 479.2 |

TABLE 6-continued

Compounds of formula I (X is N, $R^3$ is H, R is isopropyl, $R^1$ is 3-guanidinopropyl, $R^0$ is 2-thiazole, and A is $R^8$)

| Cmpd. No. | $R^8$ | Purity[a] | m/z | Calc MW |
|---|---|---|---|---|
| 126 | 2,6-Dihydroxy-pyrimidine-4-acyl | 84 | 480.3 | 479.2 |
| 127 | 3-(3-Pyridyl)-propionyl | 56 | 474.5 | 473.2 |
| 128 | (S)-5-Oxo-pyrrolidine-2-acyl | 95 | 452.0 | 451.2 |
| 129 | 4-Pyridyl-acetyl | 56 | 460.5 | 459.2 |
| 130 | 3-Pyridyl-acetyl | 56 | 460.3 | 459.3 |
| 131 | (R)-2-(3-Fluorophenyl)-2-hydroxy-acetyl | 89 | 493.6 | 492.2 |
| 132 | (S)-2-(3-Fluorophenyl)-2-hydroxy-acetyl | 87 | 493.1 | 492.2 |
| 133 | (R)-2-(4-Fluorophenyl)-2-hydroxy-acetyl | 90 | 493.2 | 492.2 |
| 134 | (R)-2-(4-Fluorophenyl)-2-hydroxy-acetyl | 86 | 493.3 | 492.2 |
| 133 | (R)-2-(3,5-Difluorophenyl)-2-hydroxy-acetyl | 90 | 511.6 | 510.2 |
| 136 | (S)-2-(3,5-Difluorophenyl)-2-hydroxy-acetyl | 87 | 511.3 | 510.2 |
| 137 | 2-(4-Pyridyl)thioacetyl | 52 | 492.0 | 491.2 |

[a]The purity percentage was determined by HPLC analysis using a C18 (3 × 30 mm, 3 μ) column with AcCN:$H_2O$ (0.1% TFA) as mobile phase.
[b]Assigned as hydrate of desired structure.

EXAMPLE 30

Synthesis of Exemplary Compounds of the Formula I where $R^3$ Together with A Forms a Ring Having the Formula XL

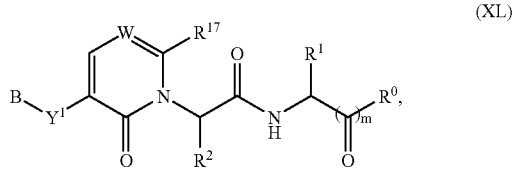

(XL)

The following procedure is representative of the preparation of compounds of formula I that conform to formula XL, wherein $R^1$ is 3-guanidinopropyl, $R^0$ is 2-thiazole, m is 1, X is N, W is N, $R^{17}$ is aryl, $R^2$ is H, $Y^1$ is NH and B is an optionally substituted alkyl, alkenyl, cycloalkylaralkyl, aralkenyl, aryl, $C_{1-9}$ heterocyclyl, heteroaralkyl, acyl, aroyl, or heteroaroyl.

2-Thiouracil (33.3 g, 0.26 mol) was dissolved in an aqueous solution of sodium hydroxide (20.8 g in 183 mL of water; ~0.52 mol). The mixture was placed in an ice bath until the internal reaction temperature was 0° C. Methyl iodide (18.5 mL, 0.29 mol) was slowly added. The resulting reaction mixture was allowed to return to room temperature and then stirred for 16 hours. The pale yellow solution was cooled to 0° C. and acidified with glacial acetic acid. The white precipitate that formed was collected by vacuum filtration, washed with cold water (3×150 mL), and dried to afford 2-methylsulfanyl-3H-pyrimidin-4-one as a white powder. (37.4 g, 98%).

A solution of 2-methylsulfanyl-3H-pyrimidin-4-one (36 g, 0.25 mol) in glacial acetic acid (500 mL) was cooled to 0° C. in an ice bath and treated with $Br_2$ (15.6 mL, 0.3 mol). The reaction mixture changed in color from yellow to brown within 0.5 hours, and was allowed to warm to room temperature where it stirred overnight. When all the starting material had been consumed (as indicated by TLC and HPLC UV detection at λ=254 nm), the reaction mixture was slowly poured into a mixture of ice/$H_2O$ (2 liters). The resulting white precipitate was collected by vacuum filtration and washed with $H_2O$ (200 mL) and $Et_2O$ (2×250 mL). The off-white solid was then suspended in anhydrous toluene (250 mL) and concentrated to dryness under reduced pressure in a 60° C. $H_2O$ bath. 5-Bromo-2-methylsulfanyl-3H-pyrimidin-4-one was obtained as a white solid (30.4 g, 55% yield).

A suspension of calcium hydride (2.3 g, 0.045 mol) in anhydrous THF (200 mL) was cooled to an internal temperature of 0° C. under an argon atmosphere, and 5-bromo-2-methylsulfanyl-3H-pyrimidin-4-one (10 g, 0.045 mol) was slowly added. The internal reaction temperature was maintained at 0° C. After 30 minutes t-butyl bromoacetate (8 mL, 0.054 mol) was added via syringe and stirred at 0° C. for 1.5 hours, then the reaction mixture was allowed to return to room temperature and stir for an additional 2 hours. The reaction mixture was then heated at reflux for 2 hours, cooled to room temperature, and slowly poured in small portions into ice water (600 mL). The mixture was vacuum-filtered, and the filtrate extracted with methylene chloride (200 mL). The aqueous layer was separated and extracted with methylene chloride (2×150 mL). The combined methylene chloride layers were then extracted with $H_2O$ (3×200 mL), dried over $MgSO_4$, and concentrated to give an off white solid (9 g). The solid was triturated in 10% $CH_2Cl_2$/hexanes (500 mL) and filtered. The filtrate was collected and saved. The trituration was repeated with the collected solid, and the combined filtrate after concentration gave compound XLI, where B—$Y^1$ is Br and $R^{17}$ is $SCH_3$, as a white solid (6.7 g, 45%, MS: m/z 336.2, M+1, calculated is 335.2).

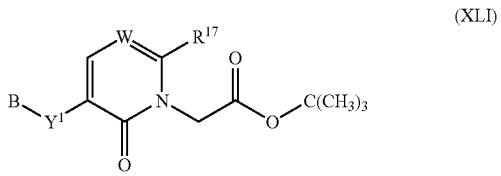

(XLI)

(5-Bromo-2-methylsulfanyl-6-oxo-6H-pyrimidin-1-yl) acetic acid, tert-butyl ester (250 mg, 0.75 mmol), cesium carbonate (269 mg, 0.83 mmol), and 2-(di-t-butylphosphino) biphenyl (23 mg, 0.08 mmol) or 2-(dicylcohexylphosphino) biphenyl (28 mg, 0.08 mmol), tris(dibenzylideneacetone) dipalladium (34 mg, 0.04 mmol) or dihydrogen dichlorobis (di-t-butylphosphinito)palladate (40 mg, 0.08 mmol) were combined in a high pressure flask under an argon atmosphere, and 10% DMF/toluene (5 mL) or dioxane (5 mL) was added. 4-Methoxybenzylamine (1.5 mmol, 2 eq.) was added, and the reaction stirred magnetically in a preheated 100° C. oil bath for 4–16 hours. The heterogenous mixture was then cooled, filtered, washed with EtOAc and the filtrate concentrated. The crude material was purified by silica gel column chromatography using a 10–20% EtOAc/hexanes to 60–70% EtOAc/hexanes gradient as eluent. In several cases, 100% EtOAc was required to elute the product. Representative compounds of formula XLI, where W is N and $R^{17}$ is —SMe, are provided in Table 7.

TABLE 7

Compounds of formula XLI (W is N, $R^{17}$ is —SMe)

| B—$Y^1$— | Purity[a] | m/z | Calc MW | Yield (%) |
|---|---|---|---|---|
| 4-methoxybenzyl | 68 | 392 | 391 | 26 |
| (5-methyl-3-isoxazolyl)methyl | 94 | 367 | 366 | 27 |
| (4-benzyl-1,4-oxazinan-2-yl)methyl | 63 | 461 | 460 | 10 |

[a]Purity estimated by HPLC analysis, 5 minutes gradient elution with 10% acetonitrile to 90% acetonitrile/water, 0.1% TFA, 1 mL/minute, Phenomenex Luna C18 column (30 × 3 mm, 4 micron).

The compound of formula XLI where B—$Y^1$ is benzyl (1 equiv.) was placed in a vial with a Teflon screw cap (8 mL), and 3-methylphenyl boronic acid (1.2 equiv.), Cu(I)-2-thiophenecarboxylate (2 equiv.), Pd(PPh$_3$)$_4$ (2.7 mole %), and THF were added under a head of argon. The reaction was heated at 70° C. with orbital shaking overnight, cooled to room temperature, and concentrated, followed by suspension in methylene chloride, filtration through Celite, and purification by silica gel flash chromatography.

Compounds of formula XL where $Y^1$ is NH and B is a substituted carbonyl or sulfonyl derivative can be prepared by methods analogous to those of Veale, vide supra, or South, vide supra, via Curtius rearrangement of a carboxylic acid to generate pyrimidinones with an amine at this position after hydrolysis of the amide. This amine can be acylated, carbamylated, or sulfonylated as previously described here to provide compounds of formula XL where $Y^1$ is NH and B is alkoxycarbonyl, cycloalkoxycarbonyl, aralkoxycarbonyl, aryloxycarbonyl, heterocyclyloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, heteroaralkylaminocarbonyl, alkylthiocarbonyl, arylthiocarbonyl, heteroarylthiocarbonyl, alkoxythiocarbonyl, cycloalkoxythiocarbonyl, aralkoxythiocarbonyl, aryloxythiocarbonyl, aminothiocarbonyl, alkylaminothiocarbonyl, dialkylaminothiocarbonyl, cycloalkylaminothiocarbonyl, aralkylaminothiocarbonyl, arylaminothiocarbonyl, heterocyclylaminothiocarbonyl, or heteroaralkylaminothiocarbonyl.

(5-Benzylamino-2-(3-methylphenyl)-6-oxo-6H-pyrimidin-1-yl)acetic acid, tert-butyl ester was suspended in 1:1 TFA/DCM for 1 hour to remove the t-butyl ester. The reaction was then concentrated, and the resulting carboxylic acid (1.0 equiv), compound XXXV (2.0 equiv.), and HOBt (1.7 equiv.) were dissolved in THF (1 mL) at room temperature. DIEA (3 equiv.) was added via syringe, and the solution was stirred until homogeneity was obtained. 1-(3-Dimethylaminopropyl)-3-ethylcarbodiimide hydrochloride (EDCI, 1.9 equiv.) was added in one portion, and the reaction was stirred at room temperature overnight. The reaction was diluted with ethyl acetate (2 mL), washed with 5% aqueous acetic acid (1×1 mL), saturated aqueous NaHCO$_3$ (2×1 mL), water (1×1 mL), and brine (1×1 mL). The organic layer was dried over Na$_2$SO$_4$, filtered, and concentrated in vacuo. Removal of the Mtr protecting group was affected with TFA (w/5% thioanisole), as previously described herein, to provide compounds of the formula XL. Representative compounds of formula XL, where $R^2$ is H, $R^1$ is 3-guanidinopropyl, and $R^0$ is 2-thiazole are provided in Table 8.

TABLE 8

Compounds of formula XL ($R^2$ is H, $R^1$ is 3-guanidinopropyl, and $R^0$ is 2-thiazole)

| Cmpd. No. | B—$Y^1$ | $R^{17}$ | Purity[a] | m/z | Calc MW |
|---|---|---|---|---|---|
| 138 | benzyl | 3-methylphenyl | 97 | 573.8 | 572.7 |
| 139 | benzyl | 2-naphthyl | 99 | 609.9 | 608.7 |
| 140 | 2-propyl | 2-naphthyl | 95 | 561.7 | 560.7 |
| 141 | 2-propyl | 3,4-dichlorophenyl | 99 | 580.6 | 579.5 |

[a]Purity estimated by HPLC analysis, 5 minute gradient elution with 10% acetonitrile to 90% acetonitrile/water, 0.1% TFA, 1 mL/minute, Phenomenex Luna C18 column (30 × 3 mm, 4 micron).

EXAMPLE 31

Exemplary Synthesis of Compounds of Formula II

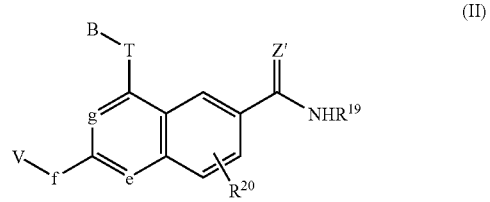

(II)

I) 8-Substituted 2-naphthamidines

The following representative procedure is for a compound of formula II, where f is a bond; each of g and e is C—H; each of V, $R^{19}$, and $R^{20}$ is H; Z' is NH, T is NH, and B is an optionally substituted natural or unnatural alpha-amino acid residue of D- or L-configuration, or an optionally substituted acyl, aroyl, aralkanoyl, heteroaralkanoyl, or heteroaroyl.

8-Amino-2-naphthol (5.0 g, 31.4 mmol) was dissolved in 1,4-dioxane (80 mL) and triethylamine (6.0 mL). A solution of N-phenyltrifluoromethanesulfonimide (11.2 g, 31.4 mmol) in dioxane (60 mL) was added slowly via an addition funnel, and the brown solution was stirred for 4 hours. The reaction was then concentrated in vacuo and triturated two times with hexanes (2×75 mL). The resulting crude naphthyl triflate (9.0 g, 30.9 mmol) was dissolved in pyridine (100 mL) and, while stirring, dimethylaminopyridine (DMAP, 250 mg, 2.0 mmol) was added in one portion. The solution was cooled to 0° C., and benzyl chloroformate (18 mL, 123 mmol) was added slowly via syringe. The reaction mixture was then allowed to warm to room temperature, stirred overnight, then quenched with H$_2$O (100 mL) and extracted with ethyl acetate (3×250 mL). The combined organic fractions were washed sequentially with saturated NaHCO$_3$ (200 mL), water (100 mL), and brine (100 mL), and then dried with MgSO$_4$. After filtration and concentration, the crude residue was purified by flash column chromatography with 15% ethyl acetate/85% hexane as eluent, which yielded compound XLII as a brown solid.

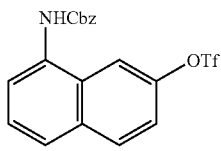

(XLII)

A Schlenk tube was flame dried under high vacuum, backfilled with Argon, and charged with CuI (110 mg), NaCN (575 mg), and Pd(PPh$_3$)$_4$ (335 mg). Compound XLII (2.5 g) was dissolved in dry acetonitrile (15 mL) and added to the Schienk flask via syringe. The solution was stirred vigorously at 80° C. for 1.5 hours. The reaction mixture was then cooled to room temperature, diluted with ethyl acetate, filtered through CELITE®, and the resulting filtrate was washed with water and brine. After drying with MgSO$_4$, the organic layer was concentrated to provide 1.42 g of 8-benzyloxycarbonylamino napththalene-2-carbonitrile which was subsequently utilized without further purification.

The Cbz group was removed by placing the Cbz-protected compound in a flask under argon. A 30% (w/w) solution of HBr/AcOH (5 mL) was added via syringe, and the solution was stirred at room temperature for 2 hours. Ether (40 mL) was added, and the solution was stirred for 10 minutes. Filtration and collection of the precipitate provided 8-aminonapththalene-2-carbonitrile (compound XLIII) as an orange powder.

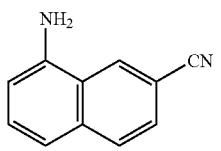

(XLIII)

Compound XLIII was dissolved in CH$_2$Cl$_2$ and triethylamine (3 equiv) and DMAP (0.05 equiv) was added. The respective acid chloride (1.5 equiv), was added in one portion and stirred overnight. The reaction mixture was quenched with water, extracted with CH$_2$Cl$_2$, and dried with MgSO$_4$. Filtration and concentration in vacuo provides the 8-amidonapththalene-2-carbonitrile intermediate.

A solution of 6N HCl/MeOH was generated by cooling a solution of anhydrous MeOH (9 mL) to 0° C. Acetyl chloride (6 mL) was added via syringe. The ice bath was removed, and the reaction was stirred for 30 minutes. To a cyanonaphthamide derivative (20–30 mg) in a 4 mL vial was placed 2 mL of the methanolic HCl solution. The vial was sealed and shaken for 3 hours. Concentration in vacuo provided a methyl imidate ester intermediate to which 2 mL of a 7N NH$_3$/MeOH solution was added. The vial was sealed and heated to 50° C. with shaking overnight. Concentration in vacuo provided a naphthamidine, which can be purified by standard chromatographic techniques.

The amidine (1.5–2 equiv) was dissolved in a 1:1 CH$_2$Cl$_2$/DMF (1 mL total volume) solution, which was then added to a vessel containing p-nitrophenyl carbonate Wang resin (1 equiv). DIEA was added (50 ul) and the mixture shaken overnight. The resin was filtered and washed sequentially with CH$_2$Cl$_2$, DMF, MeOH, CH$_2$Cl$_2$, DMF, and again with CH$_2$Cl$_2$. Added to the resin was 1:1 CH$_2$Cl$_2$/MeOH (1 mL total volume) with 5% DIEA, and the mixture was shaken for an additional 1 hour. The washing protocol was repeated. The amidine was then cleaved from the resin with 1:1 TFA/CH$_2$Cl$_2$ (1.5 mL total volume) for 1 hour, and then the reaction mixture was filtered and concentrated in vacuo. Compounds of formula II, where f is a bond; each of g and e is C—H; each of V, R$^{19}$, and R$^{20}$ is H; Z' is NH, and T is NH, are provided in Table 9.

TABLE 9

Compounds of formula II (f is a bond; g and e are C—H; V, R$^{19}$, and R$^{20}$ is H; Z' is NH, and T is NH)

| Cmpd. No. | B | m/z | Calc MW | Purity[a] |
|---|---|---|---|---|
| 142 | 2-Me-3-OH-phenyl-C(O)— | 320.2 | 319.1 | 98 |
| 143 | 3-sulfonic acid, 3-hydroxy-propyl ester phenyl-C(O)— | 428.2 | 427.1 | 90 |
| 144 | 4-pyridyl-C(O)— | | | |
| 145 | 2-thiophenyl-C(O)— | | | |

[a]Purity estimated by HPLC analysis, 5 minutes gradient elution with 10% acetonitrile to 90% acetonitrile/water, 0.1% TFA, 1 mL/minute, Phenomenex Luna C18 column (30 × 3 mm, 4 micron).

II) 6-Oxy-substituted Naphthalene-2-carboxamidines

The following representative procedure is for a compound of formula II, where T is a bond; each of g and e is C—H; each of B, R$^{19}$, and R$^{20}$ is H; Z' is NH, f is O, and V is an optionally substituted alkyl, aralkyl, or heteroaralkyl.

To 6-hydroxynaphthalene-2-carbonitrile (80 mg, 0.473 mmol) in acetone (2.0 mL) in the presence of potassium carbonate (196 mg) is added 2-bromo-1-phenyl-ethanone (95 mg, 1.2 equiv.), and the reaction mixture is stirred at room temperature overnight. The solvent is removed in vacuo and the resulting mixture is purified by preparative thick layer chromatography (EtOAc/Hexane, 1:4) to give compound XLIV. MS: m/z 288, M+1, calculated mass: 287.3.

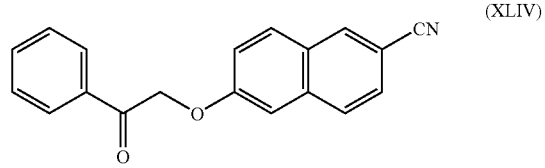

(XLIV)

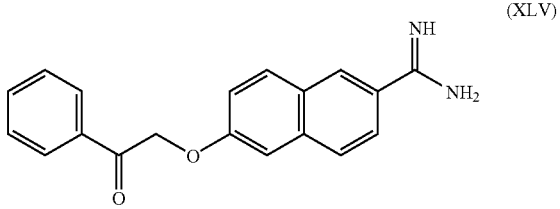

(XLV)

The product (30 mg, 0.104 mmol) is dissolved in an HCl/methanol solution (6 N) at room temperature and stirred for 1 hour. The solvent is removed in vacuo and the resulting crude mixture is immediately submitted to an ammonia/methanol solution (3.5 N) and stirred for 2 hours. The crude reaction mixture is purified with reverse-phase HPLC to give compound XLV (MS: m/z 305, M+1, calculated mass: 304.3, 85% purity[b]). The identity (m/z) of a representative sample of similarly prepared compounds is provided in Table 10 (compounds 146–148). Compounds in which f is O, and V is an optionally substituted acyl, aroyl, heterocyclylcarbonyl, alkoxycarbonyl, cycloalkoxycarbonyl, aralkoxycarbonyl, aryloxycarbonyl, heteroaralkyloxycarbonyl, heteroaryloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, or heteroaralkylaminocarbonyl can be prepared by from 6-hydroxynaphthalene-2-carbonitrile, with subsequent unmasking of the amidine groups as described herein. Alternatively, the amidine can be unmasked prior to C6-O functionalization, followed by protection with a suitable protecting group such as Boc; subsequent O-acylation, carbonylation, or carbamoylation provides, after amidine deprotection, compounds of the formula II.

III) 6-Amido-substituted Naphthalene-2-carboxamidines

The following representative procedure is for a compound of formula II, where T is a bond; each of g and e is C—H; each of B, R$^{19}$, and R$^{20}$ is H; Z' is NH, f is a covalent bond, and V is an optionally substituted aminocarbonyl, alkylaminocarbonyl, dialkylaminocarbonyl, cycloalkylaminocarbonyl, aralkylaminocarbonyl, arylaminocarbonyl, heterocyclylaminocarbonyl, or heteroaralkylaminocarbonyl.

A solution of 6-cyano-naphthalene-2-carbonyl chloride (1 mmol), prepared as described in U.S. Pat. No. 6,284,796, in THF (2 mL) in the presence of K$_2$CO$_3$ (3 equiv.) and benzyl amine (3 equiv.) was stirred overnight. The crude mixture is purified by preparative thick layer chromatography (Hexane/EtOAc 1:1) to give 6-cyano-2-benzylamidonaphthalene (m/z 287, M+1, calculated mass: 286.3).

Conversion of the cyano group to an amidine group is achieved as previously described herein to give 6-amidino-2-benzylamidonaphthalene. The crude reaction mixture is purified with reverse-phase HPLC$^a$ to give the amidine product (MS: m/z 304.3, M+1, calculated mass: 303.4). Representative compounds of formula II, where T is a bond; each of g and e is C—H; each of B, R$^{19}$, and R$^{20}$ is H; and Z' is NH, can be prepared in a similar manner and are provided in Table 10.

nocarbonyl, aralkylaminocarbonyl, arylaminocarbonyl, heterocyclylaminocarbonyl, or heteroaralkylaminocarbonyl.

Nitration of 6-cyano-naphthalene-2-carboxylic acid methyl ester, prepared as described in U.S. Pat. No. 6,284,796, is carried out with KNO$_3$ in sulfuric acid at 0° C. for 30 min. The reaction mixture is poured into ice and filtered, and the compound is washed with water and dried. The product, 6-cyano-4-nitro-naphthalene-2-carboxylic acid methyl ester is obtained and used without further purification.

The methyl ester is treated with LiOH (4 equiv.) in THF/H$_2$O for 30 min, acidified with oxalic acid, and extracted with EtOAc. After removal of the solvent, the product is obtained as a solid, which is added into SOCl$_2$ and stirred at 70° C. for 1 hour. Removal of excess thionyl chloride gives the desired acid chloride, 6-cyano-4-nitro-naphthalene-2-carbonyl chloride.

A mixture of the acid chloride, THF, K$_2$CO$_3$ (3 equiv.) and a primary or secondary amine (3 equiv.) is stirred at room temperature for 2 hours. The reaction mixture is loaded onto a preparative thick layer chromatography plate and developed with hexane/ethyl acetate (2:1) to give a compound of formula XLVI, where f is a covalent bond and V is an optionally substituted aminocarbonyl, alkylaminocarbonyl, dialkylaminocarbonyl, cycloalkylaminocarbonyl, aralkylaminocarbonyl, arylaminocarbonyl, heterocyclylaminocarbonyl, or heteroaralkylaminocarbonyl.

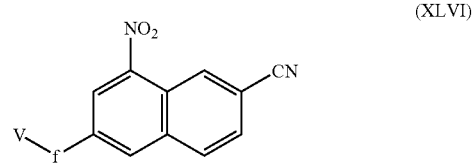

(XLVI)

In a representative example, a compound of formula XLVI, where f is a bond and V is benzylaminocarbonyl (50

TABLE 10

Compounds of formula II (T is a bond; g and e are C—H; B, R$^{19}$, and R$^{20}$ is H; and Z' is NH)

| Cmpd. No. | V | f | m/z | Calc MW | Purity$^{a,b}$ |
|---|---|---|---|---|---|
| 146 | H$_2$NC(O)CH$_2$— | O | 244.2 | 243.3 | 80 |
| 147 | HO$_2$CCH$_2$— | O | 245.2 | 244.3 | 80 |
| 148 | H$_3$CO$_2$CCH$_2$— | O | 259.2 | 258.3 | 59 |
| 149 | H$_2$NC(O)— | bond | 214.2 | 213.2 | 60 |
| 150 | (3-pyridyl)CH$_2$NHC(O)— | bond | 305.3 | 304.3 | 62 |
| 151 | morpholinyl-C(O)— | bond | 284.2 | 283.3 | 95 |
| 152 | N-methylpiperazinyl-C(O)— | bond | 230.3 | 296.4 | 98 |
| 153 | (4-methoxycarbonyl)piperidinyl-C(O)— | bond | 340.3 | 339.4 | 66 |
| 154 | (4-carboxy)piperidinyl-C(O)— | bond | 326.3 | 325.4 | 66 |
| 155 | (3-methoxycarbonyl)piperidinyl-C(O)— | bond | 340.3 | 339.4 | 64 |
| 156 | (3-carboxy)piperidinyl-C(O)— | bond | 326.3 | 325.4 | 43 |

$^a$Acetonitrile/water, 0.1% TFA, 12 mL/minute, 45 minute gradient elution (various methods), VyDac C18 column (250 × 15 mm, 5 micron).
$^b$Purity estimated by HPLC analysis, 5 minute gradient elution with 0% 10% acetonitrile to 90–100% acetonitrile/water, 0.1% TFA, 1 mL/minute, Phenomenex Luna C18 column (30 × 3 mm, 4 micron).

IV) 4,6-Disubstituted-2-carboxamidines

The following representative procedure is for a compound of formula II, where T is NH; B is an optionally substituted natural or unnatural alpha-amino acid residue of D- or L-configuration, or an optionally substituted acyl, aroyl, araalkanoyl, heteroaralkanoyl, or heteroaroyl; each of g and e is C—H; each of R$^{19}$ and R$^{20}$ is H; Z' is NH, f is a covalent bond, and V is an optionally substituted aminocarbonyl, alkylaminocarbonyl, dialkylaminocarbonyl, cycloalkylamimg, 0.151 mmol), is dissolved in methanol (3 mL) and hydrogenated in the presence of 10% Pd/C (5 mg) for 6 hours. The resulting amine is obtained after removal of the catalyst and solvent (MS: m/z 302, M+1; calculated mass: 301.3).

To a solution of the amine (15 mg, 0.031 mmol) in THF (2 mL) in the presence of K$_2$CO$_3$ (3 equiv.) is added 2-methyl-3-acetyloxybenzoic chloride (2 equiv.) and the reaction is stirred overnight. Preparative thick layer chromatography of the reaction mixture with hexane/ethyl acetate (1:1) gives a compound of formula XLVII, where f is a bond, V is benzylaminocarbonyl, T is NH and B is 2-methyl-3-acetyloxyphenylcarbonyl (MS: m/z 478, M+1; calculated mass: 477.5).

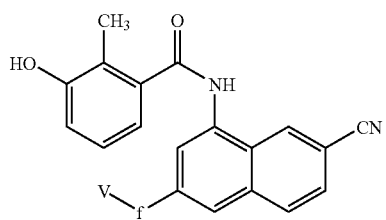

(XLVII)

Amides of formula XLVII are subjected to similar reaction conditions previously described herein for the conversion of a cyano group to an amidine group. For example, the compound of formula XLVII, where f is a bond, V is benzylaminocarbonyl, T is NH and B is 2-methyl-3-acetyloxyphenylcarbonyl (20 mg) is treated with an HCl/methanol solution (7 N, 2 mL) at room temperature for 2 hours. A solid product is obtained after removal of the solvent in vacuo, which is treated with a solution of ammonia in methanol (3.5 N, 3 mL) at 50° C. for 1.5 hours. Preparative reverse phase HPLC[a] of the crude reaction mixture affords the desired amidine product of formula XLVIII, where f is a covalent bond and V is benzylaminocarbonyl, as a trifluoroacetic acid salt (87% purity[b]; MS: m/z 453.2, M+1; calculated mass: 452.5). Representative compounds of formula XLVIII are shown in Table 11.

TABLE 11

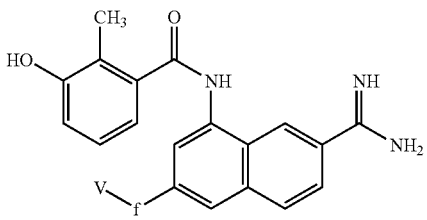

(XLVIII)

Identity and purity of compounds of the formula XLVIII

| Cmpd. No. | V | f | m/z | Calc MW | Purity[a] |
|---|---|---|---|---|---|
| 157 | $H_2NC(O)$— | bond | 363.2 | 362.4 | 61 |
| 158 | $(CH_3)_2CHCH_2NHC(O)$— | bond | 419.2 | 418.5 | 90 |
| 159 | $(3-CH_3C_6H_4)CH_2NHC(O)$— | bond | 467.3 | 466.5 | 95 |
| 160 | $(3-CH_3C_6H_4)CH_2CH_2NHC(O)$— | bond | 481.3 | 480.6 | 83 |
| 161 | $C_6H_5CH_2CH_2NHC(O)$— | bond | 467.2 | 466.5 | 84 |
| 162 | $C_6H_5CH_2CH_2CH_2NHC(O)$— | bond | 481.4 | 480.6 | 82 |
| 163 | $(4-CH_3C_6H_4)CH_2CH_2NHC(O)$— | bond | 481.3 | 480.6 | 95 |
| 164 | 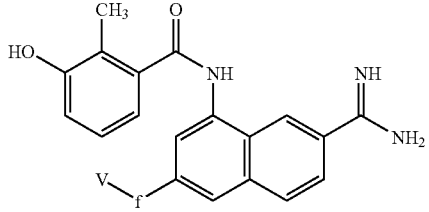 | bond | 461.3 | 460.5 | 76 |
| 165 | pyrrolidinyl methyl ester structure | bond | 475.2 | 474.5 | 77 |
| 166 | morpholine-N—(CO)— | bond | 433.2 | 432.5 | 73 |
| 167 | $(4-OHC_6H_4)CH_2CH_2NHC(O)$— | bond | 482.3 | 482.5 | 80 |
| 168 | $(3-FC_6H_4CH_2NHC(O)$— | bond | 471.2 | 470.5 | 76 |
| 169 | 3-pyridyl-NHC(O)— | bond | 440.2 | 439.4 | 60 |
| 170 | Cyclohexanylmethyl-NHC(O)— | bond | 459.4 | 458.6 | 100 |
| 171 | $(2-CH_3OC_6H_4)CH_2NHC(O)$— | bond | 483.2 | 482.5 | 80 |
| 172 | $(4-CH_3OCOC_6H_4)CH_2NHC(O)$— | bond | 511.2 | 510.5 | 55 |
| 173 | $C_6H_5NHC(O)$— | bond | 439.2 | 438.5 | 76 |
| 174 | $(3-CH_3C_6H_4CH_2NHC(O)$— | bond | — | 466.5 | 95 |
| 175 | $C_6H_4CH_2NHC(O)$— | bond | 453.2 | 452.5 | 87 |
| 176 | $CH_3OC(O)$— | bond | 378.2 | 377.4 | 80 |
| 177 | tetrahydrofuranyl-CH_2-NH(CO)— | bond | 447.2 | 446.5 | 90 |
| 178 | $(4-CH_3OCOC_6H_4)NHC(O)$— | bond | — | 496.5 | — |
| 179 | $(3-CH_3OCOC_6H_4)NHC(O)$— | bond | — | 496.5 | — |
| 180 | $(2-CH_3OCOC_6H_4)NHC(O)$— | bond | — | 496.5 | — |
| 181 | $(4-ClC_6H_4)NHC(O)$— | bond | — | 472.9 | — |
| 182 | $(3-ClC_6H_4)NHC(O)$— | bond | — | 472.9 | — |
| 183 | $(2-ClC_6H_4)NHC(O)$— | bond | — | 472.9 | — |
| 184 | $(4-FC_6H_4)NHC(O)$— | bond | — | 456.5 | — |
| 185 | $(3-FC_6H_4)NHC(O)$— | bond | — | 456.5 | — |
| 186 | $(2-FC_6H_4)NHC(O)$— | bond | — | 456.5 | — |
| 187 | $(4-OHC_6H_4)NHC(O)$— | bond | — | 454.5 | — |
| 188 | $(3-OHC_6H_4)NHC(O)$— | bond | — | 454.5 | — |
| 189 | $(2-OHC_6H_4)NHC(O)$— | bond | — | 454.5 | — |
| 190 | $(2-CH_3C_6)H_4CH_2NHC(O)$— | bond | — | 466.5 | — |
| 191 | $(4-CH_3C_6)H_4CH_2NHC(O)$— | bond | — | 466.5 | — |
| 192 | $(2-FC_6H_4)CH_2NHC(O)$— | bond | — | 470.5 | — |
| 193 | $(4-FC_6H_4)CH_2NHC(O)$— | bond | — | 470.5 | — |
| 194 | $(2-OHC_6H_4)CH_2NHC(O)$— | bond | — | 468.5 | — |
| 195 | $(3-OHC_6H_4)CH_2NHC(O)$— | bond | — | 468.5 | — |
| 196 | $(4-OHC_6H_4)CH_2NHC(O)$— | bond | — | 468.5 | — |
| 197 | $(2-ClC_6H_4)CH_2NHC(O)$— | bond | — | 487.0 | — |
| 198 | $(3-ClC_6H_4)CH_2NHC(O)$— | bond | — | 487.0 | — |
| 199 | $(4-ClC_6H_4)CH_2NHC(O)$— | bond | — | 487.0 | — |
| 200 | $(2-CH_3OCOC_6H_4)CH_2NHC(O)$— | bond | — | 510.5 | — |
| 201 | $(3-CH_3OCOC_6H_4)CH_2NHC(O)$— | bond | — | 510.5 | — |
| 202 | $(2-HO_2CC_6H_4)CH_2NHC(O)$— | bond | — | 496.5 | — |
| 203 | $(3-HO_2CC_6H_4)CH_2NHC(O)$— | bond | — | 496.5 | — |
| 204 | $(4-HO_2CC_6H_4)CH_2NHC(O)$— | bond | — | 496.5 | — |
| 205 | $(2-H_2NCOC_6H_4)CH_2NHC(O)$— | bond | — | 495.5 | — |
| 206 | $(3-H_2NCOC_6H_4)CH_2NHC(O)$— | bond | — | 495.5 | — |

TABLE 11-continued

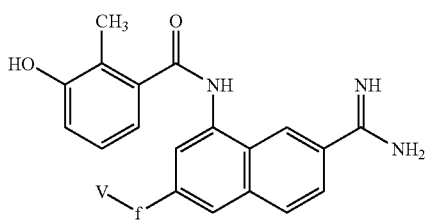

(XLVIII)

Identity and purity of compounds of the formula XLVIII

| Cmpd. No. | V | f | m/z | Calc MW | Purity[a] |
|---|---|---|---|---|---|
| 207 | (4-H$_2$NCOC$_6$H$_4$)CH$_2$NHC(O)— | bond | — | 495.5 | — |
| 208 | (2-(CH$_3$)$_2$NC$_6$H$_4$)CH$_2$NHC(O)— | bond | — | 495.6 | — |
| 209 | (3-(CH$_3$)$_2$NC$_6$H$_4$)CH$_2$NHC(O)— | bond | — | 495.6 | — |
| 210 | (4-(CH$_3$)$_2$NC$_6$H$_4$)CH$_2$NHC(O)— | bond | — | 495.6 | — |
| 207 | (3-CH$_3$OC$_6$H$_4$)CH$_2$NHC(O)— | bond | — | 482.5 | — |
| 212 | (4-CH$_3$OC$_6$H$_4$)CH$_2$NHC(O)— | bond | — | 482.5 | — |
| 213 | (2-CH$_3$OC$_6$H$_4$)NHC(O)— | bond | — | 468.5 | — |
| 214 | (3-CH$_3$OC$_6$H$_4$)NHC(O)— | bond | — | 468.5 | — |
| 215 | (4-CH$_3$OC$_6$H$_4$)NHC(O)— | bond | — | 468.5 | — |

[a]Acetonitrile/water, 0.1% TFA, 12 mL/minute, 45 minute gradient elution (various methods), VyDac C18 column (250 × 15 mm, 5 micron).
[b]Purity estimated by HPLC analysis, 5 minute gradient elution with 0%–10% acetonitrile to 90–100% acetonitrile/water, 0.1% TFA, 1 mL/minute, PHENOMENEX® LUNA® C18 column (30 × 3 mm, 4 micron).

V) Quinolines

The following representative procedures are for compounds of formula II, where T is NH; B is an optionally substituted natural or unnatural alpha-amino acid residue of D- or L-configuration, or an optionally substituted acyl, aroyl, aralkanoyl, heteroaralkanoyl, or heteroaroyl; g is C—H; e is N; each of $R^{19}$ and $R^{20}$ is H; Z' is NH, f is a covalent bond, and V is an optionally substituted alkoxycarbonyl, cycloalkoxycarbonyl, aralkoxycarbonyl, aryloxycarbonyl, heterocyclyloxycarbonyl, heteroaralkyloxycarbonyl, aminocarbonyl, alkylaminocarbonyl, dialkylaminocarbonyl, cycloalkylaminocarbonyl, aralkylaminocarbonyl, arylaminocarbonyl, heterocyclylaminocarbonyl, or heteroaralkylaminocarbonyl.

4-Amino-benzonitrile was converted to 6-cyano-4-hydroxy-quinoline-2-carboxylic acid methyl ester by Michael addition to dimethylacetylene dicarboxylate followed by thermal cyclization (see Jaen et al., J. Med. Chem. 38:4439–4445, 1995). The resulting 4-hydroxy quinoline was converted to 4-amino-6-cyano-quinoline-2-carboxylic acid methyl ester by bromination with n-butylammonium bromide and phosphorus pentoxide (see Kato et al., Tetrahedron Lett. 42:4849–4852, 2001). The 4-bromo compound is treated with with sodium azide in DMSO (see Sashida et al., Chem. Pharm. Bull. 38:2919–2925, 1990), which is subsequently reduced with sodium borohydride (see Outt et al., J. Org. Chem. 63:5762–5768, 1998). Acylation of the amine and subsequent conversion of the cyano group to an amidine group, as previously described herein, affords compounds of formula II, where T is NH; B is an optionally substituted natural or unnatural alpha-amino acid residue of D- or L-configuration, or an optionally substituted acyl, aroyl, aralkanoyl, heteroaralkanoyl, or heteroaroyl; g is C—H; e is N; each of $R^{19}$ and $R^{20}$ is H; Z' is NH, f is a covalent bond, and V is methoxycarbonyl; alternatively, the methyl ester of the 4-bromo or 4-azido intermediate can be saponified to the carboxylic, then coupled with various alcohols under ester bond-forming conditions known to those skilled in the art, followed by conversion of the 4-bromo or -azido functional group to the 4-amino group with subsequent functionalization as previously described, to afford compounds of formula II, where T is NH; B is an optionally substituted natural or unnatural alpha-amino acid residue of D- or L-configuration, or an optionally substituted acyl, aroyl, aralkanoyl, heteroaralkanoyl, or heteroaroyl; g is C—H; e is N; each of $R^{19}$ and $R^{20}$ is H; Z' is NH, f is a covalent bond, and V is an optionally substituted alkoxycarbonyl, cycloalkoxycarbonyl, aralkoxycarbonyl, aryloxycarbonyl, or heterocyclyloxycarbonyl, or heteroaralkyloxycarbonyl (e.g., V is methoxycarbonyl, B is 3-hydroxy-2-methylphenylcarbonyl; MS: m/z 378.2, M+1, calculated mass: 377.1; HPLC purity=92%). Alternatively, prior to the conversion of the cyano group to an amidine, the 2-carboxylic acid methyl ester substituent can be directly converted to an amide by treatment with an amine in the presence of Me$_3$Al (see Akakura and Yamamoto, Syn. Lett. 3:277–278, 1997). Subsequent conversion of the cyano group to an amidine using the Pinner protocol also provides compounds of the formula II, where T is NH; B is an optionally substituted natural or unnatural alpha-amino acid residue of D- or L-configuration, or an optionally substituted acyl, aroyl, aralkanoyl, heteroaralkanoyl, or heteroaroyl; g is C—H; e is N; each of $R^{19}$ and $R^{20}$ is H; Z' is NH, f is a covalent bond, and V is an optionally substituted aminocarbonyl, alkylaminocarbonyl, dialkylaminocarbonyl, cycloalkylaminocarbonyl, aralkylaminocarbonyl, arylaminocarbonyl, heterocyclylaminocarbonyl, or heteroaralkylaminocarbonyl (e.g., V is benzylaminocarbonyl, B is 3-hydroxy-2-methylphenylcarbonyl; MS: m/z 454.2, M+1, calculated mass: 453.2; HPLC purity=74%).

VI) Quinazolines

The following representative procedure is for a compound of formula II, where T is NH; B is an optionally substituted natural or unnatural alpha-amino acid residue of D- or L-configuration, or an optionally substituted alkyl, alkenyl, aralkyl, aralkenyl, heteroaralkyl, heteroaralkenyl, acyl, aroyl, aralkanoyl, heteroaralkanoyl, or heteroaroyl; each of e and g is N; each of $R^{19}$ and $R^{20}$ is H; Z' is NH, f is a covalent bond, and V is an optionally substituted $C_{1-6}$ alkyl, cycloalkyl, alkenyl, aralkyl, aralkenyl, heteroaralkyl, heteroaralkenyl, aryl, or heterocyclyl.

2-Aminobenzonitrile (2.0 g, 16.9 mmol, 1 equiv.) was dissolved in dry N,N-dimethylformamide (30 mL), and the solution was cooled to 0° C. A solution of N-iodosuccinimide, NIS (3.81 g, 16.9 mmol, 1 equiv.) in 30 mL of DMF was added dropwise with an addition funnel. After the NIS/DMF solution was, added, the ice bath was removed, and the reaction was stirred at room temperature overnight. The reaction was quenched by pouring into 3N NaOH (300 mL) and diluted with an additional 200 mL of water. 2-Amino-5-iodobenzonitrile formed as a precipitate, which was collected by filtration.

2-Amino-5-iodobenzonitrile (500 mg, 2.05 mmol, 1 equiv.), DMAP (50 mg, 0.41 mmol, 0.2 equiv.), and triethylamine (285 ul, 2.05 mmol, 1 equiv.) were dissolved in methylene chloride (10 mL). O-Acetylsalicyloyl chloride (2.0 g, 10.07 mmol, 4.9 equiv) was added in one portion, and the reaction was stirred at room temperature for 1 hour. The reaction mixture was diluted with CH$_2$Cl$_2$, washed with water, dried with MgSO$_4$, filtered, and concentrated. The resulting residue was purified by flash column chromatography (20% EtOAc/80% hexane) to provide compound XLIX (260 mg, 31% yld.), where f is a covalent bond and V is 2-acetoxyphenyl.

Compound XLIX (20 mg, 0.050 mmol, 1 equiv.) was dissolved in THF (500 ul). 4-Methoxybenzylamine (14 ul, 0.108 mmol, 2.2 equiv.) was added, and the reaction vial sealed and heated to 65° C. overnight with shaking. Concentration in vacuo provided the compound of formula L, where f is a covalent bond, V is 2-hydroxyphenyl, T is NH and B is 4-methoxybenzyl (24 mg).

Compounds of formula L where T is NH and B is a substituted carbonyl or sulfonyl derivative can be prepared by conversion of the iodo-quinazoline to the cyano-quinazoline, removal of the 4-methoxybenzyl group, and subsequent acylation or sulfonylation of the resulting free amine; conversion of the nitrile to the amidine is then effected as previously described herein. Alternatively, it can be advantageous in some cases to unmask and protect the amidine prior to effecting acylation or sulfonylation.

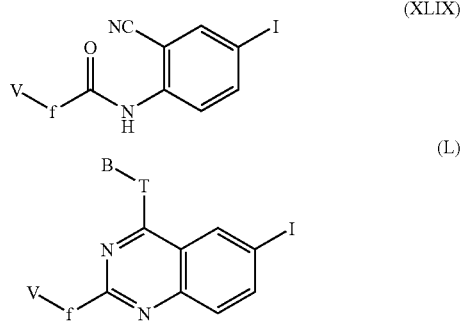

The compound for formula L, where where f is a covalent bond, V is 2-hydroxyphenyl, T is NH and B is 4-methyoxybenzyl (24 mg, 0.050 mmol, 1 equiv.) was dissolved in NMP (1 mL) and CuCN (9 mg, 0.10 mmol, 2 equiv.) was added. The vial was sealed and heated to 130° C., while shaking overnight. The reaction mixture was then poured into water (10 mL) and extracted with ethyl acetate. The organic layer was washed with brine, dried over $MgSO_4$, filtered, and then concentrated to afford the compound in which the iodo group was displaced with a cyano group to form the corresponding cyanoquinazoline. This compound was treated with 4N HCl/dioxane in MeOH to provide the intermediate methyl imidate ester, followed by aminolysis with ammonia in MeOH to provide, after concentration in vacuo, the quinazoline amidine. Alternatively, the cyanoquinazoline can be allowed to react with hydroxylamine, followed by acylation of the N-hydroxyamidine with, for example, acetic anhydride. Reduction under hydrogenolysis conditions (5% Pd/C at 50 psi under a $H_2$ atmosphere for 2 hours) resulted in the compound of formula II, where T is NH; B is 4-methoxybenzyl; each of e and g is N; each of $R^{19}$ and $R^{20}$ is H; Z' is NH; f is a covalent bond; and V is 2-hydroxyphenyl (MS: m/z 400.2, M+1, calculated mass: 399.2).

EXAMPLE 32

Pharmaceutical Compositions

Salts

Compounds of the invention may be prepared as salts. If a compound of this invention is substituted with a basic moiety, acid addition salts may be formed. The acids which can be used to prepare the acid addition salts desirably include those which produce, when combined with the free base, pharmaceutically acceptable salts, that is, salts whose anions are non-toxic to the patient in pharmaceutical doses of the salts so that the beneficial effects inherent in the free base are not modulated by side effects ascribable to the anions. Exemplary pharmaceutically acceptable salts are those derived from the following acids: acetic acid, benzenesulfonic acid, citric acid, cyclohexylsulfamic acid, ethanesulfonic acid, fumaric acid, gentisic acid, hydrochloric acid, hydrobromic acid, lactic acid, malonic acid, methanesulfonic acid, quinic acid, phosphoric acid, sulfamic acid, sulfuric acid, p-toluenesulfonic acid, and trifluoroacetic acid. Acid addition salts of the compounds of the invention are prepared by reaction of the free base with the appropriate acid by the application or adaption of methods known to those skilled in the art.

If a compound of the invention is substituted by an acidic moiety, base addition salts may be formed. The bases which can be used to prepare the base addition salts desirably include those which produce, when combined with the free acid, pharmaceutically acceptable salts, that is, salts whose effects inherent in the free acid are not modulated by side effects ascribable to the cations. Pharmaceutically acceptable salts (e.g., alkali and alkaline earth metal salts) are those derived from the following bases: aluminum hydroxide, ammonia, arginine, N-benzylphenethylamine, calcium hydroxide, chloroprocaine, choline, N,N'-dibenzylethylenediamine, diethanloamine, diethylamine, tris(hydroxymethyl)aminomethane, lithium hydroxide, lysine, magnesium hydroxide, N-methylglucamine, ornithine, piperazine, potassium hydroxide, procaine, sodium hydride, sodium hydroxide, tetramethylammonium hydroxide, triethylammonia, trimethylammonia, zinc hydroxide, and the like.

Metal salts of compounds of the invention may be obtained by contacting a hydride or hydroxide of the chosen metal in an aqueous or organic solvent with the free acid form of the compound. Amine salts of compounds of the invention may be obtained by contacting an amine in an aqueous or organic solvent with the free acid form of the compounds.

A number of methods are useful for the preparation of the salts described above and are known to those skilled in the art. For example, reaction of the free acid or free base form of a compound of the invention with one or more molar equivalents of the desired acid or base in a solvent or solvent mixture in which the salt is insoluble, or in a solvent like water after which the solvent is removed by evaporation, distillation, or freeze drying. Alternatively, the free acid or base form of the product may be passed over an ion exchange resin to form the desired salt, or one salt form of the product may be converted to another using the same general process.

Isomers

Compounds of this invention may exhibit stereoisomerism by virtue of the presence of one or more asymmetric or chiral centers in the compounds. The present invention includes the various stereoisomers and mixtures thereof. Desired isomers may be obtained by chiral synthesis or resolution of enantiomeric mixtures or chromatographic separation of enantiomers on chiral chromatography columns. Diastereomers can be resolved using, e.g., standard chromatography columns or crystallization. Compounds of this invention may also exhibit geometrical isomerism. Geometrical isomers include the cis and trans form of compounds of the invention having, for example, alkenyl moieties. Compounds of this invention may also exhibit rotameric or tautomeric isomerism. The present invention comprises the individual stereoisomers, geometrical isomers, rotameric and tautomeric isomers, and mixtures thereof.

Modifications to Increase Half-Life

Compounds of the invention may also be rendered reactive for in vivo conjugation to biological targets to substantially increase their duration of action. A pharmaceutical composition comprising a therapeutically effective amount of a compound of the formula I and II, or a pharmaceutically acceptable salt, pharmaceutically acceptable solvate, pharmaceutically active metabolite, or prodrug thereof, can be chemically modified to include linkers that can covalently bind blood components including, but not limited to, cells (e.g., red blood cells and platelets) and proteins (e.g., immunoglobulins including IgG and IgM, serum albumin, ferritin, steroid binding proteins, such as corticosteroid-binding globulin and sex hormone-binding globulin, transferrin, thyroxin binding protein, and alpha-2-macroglobulin: see, for example, Krantz et al., U.S. Pat. No. 5,942,620, 1999; Krantz et al., *J. Drug Target* 7 113, 1999; and Holmes et al., *Bioconjug. Chem.* 11, 439, 2000). Compounds of formulas LI and LII exemplify the types of modifications that can be made to compounds of the present invention to render them susceptible to selective, in vivo conjugation with the aforementioned cells and proteins. In exemplary embodiments, the linker is attached to $R^0$, $R^2$, or A, of compounds of the formula I; or to B or V of compounds of the formula II.

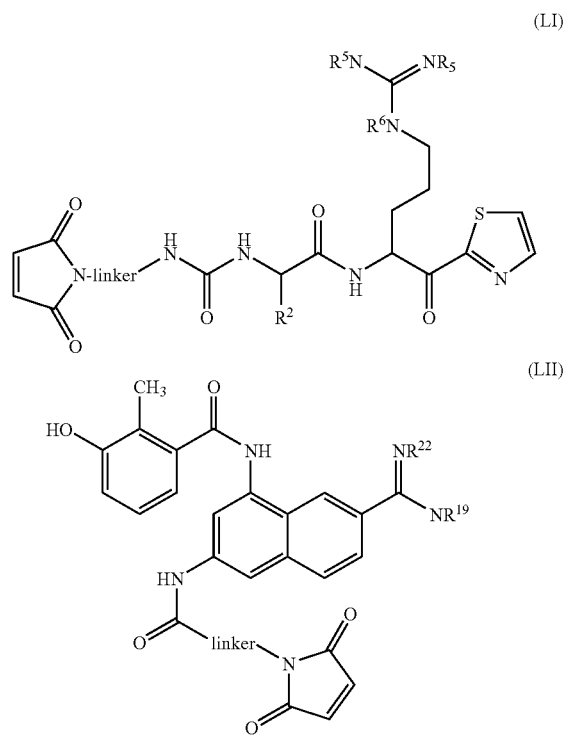

The linker is ordinarily a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparan. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

The linker group can be attached to compounds of the formula I and II through the appropriate handle (e.g., by the acylation of amino groups) and incorporate at the end of its tether a functionality, desirably a maleimide, reactive towards biomolecules. Once reacted, the conjugated compound of the invention should form a stable covalent linkage to the biomolecule via the linker moiety. In one example, the maleimide of the linker reacts with a cysteine residue (C34) of human serum albumin to form a stable, conjugated species in vivo. The linker is typically a chain of varying length, e.g., maleimide-$(CH_2)_{bb}C(O)NHCH_2CH_2(OCH_2CH_2)_{aa}OCH_2C(O)$—, maleimide-$(CH_2)_{bb}C(O)NHCH_2CH_2(OCH_2CH_2)_{aa}NHCH_2C(O)$—, maleimide-$(CH_2)_{bb}C(O)NHCH_2CH_2(OCH_2CH_2)_{aa}NHC(S)$—, maleimide-$(CH_2)_{bb}NHC(S)$—, maleimide-$(CH_2)_{bb}C(O)$—, or maleimide $(CH_2)_{bb}$— where aa is 1–10 and bb is 1–4, and desirably is attached to atoms or groups of atoms on the inhibitor which have minimal impact on the binding of the inhibitor to its protein target (e.g., atoms or groups of atoms known to have no direct or indirect binding interactions with the protein target, or solvent exposed functional groups). Desirably, the length of the linker is between 6 and 100 atoms, inclusive. In some embodiments, the reactive moiety (e.g., maleimide) covalently binds a sulfur atom in a protein, such as human serum albumin.

In other embodiments, a compound of the invention, or a pharmaceutically acceptable salt, pharmaceutically acceptable solvate, pharmaceutically active metabolite, or prodrug thereof, can be further modified to include only a polyethylglycol moiety. Such compounds are also known to increase blood serum half-life (see Yoo et al., *Chem. Pharm. Bull.* 48: 1921–1924, 2000). The polyethylene glycol moiety can be selected from the following group: $H(OCH_2CH_2)_{cc}O$—, $H_3C(OCH_2CH_2)_{cc}OC(O)$, $H(OCH_2CH_2)_{cc}OC(O)$, $H_3C(OCH_2CH_2)_{cc}NHC(O)$, $H(OCH_2CH_2)_{cc}NHC(O)$, $H_3C(OCH_2CH_2)_{cc}NHC(S)$, $H(OCH_2CH_2)_{cc}NHC(S)$, $H_3C(OCH_2CH_2)_{cc}C(O)$, $H(OCH_2CH_2)_{cc}C(O)$, $H_3C(OCH_2CH_2)_{cc}NHCH_2C(O)$, $H(OCH_2CH_2)_{cc}NHCH_2C(O)$, $H_3C(OCH_2CH_2)_{cc}OC(O)C(CH_3)_2$—, and $H(OCH_2CH_2)_{cc}OC(O)C(CH_3)_2$—, wherein cc is a range of numbers that results in an average molecular weight of said polyethylene glycol moiety of between 1,000–40,000, preferably 20,000 or 40,000.

In one example, compounds modified with a linker (e.g., a linker with a group for conjugation to a molecule of interest) have formula I:

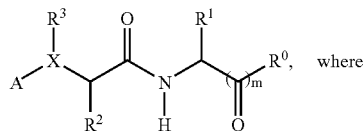

X is N, m is 1; A- is L-(CH$_2$)$_n$—K—C(O)—; R$^3$ is H, C$_{1-6}$ alkyl, or together with K forms a 5- or 6-membered ring; R$^0$ is -E-J; R$^1$ is

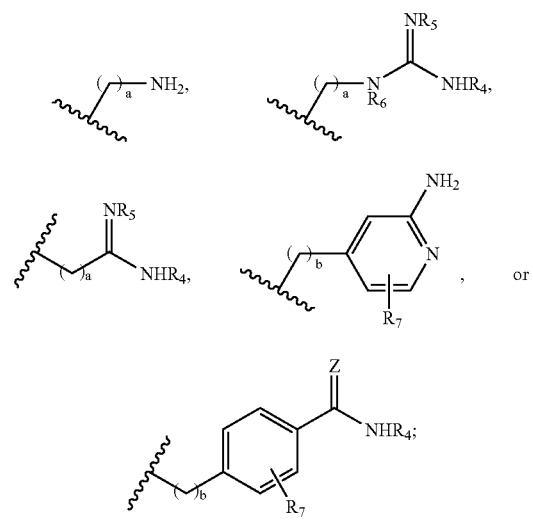

R$^2$ is selected from the group consisting of optionally substituted alkyl, alkenyl, cycloalkyl, aralkyl, aralkenyl, aryl, heterocyclyl, heteroaralkyl, heteroaralkenyl, and heteroaryl; R$^4$, R$^5$, R$^6$, R$^7$, "a", "b", "n", E, and J are as previously defined herein; and at least one of J, R$^2$, or L further includes a linker attached to a moiety reactive to a free amine or sulfhydryl contained on a blood component. Exemplary linkers can be chosen from the polyethylene glycol moieties described herein, which can, for example, be linked to a compound of the invention by attachment to an amino group contained in J, R$^2$ or L.

In another example, compounds modified with a linker have formula I where R$^1$ is

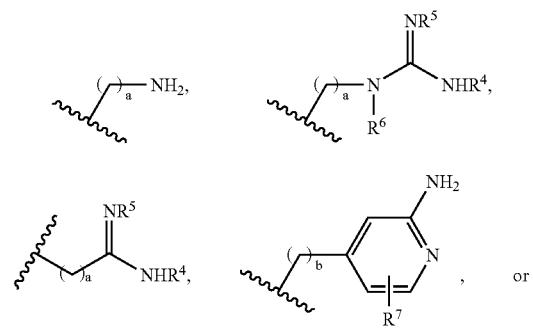

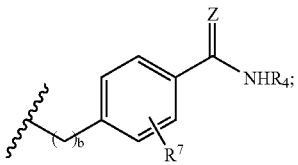

where a is an integer from 1–4, b is an integer from 0–2, R$^4$ and R$^5$ are H or C$_{1-6}$ alkyl, R$^6$ is H, OH, C$_{1-6}$ alkyl, or together with R$^4$ forms a 5- or 6-membered ring, and R$^7$ is H, OH, SH, NH$_2$, NO$_2$, optionally substituted C$_{1-6}$ alkyl, halogen, or CF$_3$; R$^2$ is and optionally substituted 2-propyl, 2-butyl, CH$_2$Ph, —CH$_2$(C$_6$H$_4$)-4-OH, cyclohexyl, or Ph; X is N; R$^3$ is H or an optionally substituted C$_{1-6}$ alkyl; A is an alpha-amino acid of the formula:

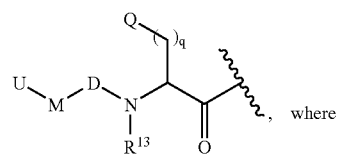

R$^{13}$ is H, C$_{1-6}$ alkyl, or together with M forms a 5- or 6-membered ring, D is C(O) or S(O)$_2$, q is an integer from 0–4; Q is an optionally substituted C$_{1-6}$ alkyl, C$_{3-8}$ cycloalkyl, C$_{1-9}$ heterocyclyl, C$_6$ or C$_{10}$ aryl, C$_{1-6}$ alkyloxy, C$_{3-8}$ cycloalkyloxy, C$_6$ or C$_{10}$ aryloxy, C$_{2-9}$ heterocyclyloxy, C$_{1-6}$ alkylthio, C$_{3-8}$ cycloalkylthio, C$_6$ or C$_{10}$ arylthio, C$_{1-6}$ alkylamino, C$_{2-12}$ dialkylamino, C$_{7-16}$ aralkylamino, C$_6$ or C$_{10}$ arylamino, C$_{2-9}$ heterocyclylamino, C$_{2-7}$ alkylaminocarbonyl, C$_{3-13}$ dialkylaminocarbonyl, amino, amidino, guanidino, hydroxy, or carboxy; M is single bond, NR$^{14}$, O, or S, wherein R$^{14}$ is H, C$_{1-6}$ alkyl, or when taken together with R$^{13}$ forms a 5- or 6-membered ring; U is an optionally substituted C$_{1-6}$alkyl, C$_{2-6}$ alkenyl, C$_{3-8}$ cycloalkyl, C$_{1-9}$ heterocyclyl, C$_{7-16}$ aralkyl, C$_{8-16}$ aralkenyl, C$_6$ or C$_{10}$ aryl, C$_{2-15}$ heteroaralkyl, or C$_{3-15}$ heteroaralkenyl, wherein when m is 1, R$^0$ is a thiazole, and when m is 0, R$^0$ is H or C$_{1-6}$ alkyl; and least one of U, R$^2$, or M when M is NR$^{14}$ further includes a linker attached to a moiety reactive to a free amine or sulfhydryl contained on a blood component. Exemplary linkers can be chosen from the polyethylene glycol moieties described herein, which can, for example, be linked to a compound of the invention by attachment to an amino group contained in U, R$^2$, or M when M is NR$^{14}$.

In yet another example, compounds modified with a linker have formula II:

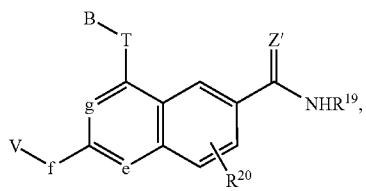

where e, g, T, B, Z', R$^{19}$, R$^{20}$, f, and V are as previously defined herein and and least one of B, or V further includes a linker attached to a moiety reactive to a free amine or sulfhydryl contained on a blood component. Exemplary linkers can be chosen from the polyethylene glycol moieties described herein, which can, for example, be linked to a compound of the invention by attachment to an amino group contained in B or V.

Other exemplary compounds of the invention further include a polyethylene glycol moiety. Desirably, the polyethylene glycol increases the half-life of the compound in vivo and/or increases the bioavailability of the compound. In various embodiments, the linear or branched polyethylene glycol is bonded to a compound of the invention via a spacer and/or has a molecular weight between 1,000 and 40,000 daltons, inclusive (e.g., approximately 1,000 daltons, 1,500 daltons, 2,000 daltons, 3,500 daltons, 5,000 daltons, 8,000 daltons, 10,000 daltons, 20,000 daltons, or 40,000 daltons). The polyethylene glycol moiety can be incorporated into the compounds of the invention by attachment to the A, $R^0$, or $R^3$ substituents of the compounds of formula I or to the B or V substituents of the compounds of formula II in the same manner as attachment of the linkers as described herein.

The present invention also includes within its scope the pharmaceutical formulations which comprise at least one of the compounds of formula I or II in association with a pharmaceutically acceptable carrier or coating (e.g., pegylation). Administration of Compounds of the Invention for the Treatment or Prevention of Excess or Undesired Thrombosis.

A compound described in any of the embodiments of the above aspects of the invention may be used in any of the following clinical applications. For example, the compounds of the invention are useful for the treatment, stabilization, or prevention of a variety of medical disorders where anticoagulant therapy is indicated in the treatment or prevention of thrombotic conditions such as coronary artery and cerebro- and peripheral vascular disease. Indications include, but are not limited to, myocardial infarction, venous or arterial thrombosis, the formation of atherosclerotic plaques, coagulation syndromes, endarterectomy, including carotid endarterectomy, envascular injury including reocclusion and restenosis following angioplasty and coronary artery bypass surgery, thrombus formation after the application of blood vessel operative techniques, the introduction of artificial heart valves or on the recirculation of blood, cerebral infarction, cerebral thrombosis, transient ischemic attacks, stroke, cerebral embolism, pulmonary embolism, ischaemia, and angina, including unstable angina. In addition, pathologic thrombus formation often occurs in the venous vasculature of the lower extremities following knee, hip, and abdominal surgery (e.g., deep vein thrombosis, DVT). DVT further predisposes the patient to a higher risk of pulmonary thromboembolism. Disseminated intravascular coagulopathy (DIC), a systemic condition that commonly occurs in vascular systems during septic shock, certain viral infections, and cancer, is also indicated for treatment by compounds of the present invention. This condition is characterized by a rapid consumption of coagulation factors and their plasma inhibitors which can result in the formation of life-threatening clots throughout the microvasculature of several organ systems. Another application of Factor XIa inhibitors is the enhancement of fibrinolysis by tissue plasminogen activator.

In addition to their use in anticoagulant therapy, Factor XIa inhibitors are useful in the treatment and prevention of other diseases in which the generation of thrombin has been implicated as playing a physiologic role. For example, thrombin has been implicated in contributing to the morbidity and mortality of chronic and degenerative diseases such as cancer, arthritis, atherosclerosis, and Alzheimer's disease by its ability to regulate many different cell types through specific cleavage and activation of a cell surface thrombin receptor, mitogenic effects, diverse cellular functions such as cell proliferation, for example, abnormal proliferation of vascular cells resulting in restenosis or angiogenesis, release of PDGF, and DNA synthesis. Inhibition of Factor XIa effectively blocks thrombin generation and therefore neutralizes any physiologic effects of thrombin on various cell types. The representative indications discussed above include some, but not all, of the potential clinical situations amenable to treatment with a Factor XIa inhibitor.

Thus, one or more compounds of the invention can be used in the manufacture of medicaments for use in the production of an antithrombotic or anticoagulant. In one aspect, the invention features a method of treating, stabilizing, or preventing a disease, disorder, or condition associated with undesirable or excess thrombosis in a mammal (e.g., a human). This method involves administering a compound of the invention to the mammal in an amount sufficient to treat, stabilize, or prevent the disease, disorder, or condition. The compound may be administered to the mammal before, during, or after the occurrence of the condition.

In various embodiments, a compound that binds to Factor XI or Factor XIa decreases the activity of Factor XIa, the binding of a Factor XIa to another molecule (e.g., a substrate for Factor XIa), or the half-life of a Factor XI protein, as measured using standard methods (see, for example, Coligan, et al. *Current Protocols in Protein Chemistry, Chapters 19 and 20*, John Wiley & Sons, New York, 2000; Ausubel et al., *Current Protocols in Molecular Biology*, Chapter 9, John Wiley & Sons, New York, 2000). For example, the compound may competitively, noncompetitively, or uncompetitively inhibit the ability of Factor XI or Factor XIa to bind one or more of its endogenous substrates. The level of protein may be determined using standard Western, blot immunoassay, or immunohistochemical analysis (see, for example, Coligan, et al., supra; Ausubel et al., supra). Desirably, the compound decreases Factor XIa activity by at least 20, 40, 60, 80, 90 or 95%. In another desirable embodiment, the level of Factor XIa activity is at least 2, 3, 5, 10, 20, or 50-fold lower in the presence of the compound. In some embodiments, the compound is administered in a dose that is sufficient to reduce thrombosis but does not eliminate normal clotting resulting from external injuries or does not induce bleeding complications. In desirable embodiments, the half-life of an injected compound is less than 7, 6, 5, 4, 3, 2, 1, or 0.5 hours. In some embodiments, the half-life is contained within one of the following ranges: 4–6 hours, 2–4 hours, 30–120 minutes, or 30–60 minutes, inclusive. In desirable embodiments, the half-life of an oral compound is less than 24, 20, 16, 12, 8, or 4 hours. In some embodiments, the half-life is contained within one of the following ranges: 20–28 hours, 14–20 hours, 10–14 hours, 6–10 hours, 2–6 hours or 30–120 minutes, inclusive. In desirable embodiments, the compound has better inhibitory activity than benzamidine for Factor XIa, such as an $IC_{50}$ value of less than 100, 10, 1, 0.1, 0.01, or 0.001 μM.

With respect to the therapeutic methods of the invention, it is not intended that the administration of compounds to a mammal be limited to a particular mode of administration, dosage, or frequency of dosing; the present invention contemplates all modes of administration, including oral, intraperitoneal, intramuscular, intravenous, intraarticular, intralesional, subcutaneous, or any other route sufficient to provide a dose adequate to prevent or treat excess or undesired Factor XIa activity (e.g., excess or undesired clotting). One or more compounds may be administered to the mammal in a single dose or multiple doses. When multiple doses are administered, the doses may be separated from one another by, for example, several hours, one day, one week, one month, or one year. It is to be understood that, for any particular subject, specific dosage regimes should be adjusted over time according to the individual need and the professional judgment of the person administering or supervising the administration of the compositions. If desired, conventional treatments such as heparin may be used in combination with the compounds of the present invention. Exemplary mammals that can be treated using the methods of the invention include humans, primates such as monkeys, animals of veterinary interest (e.g., cows, sheep, goats, buffalos, and horses), and domestic pets (e.g., dogs and cats).

For clinical applications, compounds of the present invention may generally be administered, e.g., parenterally, intravenously, subcutaneously, intramuscularly, colonically, nasally, intraperitoneally, rectally, buccally, or orally. Compositions containing at least one compound of the invention that is suitable for use in human or veterinary medicine may be presented in forms permitting administration by a suitable route. These compositions may be prepared according to the customary methods, using one or more pharmaceutically acceptable adjuvants or excipients. The adjuvants comprise, inter alia, diluents, sterile aqueous media, and various non-toxic organic solvents. Acceptable carriers or diluents for therapeutic use are well known in the pharmaceutical field, and are described, for example, in *Remington: The Science and Practice of Pharmacy* (20th ed.), ed. A. R. Gennaro, Lippincott Williams & Wilkins, 2000, Philadelphia, and *Encyclopedia of Pharmaceutical Technology*, eds. J. Swarbrick and J. C. Boylan, 1988–1999, Marcel Dekker, New York. The compositions may be presented in the form of tablets, pills, granules, powders, aqueous solutions or suspensions, injectable solutions, elixirs, or syrups, and the compositions may optionally contain one or more agents chosen from the group comprising sweeteners, flavorings, colorings, and stabilizers in order to obtain pharmaceutically acceptable preparations.

The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents which facilitate suspension. Diluents such as sucrose, ethanol, polyethylene glycol, propylene glycol, glycerol, chloroform, or mixtures thereof may also be used.

For parenteral administration, emulsions, suspensions, or solutions of the compositions of the invention in vegetable oil (e.g., sesame oil, groundnut oil, or olive oil), aqueous-organic solutions (e.g., water and propylene glycol), injectable organic esters (e.g., ethyl oleate), or sterile aqueous solutions of the pharmaceutically acceptable salts are used. The solutions of the salts of the compositions of the invention are especially useful for administration by intramuscular or subcutaneous injection. Aqueous solutions that include solutions of the salts in pure distilled water may be used for intravenous administration with the proviso that (i) their pH is adjusted suitably, (ii) they are appropriately buffered and rendered isotonic with a sufficient quantity of glucose or sodium chloride, and (iii) they are sterilized by heating, irradiation, or microfiltration. Suitable compositions containing the compounds of the invention may be dissolved or suspended in a suitable carrier for use in a nebulizer or a suspension or solution aerosol, or may be absorbed or adsorbed onto a suitable solid carrier for use in a dry powder inhaler. Solid compositions for rectal administration include suppositories formulated in accordance with known methods and containing at least one compound of formula I or II.

Dosage formulations of the compounds of this invention to be used for therapeutic administration must be sterile. Sterility is readily accomplished by filtration through sterile membranes (e.g., 0.2 micron membranes) or by other conventional methods. Formulations typically are stored in lyophilized form or as an aqueous solution. The pH of the compositions of this invention is typically between 3 and 11, more desirably between 5 and 9, and most desirably between 7 and 8, inclusive. While a desirable route of administration is by injection such as intravenously (bolus and/or infusion), other methods of administration may be used. For example, compositions may be administered subcutaneously, intramuscularly, colonically, rectally, nasally, or intrapertoneally in a variety of dosage forms such as suppositories, implanted pellets or small cylinders, aerosols, oral dosage formulations, and topical formulations such as ointments, drops, and dermal patches. The compounds of the invention are desirably incorporated into shaped articles such as implants, including but not limited to valves, stents, tubing, and prostheses, which may employ inert materials such as synthetic polymers or silicones, (e.g., Silastic, silicone rubber, or other commercially available polymers). Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the Factor XIa inhibitors of the invention may be coupled to a class of biodegradable polymers useful in achieving controlled release of a drug, for example polylactic acid, polyglycolic acid, copolymers of polylaclic and polyglycolic acid, poly-epsilon caprolactone, polyhydroxy butyric acid, polyorthoesters, polyacetals, polydihydropyrans, polycyanoacrylates, and cross linked or amphipathic block copolymers of hydrogels.

The compounds of the invention may also be administered in the form of liposome delivery systems, such as small unilamellar vesicles, large unilamellar vesicles, and multi-lamellar vesicles. Liposomes can be formed from a variety of lipids, such as cholesterol, stearylamine, or phosphatidyl-cholines. The compounds of the invention may also be delivered using antibodies, antibody fragments, growth factors, hormones, or other targeting moieties to which the compound molecules are coupled (e.g., see *Remington: The Science and Practice of Pharmacy*, vide supra), including in vivo conjugation to blood components of a suitably modified compound of the formula I or II which possesses a metastable or reactive functional group as described above.

Dosage levels of active ingredients in the pharmaceutical compositions of the invention may be varied to obtain an amount of the active compound(s) that achieves the desired therapeutic response for a particular patient, composition, and mode of administration. The selected dosage level depends upon the activity of the particular compound, the route of administration, the severity of the condition being treated, and the condition and prior medical history of the patient being treated. For adults, the doses are generally from about 0.01 to about 100 mg/kg, desirably about 0.1 to about 1 mg/kg body weight per day by inhalation, from about 0.01 to about 100 mg/kg, desirably 0.1 to 70 mg/kg, more desirably 0.5 to 10 mg/kg body weight per day by oral administration, and from about 0.01 to about 50 mg/kg, desirably 0.1 to 1 mg/kg body weight per day by intravenous administration. Doses are determined for each particular case using standard methods in accordance with factors unique to the patient, including age, weight, general state of health, and other factors which can influence the efficacy of the compound(s) of the invention.

Administration of compositions of the invention may be as frequent as necessary to obtain the desired therapeutic effect. Some patients may respond rapidly to a higher or lower dose and may find much weaker maintenance doses adequate. Other patients, however, receive long-term treatments at the rate of 1 to 4 doses per day, in accordance with the physiological requirements of each patient. The active product may be administered, e.g., orally 1 to 4 times daily.

EXAMPLE 33

Enzyme Assays

The ability of compounds of the present invention to inhibit Factor XIa and related serine proteases such as Factor Xa, thrombin, trypsin, Factor VIIa, plasma kallikrein, tissue-plasminogen activator (t-PA), urokinase-plasminogen activator (u-PA), plasmin, and activated protein C (APC) were evaluated by determining the concentration of inhibitor which resulted in a 50% reduction in enzyme activity ($IC_{50}$) using purified enzyme. Potential inhibitors of Factor XIa were evaluated using the following assay. Briefly, the inhibitors were tested against native Factor XIa (Haematological Associates, P/N FXIA01) using a custom made analog of S-2366, pyroGlu-Pro-Arg-7-methylamidocoumarin (AMC) available from American Peptide, Inc. This analog is based on the well described substrate pyro-Glu-Pro-Arg-pNA, a.k.a. S-2366, available from Diapharma Group, Inc. (Columbus, Ohio). This substrate had the p-nitroanaline group replaced with 7-methylaminocoumarin (AMC).

The final concentration of the substrate in the assay was 100 μM, and the final concentration of the enzyme was 0.25 nM. Inhibitors were tested by serial dilution over an appropriate range to yield a dose response curve for determination of the inhibitors' $IC_{50}$ value. The assay mixture was incubated for 30 minutes at 30° C., and the fluorescent yield measured using a PE-Wallac VICTOR2™ Plate Reader. Dose response curves were fit to equation 1 below in which A is the maximum inhibition, B is the minimum inhibition, C is the $IC_{50}$, and D is the Hill coefficient.

$$\left[(A-B) \bigg/ \left(1 + \left(\frac{X}{C}\right)^D\right)\right] + B \qquad \text{EQN. 1}$$

Desirable compounds have an $IC_{50}$ value for inhibiting Factor XIa of less than 1 micromolar, 100 nanomolar, 10 nanomalar, or 1 nanomolar (in order of increasing preference). Table 12 shows the $IC_{50}$ values for some of the compounds of formula I, where X is N, $R^1$ is 3-guanidinopropyl, m is 1, X is N, $R^3$ is H, and $R^0$ is 2-thiazole.

TABLE 12

Selective inhibition of factor XIa by compounds of formula I (X is N, $R^1$ is 3-guanidinopropyl, m is 1, X is N, $R^3$ is H, and $R^0$ is 2-thiazole)

| A | $R^2$ | FXIa (uM) | FXa (uM) | Thrombin (uM) |
|---|---|---|---|---|
| 3-Cl-phenyl-CH(OH)-C(O)- | isopropyl | 0.116 | 2.357 | 0.225 |
| phenyl-CH(OH)-C(O)- | isopropyl | 0.425 | 1.185 | 0.253 |
| 3-(H3CO2C)-phenyl-CH2-S(O)2-NH-CH(cyclohexyl)-C(O)- | isopropyl | 0.005 | 0.031 | 0.020 |
| 3,4-diCl-phenyl-CH2-NH-C(O)-NH-CH(isobutyl)-C(O)- | isopropyl | 0.064 | 20.000 | 0.615 |

TABLE 12-continued

Selective inhibition of factor XIa by compounds of formula I (X is N, $R^1$ is 3-guanidinopropyl, m is 1, X is N, $R^3$ is H, and $R^0$ is 2-thiazole)

| A | $R^2$ | FXIa (uM) | FXa (uM) | Thrombin (uM) |
|---|---|---|---|---|
| (3,4-dichlorobenzyl urea-Leu structure) | (isobutyl) | 0.078 | 84.872 | 2.653 |

Table 13 shows the $IC_{50}$ values for compounds of formula I, where X is N, W is N, $R^2$ is H, $R^1$ is 3-guanidinopropyl, m is 1, $R^0$ is 2-thiazole, $R^3$ together with A forms a ring having the formula:

TABLE 13

(pyrimidinone structure with B—$Y^1$ and $R^{17}$)

Selective inhibition of factor XIa by compounds of formula I

| B—$Y^1$— | $R^{17}$ | FXIa (uM) | FXa (uM) | thrombin |
|---|---|---|---|---|
| (benzylamino) | (m-tolyl) | 0.612 | 0.470 | 0.065 |

TABLE 13-continued (pyrimidinone structure with B—$Y^1$ and $R^{17}$)

Selective inhibition of factor XIa by compounds of formula I

| B—$Y^1$— | $R^{17}$ | FXIa (uM) | FXa (uM) | thrombin |
|---|---|---|---|---|
| (isopropylamino) | 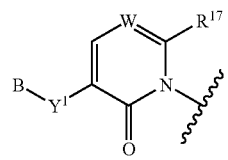 | 1.031 | 0.391 | 14.180 |

Table 14 shows the $IC_{50}$ values for compounds of formula II, where Z' is NH, each of e and g is C—H, each of $R^{19}$ and $R^{20}$ is H, f is a covalent bond, and T is NH.

TABLE 14

Selective inhibition of factor XIa by compounds of formula II (Z' is NH, each of e and g is C—H, each of $R^{19}$ and $R^{20}$ is H, f is a covalent bond, T is NH)

| V | B | FXIa (uM) | FXa (uM) | thrombin (uM) |
|---|---|---|---|---|
| (benzylamide) | (3-hydroxy-2-methylbenzoyl) | 0.076 | 1.194 | 30.7 |

TABLE 14-continued

Selective inhibition of factor XIa by compounds of formula II (Z' is NH, each of e and g is C—H, each of $R^{19}$ and $R^{20}$ is H, f is a covalent bond, T is NH)

| V | B | FXIa (uM) | FXa (uM) | thrombin (uM) |
|---|---|---|---|---|
| 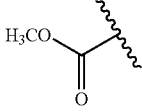 | 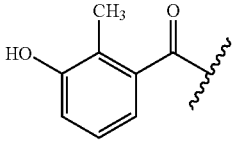 | 0.111 | 2.62 | 7.45 |
| 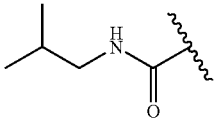 | 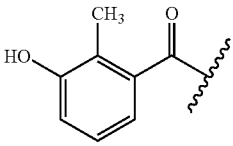 | 0.571 | 7.9 | 16.3 |
| H | 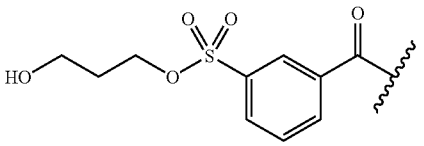 | 0.609 | 41.2 | 163 |
| H | 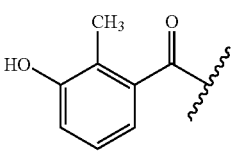 | 0.700 | 3.2 | 58.5 |

EXAMPLE 34

Clotting Assays

Human Plasma Based Clotting Assay

An activated partial thomboplastin time (aPTT) assay was used to measure the ability of compounds to inhibit the contact coagulation pathway. This pathway involves Factor XII, kallikrein, and Factor XI, which activates Factor IX and Factor VIII, leading to activation of Factor X and Factor V, and then activation of Factor II to form a blood clot (FIG. 1). For this assay, $CaCl_2$ (30 mM) was placed in a large central reagent position of a Thromboscreen 400C instrument, allowing it to equilibrate to 37° C. Plasma (50 ul) and compounds of the invention were added at different concentrations to cuvettes. After incubation for two minutes, aPTT reagent (ALEXIN®, Sigma) was added (50 ul) and incubated an additional three minutes. The cuvettes were transferred to a measuring position; prewarmed $CaCl_2$ reagent (50 ul) was added, and readings were then taken over a maximum of 300 seconds. A dose response curve was generated, and the concentration at which the clotting time was doubled (2×aPTT) was determined. Compounds which inhibit Factor XIa in the desired range desirably have an effect at less than 50 uM, more desirably at less than 10 uM.

A prothrombin time (PT) assay was also used to measure inhibition of coagulation. In this assay, the Factor XI dependent steps are bypassed. Hence, the assay measures inhibition of Factor VIIa, Factor Xa, and thrombin, but not FXI. This assay measures the ability of Factor VIIa to activate Factor X, which activates Factor II to form a blood clot. For this assay, the thromboplastin reagent (THROMBOMAX® with Calcium, Sigma) was placed in a central reagent position in a Thromboscreen 400C instrument, and allowed to equilibrate to 37° C. Plasma (50 ul of plasma prewarmed for three minutes) and compounds of the invention (different concentrations) were added to cuvettes. The cuvettes were transferred to a measuring position. The prewarmed Thromboplastin reagent (100 ul) was then added, and readings were then taken over 300 seconds. A dose response curve was generated, and the concentration at which the clotting time was doubled (2×PT) was determined.

EXAMPLE 36

Experimental In Vivo Rat Venous Thrombosis Model

The model of venous thrombosis used incorporated stenosis of the inferior vena cava with rapid infusion of hypotonic saline followed by partial stasis of blood flow (Millet, et al., (1987). *Thromb. Res.*, 45, 123–133; Schumacher et al., (1996). *J. Cardiovasc. Pharmacol.*, 28, 19–25).

Briefly, male Sprague-Dawley rats (300–400 g) were anesthetized using ketamine/xylazine I.M. A midline laparotomy was performed, and the vena cava was visualized and gently separated from the descending aorta using cotton swabs. Both iliolumbar veins were ligated with suture (3–0 silk). A loose ligature (3–0 silk) was placed around the vena cava distal to the renal veins. A 25G butterfly bent at a 90-degree angle and attached to a 5 cc syringe filled with 2.5 mL of hypotonic saline (0.225%) was inserted into the vena cava at the level of the iliolumbar veins and glued into place using VETBOND™. A 26G needle bent to a 90-degree angle was then tied tightly to the vena cava, using the loose ligature. An atraumatic clamp was placed on the vena cava proximal to the iliac bifurcation, and the hypotonic saline manually infused at a rate of 10 mL/minutes. The atraumatic clamp was removed, along with the 26G needle, creating a 26G stenosis. Organs were carefully replaced, and animals were kept normothermic until sacrifice. Animals were sacrificed by anesthetic overdose at 10 or 60 minutes post thrombus induction. Following sacrifice, the vena cava was isolated using hemostats, and the clot(s) was dissected out. Clots were removed, blotted on gauze, and then immediately weighed using an analytical balance.

Compounds under investigation along with vehicles and positive controls (heparin, enoxaparin) were administered intravenously via a catheter (PE-50 tubing) implanted in the jugular or femoral vein. In some studies, rats were administered a bolus of the test article (4 mL/kg) via the venous catheter immediately prior to initiation of intravenous infusion (4 mL/kg/h). The rats were subjected to the challenge 15 minutes post bolus/infusion initiation. All test article infusions continued to the end of the study period.

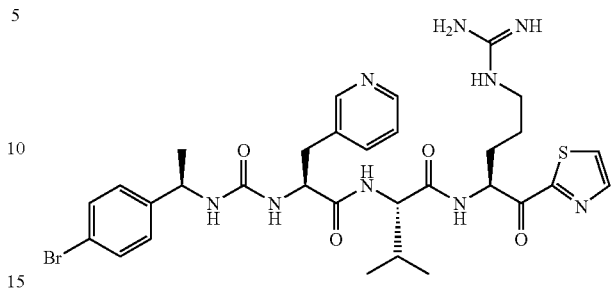

(22)

Continuous intravenous administration of compound 22 suppressed the thrombus formation induced by stenosis of the inferior vena cava with rapid infusion of hypotonic saline followed by partial stasis in the rat (FIG. 10). Administration of compound XLXI commenced 15 minutes prior to thrombotic challenge, with determination of thrombus mass at 60 minutes post challenge. Efficacy was observed at a total dose exposure of 1.4 mg/kg with no further decrease in thrombus size at 4.0 mg/kg. Despite the fact that the specificity of compound XLXI for rat Factor XIa is 11-fold less than that observed against native human Factor XIa, statistically significant efficacy was observed in a rat model of venous thrombosis.

Other Embodiments

From the foregoing description, it will be apparent that variations and modifications may be made to the invention described herein to adapt it to various usages and conditions. Such embodiments are also within the scope of the following claims.

All publications mentioned in this specification are herein incorporated by reference to the same extent as if each independent publication or patent application was specifically and individually indicated to be incorporated by reference.

---

What is claimed is:

1. A purified human Factor XI protein comprising amino acids 370–607 as set forth in SEQ ID NO: 15 and one of the following mutations at a position relative to the sequence set forth in SEQ ID NO: 15:
   (i) S434A;
   (ii) T475A;
   (iii) S434A, T475A;
   (iv) S434A, T475A, K422A
   (v) S434A, T475A, K437A;
   (vi) S434A, T475A, K486A;
   (vii) S434A, T475A, K505A;
   (viii) S434A, T475A, K509A;
   (ix) S434A, T475A, C482S;
   (x) S434A, T475A, C482S, K437A;
   (xi) S434A, T475A, C482S, R479A;
   (xii) S434A, T475A, C482S, K505A;
   (xiii) S434A, T475A, C482S, D476A;
   (xiv) S434A, T475A, C-terminal truncation of A606 and V607; or
   (xv) S434A, T475A, C482S, Y416S.

2. A purified Factor XI protein comprising amino acids 370–607 as set forth in SEQ ID NO: 15 and one or more of the following mutations:
   (a) a mutation of a residue of said protein that disrupts post-translational N-linked glycosylation when said protein is recombinantly expressed in an organism,
   (b) a mutation that eliminates a free, reactive sulfhydryl group of a cysteine residue present in said protein, or
   (c) a mutation of the $NH_2$— or COOH-terminal residue of said protein, wherein said mutation of the $NH_2$— or COOH-terminal residue of said protein promotes crystallization of said protein relative to wild-type Factor XI lacking said mutation.

3. The protein of claim 2, wherein said protein comprises a mutation of an asparagine, seine, or threonine residue within an Asn-Xaa-(Ser/Thr) N-linked glycosylation consensus sequence, wherein Xaa is any amino acid other than proline.

4. The protein of claim 3 comprising a mutation in said protein at a position relative to the mature human Factor XI polypeptide sequence set forth in SEQ ID NO: 15, wherein said mutation is selected from:
   (a) S434A;
   (b) T475A; and
   (c) S434A, T475A.

5. The protein of claim 2 comprising a mutation in said protein at a position relative to the mature human Factor XI polypeptide sequence set forth in SEQ ID NO: 15, wherein said mutation is C482S.

6. A purified Factor XI protein comprising amino acids 370–605 as set forth in SEQ ID NO: 15, wherein said protein, lacks the C-terminal alanine and valine residues at positions 606 and 607 of the mature human Factor XI polypeptide sequence set forth in SEQ ID NO: 15.

* * * * *